US009970020B2

(12) United States Patent
Yonekura et al.

(10) Patent No.: US 9,970,020 B2
(45) Date of Patent: *May 15, 2018

(54) PLANT WITH REDUCED PROTEIN PRODUCTIVITY IN SEEDS AND METHOD FOR PRODUCING SAME

(71) Applicant: TOYOTA JIDOSHA KABUSHIKI KAISHA, Toyota-shi, Aichi (JP)

(72) Inventors: Madoka Yonekura, Toyota (JP); Chikara Ohto, Toyota (JP); Nobuhiko Muramoto, Ichinomiya (JP); Norihiro Mitsukawa, Miyoshi (JP); Masaru Takagi, Tsuchiura (JP); Kyoko Matsui, Ryugasaki (JP)

(73) Assignee: TOYOTA JIDOSHA KABUSHIKI KAISHA, Tokyo-shi, Aichi-ken (JP)

( * ) Notice: Subject to any disclaimer, the term of this patent is extended or adjusted under 35 U.S.C. 154(b) by 160 days.

This patent is subject to a terminal disclaimer.

(21) Appl. No.: 14/976,291

(22) Filed: Dec. 21, 2015

(65) Prior Publication Data
US 2016/0108417 A1 Apr. 21, 2016

Related U.S. Application Data

(62) Division of application No. 13/376,169, filed as application No. PCT/JP2010/059495 on Jun. 4, 2010, now Pat. No. 9,309,531.

(30) Foreign Application Priority Data
Jun. 4, 2009 (JP) ................................. 2009-135195

(51) Int. Cl.
C12N 15/82 (2006.01)
C07K 14/415 (2006.01)

(52) U.S. Cl.
CPC ........ *C12N 15/8251* (2013.01); *C07K 14/415* (2013.01)

(58) Field of Classification Search
None
See application file for complete search history.

(56) References Cited

U.S. PATENT DOCUMENTS

| 5,516,668 | A | 5/1996 | Maruta |
| 5,783,394 | A | 7/1998 | Bestwick et al. |
| 5,914,449 | A | 6/1999 | Murase et al. |
| 6,717,034 | B2 | 4/2004 | Jiang |
| 7,342,148 | B2 | 3/2008 | Takagi et al. |
| 2003/0101481 | A1 | 5/2003 | Zhang et al. |
| 2003/0226173 | A1 | 12/2003 | Ratcliffe et al. |
| 2004/0006797 | A1 | 1/2004 | Shi et al. |
| 2004/0045049 | A1 | 3/2004 | Zhang et al. |
| 2004/0093638 | A1 | 5/2004 | Sasaki et al. |
| 2005/0005333 | A1 | 1/2005 | Ruezinsky et al. |
| 2005/0183169 | A1 | 8/2005 | Takagi et al. |
| 2006/0107345 | A1 | 5/2006 | Alexandrov et al. |
| 2006/0272060 | A1 | 11/2006 | Heard et al. |
| 2007/0022495 | A1 | 1/2007 | Reuber et al. |
| 2008/0072340 | A1 | 3/2008 | Troukhan et al. |
| 2008/0096277 | A1 | 4/2008 | Kuroda |
| 2009/0019605 | A1 | 1/2009 | Takagi et al. |
| 2009/0094717 | A1 | 4/2009 | Troukhan et al. |
| 2009/0116723 | A1 | 5/2009 | Okajima et al. |
| 2009/0178161 | A1 | 7/2009 | Arar et al. |
| 2009/0190821 | A1 | 7/2009 | Marugame |
| 2009/0300790 | A1 | 12/2009 | Aharoni et al. |
| 2010/0311994 | A1 | 12/2010 | Chatani et al. |
| 2011/0010804 | A1 | 1/2011 | Chatani et al. |
| 2011/0081691 | A1 | 4/2011 | Ohto et al. |
| 2011/0099664 | A1 | 4/2011 | Takagi et al. |
| 2011/0209244 | A1 | 8/2011 | Takagi et al. |
| 2012/0144522 | A1 | 6/2012 | Kondo et al. |
| 2012/0159673 | A1 | 6/2012 | Kondo et al. |

FOREIGN PATENT DOCUMENTS

| EP | 1586652 A1 | 10/2005 |
| EP | 1702508 A1 | 9/2006 |
| EP | 1 469 010 B1 | 11/2008 |
| EP | 1992220 A1 | 11/2008 |
| JP | 60-2023 B2 | 1/1985 |
| JP | 02-035358 A | 2/1990 |
| JP | 06-090766 A | 4/1994 |
| JP | 6-217719 A | 8/1994 |
| JP | 6-303925 A | 11/1994 |
| JP | 9-182 A | 1/1997 |
| JP | 9-65840 A | 3/1997 |
| JP | 09-313059 A | 12/1997 |
| JP | 2001-059842 A | 3/2001 |
| JP | 3149951 B2 | 3/2001 |
| JP | 2001-269176 A | 10/2001 |
| JP | 2001-269177 A | 10/2001 |

(Continued)

OTHER PUBLICATIONS

Yaklich, J Agric Food Chem 49:729-35 (2001).*
Liu et al., J Am Oil Chem Soc 72:189-92 (1995).*
S. Takada et al., Accession No. AB049071, The CUP-SHAPED COYTLEDON1 gene of *Arabidopsis* regulates shoot apical meristem formation, Database NCBI/GenBank (online), 2006, retrieved from http://www.ncbi.nlm.nih.gov/entrez/viewer.fcgi12060425:DDBJ:5636984 on Dec. 25, 2008.
Notice of Allowance dated Jan. 6, 2016, issued by the United States Patent and Trademark Office in U.S. Appl. No. 13/376,169.
Notice of Allowance dated Aug. 21, 2015, issued by the United States Patent and Trademark Office in U.S. Appl. No. 13/376,169.
Office Action, dated Jan. 2, 2015, issued by the United States Patent and Trademark Office in U.S. Appl. No. 13/376,169.

(Continued)

*Primary Examiner* — Cathy Kingdon Worley
*Assistant Examiner* — Russell T Boggs
(74) *Attorney, Agent, or Firm* — Sughrue Mion, PLLC

(57) ABSTRACT

According to the present invention, a gene having a novel function that can cause an increase or decrease in seed protein content is searched for. A chimeric protein obtained by fusing a transcription factor consisting of a protein comprising an amino acid sequence shown in any of the even-numbered SEQ ID NOS: 1 to 76 and a functional peptide capable of converting an arbitrary transcription factor into a transcriptional repressor or a transcription factor consisting of a protein comprising an amino acid sequence shown in any of the even-numbered SEQ ID NOS: 77 to 84 is expressed in a plant.

4 Claims, No Drawings

(56) References Cited

FOREIGN PATENT DOCUMENTS

| | | |
|---|---|---|
| JP | 2001-269178 A | 10/2001 |
| JP | 2001-269179 A | 10/2001 |
| JP | 2001-292776 A | 10/2001 |
| JP | 2001-292777 A | 10/2001 |
| JP | 3407034 B2 | 10/2001 |
| JP | 2001-333705 A | 12/2001 |
| JP | 3289043 B2 | 6/2002 |
| JP | 2002-524028 A | 8/2002 |
| JP | 3407033 B2 | 3/2003 |
| JP | 3407035 B2 | 3/2003 |
| JP | 3409079 B2 | 3/2003 |
| JP | 3407036 B2 | 5/2003 |
| JP | 3421740 B2 | 5/2003 |
| JP | 2004-500823 A | 1/2004 |
| JP | 2004-286666 A | 10/2004 |
| JP | 2005-013214 A | 1/2005 |
| JP | 2005-027654 A | 2/2005 |
| JP | 2005-052114 A | 3/2005 |
| JP | 3656104 B2 | 3/2005 |
| JP | 2005-192483 A | 7/2005 |
| JP | 2005-204573 A | 8/2005 |
| JP | 2005-204657 A | 10/2005 |
| JP | 2005-278422 A | 10/2005 |
| JP | 2005-295878 A | 10/2005 |
| JP | 2005-295879 A | 10/2005 |
| JP | 2005-325136 A | 11/2005 |
| JP | 2005-352571 A | 12/2005 |
| JP | 2006-006248 A | 1/2006 |
| JP | 2006-020607 A | 1/2006 |
| JP | 2006-034218 A | 2/2006 |
| JP | 2006-42729 A | 2/2006 |
| JP | 2006-042730 A | 2/2006 |
| JP | 2006-055125 A | 3/2006 |
| JP | 2006-101827 A | 4/2006 |
| JP | 2006-134188 A | 5/2006 |
| JP | 2006-280242 A | 10/2006 |
| JP | 3829200 B2 | 10/2006 |
| JP | 2006-325588 A | 12/2006 |
| JP | 3995211 B2 | 10/2007 |
| JP | 2008-502358 A | 1/2008 |
| JP | 2009-009290 A | 1/2009 |
| JP | 2009-115598 A | 5/2009 |
| JP | 2009-180539 A | 8/2009 |
| JP | 2009-210409 A | 9/2009 |
| WO | 00/05385 A1 | 2/2000 |
| WO | 01/35727 A1 | 5/2001 |
| WO | 01/36597 A1 | 5/2001 |
| WO | 01/64022 A2 | 9/2001 |
| WO | 03/013227 A2 | 2/2003 |
| WO | 03/055903 A1 | 7/2003 |
| WO | 2004/046336 A2 | 6/2004 |
| WO | 2004/056993 A1 | 7/2004 |
| WO | 2005047516 A2 | 5/2005 |
| WO | 2005/085467 A1 | 9/2005 |
| WO | 2005120215 A1 | 12/2005 |
| WO | 2006/056701 A1 | 6/2006 |
| WO | 2006133461 A1 | 12/2006 |
| WO | 2007/102346 A1 | 9/2007 |
| WO | 2007/117693 A2 | 10/2007 |
| WO | 2008/041693 A1 | 4/2008 |
| WO | 2008/074891 A2 | 6/2008 |
| WO | 2010/035618 A1 | 4/2010 |
| WO | 2010/041423 A1 | 4/2010 |

OTHER PUBLICATIONS

Office Action, dated May 27, 2014, issued by the United States Patent and Trademark Office in U.S. Appl. No. 13/376,169.
Office Action, dated Feb. 27, 2014, issued by the United States Patent and Trademark Office in U.S. Appl. No. 13/376,169.
Communication, dated Apr. 22, 2015, issued by the United States Patent and Trademark Office in U.S. Appl. No. 13/376,169.
Communication, dated Jun. 26, 2015, issued by the United States Patent and Trademark Office in U.S. Appl. No. 13/376,169.
Akio Ohyama, et al., "Environmental risk evaluation of rice plants transformed with chimeric antisense cDNA for glutenin", Breeding Research, 2001, pp. 139-149, vol. 3.
Antony N. Dodd, et al., "Plant Circadian Clocks Increase Photosynthesis, Growth, Survival, and Competitive Advantage", Science, Jul. 22, 2005, pp. 630-633, vol. 309.
Heyl et al., The Transcriptional Repressor ARR1-SRDX Suppresses Pleiotropic Cytokinin Activities in *Arabidopsis*, Plant Physiology, Jul. 2008, vol. 147, pp. 1380-1395, 21 pages total.
Hon-Ming Lam, et al., "Overexpression of the ASN1 Gene Enhances Nitrogen Status in Seeds of *Arabidopsis*", Plant Physiology, Jun. 2003, pp. 926-935, vol. 132.
Iwase et al., Manipulation of plant metabolic pathways by transcript factors, Plant Biotechnology, 2009, vol. 26, pp. 29-38.
John Doebley, et al., "The evolution of apical dominance in maize", Nature, Apr. 3, 1997, pp. 485-488, vol. 386.
Keiichiro Hiratsu, et al., "Dominant repression of target genes by chimeric repressors that include the EAR motif, a repression domain, in *Arabidopsis*", The Plant Journal, 2003, pp. 733-739, vol. 34.
Kyoko Matsui, et al., "AtMYBL2, a protein with a single MYB domain, acts as a negative regulator of anthocyanin biosynthesis in *Arabidopsis*", The Plant Journal, 2008, pp. 954-967, vol. 55.
Makoto Kusaba, et al., "Low glutelin content1: A Dominant Mutation That Suppresses the Glutelin Multigene Family via RNA Silencing in Rice", The Plant Cell, Jun. 2003, pp. 1455-1467, vol. 15.
Mingjie Chen, et al., "System Analysis of an *Arabidopsis* Mutant Altered in de Novo Fatty Acid Synthesis Reveals Diverse Changes in Seed Composition and Metabolism", Plant Physiology, May 2009, pp. 27-41, vol. 150.
Minoru Kubo, et al., "Transcription switches for protoxylem and metaxylem vessel formation", Genes & Development, 2005, pp. 1855-1860, vol. 19.
Monica Santos-Mendoza, et al., "Deciphering gene regulatory networks that control seed development and maturation in *Arabidopsis*", The Plant Journal, 2008, pp. 608-620, vol. 54.
Nobutaka Mitsuda, et al., "NAC Transcription Factors, NST1 and NST3, Are Key Regulators of the Formation of Secondary Walls in Woody Tissues of *Arabidopsis*", The Plant Cell, Jan. 2007, pp. 270-280, vol. 19.
Norihito Kuno, et al., "The Novel MYB Protein EARLY-PHYTOCHROME-RESPONSIVE1 Is a Component of a Slave Circadian Oscillator in *Arabidopsis*", The Plant Cell, Oct. 2003, pp. 2476-2488, vol. 15.
Taito Takeda, et al., "RNA interference of the *Arabidopsis* putative transcription factor TCP16 gene results in abortion of early pollen development", Plant Molecular Biology, 2006, pp. 165-177, vol. 61.
Tomotsugu Koyama, et al., "TCP Transcription Factors Control the Morphology of Shoot Lateral Organs via Negative Regulation of the Expression of Boundary-Specific Genes in *Arabidopsis*", The Plant Cell, Feb. 2007, pp. 473-484, vol. 19.
Yongfeng Guo, et al., "AtNAP, a NAC family transcription factor, has an important role in leaf senescence", The Plant Journal, 2006, pp. 601-612, vol. 46.
Yoshiyuki Maruta, et al., "Transgenic rice with reduced glutelin content by transformation with glutelin a antisense gene", Molecular Breeding, 2001, pp. 273-284, vol. 8.
Communication from the United State Patent and Trademark Office dated Feb. 11, 2015 from counterpart U.S. Appl. No. 12/921,060.
Communication from the United State Patent and Trademark Office dated Oct. 23, 2013 from counterpart U.S. Appl. No. 12/746,577.
Communication from the United States Patent and Trademark Office dated Oct. 8, 2013 from counterpart U.S. Appl. No. 12/921,060.
V.R. Bautista et al., "*Arabidopsis* ORF clones", GenBank Accession BT029518, 2006, retrieved from: http://wvvw.ncbi.nlm.nih.gov/entrez/viewer.fcgi?119360090:NCBI:15965543 on Dec. 25, 2008.
John L. Bowman, et al., "SUPERMAN, a regulator of floral homeotic genes in *Arabidopsis*", Development, 1992, pp. 599-615, vol. 114, The Company of Biologists Limited, Great Britain.

(56) References Cited

OTHER PUBLICATIONS

Xiaofeng Cao, et al., "Locus-specific control of asymmetric and CpNpG methylation by the DRM and CMT3 methyltransferase genes", PNAS, Dec. 2002, pp. 16491-16498, vol. 99, Suppl. 4.
Xiaofeng Cao, et al., "Role of the *Arabidopsis* DRM Methyltransferases in De Novo DNA Methylation and Gene Silencing", Current Biology, Jul. 2002, pp. 1138-1144, vol. 12, Elsevier Science Ltd.
Alex Cernac, et al., "WRINKLED1 encodes an AP2/EREB domain protein involved in the control of storage compound biosynthesis in *Arabidopsis*", The Plant Journal, 2004, pp. 575-585, vol. 40, Blackwell Publishing Ltd.
Christian Dubos et al., "MYB transcription factors in *Arabidopsis*", Trends in Plant Science, 2010, 15(10): 573-581.
Extended European Search Report (EESR) for corresponding European Patent Application No. 08 85 6425.7, dated Nov. 3, 2010.
Extended European Search Report (EESR) for corresponding European Patent Application No. 08858128.5, dated Nov. 15, 2010.
J. Christopher Gaiser, et al., "The *Arabidopsis* SUPERMAN Gene Mediates Asymmetric Growth of the Outer Integument of Ovules", The Plant Cell, Mar. 1995, pp. 333-345, vol. 7, American Society of Plant Physiologists.
Koji Goto, et al., "Function and regulation of the *Arabidopsis* floral homeotic gene PISTILLATA", Genes & Development, 1994, pp. 1548-1560, vol. 8, Cold Spring Harbor Laboratory Press.
Haiwei H. Guo et al., "Protein tolerance to random amino acid change", PNAS, 2004, 101(25): 9205-9210.
Keiichiro Hiratsu, et al., "Identification of the minimal repression domain of SUPERMAN shows that the DLELRL hexapeptide is both necessary and sufficient for repression of transcription in *Arabidopsis*", Biochemical and Biophysical Research Communications, 2004, pp. 172-178, vol. 321, Elsevier Inc.
Keiichiro Hiratsu, et al., "The SUPERMAN protein is an active repressor whose carboxy-terminal repression domain is required for the development of normal flowers", Federation of European Biochemical Societies, 2002, pp. 351-354, vol. 514, Elsevier Science B.V.
Yuxin Hu et al., "The *Arabidopsis* Auxin-Inducible Gene ARGOS Controls Lateral Organ Size", The Plant Cell, 2003, 15: 1951-1961.
Yuxin Hu. et al., "The *Arabidopsis* ARGOS-LIKE gene regulates cell expansion during organ growth", The Plant Journal, 2006, 47:1-9.
International Search Report for International Application No. PCT/JP2008/072158, dated Feb. 24, 2009.
International Search Report for International Application No. PCT/JP2010/059543, dated Aug. 17, 2010.
James P. Jackson, et al., "Control of CpNpG DNA methylation by the KRYPTONITE histone H3 methyltransferase", Letters to Nature, Apr. 2002, pp. 556-560, vol. 416, Macmillan Magazines Ltd.
Steven E. Jacobsen, et al., "Hypermethylated SUPERMAN Epigenetic Alleles in *Arabidopsis*", Science, Aug. 1997, pp. 1100-1103, vol. 277, American Association for the Advancement of Science, Washington, DC.
Steven E. Jacobsen, et al., "Ectopic hypermethylation of flower-specific genes in *Arabidopsis*", Current Biology, 2000, pp. 179-186, vol. 10, No. 4, Elsevier Science Ltd.
Colette Jako, et al., "Seed-Specific Over-Expression of an *Arabidopsis* cDNA Encoding a Diacylglycerol Acyltransferase Enhances Seed Oil Content and Seed Weight", Plant Physiology, Jun. 2001, pp. 861-874, vol. 126, American Society of Plant Physiologists.
K. Diane Jofuku et al., "Control of seed mass and seed yield by the floral homeotic gene APETALA2", PNAS, 2005, 102(8): 3117-3122.
Jisheng Li et al., "*Arabidopsis* H+ -PPase AVP1 Regulates Auxin-Mediated Organ Development", Science, 2005, 310: 121-125.
Anders M. Lindroth, et al., "Requirement of CHROMOMETHYLASE3 for Maintenance of CpXpG Methylation", Science, Jun. 2001, pp. 2077-2080, vol. 292, American Association for the Advancement of Science, Washington, DC.
Kyoko Matsui, et al., "Suppression of the biosynthesis of proanthocyanidin in *Arabidopsis* by a chimeric PAP1 repressor", Plant Biotechnology Journal, 2004, pp. 487-493, vol. 2, Blackwell Publishing Ltd.
Kyoko Matsui, "A Chimeric AtMYB23 Repressor Induces Hairy Roots, Elongation of Leaves and Stems, and Inhibition of the Deposition of Mucilage on Seed Coats in *Arabidopsis*", Plant Cell Physiology, 2005, pp. 147-155, vol. 46(1).
Kyoko Matsui, et al., "Bio Medical Quick Review Net", 2004, pp. 1-6, vol. 4006.
Akane Matsushita et al., "AGF1, an AT-Hook Protein, Is Necessary for the Negative Feedback of AtGA3ox1 Encoding GA 3-Oxidase", Plant Physiology, 2007, 143: 1152-1162.
Nobutaka Mitsuda et al., "Comprehensive functional analysis of plant-specific NAC transcription factor family using the CRES-T method", Abstracts of the 45th Annual Meeting of the Japanese Society of Plant Physiologists, Mar. 2004, P4-B-16 (813).
Yukiko Mizukami et al., "Plant organ size control: AINTEGUMENTA regulates growth and cell numbers during organogenesis", PNAS, 2000, 97(2): 942-947.
Nobuhiko Muramoto et al., "Identification of transcription factors responsible for seed oil content by Chimeric Repressor Gene-Silencing Technology (CRES-T)", Supplemental to Plant and Cell Physiology, 2008, 49: 152.
Toshitsugu Nakano et al., "Genome-Wide Analysis of the ERF Gene Family in *Arabidopsis* and Rice", Plant Physiology, 2006, 140: 411-432.
Zhongfu Ni et al., "Altered circadian rhythms regulate growth vigour in hybrids and allopolyploids", Nature, 2009, 457: 327-331.
Masaru Ohta, et al., "Repression Domains of Class II ERF Transcriptional Repressors Share and Essential Motif for Active Repression", The Plant Cell, Aug. 2001, pp. 1959-1968, vol. 13, American Society of Plant Biologists.
Ohto, 22nd International Conference on *Arabidopsis* Research, 2011, Pub: 501746623.
Y. Pan et al., "Molecular Cloning, Expression, Phylogenetic and Functional Characterization of the *Arabidopsis* AP2/EREBP Transcription Factor Family", GenBank Accession AY560877, 2004 retrieved from: http://www.ncbi.nlm.nih.gov/entrez/viewer.fcgi?48479345:NCBI:6713742 on Dec. 25, 2008.
"Represent" from Merriam-Webster Dictionary, Retrieved from http://www.merriam-webster.com/dictionary/represents on Feb. 5, 2013.
Diego Mauricio Riaño-Pachón et al., "Pln TFDB an integrative plant transcription factor database", BMC Bioinformatics, 2007, 8(42): 1-10.
Keith Roesler, et al., "Targeting of the *Arabidopsis* Homomeric Acetyl-Coenzyme A Carboxylase to Plastids of Rapeseeds", Plant Physiology, 1997, pp. 75-81, vol. 113, Clearance Center.
Shinchiro Sawa, "Overexpression of the AtmybL2 Gene Represses Trichome Development in *Arabidopsis*", DNA Research, 2002, pp. 31-34, vol. 9, No. 2.
Marie C. Schruff et al., "The AUXIN RESPONSE FACTOR 2 gene of *Arabidopsis* links auxin signaling, cell division, and the size of seeds and other organs", Development, 2005, 133: 251-261.
Bo Shen et al., "The homeobox gene GLABRA2 affects seed oil content in *Arabidopsis*", Plant Molecular Biology, 2006, 60: 377-387.
Ralf Stracke et al., "The R2R3-MYB gene family in *Arabidopsis thaliana*", Current Opinion in Plant Biology, 2001, 4: 447-456.
S. Takada et al., Accession No. AB049071, The CUP-SHAPED COYTLEDON1 gene of *Arabidopsis* regulates shoot apical meristem formation, Database NCBI/GenBank (online), 2006, retrieved from http://www.ncbi.nlm.nih.gov/entrez/viewer.fcgi712060425:DDBJ:5636984 on Dec. 25, 2008.
Lu Tian et al., "Blocking histone deacetylation in *Arabidopsis* induces pleiotropic effects on plant gene regulation and development", PNAS, Jan. 2001, pp. 200-205, vol. 98, No. 1.
At1G43160, 2014, https://www.arabidopsis.org/servlets/TairObject?id=28442&type=locus.

(56) References Cited

OTHER PUBLICATIONS

At2G23760, 2014, https://www.arabidopsis.org/servlets/TairObject?id=32802&type=locus.

Judy Meinkoth, et al., "Hybridization of Nucleic Acids Immobilized on Solid Supports," Analytical Biochemistry, 1984, vol. 138, pp. 267-284.

Zhe Wang, et al., "Identification and Characterization of COI1-Dependent Transcription Factor Genes Involved in JA-Mediated Response to Wounding in *Arabidopsis* Plants," Plant Cell Resp, 2008, vol. 27, pp. 125-135.

Qiang Zhu, et al., "The *Arabidopsis* AP2/ERF Transcription Factor RAP2.6 Participates in ABA, Salt, and Osmotic Stress Response," Gene, Feb. 26, 2010, vol. 457, pp. 1-12.

James Z. Zhang, "Overexpression Analysis of Plant Transcription Factors," Current Opinion in Plant Biology, 2003, vol. 6, pp. 430-440.

Haiwei Guo, et al., "Protein Tolerance to Random Amino Acid Change," PNAS, Jun. 22, 2004, vol. 101, No. 25, pp. 9205-9210.

James C. Whisstock, et al., "Prediction of Protein Function from Protein Sequence and Structure," Cambridge University Press, Quarterly Review of Biophysics, 2003, vol. 36, No. 3, pp. 307-340.

Final Office Action issued in U.S. Appl. No. 12/746,640, dated Jul. 2, 2013.

Non-Final Office Action issued in U.S. Appl. No. 12/746,640, dated Nov. 27, 2012.

Notice to Comply issued in U.S. Appl. No. 12/746,640, dated Aug. 16, 2012.

Non-Final Office Action issued in U.S. Appl. No. 12/921,060, dated Feb. 19, 2013.

Non-Final Office Action issued in U.S. Appl. No. 12/746,577, dated Feb. 15, 2013.

Restriction/Election of Species Requirement issued in U.S. Appl. No. 12/746,577, dated Aug. 16, 2013.

Daniel Zilberman, et al., "ARGONAUTE4 Control of Locus-Specific siRNA Accumulation and DNA and Histone Methylation", Science, Jan. 2003, pp. 716-719, vol. 299, American Association for the Advancement of Science.

Gaiyun Zhang et al., Phylogeny, gene structures, and expression patterns of the ERF gene family in soybean (*Glycine max* L.), Journal of Experimental Botany, 2008, 59(15): 4095-4107.

Chen Yanhui et al., "The MYB transcription factor superfamily of *Arabidopsis*: expression analysis and phylogenetic comparison with the rice MYB family", Plant Molecular Biology, 2006, 60(1): 107-124.

K. Yamada et al., Accession No. BT005044, *Arabidopsis* Open Reading Frame (ORF) Clones, Database NCBI/GenBank (online), 2003, retrieved from httD://www.ncbi.nlm.nih.jTOv/entrez/viewer.fcgi?28827465:NCBI:4515668 on Dec. 25, 2008.

Joseph A. White et al., "Genomic approaches towards the engineering of oil seeds", Plant Physiology and Biochemistry, 2001, 39: 263-270.

Randall J. Weselake et al., "Increasing the flow of carbon into seed oil", Biotechnology Advances, 2009, 27: 866-878.

Geoffrey M. Wahl et al., "Molecular Hybridization of Immobilized Nucleic Acids: Theoretical Concepts and Practical Considerations", Methods in Enzymology, 1987, 152: 399-407.

Communication, dated Aug. 7, 2017, issued by the United States Patent and Trademark Office in counterpart U.S. Appl. No. 14/976,425.

Notice of Allowance, dated Sep. 1, 2017, issued by the United States Patent and Trademark Office in U.S. Appl. No. 14/976,233.

\* cited by examiner

SEQUENCE LISTING

```
<160> NUMBER OF SEQ ID NOS: 398

<210> SEQ ID NO 1
<211> LENGTH: 1884
<212> TYPE: DNA
<213> ORGANISM: Arabidopsis thaliana
<220> FEATURE:
<221> NAME/KEY: CDS
<222> LOCATION: (1)..(1884)

<400> SEQUENCE: 1 atg ggt tta gct act aca act tct tct atg tca caa gat tat cat cat      48
Met Gly Leu Ala Thr Thr Thr Ser Ser Met Ser Gln Asp Tyr His His
1               5                   10                  15 cac caa gga atc ttt tcc ttc tct aat gga ttc cac cga tca tca tca      96
His Gln Gly Ile Phe Ser Phe Ser Asn Gly Phe His Arg Ser Ser Ser
            20                  25                  30 acc act cat caa gag gaa gta gat gaa tcc gcc gtc gtc tcc ggt gct     144
Thr Thr His Gln Glu Glu Val Asp Glu Ser Ala Val Val Ser Gly Ala
        35                  40                  45 caa att ccg gtt tat gaa acc gcc gga atg ttg tct gaa atg ttt gct     192
Gln Ile Pro Val Tyr Glu Thr Ala Gly Met Leu Ser Glu Met Phe Ala
    50                  55                  60 tac cct ggc gga ggt ggc ggc ggt tcc ggt gga gag att ctt gat cag     240
Tyr Pro Gly Gly Gly Gly Gly Gly Ser Gly Gly Glu Ile Leu Asp Gln
65                  70                  75                  80 tct act aaa cag ttg cta gag caa caa aac cgt cac aac aac aac aat     288
Ser Thr Lys Gln Leu Leu Glu Gln Gln Asn Arg His Asn Asn Asn Asn
                85                  90                  95 aac tca act ctt cat atg tta tta cca aat cat cat caa ggt ttt gct     336
Asn Ser Thr Leu His Met Leu Leu Pro Asn His His Gln Gly Phe Ala
            100                 105                 110 ttc acc gac gaa aac act atg cag ccg cag caa caa caa cac ttt aca     384
Phe Thr Asp Glu Asn Thr Met Gln Pro Gln Gln Gln Gln His Phe Thr
        115                 120                 125 tgg cca tct tcc tcc tcc gat cat cat caa aac cga gat atg atc gga     432
Trp Pro Ser Ser Ser Ser Asp His His Gln Asn Arg Asp Met Ile Gly
    130                 135                 140 acc gtc cac gtg gaa gga gga aag ggt ttg tct tta tct ctc tca tct     480
Thr Val His Val Glu Gly Gly Lys Gly Leu Ser Leu Ser Leu Ser Ser
145                 150                 155                 160 tca tta gcc gca gct aaa gcc gag gaa tat aga agc att tat tgt gca     528
Ser Leu Ala Ala Ala Lys Ala Glu Glu Tyr Arg Ser Ile Tyr Cys Ala
                165                 170                 175 gcc gtt gat gga act tct tct tct tct aac gca tcc gct cat cat cat     576
```

```
Ala Val Asp Gly Thr Ser Ser Ser Asn Ala Ser Ala His His
            180              185              190 caa ttc aat cag ttc aag aat ctt ctt ctt gag aat tct tct tct caa    624
Gln Phe Asn Gln Phe Lys Asn Leu Leu Leu Glu Asn Ser Ser Ser Gln
        195              200              205 cat cat cac cat caa gtt gtt gga cat ttt ggt tca tca tca tca tct    672
His His His His Gln Val Val Gly His Phe Gly Ser Ser Ser Ser Ser
210              215              220 ccc atg gcg gct tct tca tcc att gga ggg atc tac acg ttg agg aat    720
Pro Met Ala Ala Ser Ser Ser Ile Gly Gly Ile Tyr Thr Leu Arg Asn
225              230              235              240 tcg aaa tat acg aaa ccg gct caa gag ttg ttg gaa gag ttt tgt agt    768
Ser Lys Tyr Thr Lys Pro Ala Gln Glu Leu Leu Glu Glu Phe Cys Ser
        245              250              255 gtt gga aga gga cat ttc aag aag aac aaa ctt agt agg aac aac tca    816
Val Gly Arg Gly His Phe Lys Lys Asn Lys Leu Ser Arg Asn Asn Ser
            260              265              270 aac cct aat act acc ggt gga gga gga ggc gga ggg tcc tcg tca tcg    864
Asn Pro Asn Thr Thr Gly Gly Gly Gly Gly Gly Gly Ser Ser Ser Ser
                275              280              285 gcc gga aca gct aat gat agt cct cct ttg tct ccg gct gat cgg att    912
Ala Gly Thr Ala Asn Asp Ser Pro Pro Leu Ser Pro Ala Asp Arg Ile
290              295              300 gaa cat caa aga aga aaa gtc aag cta cta tct atg ctt gaa gag gtg    960
Glu His Gln Arg Arg Lys Val Lys Leu Leu Ser Met Leu Glu Glu Val
305              310              315              320 gac cga cgg tac aac cac tac tgc gaa caa atg caa atg gta gtg aac   1008
Asp Arg Arg Tyr Asn His Tyr Cys Glu Gln Met Gln Met Val Val Asn
        325              330              335 tca ttc gac caa gta atg ggt tac ggc gcg gcg gtt ccg tac acg aca   1056
Ser Phe Asp Gln Val Met Gly Tyr Gly Ala Ala Val Pro Tyr Thr Thr
            340              345              350 tta gct caa aag gca atg tct agg cat ttc cgg tgt ttg aaa gac gcg   1104
Leu Ala Gln Lys Ala Met Ser Arg His Phe Arg Cys Leu Lys Asp Ala
                355              360              365 gta gcg gtt cag ctt aaa cgc agc tgt gag ctt cta ggg gat aaa gag   1152
Val Ala Val Gln Leu Lys Arg Ser Cys Glu Leu Leu Gly Asp Lys Glu
370              375              380 gcg gca ggg gct gca tcc tcg ggg tta acc aaa ggg gaa acg ccg cga   1200
Ala Ala Gly Ala Ala Ser Ser Gly Leu Thr Lys Gly Glu Thr Pro Arg
385              390              395              400 ttg cgt ttg cta gag cag agt ttg cgt cag caa cga gcg ttt cat cat   1248
Leu Arg Leu Leu Glu Gln Ser Leu Arg Gln Gln Arg Ala Phe His His
        405              410              415 atg ggt atg atg gag caa gag gca tgg aga ccg caa cgt ggt ttg cct   1296
Met Gly Met Met Glu Gln Glu Ala Trp Arg Pro Gln Arg Gly Leu Pro
            420              425              430 gaa cgc tcc gtt aat atc ctt aga gct tgg cta ttc gag cat ttt ctt   1344
Glu Arg Ser Val Asn Ile Leu Arg Ala Trp Leu Phe Glu His Phe Leu
                435              440              445 aat ccg tac cca agc gat gct gat aag cac ctc tta gca cga cag act   1392
Asn Pro Tyr Pro Ser Asp Ala Asp Lys His Leu Leu Ala Arg Gln Thr
450              455              460 ggt tta tcc aga aat cag gtg tca aat tgg ttc ata aat gct agg gtt   1440
Gly Leu Ser Arg Asn Gln Val Ser Asn Trp Phe Ile Asn Ala Arg Val
465              470              475              480 cgc cta tgg aaa cca atg gtg gaa gag atg tat caa caa gaa gca aaa   1488
Arg Leu Trp Lys Pro Met Val Glu Glu Met Tyr Gln Gln Glu Ala Lys
        485              490              495
```

-continued

```
gaa aga gaa gaa gca gaa gaa gaa aat gaa aat caa caa caa caa aga    1536
Glu Arg Glu Glu Ala Glu Glu Glu Asn Glu Asn Gln Gln Gln Gln Arg
        500                 505                 510 aga cag caa caa aca aac aac aac gac acg aaa ccc aac aac aat gaa    1584
Arg Gln Gln Gln Thr Asn Asn Asn Asp Thr Lys Pro Asn Asn Asn Glu
        515                 520                 525 aac aac ttc act gtc ata acc gca caa act cca acg acg atg aca tcg    1632
Asn Asn Phe Thr Val Ile Thr Ala Gln Thr Pro Thr Thr Met Thr Ser
        530                 535                 540 aca cat cac gaa aac gac tct tca ttc ctc tct tcc gtc gcc gcc gct    1680
Thr His His Glu Asn Asp Ser Ser Phe Leu Ser Ser Val Ala Ala Ala
545                 550                 555                 560 tct cac ggc ggt tca gac gcg ttc acc gtc gcc acg tgt cag caa gac    1728
Ser His Gly Gly Ser Asp Ala Phe Thr Val Ala Thr Cys Gln Gln Asp
                565                 570                 575 gtc agt gac ttc cac gtc gac gga gat ggt gtg aac gtc ata aga ttc    1776
Val Ser Asp Phe His Val Asp Gly Asp Gly Val Asn Val Ile Arg Phe
                580                 585                 590 ggg acc aaa cag act ggt gac gtg tct ctt acg ctt ggt cta cgc cac    1824
Gly Thr Lys Gln Thr Gly Asp Val Ser Leu Thr Leu Gly Leu Arg His
                595                 600                 605 tct ggc aat att cct gat aag aac act tct ttc tcc gtt aga gac ttt    1872
Ser Gly Asn Ile Pro Asp Lys Asn Thr Ser Phe Ser Val Arg Asp Phe
        610                 615                 620 gga gat ttt tag                                                    1884
Gly Asp Phe
625

<210> SEQ ID NO 2
<211> LENGTH: 627
<212> TYPE: PRT
<213> ORGANISM: Arabidopsis thaliana

<400> SEQUENCE: 2

Met Gly Leu Ala Thr Thr Thr Ser Ser Met Ser Gln Asp Tyr His His
1               5                   10                  15

His Gln Gly Ile Phe Ser Phe Ser Asn Gly Phe His Arg Ser Ser Ser
            20                  25                  30

Thr Thr His Gln Glu Glu Val Asp Glu Ser Ala Val Val Ser Gly Ala
        35                  40                  45

Gln Ile Pro Val Tyr Glu Thr Ala Gly Met Leu Ser Glu Met Phe Ala
    50                  55                  60

Tyr Pro Gly Gly Gly Gly Gly Ser Gly Gly Glu Ile Leu Asp Gln
65                  70                  75                  80

Ser Thr Lys Gln Leu Leu Glu Gln Gln Asn Arg His Asn Asn Asn Asn
                85                  90                  95

Asn Ser Thr Leu His Met Leu Leu Pro Asn His Gln Gly Phe Ala
            100                 105                 110

Phe Thr Asp Glu Asn Thr Met Gln Pro Gln Gln Gln His Phe Thr
        115                 120                 125

Trp Pro Ser Ser Ser Asp His His Gln Asn Arg Asp Met Ile Gly
    130                 135                 140

Thr Val His Val Glu Gly Gly Lys Gly Leu Ser Leu Ser Leu Ser Ser
145                 150                 155                 160

Ser Leu Ala Ala Ala Lys Ala Glu Glu Tyr Arg Ser Ile Tyr Cys Ala
                165                 170                 175

Ala Val Asp Gly Thr Ser Ser Ser Asn Ala Ser Ala His His His
            180                 185                 190
```

```
Gln Phe Asn Gln Phe Lys Asn Leu Leu Glu Asn Ser Ser Gln
    195                 200                 205

His His His Gln Val Val Gly His Phe Gly Ser Ser Ser Ser
    210                 215                 220

Pro Met Ala Ala Ser Ser Ile Gly Gly Ile Tyr Thr Leu Arg Asn
225                 230                 235                 240

Ser Lys Tyr Thr Lys Pro Ala Gln Glu Leu Leu Glu Glu Phe Cys Ser
            245                 250                 255

Val Gly Arg Gly His Phe Lys Lys Asn Lys Leu Ser Arg Asn Asn Ser
        260                 265                 270

Asn Pro Asn Thr Thr Gly Gly Gly Gly Gly Gly Ser Ser Ser Ser
            275                 280                 285

Ala Gly Thr Ala Asn Asp Ser Pro Pro Leu Ser Pro Ala Asp Arg Ile
    290                 295                 300

Glu His Gln Arg Arg Lys Val Lys Leu Leu Ser Met Leu Glu Glu Val
305                 310                 315                 320

Asp Arg Arg Tyr Asn His Tyr Cys Glu Gln Met Gln Met Val Val Asn
                    325                 330                 335

Ser Phe Asp Gln Val Met Gly Tyr Gly Ala Ala Val Pro Tyr Thr Thr
            340                 345                 350

Leu Ala Gln Lys Ala Met Ser Arg His Phe Arg Cys Leu Lys Asp Ala
            355                 360                 365

Val Ala Val Gln Leu Lys Arg Ser Cys Glu Leu Leu Gly Asp Lys Glu
    370                 375                 380

Ala Ala Gly Ala Ala Ser Ser Gly Leu Thr Lys Gly Glu Thr Pro Arg
385                 390                 395                 400

Leu Arg Leu Leu Glu Gln Ser Leu Arg Gln Gln Arg Ala Phe His His
                405                 410                 415

Met Gly Met Met Glu Gln Glu Ala Trp Arg Pro Gln Arg Gly Leu Pro
            420                 425                 430

Glu Arg Ser Val Asn Ile Leu Arg Ala Trp Leu Phe Glu His Phe Leu
    435                 440                 445

Asn Pro Tyr Pro Ser Asp Ala Asp Lys His Leu Leu Ala Arg Gln Thr
    450                 455                 460

Gly Leu Ser Arg Asn Gln Val Ser Asn Trp Phe Ile Asn Ala Arg Val
465                 470                 475                 480

Arg Leu Trp Lys Pro Met Val Glu Glu Met Tyr Gln Gln Glu Ala Lys
                485                 490                 495

Glu Arg Glu Glu Ala Glu Glu Glu Asn Glu Asn Gln Gln Gln Gln Arg
            500                 505                 510

Arg Gln Gln Gln Thr Asn Asn Asn Asp Thr Lys Pro Asn Asn Asn Glu
    515                 520                 525

Asn Asn Phe Thr Val Ile Thr Ala Gln Thr Pro Thr Thr Met Thr Ser
    530                 535                 540

Thr His His Glu Asn Asp Ser Ser Phe Leu Ser Ser Val Ala Ala Ala
545                 550                 555                 560

Ser His Gly Gly Ser Asp Ala Phe Thr Val Ala Thr Cys Gln Gln Asp
            565                 570                 575

Val Ser Asp Phe His Val Asp Gly Asp Val Asn Val Ile Arg Phe
            580                 585                 590

Gly Thr Lys Gln Thr Gly Asp Val Ser Leu Thr Leu Gly Leu Arg His
        595                 600                 605
```

```
Ser Gly Asn Ile Pro Asp Lys Asn Thr Ser Phe Ser Val Arg Asp Phe
    610                 615                 620

Gly Asp Phe
625

<210> SEQ ID NO 3
<211> LENGTH: 1119
<212> TYPE: DNA
<213> ORGANISM: Arabidopsis thaliana
<220> FEATURE:
<221> NAME/KEY: CDS
<222> LOCATION: (1)..(1119)

<400> SEQUENCE: 3 atg ctc tgt ttt gtt cgc ttt cag gct ggt ttt gtg aga att ata gtt        48
Met Leu Cys Phe Val Arg Phe Gln Ala Gly Phe Val Arg Ile Ile Val
1               5                   10                  15 gca gca aga aag cgt ttc aga tat ttt tta atg gcc gct gag gat cga        96
Ala Ala Arg Lys Arg Phe Arg Tyr Phe Leu Met Ala Ala Glu Asp Arg
                20                  25                  30 agt gag gaa cta agc agc aat gta gaa aat gga agt tgc aat tcc aat       144
Ser Glu Glu Leu Ser Ser Asn Val Glu Asn Gly Ser Cys Asn Ser Asn
            35                  40                  45 gaa gga att aat cct gaa acc agc agt cat tgg att gaa aac gtt gtc       192
Glu Gly Ile Asn Pro Glu Thr Ser Ser His Trp Ile Glu Asn Val Val
        50                  55                  60 aag gtt agg aaa ccg tac aca gta act aag cag aga gag aag tgg agt       240
Lys Val Arg Lys Pro Tyr Thr Val Thr Lys Gln Arg Glu Lys Trp Ser
65                  70                  75                  80 gag gaa gag cat gat agg ttt ctt gaa gct atc aag ctt tat ggt cgt       288
Glu Glu Glu His Asp Arg Phe Leu Glu Ala Ile Lys Leu Tyr Gly Arg
                85                  90                  95 ggt tgg cgt caa atc caa gaa cac ata ggt aca aaa acc gct gta cag       336
Gly Trp Arg Gln Ile Gln Glu His Ile Gly Thr Lys Thr Ala Val Gln
                100                 105                 110 ata cga agc cat gct caa aag ttc ttc tcc aag atg gct cag gaa gct       384
Ile Arg Ser His Ala Gln Lys Phe Phe Ser Lys Met Ala Gln Glu Ala
            115                 120                 125 gac agt aga agt gaa gga tcg gtt aaa gcg att gtg atc ccg cct cct       432
Asp Ser Arg Ser Glu Gly Ser Val Lys Ala Ile Val Ile Pro Pro Pro
        130                 135                 140 cgt cca aag aga aaa ccg gca cat cct tat cct cgg aaa tcg cct gtt       480
Arg Pro Lys Arg Lys Pro Ala His Pro Tyr Pro Arg Lys Ser Pro Val
145                 150                 155                 160 cca tat act cag tct cct cca cca aat ttg tca gct atg gag aaa gga       528
Pro Tyr Thr Gln Ser Pro Pro Pro Asn Leu Ser Ala Met Glu Lys Gly
                165                 170                 175 acc aag tct cca acc tca gtg tta tca tcg ttt ggt tca gag gat caa       576
Thr Lys Ser Pro Thr Ser Val Leu Ser Ser Phe Gly Ser Glu Asp Gln
            180                 185                 190 gtc aat aga tgc tct tcg cct aat tcg tgt acc agt gac atc caa tcc       624
Val Asn Arg Cys Ser Ser Pro Asn Ser Cys Thr Ser Asp Ile Gln Ser
        195                 200                 205 att ggt gca act tcc att gat aaa aag aat aac tac aca aca tcc aag       672
Ile Gly Ala Thr Ser Ile Asp Lys Lys Asn Asn Tyr Thr Thr Ser Lys
    210                 215                 220 caa cct ttc aaa gat gat tct gac att ggt tca aca ccc att tca agc       720
Gln Pro Phe Lys Asp Asp Ser Asp Ile Gly Ser Thr Pro Ile Ser Ser
225                 230                 235                 240 att act ctt ttc ggg aag att gtc ctt gtc gcg gaa gaa tct cac aaa       768
Ile Thr Leu Phe Gly Lys Ile Val Leu Val Ala Glu Glu Ser His Lys
```

|  |  |  |  |  |  |  |  |  |  | 245 |  |  |  |  | 250 |  |  |  |  | 255 |  |  |  |  |  |
|---|---|---|---|---|---|---|---|---|---|---|---|---|---|---|---|---|---|---|---|---|---|---|---|---|---|

```
cca tcc tct tac aat gat gat gat ctt aaa caa atg acg tgt cag gag      816
Pro Ser Ser Tyr Asn Asp Asp Asp Leu Lys Gln Met Thr Cys Gln Glu
            260                 265                 270 aat cac tac tca ggg atg cta gtt gac act aat tta tct ctt ggt gta      864
Asn His Tyr Ser Gly Met Leu Val Asp Thr Asn Leu Ser Leu Gly Val
            275                 280                 285 tgg gaa acg ttt tgt act ggt tct aat gca ttt ggc tcg gtt aca gaa      912
Trp Glu Thr Phe Cys Thr Gly Ser Asn Ala Phe Gly Ser Val Thr Glu
290                 295                 300 gca tct gag aac ttg gag aaa agt gca gag ccg ata agt tct tca tgg      960
Ala Ser Glu Asn Leu Glu Lys Ser Ala Glu Pro Ile Ser Ser Ser Trp
305                 310                 315                 320 aaa cgg tta agc tcc tta gaa aaa caa gga tct tgt aat cct gta aat     1008
Lys Arg Leu Ser Ser Leu Glu Lys Gln Gly Ser Cys Asn Pro Val Asn
                325                 330                 335 gca agt ggg ttc agg cca tac aag aga tgc cta tca gaa aga gaa gta     1056
Ala Ser Gly Phe Arg Pro Tyr Lys Arg Cys Leu Ser Glu Arg Glu Val
            340                 345                 350 aca tca tca ttg acg ctg gta gct tca gat gaa aag aaa agc caa aga     1104
Thr Ser Ser Leu Thr Leu Val Ala Ser Asp Glu Lys Lys Ser Gln Arg
            355                 360                 365 gca cgt ata tgc tag                                                 1119
Ala Arg Ile Cys
    370
```

<210> SEQ ID NO 4
<211> LENGTH: 372
<212> TYPE: PRT
<213> ORGANISM: Arabidopsis thaliana

<400> SEQUENCE: 4

```
Met Leu Cys Phe Val Arg Phe Gln Ala Gly Phe Val Arg Ile Ile Val
1               5                   10                  15

Ala Ala Arg Lys Arg Phe Arg Tyr Phe Leu Met Ala Ala Glu Asp Arg
            20                  25                  30

Ser Glu Glu Leu Ser Ser Asn Val Glu Asn Gly Ser Cys Asn Ser Asn
        35                  40                  45

Glu Gly Ile Asn Pro Glu Thr Ser Ser His Trp Ile Glu Asn Val Val
    50                  55                  60

Lys Val Arg Lys Pro Tyr Thr Val Thr Lys Gln Arg Glu Lys Trp Ser
65                  70                  75                  80

Glu Glu Glu His Asp Arg Phe Leu Glu Ala Ile Lys Leu Tyr Gly Arg
                85                  90                  95

Gly Trp Arg Gln Ile Gln Glu His Ile Gly Thr Lys Thr Ala Val Gln
            100                 105                 110

Ile Arg Ser His Ala Gln Lys Phe Phe Ser Lys Met Ala Gln Glu Ala
        115                 120                 125

Asp Ser Arg Ser Glu Gly Ser Val Lys Ala Ile Val Ile Pro Pro Pro
    130                 135                 140

Arg Pro Lys Arg Lys Pro Ala His Pro Tyr Pro Arg Lys Ser Pro Val
145                 150                 155                 160

Pro Tyr Thr Gln Ser Pro Pro Asn Leu Ser Ala Met Glu Lys Gly
                165                 170                 175

Thr Lys Ser Pro Thr Ser Val Leu Ser Ser Phe Gly Ser Glu Asp Gln
            180                 185                 190

Val Asn Arg Cys Ser Ser Pro Asn Ser Cys Thr Ser Asp Ile Gln Ser
```

```
                        195                 200                 205
Ile Gly Ala Thr Ser Ile Asp Lys Lys Asn Asn Tyr Thr Thr Ser Lys
    210                 215                 220

Gln Pro Phe Lys Asp Asp Ser Asp Ile Gly Ser Thr Pro Ile Ser Ser
225                 230                 235                 240

Ile Thr Leu Phe Gly Lys Ile Val Leu Val Ala Glu Glu Ser His Lys
                245                 250                 255

Pro Ser Ser Tyr Asn Asp Asp Leu Lys Gln Met Thr Cys Gln Glu
            260                 265                 270

Asn His Tyr Ser Gly Met Leu Val Asp Thr Asn Leu Ser Leu Gly Val
                275                 280                 285

Trp Glu Thr Phe Cys Thr Gly Ser Asn Ala Phe Gly Ser Val Thr Glu
290                 295                 300

Ala Ser Glu Asn Leu Glu Lys Ser Ala Glu Pro Ile Ser Ser Ser Trp
305                 310                 315                 320

Lys Arg Leu Ser Ser Leu Glu Lys Gln Gly Ser Cys Asn Pro Val Asn
                325                 330                 335

Ala Ser Gly Phe Arg Pro Tyr Lys Arg Cys Leu Ser Glu Arg Glu Val
                340                 345                 350

Thr Ser Ser Leu Thr Leu Val Ala Ser Asp Glu Lys Lys Ser Gln Arg
            355                 360                 365

Ala Arg Ile Cys
    370

<210> SEQ ID NO 5
<211> LENGTH: 1809
<212> TYPE: DNA
<213> ORGANISM: Arabidopsis thaliana
<220> FEATURE:
<221> NAME/KEY: CDS
<222> LOCATION: (1)..(1809)

<400> SEQUENCE: 5 atg gct gct tct tca tcc tcc gct gct tcc ttc ttt gga gtc cga caa    48
Met Ala Ala Ser Ser Ser Ser Ala Ala Ser Phe Phe Gly Val Arg Gln
1               5                   10                  15 gat gac caa tct cac ctc ctc cca cct aat tcc tcc gcc gct gct cct    96
Asp Asp Gln Ser His Leu Leu Pro Pro Asn Ser Ser Ala Ala Ala Pro
                20                  25                  30 cct cct cca cct cct cac cac cag gca ccg ctg cca ccg ctt gaa gct   144
Pro Pro Pro Pro Pro His His Gln Ala Pro Leu Pro Pro Leu Glu Ala
            35                  40                  45 cca ccg cag aaa aag aag aga aac caa cca aga act cca aat tcc gat   192
Pro Pro Gln Lys Lys Lys Arg Asn Gln Pro Arg Thr Pro Asn Ser Asp
50                  55                  60 gcg gaa gtg ata gct tta tct cca aag aca cta atg gct aca aac aga   240
Ala Glu Val Ile Ala Leu Ser Pro Lys Thr Leu Met Ala Thr Asn Arg
65                  70                  75                  80 ttc ata tgt gaa gta tgc aac aaa ggg ttt caa aga gaa cag aat cta   288
Phe Ile Cys Glu Val Cys Asn Lys Gly Phe Gln Arg Glu Gln Asn Leu
                85                  90                  95 caa ctt cac cga aga gga cac aat ctt cca tgg aag ctc aaa cag aaa   336
Gln Leu His Arg Arg Gly His Asn Leu Pro Trp Lys Leu Lys Gln Lys
                100                 105                 110 tcg acc aaa gaa gtg aag aga aaa gtg tat ctt tgt ccg gag ccc tcg   384
Ser Thr Lys Glu Val Lys Arg Lys Val Tyr Leu Cys Pro Glu Pro Ser
            115                 120                 125 tgc gtc cac cat gac ccg tca cgt gct ctc gga gac ctc acc gga atc   432
```

```
                Cys Val His His Asp Pro Ser Arg Ala Leu Gly Asp Leu Thr Gly Ile
                    130                 135                 140 aag aaa cat tat tac cgt aaa cac ggt gaa aag aag tgg aaa tgc gat       480
Lys Lys His Tyr Tyr Arg Lys His Gly Glu Lys Lys Trp Lys Cys Asp
145                 150                 155                 160 aaa tgc tct aag cgt tac gct gtt caa tcg gat tgg aaa gct cac tcc       528
Lys Cys Ser Lys Arg Tyr Ala Val Gln Ser Asp Trp Lys Ala His Ser
                165                 170                 175 aag act tgt ggt acc aaa gag tat cgt tgt gac tgt ggt aca ctc ttc       576
Lys Thr Cys Gly Thr Lys Glu Tyr Arg Cys Asp Cys Gly Thr Leu Phe
            180                 185                 190 tct cgg cga gac agt ttc atc aca cat aga gct ttc tgt gac gcg ttg       624
Ser Arg Arg Asp Ser Phe Ile Thr His Arg Ala Phe Cys Asp Ala Leu
                195                 200                 205 gct caa gag agt gcg aga cac cca act tca ttg act tct ttg cca agt       672
Ala Gln Glu Ser Ala Arg His Pro Thr Ser Leu Thr Ser Leu Pro Ser
    210                 215                 220 cat cac ttc ccg tac gga caa aac aca aac aac tcc aac aac aac gct       720
His His Phe Pro Tyr Gly Gln Asn Thr Asn Asn Ser Asn Asn Asn Ala
225                 230                 235                 240 tca agc atg atc ctt ggt ctg tcc cac atg ggg gcc cca cag aat ctt       768
Ser Ser Met Ile Leu Gly Leu Ser His Met Gly Ala Pro Gln Asn Leu
                245                 250                 255 gat cac cag ccc ggt gac gtt ctc cgt ctt gga agc gga gga gga gga       816
Asp His Gln Pro Gly Asp Val Leu Arg Leu Gly Ser Gly Gly Gly Gly
            260                 265                 270 gga gga gcc gct tca cgc tct tct tct gat ctc att gct gcg aat gct       864
Gly Gly Ala Ala Ser Arg Ser Ser Ser Asp Leu Ile Ala Ala Asn Ala
        275                 280                 285 tca ggc tac ttc atg caa gag caa aac cct agc ttt cat gat caa caa       912
Ser Gly Tyr Phe Met Gln Glu Gln Asn Pro Ser Phe His Asp Gln Gln
    290                 295                 300 gat cat cat cat cat cat caa caa ggg ttt ttg gct ggg aac aat aac       960
Asp His His His His His Gln Gln Gly Phe Leu Ala Gly Asn Asn Asn
305                 310                 315                 320 atc aag caa tca cca atg agt ttt caa cag aat ctg atg cag ttc tca      1008
Ile Lys Gln Ser Pro Met Ser Phe Gln Gln Asn Leu Met Gln Phe Ser
                325                 330                 335 cat gat aac cat aat tct gct ccc tcc aat gtc ttc aat ctc agc ttc      1056
His Asp Asn His Asn Ser Ala Pro Ser Asn Val Phe Asn Leu Ser Phe
            340                 345                 350 ctc tcc gga aac aac gga gtt act tct gcc aca agt aac cct aat gct      1104
Leu Ser Gly Asn Asn Gly Val Thr Ser Ala Thr Ser Asn Pro Asn Ala
        355                 360                 365 gcc gcc gct gct gct gtt tct tct ggt aat ctt atg ata tca aac cat      1152
Ala Ala Ala Ala Ala Val Ser Ser Gly Asn Leu Met Ile Ser Asn His
    370                 375                 380 tat gat ggc gaa aat gct gtt gga gga gga gga gaa gga agc act ggt      1200
Tyr Asp Gly Glu Asn Ala Val Gly Gly Gly Gly Glu Gly Ser Thr Gly
385                 390                 395                 400 ctc ttc cct aac aat ctg atg agc tcg gca gat aga att agc tca gga      1248
Leu Phe Pro Asn Asn Leu Met Ser Ser Ala Asp Arg Ile Ser Ser Gly
                405                 410                 415 tca gtc cct tca ctc ttt agc tca tca atg caa agt cca aat tca gca      1296
Ser Val Pro Ser Leu Phe Ser Ser Ser Met Gln Ser Pro Asn Ser Ala
            420                 425                 430 cct cac atg tca gcc act gcc ctt cta cag aaa gct gct caa atg ggt      1344
Pro His Met Ser Ala Thr Ala Leu Leu Gln Lys Ala Ala Gln Met Gly
        435                 440                 445
```

```
tca acc tca agc aac aac aac gga agc aac acc aac aac aat aac      1392
Ser Thr Ser Ser Asn Asn Asn Gly Ser Asn Thr Asn Asn Asn Asn
    450             455                 460 aat gcc tca tcg atc cta aga agc ttt ggg agt gga atc tac gga gaa  1440
Asn Ala Ser Ser Ile Leu Arg Ser Phe Gly Ser Gly Ile Tyr Gly Glu
465             470                 475                 480 aat gag agt aat ctt cag gat ttg atg aat tct ttc tct aac ccc ggc  1488
Asn Glu Ser Asn Leu Gln Asp Leu Met Asn Ser Phe Ser Asn Pro Gly
                485                 490                 495 gca acg gga aac gtt aac gga gtt gat tct cct ttt ggt tcg tac gga  1536
Ala Thr Gly Asn Val Asn Gly Val Asp Ser Pro Phe Gly Ser Tyr Gly
            500                 505                 510 gga gtg aac aaa gga tta agc gct gac aaa cag agc atg act aga gac  1584
Gly Val Asn Lys Gly Leu Ser Ala Asp Lys Gln Ser Met Thr Arg Asp
        515                 520                 525 ttt ctt gga gtt gga cag atc gta aaa agc atg agt gga agc gga ggg  1632
Phe Leu Gly Val Gly Gln Ile Val Lys Ser Met Ser Gly Ser Gly Gly
    530                 535                 540 ttt caa caa cag caa caa cag caa cag cag caa caa caa caa caa       1680
Phe Gln Gln Gln Gln Gln Gln Gln Gln Gln Gln Gln Gln Gln Gln
545             550                 555                 560 cat gga aat agt aga gaa aga gtt ggc tcg tcg tcg gat tcc gct gat  1728
His Gly Asn Ser Arg Glu Arg Val Gly Ser Ser Ser Asp Ser Ala Asp
                565                 570                 575 aga agc agc atg aat gtg aat acc gga ggt ggt ccg gca agt act tca  1776
Arg Ser Ser Met Asn Val Asn Thr Gly Gly Gly Pro Ala Ser Thr Ser
            580                 585                 590 cca cct tat gga atc cat cat gcg agt ttc taa                      1809
Pro Pro Tyr Gly Ile His His Ala Ser Phe
        595                 600

<210> SEQ ID NO 6
<211> LENGTH: 602
<212> TYPE: PRT
<213> ORGANISM: Arabidopsis thaliana

<400> SEQUENCE: 6

Met Ala Ala Ser Ser Ser Ala Ala Ser Phe Phe Gly Val Arg Gln
1               5                   10                  15

Asp Asp Gln Ser His Leu Leu Pro Asn Ser Ser Ala Ala Ala Pro
                20                  25                  30

Pro Pro Pro Pro His His Gln Ala Pro Leu Pro Pro Leu Glu Ala
            35                  40                  45

Pro Pro Gln Lys Lys Arg Asn Gln Pro Arg Thr Pro Asn Ser Asp
    50                  55                  60

Ala Glu Val Ile Ala Leu Ser Pro Lys Thr Leu Met Ala Thr Asn Arg
65                  70                  75                  80

Phe Ile Cys Glu Val Cys Asn Lys Gly Phe Gln Arg Glu Gln Asn Leu
                85                  90                  95

Gln Leu His Arg Arg Gly His Asn Leu Pro Trp Lys Leu Lys Gln Lys
            100                 105                 110

Ser Thr Lys Glu Val Lys Arg Lys Val Tyr Leu Cys Pro Glu Pro Ser
        115                 120                 125

Cys Val His His Asp Pro Ser Arg Ala Leu Gly Asp Leu Thr Gly Ile
    130                 135                 140

Lys Lys His Tyr Tyr Arg Lys His Gly Glu Lys Lys Trp Lys Cys Asp
145                 150                 155                 160

Lys Cys Ser Lys Arg Tyr Ala Val Gln Ser Asp Trp Lys Ala His Ser
```

```
                    165                 170                 175
Lys Thr Cys Gly Thr Lys Glu Tyr Arg Cys Asp Cys Gly Thr Leu Phe
                180                 185                 190

Ser Arg Arg Asp Ser Phe Ile Thr His Arg Ala Phe Cys Asp Ala Leu
            195                 200                 205

Ala Gln Glu Ser Ala Arg His Pro Thr Ser Leu Thr Ser Leu Pro Ser
        210                 215                 220

His His Phe Pro Tyr Gly Gln Asn Thr Asn Asn Ser Asn Asn Asn Ala
225                 230                 235                 240

Ser Ser Met Ile Leu Gly Leu Ser His Met Gly Ala Pro Gln Asn Leu
                245                 250                 255

Asp His Gln Pro Gly Asp Val Leu Arg Leu Gly Ser Gly Gly Gly Gly
            260                 265                 270

Gly Gly Ala Ala Ser Arg Ser Ser Ser Asp Leu Ile Ala Ala Asn Ala
        275                 280                 285

Ser Gly Tyr Phe Met Gln Glu Gln Asn Pro Ser Phe His Asp Gln Gln
    290                 295                 300

Asp His His His His Gln Gln Gly Phe Leu Ala Gly Asn Asn Asn
305                 310                 315                 320

Ile Lys Gln Ser Pro Met Ser Phe Gln Gln Asn Leu Met Gln Phe Ser
                325                 330                 335

His Asp Asn His Asn Ser Ala Pro Ser Asn Val Phe Asn Leu Ser Phe
            340                 345                 350

Leu Ser Gly Asn Asn Gly Val Thr Ser Ala Thr Ser Asn Pro Asn Ala
        355                 360                 365

Ala Ala Ala Ala Ala Val Ser Ser Gly Asn Leu Met Ile Ser Asn His
    370                 375                 380

Tyr Asp Gly Glu Asn Ala Val Gly Gly Gly Glu Gly Ser Thr Gly
385                 390                 395                 400

Leu Phe Pro Asn Asn Leu Met Ser Ser Ala Asp Arg Ile Ser Ser Gly
                405                 410                 415

Ser Val Pro Ser Leu Phe Ser Ser Ser Met Gln Ser Pro Asn Ser Ala
            420                 425                 430

Pro His Met Ser Ala Thr Ala Leu Leu Gln Lys Ala Ala Gln Met Gly
        435                 440                 445

Ser Thr Ser Ser Asn Asn Asn Asn Gly Ser Asn Thr Asn Asn Asn Asn
    450                 455                 460

Asn Ala Ser Ser Ile Leu Arg Ser Phe Gly Ser Gly Ile Tyr Gly Glu
465                 470                 475                 480

Asn Glu Ser Asn Leu Gln Asp Leu Met Asn Ser Phe Ser Asn Pro Gly
                485                 490                 495

Ala Thr Gly Asn Val Asn Gly Val Asp Ser Pro Phe Gly Ser Tyr Gly
            500                 505                 510

Gly Val Asn Lys Gly Leu Ser Ala Asp Lys Gln Ser Met Thr Arg Asp
        515                 520                 525

Phe Leu Gly Val Gly Gln Ile Val Lys Ser Met Ser Gly Ser Gly Gly
    530                 535                 540

Phe Gln Gln Gln Gln Gln Gln Gln Gln Gln Gln Gln Gln Gln Gln Gln
545                 550                 555                 560

His Gly Asn Ser Arg Glu Arg Val Gly Ser Ser Asp Ser Ala Asp
                565                 570                 575

Arg Ser Ser Met Asn Val Asn Thr Gly Gly Gly Pro Ala Ser Thr Ser
            580                 585                 590
```

```
Pro Pro Tyr Gly Ile His His Ala Ser Phe
        595                 600

<210> SEQ ID NO 7
<211> LENGTH: 987
<212> TYPE: DNA
<213> ORGANISM: Arabidopsis thaliana
<220> FEATURE:
<221> NAME/KEY: CDS
<222> LOCATION: (1)..(987)

<400> SEQUENCE: 7 atg gaa aaa gcc ttg aga aac ttc acc gaa tct acc cac tca cca gac        48
Met Glu Lys Ala Leu Arg Asn Phe Thr Glu Ser Thr His Ser Pro Asp
1               5                  10                  15 cct aat cct ctc aca aaa ttc ttc act gaa cct aca gcc tca cct gtt        96
Pro Asn Pro Leu Thr Lys Phe Phe Thr Glu Pro Thr Ala Ser Pro Val
                20                  25                  30 agc cgc aac cgc aaa ctg tct tca aaa gat acc act gta acc atc gcc       144
Ser Arg Asn Arg Lys Leu Ser Ser Lys Asp Thr Thr Val Thr Ile Ala
            35                  40                  45 gga gct ggc agc agc acg acg agg tac cgc ggc gta cgc cgg agg ccg       192
Gly Ala Gly Ser Ser Thr Thr Arg Tyr Arg Gly Val Arg Arg Arg Pro
        50                  55                  60 tgg gga cga tac gcg gcg gag ata cgt gac cca atg tcg aag gag aga       240
Trp Gly Arg Tyr Ala Ala Glu Ile Arg Asp Pro Met Ser Lys Glu Arg
65                  70                  75                  80 cgt tgg ctc gga aca ttt gac acg gcg gaa caa gcc gct tgt gct tac       288
Arg Trp Leu Gly Thr Phe Asp Thr Ala Glu Gln Ala Ala Cys Ala Tyr
                85                  90                  95 gac tct gcg gct cgt gcc ttt cgt gga gca aag gct cgt act aat ttt       336
Asp Ser Ala Ala Arg Ala Phe Arg Gly Ala Lys Ala Arg Thr Asn Phe
                100                 105                 110 act tat ccg aca gct gtc att atg cct gaa cca agg ttt tct ttt tcc       384
Thr Tyr Pro Thr Ala Val Ile Met Pro Glu Pro Arg Phe Ser Phe Ser
            115                 120                 125 aac aag aaa tct tcg ccg tct gct cgt tgt cct ctt cct tct cta ccg       432
Asn Lys Lys Ser Ser Pro Ser Ala Arg Cys Pro Leu Pro Ser Leu Pro
        130                 135                 140 tta gat tcc tct acc caa aac ttt tac ggt gca ccg gca gcg cag agg       480
Leu Asp Ser Ser Thr Gln Asn Phe Tyr Gly Ala Pro Ala Ala Gln Arg
145                 150                 155                 160 atc tat aat aca cag tct atc ttc tta cgc gac gcc tcg tgt tcc tct       528
Ile Tyr Asn Thr Gln Ser Ile Phe Leu Arg Asp Ala Ser Cys Ser Ser
                165                 170                 175 cgt aaa acg act ccg tat aat aac tct ttc aac ggc tca tca tct tct       576
Arg Lys Thr Thr Pro Tyr Asn Asn Ser Phe Asn Gly Ser Ser Ser Ser
                180                 185                 190 tac tca gca tcg aaa acg gca tgc gtt tct tat tcc gaa aac gaa aac       624
Tyr Ser Ala Ser Lys Thr Ala Cys Val Ser Tyr Ser Glu Asn Glu Asn
            195                 200                 205 aac gag tcg ttt ttc ccg gaa gaa tct tct gat act ggc cta tta caa       672
Asn Glu Ser Phe Phe Pro Glu Glu Ser Ser Asp Thr Gly Leu Leu Gln
        210                 215                 220 gag gtc gtt caa gag ttc ttg aag aaa aat cgc ggc gtt cct cct tct       720
Glu Val Val Gln Glu Phe Leu Lys Lys Asn Arg Gly Val Pro Pro Ser
225                 230                 235                 240 cca cca aca cca ccg ccg gtg act agc cat cat gac aac tct ggt tat       768
Pro Pro Thr Pro Pro Pro Val Thr Ser His His Asp Asn Ser Gly Tyr
                245                 250                 255
```

| | | | | | | | | | | | | | | | |
|---|---|---|---|---|---|---|---|---|---|---|---|---|---|---|---|
| ttc | tct | aat | ctc | act | ata | tac | tct | gaa | aat | atg | gtt | caa | gag | act | aag |
| Phe | Ser | Asn | Leu | Thr | Ile | Tyr | Ser | Glu | Asn | Met | Val | Gln | Glu | Thr | Lys |
| | | | 260 | | | | 265 | | | | | 270 | | | |

816

| gag | act | ttg | tcg | tcg | aaa | cta | gat | cgc | tac | ggg | aat | ttt | caa | gct | aat |
|---|---|---|---|---|---|---|---|---|---|---|---|---|---|---|---|
| Glu | Thr | Leu | Ser | Ser | Lys | Leu | Asp | Arg | Tyr | Gly | Asn | Phe | Gln | Ala | Asn |
| | | | 275 | | | | 280 | | | | | 285 | | | |

864

| gac | gac | ggc | gta | aga | gcc | gtc | gca | gac | ggt | ggt | tta | tcg | ttg | gga | tca |
|---|---|---|---|---|---|---|---|---|---|---|---|---|---|---|---|
| Asp | Asp | Gly | Val | Arg | Ala | Val | Ala | Asp | Gly | Gly | Leu | Ser | Leu | Gly | Ser |
| | | | 290 | | | | 295 | | | | | 300 | | | |

912

| aac | gag | tgg | ggg | tat | caa | gaa | atg | ttg | atg | tac | gga | act | cag | tta | ggc |
|---|---|---|---|---|---|---|---|---|---|---|---|---|---|---|---|
| Asn | Glu | Trp | Gly | Tyr | Gln | Glu | Met | Leu | Met | Tyr | Gly | Thr | Gln | Leu | Gly |
| 305 | | | | 310 | | | | | 315 | | | | | | 320 |

960

| tgt | act | tgc | cga | aga | tcg | tgg | gga | tag | | | | | | | |
|---|---|---|---|---|---|---|---|---|---|---|---|---|---|---|---|
| Cys | Thr | Cys | Arg | Arg | Ser | Trp | Gly | | | | | | | | |
| | | | 325 | | | | | | | | | | | | |

987

```
<210> SEQ ID NO 8
<211> LENGTH: 328
<212> TYPE: PRT
<213> ORGANISM: Arabidopsis thaliana

<400> SEQUENCE: 8
```

| Met | Glu | Lys | Ala | Leu | Arg | Asn | Phe | Thr | Glu | Ser | Thr | His | Ser | Pro | Asp |
|---|---|---|---|---|---|---|---|---|---|---|---|---|---|---|---|
| 1 | | | | 5 | | | | | 10 | | | | | 15 | |

| Pro | Asn | Pro | Leu | Thr | Lys | Phe | Phe | Thr | Glu | Pro | Thr | Ala | Ser | Pro | Val |
|---|---|---|---|---|---|---|---|---|---|---|---|---|---|---|---|
| | | | | 20 | | | | | 25 | | | | | 30 | |

| Ser | Arg | Asn | Arg | Lys | Leu | Ser | Ser | Lys | Asp | Thr | Thr | Val | Thr | Ile | Ala |
|---|---|---|---|---|---|---|---|---|---|---|---|---|---|---|---|
| | | | 35 | | | | | 40 | | | | | 45 | | |

| Gly | Ala | Gly | Ser | Ser | Thr | Thr | Arg | Tyr | Arg | Gly | Val | Arg | Arg | Pro |
|---|---|---|---|---|---|---|---|---|---|---|---|---|---|---|
| | 50 | | | | | 55 | | | | | 60 | | | |

| Trp | Gly | Arg | Tyr | Ala | Ala | Glu | Ile | Arg | Asp | Pro | Met | Ser | Lys | Glu | Arg |
|---|---|---|---|---|---|---|---|---|---|---|---|---|---|---|---|
| 65 | | | | | 70 | | | | | 75 | | | | | 80 |

| Arg | Trp | Leu | Gly | Thr | Phe | Asp | Thr | Ala | Glu | Gln | Ala | Ala | Cys | Ala | Tyr |
|---|---|---|---|---|---|---|---|---|---|---|---|---|---|---|---|
| | | | | 85 | | | | | 90 | | | | | 95 | |

| Asp | Ser | Ala | Ala | Arg | Ala | Phe | Arg | Gly | Ala | Lys | Ala | Arg | Thr | Asn | Phe |
|---|---|---|---|---|---|---|---|---|---|---|---|---|---|---|---|
| | | | 100 | | | | | 105 | | | | | 110 | | |

| Thr | Tyr | Pro | Thr | Ala | Val | Ile | Met | Pro | Glu | Pro | Arg | Phe | Ser | Phe | Ser |
|---|---|---|---|---|---|---|---|---|---|---|---|---|---|---|---|
| | | 115 | | | | | 120 | | | | | 125 | | | |

| Asn | Lys | Lys | Ser | Ser | Pro | Ser | Ala | Arg | Cys | Pro | Leu | Pro | Ser | Leu | Pro |
|---|---|---|---|---|---|---|---|---|---|---|---|---|---|---|---|
| | 130 | | | | | 135 | | | | | 140 | | | | |

| Leu | Asp | Ser | Ser | Thr | Gln | Asn | Phe | Tyr | Gly | Ala | Pro | Ala | Ala | Gln | Arg |
|---|---|---|---|---|---|---|---|---|---|---|---|---|---|---|---|
| 145 | | | | | 150 | | | | | 155 | | | | | 160 |

| Ile | Tyr | Asn | Thr | Gln | Ser | Ile | Phe | Leu | Arg | Asp | Ala | Ser | Cys | Ser | Ser |
|---|---|---|---|---|---|---|---|---|---|---|---|---|---|---|---|
| | | | | 165 | | | | | 170 | | | | | 175 | |

| Arg | Lys | Thr | Thr | Pro | Tyr | Asn | Asn | Ser | Phe | Asn | Gly | Ser | Ser | Ser | Ser |
|---|---|---|---|---|---|---|---|---|---|---|---|---|---|---|---|
| | | | 180 | | | | | 185 | | | | | 190 | | |

| Tyr | Ser | Ala | Ser | Lys | Thr | Ala | Cys | Val | Ser | Tyr | Ser | Glu | Asn | Glu | Asn |
|---|---|---|---|---|---|---|---|---|---|---|---|---|---|---|---|
| | | | 195 | | | | | 200 | | | | | 205 | | |

| Asn | Glu | Ser | Phe | Phe | Pro | Glu | Glu | Ser | Ser | Asp | Thr | Gly | Leu | Leu | Gln |
|---|---|---|---|---|---|---|---|---|---|---|---|---|---|---|---|
| | 210 | | | | | 215 | | | | | 220 | | | | |

| Glu | Val | Gln | Glu | Phe | Leu | Lys | Lys | Asn | Arg | Gly | Val | Pro | Pro | Ser |
|---|---|---|---|---|---|---|---|---|---|---|---|---|---|---|
| 225 | | | | 230 | | | | | 235 | | | | | 240 |

| Pro | Pro | Thr | Pro | Pro | Val | Thr | Ser | His | His | Asp | Asn | Ser | Gly | Tyr |
|---|---|---|---|---|---|---|---|---|---|---|---|---|---|---|
| | | | 245 | | | | | 250 | | | | | 255 | |

| Phe | Ser | Asn | Leu | Thr | Ile | Tyr | Ser | Glu | Asn | Met | Val | Gln | Glu | Thr | Lys |
|---|---|---|---|---|---|---|---|---|---|---|---|---|---|---|---|
| | | | 260 | | | | 265 | | | | | 270 | | | |

-continued

```
            Glu Thr Leu Ser Ser Lys Leu Asp Arg Tyr Gly Asn Phe Gln Ala Asn
                            275                 280                 285
            Asp Asp Gly Val Arg Ala Val Ala Asp Gly Gly Leu Ser Leu Gly Ser
                        290                 295                 300
            Asn Glu Trp Gly Tyr Gln Glu Met Leu Met Tyr Gly Thr Gln Leu Gly
            305                 310                 315                 320
            Cys Thr Cys Arg Arg Ser Trp Gly
                            325

<210> SEQ ID NO 9
<211> LENGTH: 1047
<212> TYPE: DNA
<213> ORGANISM: Arabidopsis thaliana
<220> FEATURE:
<221> NAME/KEY: CDS
<222> LOCATION: (1)..(1047)

<400> SEQUENCE: 9 atg gaa agt ctc gca cac att cct ccc ggt tat cga ttc cat ccg acc      48
Met Glu Ser Leu Ala His Ile Pro Pro Gly Tyr Arg Phe His Pro Thr
1               5                   10                  15 gat gaa gaa ctc gtt gac tat tat ctc aag aac aaa gtt gca ttc ccg      96
Asp Glu Glu Leu Val Asp Tyr Tyr Leu Lys Asn Lys Val Ala Phe Pro
                20                  25                  30 gga atg caa gtt gat gtt atc aaa gat gtt gat ctc tac aaa atc gag     144
Gly Met Gln Val Asp Val Ile Lys Asp Val Asp Leu Tyr Lys Ile Glu
            35                  40                  45 cca tgg gac atc caa gag tta tgt gga aga ggg aca gga gaa gag agg     192
Pro Trp Asp Ile Gln Glu Leu Cys Gly Arg Gly Thr Gly Glu Glu Arg
        50                  55                  60 gaa tgg tat ttc ttt agc cac aag gac aag aaa tat cca act ggg aca     240
Glu Trp Tyr Phe Phe Ser His Lys Asp Lys Lys Tyr Pro Thr Gly Thr
65                  70                  75                  80 cga acc aat aga gca acg ggc tcc gga ttt tgg aaa gca acg ggt cga     288
Arg Thr Asn Arg Ala Thr Gly Ser Gly Phe Trp Lys Ala Thr Gly Arg
                85                  90                  95 gac aag gcc att tac tca aag caa gag ctt gtt ggg atg agg aag act     336
Asp Lys Ala Ile Tyr Ser Lys Gln Glu Leu Val Gly Met Arg Lys Thr
                100                 105                 110 ctt gtc ttt tac aaa ggt agg gcc cca aat ggt cag aaa tct gat tgg     384
Leu Val Phe Tyr Lys Gly Arg Ala Pro Asn Gly Gln Lys Ser Asp Trp
            115                 120                 125 ata atg cac gaa tac cgt ctt gag acc gat gaa aat gga ccg cct cat     432
Ile Met His Glu Tyr Arg Leu Glu Thr Asp Glu Asn Gly Pro Pro His
        130                 135                 140 gag gaa gga tgg gtg gtt tgt cgc gct ttc aag aag aag cta acc acg     480
Glu Glu Gly Trp Val Val Cys Arg Ala Phe Lys Lys Lys Leu Thr Thr
145                 150                 155                 160 atg aac tac aac aat cca aga aca atg atg gga tca tca tca ggc caa     528
Met Asn Tyr Asn Asn Pro Arg Thr Met Met Gly Ser Ser Ser Gly Gln
                165                 170                 175 gaa tct aac tgg ttc acg cag caa atg gat gtg ggg aat ggt aat tac     576
Glu Ser Asn Trp Phe Thr Gln Gln Met Asp Val Gly Asn Gly Asn Tyr
                180                 185                 190 tat cat ctt cct gat cta gag agt ccg aga atg ttt caa ggc tca tca     624
Tyr His Leu Pro Asp Leu Glu Ser Pro Arg Met Phe Gln Gly Ser Ser
            195                 200                 205 tca tca tca cta tca tca tta cat cag aat gat caa gac cct tat ggt     672
Ser Ser Ser Leu Ser Ser Leu His Gln Asn Asp Gln Asp Pro Tyr Gly
        210                 215                 220
```

| | | | | | | | | | | | | | | | |
|---|---|---|---|---|---|---|---|---|---|---|---|---|---|---|---|
| gtc | gta | ctc | agc | act | att | aac | gca | acc | cca | act | aca | ata | atg | caa | cga | 720 |
| Val | Val | Leu | Ser | Thr | Ile | Asn | Ala | Thr | Pro | Thr | Thr | Ile | Met | Gln | Arg | |
| 225 | | | | 230 | | | | | 235 | | | | | 240 | | |

| | | | | | | | | | | | | | | | |
|---|---|---|---|---|---|---|---|---|---|---|---|---|---|---|---|
| gat | gat | ggt | cat | gtg | att | acc | aat | gat | gat | gat | cat | atg | atc | atg | atg | 768 |
| Asp | Asp | Gly | His | Val | Ile | Thr | Asn | Asp | Asp | Asp | His | Met | Ile | Met | Met | |
| | | | | 245 | | | | | 250 | | | | | 255 | | |

| | | | | | | | | | | | | | | | |
|---|---|---|---|---|---|---|---|---|---|---|---|---|---|---|---|
| aac | aca | agt | act | ggt | gat | cat | cat | caa | tca | gga | tta | cta | gtc | aat | gat | 816 |
| Asn | Thr | Ser | Thr | Gly | Asp | His | His | Gln | Ser | Gly | Leu | Leu | Val | Asn | Asp | |
| | | 260 | | | | | 265 | | | | | 270 | | | | |

| | | | | | | | | | | | | | | | |
|---|---|---|---|---|---|---|---|---|---|---|---|---|---|---|---|
| gat | cat | aat | gat | caa | gta | atg | gat | tgg | caa | acg | ctt | gac | aag | ttt | gtt | 864 |
| Asp | His | Asn | Asp | Gln | Val | Met | Asp | Trp | Gln | Thr | Leu | Asp | Lys | Phe | Val | |
| | | 275 | | | | | 280 | | | | | 285 | | | | |

| | | | | | | | | | | | | | | | |
|---|---|---|---|---|---|---|---|---|---|---|---|---|---|---|---|
| gct | tct | cag | cta | atc | atg | agc | caa | gaa | gag | gaa | gaa | gtt | aac | aaa | gat | 912 |
| Ala | Ser | Gln | Leu | Ile | Met | Ser | Gln | Glu | Glu | Glu | Glu | Val | Asn | Lys | Asp | |
| | | 290 | | | | | 295 | | | | | 300 | | | | |

| | | | | | | | | | | | | | | | |
|---|---|---|---|---|---|---|---|---|---|---|---|---|---|---|---|
| cca | tca | gat | aat | tct | tcg | aat | gaa | aca | ttt | cat | cat | ctc | tct | gaa | gag | 960 |
| Pro | Ser | Asp | Asn | Ser | Ser | Asn | Glu | Thr | Phe | His | His | Leu | Ser | Glu | Glu | |
| 305 | | | | | 310 | | | | | 315 | | | | | 320 | |

| | | | | | | | | | | | | | | | |
|---|---|---|---|---|---|---|---|---|---|---|---|---|---|---|---|
| caa | gct | gca | aca | atg | gtt | tcg | atg | aat | gct | tct | tcc | tct | tct | tct | cca | 1008 |
| Gln | Ala | Ala | Thr | Met | Val | Ser | Met | Asn | Ala | Ser | Ser | Ser | Ser | Ser | Pro | |
| | | | | 325 | | | | | 330 | | | | | 335 | | |

| | | | | | | | | | | |
|---|---|---|---|---|---|---|---|---|---|---|
| tgt | tcc | ttc | tac | tct | tgg | gct | caa | aat | aca | cac | acg | taa | 1047 |
| Cys | Ser | Phe | Tyr | Ser | Trp | Ala | Gln | Asn | Thr | His | Thr | | |
| | | | | 340 | | | | | 345 | | | | |

<210> SEQ ID NO 10
<211> LENGTH: 348
<212> TYPE: PRT
<213> ORGANISM: Arabidopsis thaliana

<400> SEQUENCE: 10

Met Glu Ser Leu Ala His Ile Pro Pro Gly Tyr Arg Phe His Pro Thr
1               5                   10                  15

Asp Glu Glu Leu Val Asp Tyr Tyr Leu Lys Asn Lys Val Ala Phe Pro
            20                  25                  30

Gly Met Gln Val Asp Val Ile Lys Asp Val Asp Leu Tyr Lys Ile Glu
        35                  40                  45

Pro Trp Asp Ile Gln Glu Leu Cys Gly Arg Gly Thr Gly Glu Glu Arg
    50                  55                  60

Glu Trp Tyr Phe Phe Ser His Lys Asp Lys Lys Tyr Pro Thr Gly Thr
65                  70                  75                  80

Arg Thr Asn Arg Ala Thr Gly Ser Gly Phe Trp Lys Ala Thr Gly Arg
                85                  90                  95

Asp Lys Ala Ile Tyr Ser Lys Gln Glu Leu Val Gly Met Arg Lys Thr
            100                 105                 110

Leu Val Phe Tyr Lys Gly Arg Ala Pro Asn Gly Gln Lys Ser Asp Trp
        115                 120                 125

Ile Met His Glu Tyr Arg Leu Glu Thr Asp Glu Asn Gly Pro Pro His
    130                 135                 140

Glu Glu Gly Trp Val Val Cys Arg Ala Phe Lys Lys Lys Leu Thr Thr
145                 150                 155                 160

Met Asn Tyr Asn Asn Pro Arg Thr Met Met Gly Ser Ser Ser Gly Gln
                165                 170                 175

Glu Ser Asn Trp Phe Thr Gln Gln Met Asp Val Gly Asn Gly Asn Tyr
            180                 185                 190

Tyr His Leu Pro Asp Leu Glu Ser Pro Arg Met Phe Gln Gly Ser Ser
        195                 200                 205

```
Ser Ser Ser Leu Ser Ser Leu His Gln Asn Asp Gln Asp Pro Tyr Gly
    210                 215                 220

Val Val Leu Ser Thr Ile Asn Ala Thr Pro Thr Thr Ile Met Gln Arg
225                 230                 235                 240

Asp Asp Gly His Val Ile Thr Asn Asp Asp His Met Ile Met Met
                245                 250                 255

Asn Thr Ser Thr Gly Asp His His Gln Ser Gly Leu Leu Val Asn Asp
            260                 265                 270

Asp His Asn Asp Gln Val Met Asp Trp Gln Thr Leu Asp Lys Phe Val
                275                 280                 285

Ala Ser Gln Leu Ile Met Ser Gln Glu Glu Glu Val Asn Lys Asp
        290                 295                 300

Pro Ser Asp Asn Ser Ser Asn Glu Thr Phe His His Leu Ser Glu Glu
305                 310                 315                 320

Gln Ala Ala Thr Met Val Ser Met Asn Ala Ser Ser Ser Ser Pro
                325                 330                 335

Cys Ser Phe Tyr Ser Trp Ala Gln Asn Thr His Thr
            340                 345

<210> SEQ ID NO 11
<211> LENGTH: 1032
<212> TYPE: DNA
<213> ORGANISM: Arabidopsis thaliana
<220> FEATURE:
<221> NAME/KEY: CDS
<222> LOCATION: (1)..(1032)

<400> SEQUENCE: 11 atg gaa gcg gag aag aaa atg gtt cta ccg aga atc aaa ttc aca gag      48
Met Glu Ala Glu Lys Lys Met Val Leu Pro Arg Ile Lys Phe Thr Glu
1               5                   10                  15 cac aaa acc aac acg aca aca atc gta tcg gag tta acc aac act cac      96
His Lys Thr Asn Thr Thr Thr Ile Val Ser Glu Leu Thr Asn Thr His
                20                  25                  30 caa acc agg att ctt cgt atc tca gtc act gac cca gac gct act gat     144
Gln Thr Arg Ile Leu Arg Ile Ser Val Thr Asp Pro Asp Ala Thr Asp
            35                  40                  45 tcc tcc agt gac gac gaa gaa gaa cat caa cgc ttt gtc tct aaa         192
Ser Ser Ser Asp Asp Glu Glu Glu Glu His Gln Arg Phe Val Ser Lys
        50                  55                  60 cgc cgt cgt gtt aag aag ttt gtc aac gaa gtc tat ctc gat tcc ggt     240
Arg Arg Arg Val Lys Lys Phe Val Asn Glu Val Tyr Leu Asp Ser Gly
65                  70                  75                  80 gct gtt gtt act ggt agt tgt ggt caa atg gag tcg aag aag aga caa     288
Ala Val Val Thr Gly Ser Cys Gly Gln Met Glu Ser Lys Lys Arg Gln
                85                  90                  95 aag aga gcg gtt aaa tcg gag tct act gtt tct ccg gtt gtt tca gcg     336
Lys Arg Ala Val Lys Ser Glu Ser Thr Val Ser Pro Val Val Ser Ala
            100                 105                 110 acg acg act acg acg gga gag aag aag ttc cga gga gtg aga cag cgt     384
Thr Thr Thr Thr Thr Gly Glu Lys Lys Phe Arg Gly Val Arg Gln Arg
        115                 120                 125 cca tgg gga aaa tgg gcg gcg gag ata aga gat ccg ttg aaa cgt gta     432
Pro Trp Gly Lys Trp Ala Ala Glu Ile Arg Asp Pro Leu Lys Arg Val
130                 135                 140 cgg ctc tgg tta ggt act tac aac acg gcg gaa gaa gct gct atg gtt     480
Arg Leu Trp Leu Gly Thr Tyr Asn Thr Ala Glu Glu Ala Ala Met Val
145                 150                 155                 160 tac gat aac gcc gct att cag ctt cgt ggt ccc gac gct ctg act aat     528
```

```
Tyr Asp Asn Ala Ala Ile Gln Leu Arg Gly Pro Asp Ala Leu Thr Asn
                165                 170                 175 ttc tca gtc act ccg aca aca gcg acg gag aag aaa gcc cca cca ccg      576
Phe Ser Val Thr Pro Thr Thr Ala Thr Glu Lys Lys Ala Pro Pro Pro
            180                 185                 190 tct ccg gtg aag aag aag aag aag aaa aac aac aaa agc aaa aaa tcc      624
Ser Pro Val Lys Lys Lys Lys Lys Asn Asn Lys Ser Lys Lys Ser
        195                 200                 205 gtt act gct tct tcc tcc atc agc aga agc agc agc aac gat tgt ctc      672
Val Thr Ala Ser Ser Ser Ile Ser Arg Ser Ser Ser Asn Asp Cys Leu
    210                 215                 220 tgc tct ccg gtg tct gtt ctc cga tct cct ttc gcc gtc gac gaa ttc      720
Cys Ser Pro Val Ser Val Leu Arg Ser Pro Phe Ala Val Asp Glu Phe
225                 230                 235                 240 tcc ggc att tct tca tca cca gtc gcg gcc gtt gta gtc aag gaa gag      768
Ser Gly Ile Ser Ser Ser Pro Val Ala Ala Val Val Lys Glu Glu
                245                 250                 255 cca tcc atg aca acg gta tct gaa act ttc tct gat ttc tcg gcg ccc      816
Pro Ser Met Thr Thr Val Ser Glu Thr Phe Ser Asp Phe Ser Ala Pro
            260                 265                 270 ttg ttc tca gat gat gac gtg ttc gat ttc cgg agc tca gtg gtt ccc      864
Leu Phe Ser Asp Asp Asp Val Phe Asp Phe Arg Ser Ser Val Val Pro
        275                 280                 285 gac tat ctc ggc ggc gat tta ttt ggg gaa gat cta ttc acg gcg gat      912
Asp Tyr Leu Gly Gly Asp Leu Phe Gly Glu Asp Leu Phe Thr Ala Asp
    290                 295                 300 atg tgt acg gat atg aac ttc gga ttc gat ttc gga tcc gga tta tcc      960
Met Cys Thr Asp Met Asn Phe Gly Phe Asp Phe Gly Ser Gly Leu Ser
305                 310                 315                 320 agc tgg cac atg gag gac cat ttt caa gat atc ggg gat cta ttc ggg     1008
Ser Trp His Met Glu Asp His Phe Gln Asp Ile Gly Asp Leu Phe Gly
                325                 330                 335 tcg gat cct ctt tta gct gtt taa                                     1032
Ser Asp Pro Leu Leu Ala Val
            340

<210> SEQ ID NO 12
<211> LENGTH: 343
<212> TYPE: PRT
<213> ORGANISM: Arabidopsis thaliana

<400> SEQUENCE: 12

Met Glu Ala Glu Lys Lys Met Val Leu Pro Arg Ile Lys Phe Thr Glu
1               5                   10                  15

His Lys Thr Asn Thr Thr Thr Ile Val Ser Glu Leu Thr Asn Thr His
                20                  25                  30

Gln Thr Arg Ile Leu Arg Ile Ser Val Thr Asp Pro Asp Ala Thr Asp
            35                  40                  45

Ser Ser Asp Asp Glu Glu Glu His Gln Arg Phe Val Ser Lys
        50                  55                  60

Arg Arg Arg Val Lys Lys Phe Val Asn Glu Val Tyr Leu Asp Ser Gly
65                  70                  75                  80

Ala Val Val Thr Gly Ser Cys Gly Gln Met Glu Ser Lys Lys Arg Gln
                85                  90                  95

Lys Arg Ala Val Lys Ser Glu Ser Thr Val Ser Pro Val Val Ser Ala
            100                 105                 110

Thr Thr Thr Thr Gly Glu Lys Lys Phe Arg Gly Val Arg Gln Arg
        115                 120                 125
```

```
Pro Trp Gly Lys Trp Ala Ala Glu Ile Arg Asp Pro Leu Lys Arg Val
    130                 135                 140

Arg Leu Trp Leu Gly Thr Tyr Asn Thr Ala Glu Glu Ala Ala Met Val
145                 150                 155                 160

Tyr Asp Asn Ala Ala Ile Gln Leu Arg Gly Pro Asp Ala Leu Thr Asn
                    165                 170                 175

Phe Ser Val Thr Pro Thr Thr Ala Thr Glu Lys Lys Ala Pro Pro Pro
                180                 185                 190

Ser Pro Val Lys Lys Lys Lys Lys Asn Asn Lys Ser Lys Lys Ser
            195                 200                 205

Val Thr Ala Ser Ser Ser Ile Ser Arg Ser Ser Asn Asp Cys Leu
    210                 215                 220

Cys Ser Pro Val Ser Val Leu Arg Ser Pro Phe Ala Val Asp Glu Phe
225                 230                 235                 240

Ser Gly Ile Ser Ser Ser Pro Val Ala Ala Val Val Lys Glu Glu
                    245                 250                 255

Pro Ser Met Thr Thr Val Ser Glu Thr Phe Ser Asp Phe Ser Ala Pro
                260                 265                 270

Leu Phe Ser Asp Asp Asp Val Phe Asp Phe Arg Ser Ser Val Val Pro
    275                 280                 285

Asp Tyr Leu Gly Gly Asp Leu Phe Gly Glu Asp Leu Phe Thr Ala Asp
290                 295                 300

Met Cys Thr Asp Met Asn Phe Gly Phe Asp Phe Gly Ser Gly Leu Ser
305                 310                 315                 320

Ser Trp His Met Glu Asp His Phe Gln Asp Ile Gly Asp Leu Phe Gly
                    325                 330                 335

Ser Asp Pro Leu Leu Ala Val
                340

<210> SEQ ID NO 13
<211> LENGTH: 666
<212> TYPE: DNA
<213> ORGANISM: Arabidopsis thaliana
<220> FEATURE:
<221> NAME/KEY: CDS
<222> LOCATION: (1)..(666)

<400> SEQUENCE: 13 atg gcg gat tcg tct tcc gac aag gag aag aag gaa aat aat aag cag      48
Met Ala Asp Ser Ser Ser Asp Lys Glu Lys Lys Glu Asn Asn Lys Gln
1               5                   10                  15 ccc gtg tat cgt gga gtc cgt atg agg agc tgg gga aaa tgg gta tcg      96
Pro Val Tyr Arg Gly Val Arg Met Arg Ser Trp Gly Lys Trp Val Ser
            20                  25                  30 gag att cgc gaa ccg agg aag aaa tcg aga atc tgg ctc ggg act ttt     144
Glu Ile Arg Glu Pro Arg Lys Lys Ser Arg Ile Trp Leu Gly Thr Phe
        35                  40                  45 ccg acg gcg gag atg gct atg cgt gct cac gac gtg gcg gct atg agt     192
Pro Thr Ala Glu Met Ala Met Arg Ala His Asp Val Ala Ala Met Ser
    50                  55                  60 atc aaa gga act tca gcc att ctc aat ttc cct gag ctc tct aaa ctt     240
Ile Lys Gly Thr Ser Ala Ile Leu Asn Phe Pro Glu Leu Ser Lys Leu
65                  70                  75                  80 ctt ccc cga ccc gtt tcg ctc agc cct cgt gac gtc aga gct gcg gcg     288
Leu Pro Arg Pro Val Ser Leu Ser Pro Arg Asp Val Arg Ala Ala Ala
                85                  90                  95 acc aaa gct gct ctc atg gac ttc gat acg acg gcg ttt cgt tcg gat     336
Thr Lys Ala Ala Leu Met Asp Phe Asp Thr Thr Ala Phe Arg Ser Asp
```

```
                  100                 105                 110
act gag act agc gaa acg acg tcg aat aaa atg tca gag agt agt    384
Thr Glu Thr Ser Glu Thr Thr Ser Asn Lys Met Ser Glu Ser Ser
        115                 120                 125 gag agt aac gaa acg gtg tcg ttc tca tcg tcg tct tgg tcc tct gtt    432
Glu Ser Asn Glu Thr Val Ser Phe Ser Ser Ser Ser Trp Ser Ser Val
    130                 135                 140 acg agc att gag gaa agt aca gtc tcc gac gat ctt gac gag atc gta    480
Thr Ser Ile Glu Glu Ser Thr Val Ser Asp Asp Leu Asp Glu Ile Val
145                 150                 155                 160 aag tta ccg agt cta gga acg agc cta aac gag tcg aac gag ttc gtg    528
Lys Leu Pro Ser Leu Gly Thr Ser Leu Asn Glu Ser Asn Glu Phe Val
                165                 170                 175 ata ttt gac tcg ttg gag gat ttg gtg tac atg cct cgg tgg tta agc    576
Ile Phe Asp Ser Leu Glu Asp Leu Val Tyr Met Pro Arg Trp Leu Ser
            180                 185                 190 ggt acg gaa gaa gaa gtt ttt acg tat aat aac aat gat tct tcg ttg    624
Gly Thr Glu Glu Glu Val Phe Thr Tyr Asn Asn Asn Asp Ser Ser Leu
        195                 200                 205 aat tac tca tca gtt ttc gaa tct tgg aaa cat ttt ccc tga    666
Asn Tyr Ser Ser Val Phe Glu Ser Trp Lys His Phe Pro
    210                 215                 220

<210> SEQ ID NO 14
<211> LENGTH: 221
<212> TYPE: PRT
<213> ORGANISM: Arabidopsis thaliana

<400> SEQUENCE: 14

Met Ala Asp Ser Ser Ser Asp Lys Glu Lys Lys Glu Asn Asn Lys Gln
1               5                   10                  15

Pro Val Tyr Arg Gly Val Arg Met Arg Ser Trp Gly Lys Trp Val Ser
            20                  25                  30

Glu Ile Arg Glu Pro Arg Lys Lys Ser Arg Ile Trp Leu Gly Thr Phe
        35                  40                  45

Pro Thr Ala Glu Met Ala Met Arg Ala His Asp Val Ala Ala Met Ser
    50                  55                  60

Ile Lys Gly Thr Ser Ala Ile Leu Asn Phe Pro Glu Leu Ser Lys Leu
65              70                  75                  80

Leu Pro Arg Pro Val Ser Leu Ser Pro Arg Asp Val Arg Ala Ala Ala
                85                  90                  95

Thr Lys Ala Ala Leu Met Asp Phe Asp Thr Thr Ala Phe Arg Ser Asp
            100                 105                 110

Thr Glu Thr Ser Glu Thr Thr Thr Ser Asn Lys Met Ser Glu Ser Ser
        115                 120                 125

Glu Ser Asn Glu Thr Val Ser Phe Ser Ser Ser Ser Trp Ser Ser Val
    130                 135                 140

Thr Ser Ile Glu Glu Ser Thr Val Ser Asp Asp Leu Asp Glu Ile Val
145                 150                 155                 160

Lys Leu Pro Ser Leu Gly Thr Ser Leu Asn Glu Ser Asn Glu Phe Val
                165                 170                 175

Ile Phe Asp Ser Leu Glu Asp Leu Val Tyr Met Pro Arg Trp Leu Ser
            180                 185                 190

Gly Thr Glu Glu Glu Val Phe Thr Tyr Asn Asn Asn Asp Ser Ser Leu
        195                 200                 205

Asn Tyr Ser Ser Val Phe Glu Ser Trp Lys His Phe Pro
    210                 215                 220
```

```
<210> SEQ ID NO 15
<211> LENGTH: 921
<212> TYPE: DNA
<213> ORGANISM: Arabidopsis thaliana
<220> FEATURE:
<221> NAME/KEY: CDS
<222> LOCATION: (1)..(921)

<400> SEQUENCE: 15 atg gaa gaa gca atc atg aga ctc gaa ggt gcc gag cac aga gaa acc      48
Met Glu Glu Ala Ile Met Arg Leu Glu Gly Ala Glu His Arg Glu Thr
1               5                   10                  15 aac atc cat tct ttg aaa aga aag cca tca aga act tcc tcg aca gct      96
Asn Ile His Ser Leu Lys Arg Lys Pro Ser Arg Thr Ser Ser Thr Ala
                20                  25                  30 cct ggc tct ccc gga gga gta act acc gca aaa gct gcc tcc ggc gcc     144
Pro Gly Ser Pro Gly Gly Val Thr Thr Ala Lys Ala Ala Ser Gly Ala
            35                  40                  45 ggc gct tcc ggt gtc tct acg ata agg tac cga ggc gtg agg cgt agg     192
Gly Ala Ser Gly Val Ser Thr Ile Arg Tyr Arg Gly Val Arg Arg Arg
        50                  55                  60 cca tgg ggt cgt tac gca gct gaa ata cgg gac cca ttg tcc aag gag     240
Pro Trp Gly Arg Tyr Ala Ala Glu Ile Arg Asp Pro Leu Ser Lys Glu
65                  70                  75                  80 aga cga tgg ctc gga aca ttt gac acg gcc gag gaa gca gct tgc gca     288
Arg Arg Trp Leu Gly Thr Phe Asp Thr Ala Glu Glu Ala Ala Cys Ala
                85                  90                  95 tat gac tgc gcc gct cga gcc atg cgt ggt ctt aaa gct cga acc aac     336
Tyr Asp Cys Ala Ala Arg Ala Met Arg Gly Leu Lys Ala Arg Thr Asn
                100                 105                 110 ttc gtc tac cca atg cct tct ctc gac tct tat cac cac cgt att ttc     384
Phe Val Tyr Pro Met Pro Ser Leu Asp Ser Tyr His His Arg Ile Phe
            115                 120                 125 tcg tct cct cca atg aat atg ttc ctt cta cga gac gtg tta aac tct     432
Ser Ser Pro Pro Met Asn Met Phe Leu Leu Arg Asp Val Leu Asn Ser
        130                 135                 140 cag tct ctt tct ccg tta acc act ttc gct tac ccg cct tgt aat ctt     480
Gln Ser Leu Ser Pro Leu Thr Thr Phe Ala Tyr Pro Pro Cys Asn Leu
145                 150                 155                 160 tct aac gta aac gac gtt gtt cac gag tcc ttc act aac gtc aac gat     528
Ser Asn Val Asn Asp Val Val His Glu Ser Phe Thr Asn Val Asn Asp
                165                 170                 175 gtc tgt gaa gat ctc tcg cct aaa gct aag agg tca agt acc att gag     576
Val Cys Glu Asp Leu Ser Pro Lys Ala Lys Arg Ser Ser Thr Ile Glu
                180                 185                 190 aac gag agc ctg ata tca aat atc ttt gaa cca gaa cca gct agt tct     624
Asn Glu Ser Leu Ile Ser Asn Ile Phe Glu Pro Glu Pro Ala Ser Ser
            195                 200                 205 ggt ctt ctt caa gaa att gtt caa ggc ttc tta cca aaa cct atc tct     672
Gly Leu Leu Gln Glu Ile Val Gln Gly Phe Leu Pro Lys Pro Ile Ser
        210                 215                 220 caa cat gct tct ata cct cca aag agc aac caa cag tcg gtt ggt gtt     720
Gln His Ala Ser Ile Pro Pro Lys Ser Asn Gln Gln Ser Val Gly Val
225                 230                 235                 240 ttc ccg acg atg cca gag agc ggt ttt cag aca gat gtt cgt tta gct     768
Phe Pro Thr Met Pro Glu Ser Gly Phe Gln Thr Asp Val Arg Leu Ala
                245                 250                 255 gac ttc cat gtc gaa gga aac gga ttc ggt cag gtt aaa tat cat gga     816
Asp Phe His Val Glu Gly Asn Gly Phe Gly Gln Val Lys Tyr His Gly
                260                 265                 270
```

```
gag tta ggt tgg gct gat cat gag aat ggg ttt gat tca gct aag atg      864
Glu Leu Gly Trp Ala Asp His Glu Asn Gly Phe Asp Ser Ala Lys Met
        275                 280                 285 cag cag aac gga aat ggt gga atg ttt tat cag tat tgc ttt cat gat      912
Gln Gln Asn Gly Asn Gly Gly Met Phe Tyr Gln Tyr Cys Phe His Asp
290                 295                 300 gat tat tag                                                          921
Asp Tyr
305

<210> SEQ ID NO 16
<211> LENGTH: 306
<212> TYPE: PRT
<213> ORGANISM: Arabidopsis thaliana

<400> SEQUENCE: 16
```

Met Glu Glu Ala Ile Met Arg Leu Glu Gly Ala Glu His Arg Glu Thr
1               5                   10                  15

Asn Ile His Ser Leu Lys Arg Lys Pro Ser Arg Thr Ser Ser Thr Ala
            20                  25                  30

Pro Gly Ser Pro Gly Gly Val Thr Thr Ala Lys Ala Ala Ser Gly Ala
        35                  40                  45

Gly Ala Ser Gly Val Ser Thr Ile Arg Tyr Arg Gly Val Arg Arg Arg
    50                  55                  60

Pro Trp Gly Arg Tyr Ala Ala Glu Ile Arg Asp Pro Leu Ser Lys Glu
65                  70                  75                  80

Arg Arg Trp Leu Gly Thr Phe Asp Thr Ala Glu Glu Ala Ala Cys Ala
                85                  90                  95

Tyr Asp Cys Ala Ala Arg Ala Met Arg Gly Leu Lys Ala Arg Thr Asn
            100                 105                 110

Phe Val Tyr Pro Met Pro Ser Leu Asp Ser Tyr His His Arg Ile Phe
        115                 120                 125

Ser Ser Pro Pro Met Asn Met Phe Leu Leu Arg Asp Val Leu Asn Ser
    130                 135                 140

Gln Ser Leu Ser Pro Leu Thr Thr Phe Ala Tyr Pro Pro Cys Asn Leu
145                 150                 155                 160

Ser Asn Val Asn Asp Val Val His Glu Ser Phe Thr Asn Val Asn Asp
                165                 170                 175

Val Cys Glu Asp Leu Ser Pro Lys Ala Lys Arg Ser Ser Thr Ile Glu
            180                 185                 190

Asn Glu Ser Leu Ile Ser Asn Ile Phe Glu Pro Glu Pro Ala Ser Ser
        195                 200                 205

Gly Leu Leu Gln Glu Ile Val Gln Gly Phe Leu Pro Lys Pro Ile Ser
    210                 215                 220

Gln His Ala Ser Ile Pro Pro Lys Ser Asn Gln Gln Ser Val Gly Val
225                 230                 235                 240

Phe Pro Thr Met Pro Glu Ser Gly Phe Gln Thr Asp Val Arg Leu Ala
                245                 250                 255

Asp Phe His Val Glu Gly Asn Gly Phe Gly Gln Val Lys Tyr His Gly
            260                 265                 270

Glu Leu Gly Trp Ala Asp His Glu Asn Gly Phe Asp Ser Ala Lys Met
        275                 280                 285

Gln Gln Asn Gly Asn Gly Gly Met Phe Tyr Gln Tyr Cys Phe His Asp
    290                 295                 300

Asp Tyr
305

```
<210> SEQ ID NO 17
<211> LENGTH: 1011
<212> TYPE: DNA
<213> ORGANISM: Arabidopsis thaliana
<220> FEATURE:
<221> NAME/KEY: CDS
<222> LOCATION: (1)..(1011)

<400> SEQUENCE: 17
```

| | | | | | | | | | | | | | | | | |
|---|---|---|---|---|---|---|---|---|---|---|---|---|---|---|---|---|
| atg | tca | aga | aag | cca | tgt | tgt | gtg | gga | gaa | gga | ctg | aag | aaa | gga | gca | 48 |
| Met | Ser | Arg | Lys | Pro | Cys | Cys | Val | Gly | Glu | Gly | Leu | Lys | Lys | Gly | Ala | |
| 1 | | | 5 | | | | | 10 | | | | | 15 | | | |
| tgg | act | gcc | gaa | gaa | gac | aag | aaa | ctc | atc | tct | tac | att | cat | gaa | cac | 96 |
| Trp | Thr | Ala | Glu | Glu | Asp | Lys | Lys | Leu | Ile | Ser | Tyr | Ile | His | Glu | His | |
| | | | 20 | | | | | 25 | | | | | 30 | | | |
| ggt | gaa | gga | ggc | tgg | cgt | gac | att | ccc | caa | aaa | gct | gga | cta | aaa | cga | 144 |
| Gly | Glu | Gly | Gly | Trp | Arg | Asp | Ile | Pro | Gln | Lys | Ala | Gly | Leu | Lys | Arg | |
| | | 35 | | | | | 40 | | | | | 45 | | | | |
| tgt | gga | aag | agt | tgt | aga | ttg | cga | tgg | gct | aac | tat | ttg | aaa | cct | gac | 192 |
| Cys | Gly | Lys | Ser | Cys | Arg | Leu | Arg | Trp | Ala | Asn | Tyr | Leu | Lys | Pro | Asp | |
| | 50 | | | | | 55 | | | | | 60 | | | | | |
| atc | aag | aga | gga | gag | ttt | agc | tat | gag | gag | gaa | cag | att | atc | atc | atg | 240 |
| Ile | Lys | Arg | Gly | Glu | Phe | Ser | Tyr | Glu | Glu | Glu | Gln | Ile | Ile | Ile | Met | |
| 65 | | | | | 70 | | | | | 75 | | | | | 80 | |
| cta | cac | gct | tct | cgc | ggc | aac | aag | tgg | tca | gtc | ata | gcg | aga | cat | ttg | 288 |
| Leu | His | Ala | Ser | Arg | Gly | Asn | Lys | Trp | Ser | Val | Ile | Ala | Arg | His | Leu | |
| | | | | 85 | | | | | 90 | | | | | 95 | | |
| ccc | aaa | aga | aca | gat | aac | gag | att | aag | aac | tac | tgg | aac | acg | cat | ctc | 336 |
| Pro | Lys | Arg | Thr | Asp | Asn | Glu | Ile | Lys | Asn | Tyr | Trp | Asn | Thr | His | Leu | |
| | | | 100 | | | | | 105 | | | | | 110 | | | |
| aaa | aag | ctc | ctg | atc | gat | aag | gga | atc | gat | ccc | gtg | acc | cac | aag | cca | 384 |
| Lys | Lys | Leu | Leu | Ile | Asp | Lys | Gly | Ile | Asp | Pro | Val | Thr | His | Lys | Pro | |
| | | | 115 | | | | | 120 | | | | | 125 | | | |
| ctt | gcc | tat | gac | tca | aac | ccg | gat | gag | caa | tcg | caa | tcg | ggt | tcc | atc | 432 |
| Leu | Ala | Tyr | Asp | Ser | Asn | Pro | Asp | Glu | Gln | Ser | Gln | Ser | Gly | Ser | Ile | |
| | 130 | | | | | 135 | | | | | 140 | | | | | |
| tct | cca | aag | tct | ctt | cct | cct | tca | agc | tcc | aaa | aat | gta | ccg | gag | ata | 480 |
| Ser | Pro | Lys | Ser | Leu | Pro | Pro | Ser | Ser | Ser | Lys | Asn | Val | Pro | Glu | Ile | |
| 145 | | | | | 150 | | | | | 155 | | | | | 160 | |
| acc | agc | agt | gac | gag | aca | ccg | aaa | tat | gat | gct | tcc | ttg | agc | tcc | aag | 528 |
| Thr | Ser | Ser | Asp | Glu | Thr | Pro | Lys | Tyr | Asp | Ala | Ser | Leu | Ser | Ser | Lys | |
| | | | | 165 | | | | | 170 | | | | | 175 | | |
| aaa | cgt | tgt | ttt | aag | aga | tcg | agt | tct | aca | tca | aaa | ctg | tta | aac | aaa | 576 |
| Lys | Arg | Cys | Phe | Lys | Arg | Ser | Ser | Ser | Thr | Ser | Lys | Leu | Leu | Asn | Lys | |
| | | | 180 | | | | | 185 | | | | | 190 | | | |
| gtt | gca | gct | agg | gct | tct | tcc | atg | gga | act | ata | cta | ggc | gcc | tcc | atc | 624 |
| Val | Ala | Ala | Arg | Ala | Ser | Ser | Met | Gly | Thr | Ile | Leu | Gly | Ala | Ser | Ile | |
| | | | 195 | | | | | 200 | | | | | 205 | | | |
| gaa | gga | acc | ttg | atc | agc | tct | aca | ccg | ttg | tct | tca | tgt | cta | aat | gat | 672 |
| Glu | Gly | Thr | Leu | Ile | Ser | Ser | Thr | Pro | Leu | Ser | Ser | Cys | Leu | Asn | Asp | |
| | 210 | | | | | 215 | | | | | 220 | | | | | |
| gac | ttt | tct | gaa | aca | agt | caa | ttt | cag | atg | gaa | gaa | ttt | gat | cca | ttc | 720 |
| Asp | Phe | Ser | Glu | Thr | Ser | Gln | Phe | Gln | Met | Glu | Glu | Phe | Asp | Pro | Phe | |
| 225 | | | | | 230 | | | | | 235 | | | | | 240 | |
| tat | cag | tca | tct | gaa | cac | ata | att | gat | cat | atg | aaa | gaa | gat | atc | agc | 768 |
| Tyr | Gln | Ser | Ser | Glu | His | Ile | Ile | Asp | His | Met | Lys | Glu | Asp | Ile | Ser | |
| | | | | 245 | | | | | 250 | | | | | 255 | | |
| atc | aac | aat | tcc | gaa | tac | gat | ttc | tcg | cag | ttt | ctc | gag | cag | ttt | agt | 816 |
| Ile | Asn | Asn | Ser | Glu | Tyr | Asp | Phe | Ser | Gln | Phe | Leu | Glu | Gln | Phe | Ser | |

```
             260                 265                 270
aac aac gaa ggg gaa gaa gct gac aat act gga gga gga tat aac caa    864
Asn Asn Glu Gly Glu Glu Ala Asp Asn Thr Gly Gly Gly Tyr Asn Gln
        275                 280                 285 gat ctt ctt atg tct gat gtc tca tca aca agc gtt gat gaa gac gag    912
Asp Leu Leu Met Ser Asp Val Ser Ser Thr Ser Val Asp Glu Asp Glu
    290                 295                 300 atg atg caa aac ata act ggt tgg tca aat tat ctc ctt gac cat tcc    960
Met Met Gln Asn Ile Thr Gly Trp Ser Asn Tyr Leu Leu Asp His Ser
305                 310                 315                 320 gat ttc aat tat gac acg agc caa gat tac gac gac aag aac ttc ata   1008
Asp Phe Asn Tyr Asp Thr Ser Gln Asp Tyr Asp Asp Lys Asn Phe Ile
                325                 330                 335 tga                                                               1011
```

<210> SEQ ID NO 18
<211> LENGTH: 336
<212> TYPE: PRT
<213> ORGANISM: Arabidopsis thaliana

<400> SEQUENCE: 18

```
Met Ser Arg Lys Pro Cys Cys Val Gly Glu Gly Leu Lys Lys Gly Ala
1               5                   10                  15

Trp Thr Ala Glu Glu Asp Lys Lys Leu Ile Ser Tyr Ile His Glu His
            20                  25                  30

Gly Glu Gly Gly Trp Arg Asp Ile Pro Gln Lys Ala Gly Leu Lys Arg
        35                  40                  45

Cys Gly Lys Ser Cys Arg Leu Arg Trp Ala Asn Tyr Leu Lys Pro Asp
    50                  55                  60

Ile Lys Arg Gly Glu Phe Ser Tyr Glu Glu Gln Ile Ile Ile Met
65                  70                  75                  80

Leu His Ala Ser Arg Gly Asn Lys Trp Ser Val Ile Ala Arg His Leu
                85                  90                  95

Pro Lys Arg Thr Asp Asn Glu Ile Lys Asn Tyr Trp Asn Thr His Leu
            100                 105                 110

Lys Lys Leu Leu Ile Asp Lys Gly Ile Asp Pro Val Thr His Lys Pro
        115                 120                 125

Leu Ala Tyr Asp Ser Asn Pro Asp Glu Gln Ser Gln Ser Gly Ser Ile
    130                 135                 140

Ser Pro Lys Ser Leu Pro Pro Ser Ser Lys Asn Val Pro Glu Ile
145                 150                 155                 160

Thr Ser Ser Asp Glu Thr Pro Lys Tyr Asp Ala Ser Leu Ser Ser Lys
                165                 170                 175

Lys Arg Cys Phe Lys Arg Ser Ser Thr Ser Lys Leu Leu Asn Lys
            180                 185                 190

Val Ala Ala Arg Ala Ser Ser Met Gly Thr Ile Leu Gly Ala Ser Ile
        195                 200                 205

Glu Gly Thr Leu Ile Ser Ser Thr Pro Leu Ser Ser Cys Leu Asn Asp
    210                 215                 220

Asp Phe Ser Glu Thr Ser Gln Phe Gln Met Glu Glu Phe Asp Pro Phe
225                 230                 235                 240

Tyr Gln Ser Ser Glu His Ile Ile Asp His Met Lys Glu Asp Ile Ser
                245                 250                 255

Ile Asn Asn Ser Glu Tyr Asp Phe Ser Gln Phe Leu Glu Gln Phe Ser
            260                 265                 270
```

```
Asn Asn Glu Gly Glu Glu Ala Asp Asn Thr Gly Gly Tyr Asn Gln
            275                 280                 285

Asp Leu Leu Met Ser Asp Val Ser Ser Thr Ser Val Asp Glu Asp
            290                 295                 300

Met Met Gln Asn Ile Thr Gly Trp Ser Asn Tyr Leu Leu Asp His Ser
305                 310                 315                 320

Asp Phe Asn Tyr Asp Thr Ser Gln Asp Tyr Asp Asp Lys Asn Phe Ile
                325                 330                 335

<210> SEQ ID NO 19
<211> LENGTH: 636
<212> TYPE: DNA
<213> ORGANISM: Arabidopsis thaliana
<220> FEATURE:
<221> NAME/KEY: CDS
<222> LOCATION: (1)..(636)

<400> SEQUENCE: 19 atg gct cgt gga aag att cag ctt aag agg att gag aac ccg gtt cac      48
Met Ala Arg Gly Lys Ile Gln Leu Lys Arg Ile Glu Asn Pro Val His
1               5                   10                  15 aga caa gtg act ttt tgc aag agg aga act ggt ctt ctc aag aag gct      96
Arg Gln Val Thr Phe Cys Lys Arg Arg Thr Gly Leu Leu Lys Lys Ala
            20                  25                  30 aag gag ctc tct gtg ctc tgt gat gcc gag atc ggt gtt gtg atc ttc     144
Lys Glu Leu Ser Val Leu Cys Asp Ala Glu Ile Gly Val Val Ile Phe
        35                  40                  45 tct cct cag ggc aag ctc ttt gag ctc gct act aaa gga aca atg gag     192
Ser Pro Gln Gly Lys Leu Phe Glu Leu Ala Thr Lys Gly Thr Met Glu
    50                  55                  60 gga atg att gat aag tac atg aag tgt act ggt ggt ggt cgt ggt tct     240
Gly Met Ile Asp Lys Tyr Met Lys Cys Thr Gly Gly Gly Arg Gly Ser
65                  70                  75                  80 tct tct gct act ttt act gct caa gaa caa ctt caa cca cca aat ctt     288
Ser Ser Ala Thr Phe Thr Ala Gln Glu Gln Leu Gln Pro Pro Asn Leu
                85                  90                  95 gat ccg aaa gat gag atc aac gtg ctt aag caa gag att gag atg ctt     336
Asp Pro Lys Asp Glu Ile Asn Val Leu Lys Gln Glu Ile Glu Met Leu
            100                 105                 110 cag aaa ggg ata agc tat atg ttt gga gga gga gat ggg gct atg aat     384
Gln Lys Gly Ile Ser Tyr Met Phe Gly Gly Gly Asp Gly Ala Met Asn
        115                 120                 125 ctt gaa gaa ctt ctt ttg ctt gag aag cat ctt gag tat tgg att tct     432
Leu Glu Glu Leu Leu Leu Leu Glu Lys His Leu Glu Tyr Trp Ile Ser
    130                 135                 140 cag att cgc tct gct aag atg gat gtt atg ctt caa gaa att cag tca     480
Gln Ile Arg Ser Ala Lys Met Asp Val Met Leu Gln Glu Ile Gln Ser
145                 150                 155                 160 ttg agg aac aag gaa gga gtc ctc aaa aac acc aac aag tat ctc ctc     528
Leu Arg Asn Lys Glu Gly Val Leu Lys Asn Thr Asn Lys Tyr Leu Leu
                165                 170                 175 gaa aag ata gag gaa aac aac aat agc ata tta gat gct aac ttc gca     576
Glu Lys Ile Glu Glu Asn Asn Asn Ser Ile Leu Asp Ala Asn Phe Ala
            180                 185                 190 gtc atg gag aca aac tat tcc tat ccg cta aca atg cca agt gaa ata     624
Val Met Glu Thr Asn Tyr Ser Tyr Pro Leu Thr Met Pro Ser Glu Ile
        195                 200                 205 ttt cag ttc tag                                                      636
Phe Gln Phe
    210
```

<210> SEQ ID NO 20
<211> LENGTH: 211
<212> TYPE: PRT
<213> ORGANISM: Arabidopsis thaliana

<400> SEQUENCE: 20

```
Met Ala Arg Gly Lys Ile Gln Leu Lys Arg Ile Glu Asn Pro Val His
1               5                   10                  15

Arg Gln Val Thr Phe Cys Lys Arg Thr Gly Leu Leu Lys Lys Ala
            20                  25                  30

Lys Glu Leu Ser Val Leu Cys Asp Ala Glu Ile Gly Val Val Ile Phe
        35                  40                  45

Ser Pro Gln Gly Lys Leu Phe Glu Leu Ala Thr Lys Gly Thr Met Glu
    50                  55                  60

Gly Met Ile Asp Lys Tyr Met Lys Cys Thr Gly Gly Arg Gly Ser
65                  70                  75                  80

Ser Ser Ala Thr Phe Thr Ala Gln Glu Gln Leu Gln Pro Asn Leu
                85                  90                  95

Asp Pro Lys Asp Glu Ile Asn Val Leu Lys Gln Glu Ile Glu Met Leu
            100                 105                 110

Gln Lys Gly Ile Ser Tyr Met Phe Gly Gly Asp Gly Ala Met Asn
            115                 120                 125

Leu Glu Glu Leu Leu Leu Glu Lys His Leu Glu Tyr Trp Ile Ser
    130                 135                 140

Gln Ile Arg Ser Ala Lys Met Asp Val Met Leu Gln Glu Ile Gln Ser
145                 150                 155                 160

Leu Arg Asn Lys Glu Gly Val Leu Lys Asn Thr Asn Lys Tyr Leu Leu
                165                 170                 175

Glu Lys Ile Glu Glu Asn Asn Asn Ser Ile Leu Asp Ala Asn Phe Ala
            180                 185                 190

Val Met Glu Thr Asn Tyr Ser Tyr Pro Leu Thr Met Pro Ser Glu Ile
            195                 200                 205

Phe Gln Phe
    210
```

<210> SEQ ID NO 21
<211> LENGTH: 2514
<212> TYPE: DNA
<213> ORGANISM: Arabidopsis thaliana
<220> FEATURE:
<221> NAME/KEY: CDS
<222> LOCATION: (1)..(2514)

<400> SEQUENCE: 21

```
atg gca atg tct tgc aag gat ggt aag ttg gga tgt ttg gat aat ggg      48
Met Ala Met Ser Cys Lys Asp Gly Lys Leu Gly Cys Leu Asp Asn Gly
1               5                   10                  15 aag tat gtg agg tat aca cct gaa caa gtt gaa gca ctt gag agg ctt      96
Lys Tyr Val Arg Tyr Thr Pro Glu Gln Val Glu Ala Leu Glu Arg Leu
            20                  25                  30 tat cat gac tgt cct aaa ccg agt tct att cgc gtt cag cag ttg atc     144
Tyr His Asp Cys Pro Lys Pro Ser Ser Ile Arg Arg Gln Gln Leu Ile
        35                  40                  45 aga gag tgt cct att ctc tct aac att gag cct aaa cag atc aaa gtg     192
Arg Glu Cys Pro Ile Leu Ser Asn Ile Glu Pro Lys Gln Ile Lys Val
    50                  55                  60 tgg ttt cag aac cga aga tgt aga gag aaa caa agg aaa gag gct tca     240
Trp Phe Gln Asn Arg Arg Cys Arg Glu Lys Gln Arg Lys Glu Ala Ser
```

```
               65                  70                  75                  80
cgg ctt caa gct gtg aat cgg aag ttg acg gca atg aac aag ctc ttg        288
Arg Leu Gln Ala Val Asn Arg Lys Leu Thr Ala Met Asn Lys Leu Leu
                    85                  90                  95 atg gag gag aat gac agg ttg cag aag caa gtg tca cag ctg gtc cat        336
Met Glu Glu Asn Asp Arg Leu Gln Lys Gln Val Ser Gln Leu Val His
                100                 105                 110 gaa aac agc tac ttc cgt caa cat act cca aat cct tca ctc cca gct        384
Glu Asn Ser Tyr Phe Arg Gln His Thr Pro Asn Pro Ser Leu Pro Ala
                115                 120                 125 aaa gac aca agc tgt gaa tcg gtg gtg acg agt ggt cag cac caa ttg        432
Lys Asp Thr Ser Cys Glu Ser Val Val Thr Ser Gly Gln His Gln Leu
130                 135                 140 gca tct caa aat cct cag aga gat gct agt cct gca gga ctt tgt tcc       480
Ala Ser Gln Asn Pro Gln Arg Asp Ala Ser Pro Ala Gly Leu Leu Ser
145                 150                 155                 160 att gca gaa gaa act tta gca gag ttt ctt tca aag gca act gga acc       528
Ile Ala Glu Glu Thr Leu Ala Glu Phe Leu Ser Lys Ala Thr Gly Thr
                165                 170                 175 gct gtt gag tgg gtt cag atg cct gga atg aag cct ggt ccg gat tcc       576
Ala Val Glu Trp Val Gln Met Pro Gly Met Lys Pro Gly Pro Asp Ser
                180                 185                 190 att gga atc atc gct att tct cat ggt tgc act ggt gtg gca gca cgc       624
Ile Gly Ile Ile Ala Ile Ser His Gly Cys Thr Gly Val Ala Ala Arg
                195                 200                 205 gcc tgt ggc cta gtg ggt ctt gag cct aca agg gtt gca gag att gtc       672
Ala Cys Gly Leu Val Gly Leu Glu Pro Thr Arg Val Ala Glu Ile Val
210                 215                 220 aag gat cgt cct tcg tgg ttc cgc gaa tgt cga gct gtt gaa gtt atg       720
Lys Asp Arg Pro Ser Trp Phe Arg Glu Cys Arg Ala Val Glu Val Met
225                 230                 235                 240 aac gtg ttg cca act gcc aat ggt gga acc gtt gag ctg ctt tat atg       768
Asn Val Leu Pro Thr Ala Asn Gly Gly Thr Val Glu Leu Leu Tyr Met
                245                 250                 255 cag ctc tat gca cca act aca ttg gcc cca cca cgc gat ttc tgg ctg       816
Gln Leu Tyr Ala Pro Thr Thr Leu Ala Pro Pro Arg Asp Phe Trp Leu
                260                 265                 270 tta cgt tac acc tct gtt tta gaa gat ggc agc ctt gtg gtg tgc gag       864
Leu Arg Tyr Thr Ser Val Leu Glu Asp Gly Ser Leu Val Val Cys Glu
                275                 280                 285 aga tct ctt aag agc act caa aat ggt cct agt atg cca ctg gtt cag       912
Arg Ser Leu Lys Ser Thr Gln Asn Gly Pro Ser Met Pro Leu Val Gln
                290                 295                 300 aat ttt gtg aga gca gag atg ctt tcc agt ggg tac ttg ata cgg cct       960
Asn Phe Val Arg Ala Glu Met Leu Ser Ser Gly Tyr Leu Ile Arg Pro
305                 310                 315                 320 tgt gat ggt ggt ggc tca atc ata cac ata gtg gat cat atg gat ttg      1008
Cys Asp Gly Gly Gly Ser Ile Ile His Ile Val Asp His Met Asp Leu
                325                 330                 335 gag gct tgt agc gtg cct gag gtc ttg cgc ccg ctc tat gag tca ccc      1056
Glu Ala Cys Ser Val Pro Glu Val Leu Arg Pro Leu Tyr Glu Ser Pro
                340                 345                 350 aaa gta ctt gca cag aag aca aca atg gcg gca ctg cgt cag ctc aag      1104
Lys Val Leu Ala Gln Lys Thr Thr Met Ala Ala Leu Arg Gln Leu Lys
                355                 360                 365 caa ata gct cag gag gtt act cag act aat agt agt gtt aat ggg tgg      1152
Gln Ile Ala Gln Glu Val Thr Gln Thr Asn Ser Ser Val Asn Gly Trp
                370                 375                 380 gga cgg cgt cct gct gcc tta aga gct ctc agc cag agg cta agc aga      1200
```

| | | | | | | | | | | | | | | |
|---|---|---|---|---|---|---|---|---|---|---|---|---|---|---|
| Gly | Arg | Arg | Pro | Ala | Ala | Leu | Arg | Ala | Leu | Ser | Gln | Arg | Leu | Ser | Arg |
| 385 | | | | | 390 | | | | | 395 | | | | | 400 |

```
ggc ttc aat gaa gct gta aat ggt ttc act gat gaa gga tgg tca gtg      1248
Gly Phe Asn Glu Ala Val Asn Gly Phe Thr Asp Glu Gly Trp Ser Val
            405                 410                 415 ata gga gat agc atg gat gat gtc aca atc act gta aac tct tct cca      1296
Ile Gly Asp Ser Met Asp Asp Val Thr Ile Thr Val Asn Ser Ser Pro
                420                 425                 430 gac aag cta atg ggt cta aat ctt aca ttt gcc aat ggc ttt gct cct      1344
Asp Lys Leu Met Gly Leu Asn Leu Thr Phe Ala Asn Gly Phe Ala Pro
            435                 440                 445 gta agc aat gtt gtt tta tgc gca aaa gca tca atg ctt tta cag aat      1392
Val Ser Asn Val Val Leu Cys Ala Lys Ala Ser Met Leu Leu Gln Asn
450                 455                 460 gtt cct ccg gcg atc ctg ctt cgg ttt ctg agg gag cat agg tca gaa      1440
Val Pro Pro Ala Ile Leu Leu Arg Phe Leu Arg Glu His Arg Ser Glu
465                 470                 475                 480 tgg gct gac aac aac att gat gcg tat cta gca gca gca gtt aaa gta      1488
Trp Ala Asp Asn Asn Ile Asp Ala Tyr Leu Ala Ala Ala Val Lys Val
                485                 490                 495 ggg cct tgt agt gcc cga gtt gga gga ttt gga ggg cag gta ata ctt      1536
Gly Pro Cys Ser Ala Arg Val Gly Gly Phe Gly Gly Gln Val Ile Leu
            500                 505                 510 cca ctt gct cat act att gag cat gaa gag ttt atg gaa gtc atc aaa      1584
Pro Leu Ala His Thr Ile Glu His Glu Glu Phe Met Glu Val Ile Lys
            515                 520                 525 ttg gaa ggt ctt ggt cat tcc cct gaa gat gca atc gtt cca aga gat      1632
Leu Glu Gly Leu Gly His Ser Pro Glu Asp Ala Ile Val Pro Arg Asp
530                 535                 540 atc ttc ctt ctt caa ctt tgt agc gga atg gat gaa aat gct gta gga      1680
Ile Phe Leu Leu Gln Leu Cys Ser Gly Met Asp Glu Asn Ala Val Gly
545                 550                 555                 560 acc tgt gcg gaa ctt ata ttt gct cca atc gat gct tcg ttt gcg gat      1728
Thr Cys Ala Glu Leu Ile Phe Ala Pro Ile Asp Ala Ser Phe Ala Asp
                565                 570                 575 gat gca cct ctg ctt cct tct ggt ttt cgt att atc cct ctt gat tcc      1776
Asp Ala Pro Leu Leu Pro Ser Gly Phe Arg Ile Ile Pro Leu Asp Ser
            580                 585                 590 gca aag cag gaa gta tct agc cca aac cga acc ttg gat ctt gct tcg      1824
Ala Lys Gln Glu Val Ser Ser Pro Asn Arg Thr Leu Asp Leu Ala Ser
            595                 600                 605 gca ctg gaa att ggt tca gct gga aca aaa gcc tca act gat caa tca      1872
Ala Leu Glu Ile Gly Ser Ala Gly Thr Lys Ala Ser Thr Asp Gln Ser
610                 615                 620 gga aac tcc aca tgt gca aga tct gtg atg aca ata gca ttt gag ttt      1920
Gly Asn Ser Thr Cys Ala Arg Ser Val Met Thr Ile Ala Phe Glu Phe
625                 630                 635                 640 ggt atc gag agc cat atg caa gaa cat gta gca tcc atg gct agg cag      1968
Gly Ile Glu Ser His Met Gln Glu His Val Ala Ser Met Ala Arg Gln
                645                 650                 655 tat gtt cga ggt atc ata tca tcg gtg cag aga gta gca ttg gct ctt      2016
Tyr Val Arg Gly Ile Ile Ser Ser Val Gln Arg Val Ala Leu Ala Leu
            660                 665                 670 tct cct tct cat atc agc tca caa gtt ggt cta cgc act cct ttg ggt      2064
Ser Pro Ser His Ile Ser Ser Gln Val Gly Leu Arg Thr Pro Leu Gly
            675                 680                 685 act cct gaa gcc caa aca ctt gct cgt tgg att tgc cag agt tac agg      2112
Thr Pro Glu Ala Gln Thr Leu Ala Arg Trp Ile Cys Gln Ser Tyr Arg
690                 695                 700
```

-continued

```
ggc tac atg ggt gtt gag cta ctt aaa tca aac agt gac ggc aat gaa      2160
Gly Tyr Met Gly Val Glu Leu Leu Lys Ser Asn Ser Asp Gly Asn Glu
705                 710                 715                 720 tct att ctt aag aat ctt tgg cat cac act gat gct ata atc tgc tgc      2208
Ser Ile Leu Lys Asn Leu Trp His His Thr Asp Ala Ile Ile Cys Cys
                725                 730                 735 tca atg aag gcc ttg ccc gtc ttc aca ttt gca aac cag gcg gga ctt      2256
Ser Met Lys Ala Leu Pro Val Phe Thr Phe Ala Asn Gln Ala Gly Leu
            740                 745                 750 gac atg ctg gag act aca tta gtt gct ctt caa gac atc tct tta gag      2304
Asp Met Leu Glu Thr Thr Leu Val Ala Leu Gln Asp Ile Ser Leu Glu
        755                 760                 765 aag ata ttt gat gac aat gga aga aag act ctt tgc tct gag ttc cca      2352
Lys Ile Phe Asp Asp Asn Gly Arg Lys Thr Leu Cys Ser Glu Phe Pro
    770                 775                 780 cag atc atg caa cag ggc ttc gcg tgc ctt caa ggc ggg ata tgt ctc      2400
Gln Ile Met Gln Gln Gly Phe Ala Cys Leu Gln Gly Gly Ile Cys Leu
785                 790                 795                 800 tca agc atg ggg aga cca gtt tcg tat gag aga gca gtt gct tgg aaa      2448
Ser Ser Met Gly Arg Pro Val Ser Tyr Glu Arg Ala Val Ala Trp Lys
                805                 810                 815 gta ctc aat gaa gaa gaa aat gct cat tgc atc tgc ttt gtg ttc atc      2496
Val Leu Asn Glu Glu Glu Asn Ala His Cys Ile Cys Phe Val Phe Ile
                820                 825                 830 aat tgg tcc ttt gtg tga                                              2514
Asn Trp Ser Phe Val
            835

<210> SEQ ID NO 22
<211> LENGTH: 837
<212> TYPE: PRT
<213> ORGANISM: Arabidopsis thaliana

<400> SEQUENCE: 22

Met Ala Met Ser Cys Lys Asp Gly Lys Leu Gly Cys Leu Asp Asn Gly
1               5                   10                  15

Lys Tyr Val Arg Tyr Thr Pro Glu Gln Val Glu Ala Leu Glu Arg Leu
            20                  25                  30

Tyr His Asp Cys Pro Lys Pro Ser Ser Ile Arg Arg Gln Leu Ile
        35                  40                  45

Arg Glu Cys Pro Ile Leu Ser Asn Ile Glu Pro Lys Gln Ile Lys Val
    50                  55                  60

Trp Phe Gln Asn Arg Arg Cys Arg Glu Lys Gln Arg Lys Glu Ala Ser
65                  70                  75                  80

Arg Leu Gln Ala Val Asn Arg Lys Leu Thr Ala Met Asn Lys Leu Leu
                85                  90                  95

Met Glu Glu Asn Asp Arg Leu Gln Lys Gln Val Ser Gln Leu Val His
            100                 105                 110

Glu Asn Ser Tyr Phe Arg Gln His Thr Pro Asn Pro Ser Leu Pro Ala
        115                 120                 125

Lys Asp Thr Ser Cys Glu Ser Val Val Thr Ser Gly Gln His Gln Leu
    130                 135                 140

Ala Ser Gln Asn Pro Gln Arg Asp Ala Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Glu Trp Val Gln Met Pro Gly Met Lys Pro Gly Pro Asp Ser
            180                 185                 190
```

```
Ile Gly Ile Ile Ala Ile Ser His Gly Cys Thr Gly Val Ala Arg
    195                 200                 205

Ala Cys Gly Leu Val Gly Leu Glu Pro Thr Arg Val Ala Glu Ile Val
    210                 215                 220

Lys Asp Arg Pro Ser Trp Phe Arg Glu Cys Arg Ala Val Glu Val Met
225                 230                 235                 240

Asn Val Leu Pro Thr Ala Asn Gly Gly Thr Val Glu Leu Leu Tyr Met
                245                 250                 255

Gln Leu Tyr Ala Pro Thr Thr Leu Ala Pro Pro Arg Asp Phe Trp Leu
                260                 265                 270

Leu Arg Tyr Thr Ser Val Leu Glu Asp Gly Ser Leu Val Val Cys Glu
            275                 280                 285

Arg Ser Leu Lys Ser Thr Gln Asn Gly Pro Ser Met Pro Leu Val Gln
    290                 295                 300

Asn Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Met Asp Leu
                325                 330                 335

Glu Ala Cys Ser Val Pro Glu Val Leu Arg Pro Leu Tyr Glu Ser Pro
                340                 345                 350

Lys Val Leu Ala Gln Lys Thr Thr Met Ala Ala Leu Arg Gln Leu Lys
            355                 360                 365

Gln Ile Ala Gln Glu Val Thr Gln Thr Asn Ser Ser Val Asn Gly Trp
    370                 375                 380

Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
                405                 410                 415

Ile Gly Asp Ser Met Asp Asp Val Thr Ile Thr Val Asn Ser Ser Pro
                420                 425                 430

Asp Lys Leu Met Gly Leu Asn Leu Thr Phe Ala Asn Gly Phe Ala Pro
            435                 440                 445

Val Ser Asn Val Val Leu Cys Ala Lys Ala Ser Met Leu Leu Gln Asn
    450                 455                 460

Val Pro Pro Ala Ile Leu Leu Arg Phe Leu Arg Glu His Arg Ser Glu
465                 470                 475                 480

Trp Ala Asp Asn Asn Ile Asp Ala Tyr Leu Ala Ala Ala Val Lys Val
                485                 490                 495

Gly Pro Cys Ser Ala Arg Val Gly Gly Phe Gly Gly Gln Val Ile Leu
                500                 505                 510

Pro Leu Ala His Thr Ile Glu His Glu Glu Phe Met Glu Val Ile Lys
            515                 520                 525

Leu Glu Gly Leu Gly His Ser Pro Glu Asp Ala Ile Val Pro Arg Asp
    530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                565                 570                 575

Asp Ala Pro Leu Leu Pro Ser Gly Phe Arg Ile Ile Pro Leu Asp Ser
            580                 585                 590

Ala Lys Gln Glu Val Ser Ser Pro Asn Arg Thr Leu Asp Leu Ala Ser
            595                 600                 605
```

```
Ala Leu Glu Ile Gly Ser Ala Gly Thr Lys Ala Ser Thr Asp Gln Ser
610             615                 620

Gly Asn Ser Thr Cys Ala Arg Ser Val Met Thr Ile Ala Phe Glu Phe
625                 630                 635                 640

Gly Ile Glu Ser His Met Gln Glu His Val Ala Ser Met Ala Arg Gln
            645                 650                 655

Tyr Val Arg Gly Ile Ile Ser Ser Val Gln Arg Val Ala Leu Ala Leu
            660                 665                 670

Ser Pro Ser His Ile Ser Ser Gln Val Gly Leu Arg Thr Pro Leu Gly
            675                 680                 685

Thr Pro Glu Ala Gln Thr Leu Ala Arg Trp Ile Cys Gln Ser Tyr Arg
690                 695                 700

Gly Tyr Met Gly Val Glu Leu Leu Lys Ser Asn Ser Asp Gly Asn Glu
705                 710                 715                 720

Ser Ile Leu Lys Asn Leu Trp His His Thr Asp Ala Ile Ile Cys Cys
                725                 730                 735

Ser Met Lys Ala Leu Pro Val Phe Thr Phe Ala Asn Gln Ala Gly Leu
                740                 745                 750

Asp Met Leu Glu Thr Thr Leu Val Ala Leu Gln Asp Ile Ser Leu Glu
            755                 760                 765

Lys Ile Phe Asp Asp Asn Gly Arg Lys Thr Leu Cys Ser Glu Phe Pro
770                 775                 780

Gln Ile Met Gln Gln Gly Phe Ala Cys Leu Gln Gly Gly Ile Cys Leu
785                 790                 795                 800

Ser Ser Met Gly Arg Pro Val Ser Tyr Glu Arg Ala Val Ala Trp Lys
                805                 810                 815

Val Leu Asn Glu Glu Glu Asn Ala His Cys Ile Cys Phe Val Phe Ile
            820                 825                 830

Asn Trp Ser Phe Val
            835

<210> SEQ ID NO 23
<211> LENGTH: 999
<212> TYPE: DNA
<213> ORGANISM: Arabidopsis thaliana
<220> FEATURE:
<221> NAME/KEY: CDS
<222> LOCATION: (1)..(999)

<400> SEQUENCE: 23 atg gct gaa cga aag aaa cgc tct tct att caa acc aat aaa ccc aac      48
Met Ala Glu Arg Lys Lys Arg Ser Ser Ile Gln Thr Asn Lys Pro Asn
1               5                   10                  15 aaa aaa ccc atg aag aag aaa cct ttt cag cta aat cac ctc cca ggt      96
Lys Lys Pro Met Lys Lys Lys Pro Phe Gln Leu Asn His Leu Pro Gly
            20                  25                  30 tta tct gaa gat ttg aag act atg aga aaa ctc cgt ttc gtt gtg aat     144
Leu Ser Glu Asp Leu Lys Thr Met Arg Lys Leu Arg Phe Val Val Asn
        35                  40                  45 gat cct tac gct act gac tac tca tca agc gaa gaa gaa gaa agg agt     192
Asp Pro Tyr Ala Thr Asp Tyr Ser Ser Ser Glu Glu Glu Glu Arg Ser
    50                  55                  60 cag aga agg aaa cgt tat gtc tgt gag atc gat ctt cct ttc gct caa     240
Gln Arg Arg Lys Arg Tyr Val Cys Glu Ile Asp Leu Pro Phe Ala Gln
65                  70                  75                  80 gct gct act caa gca gaa tct gaa agc tca tat tgt cag gag agt aac     288
Ala Ala Thr Gln Ala Glu Ser Glu Ser Ser Tyr Cys Gln Glu Ser Asn
                85                  90                  95
```

```
aat aat ggt gta agc aag act aaa atc tca gct tgt agc aaa aag gtt       336
Asn Asn Gly Val Ser Lys Thr Lys Ile Ser Ala Cys Ser Lys Lys Val
        100                 105                 110 tta cgc agc aaa gca tct ccg gtc gtt gga cgt tct tct act act gtc       384
Leu Arg Ser Lys Ala Ser Pro Val Val Gly Arg Ser Ser Thr Thr Val
    115                 120                 125 tcg aag cct gtt ggt gtt agg cag agg aaa tgg ggt aaa tgg gct gct       432
Ser Lys Pro Val Gly Val Arg Gln Arg Lys Trp Gly Lys Trp Ala Ala
130                 135                 140 gag att aga cat cca atc acc aaa gta aga act tgg ttg ggt act tac       480
Glu Ile Arg His Pro Ile Thr Lys Val Arg Thr Trp Leu Gly Thr Tyr
145                 150                 155                 160 gag acg ctt gaa caa gca gct gat gct tat gct acc aag aag ctt gag       528
Glu Thr Leu Glu Gln Ala Ala Asp Ala Tyr Ala Thr Lys Lys Leu Glu
                165                 170                 175 ttt gat gct ctg gct gca gcc act tct gct gct tcc tct gtt ttg tca       576
Phe Asp Ala Leu Ala Ala Ala Thr Ser Ala Ala Ser Ser Val Leu Ser
            180                 185                 190 aat gag tct ggt tct atg atc tca gcc tca ggg tca agc att gat ctt       624
Asn Glu Ser Gly Ser Met Ile Ser Ala Ser Gly Ser Ser Ile Asp Leu
        195                 200                 205 gac aag aag cta gtt gat tcg act ctt gat caa caa gct ggt gaa tcg       672
Asp Lys Lys Leu Val Asp Ser Thr Leu Asp Gln Gln Ala Gly Glu Ser
    210                 215                 220 aag aaa gcg agt ttt gat ttc gac ttt gca gat cta cag att cct gaa       720
Lys Lys Ala Ser Phe Asp Phe Asp Phe Ala Asp Leu Gln Ile Pro Glu
225                 230                 235                 240 atg ggt tgc ttc att gat gac tca ttc atc cca aat gct tgt gag ctt       768
Met Gly Cys Phe Ile Asp Asp Ser Phe Ile Pro Asn Ala Cys Glu Leu
                245                 250                 255 gat ttt ctc tta aca gaa gag aac aac aac caa atg ttg gat gat tac       816
Asp Phe Leu Leu Thr Glu Glu Asn Asn Asn Gln Met Leu Asp Asp Tyr
            260                 265                 270 tgt ggc ata gat gat ctg gac atc att ggt ctt gaa tgt gac ggt cca       864
Cys Gly Ile Asp Asp Leu Asp Ile Ile Gly Leu Glu Cys Asp Gly Pro
        275                 280                 285 agc gaa ctt cca gac tat gat ttc tca gat gtg gag atc gat ctt ggt       912
Ser Glu Leu Pro Asp Tyr Asp Phe Ser Asp Val Glu Ile Asp Leu Gly
    290                 295                 300 ctc att gga acc acc att gac aag tat gct ttc gtt gat cat atc gca       960
Leu Ile Gly Thr Thr Ile Asp Lys Tyr Ala Phe Val Asp His Ile Ala
305                 310                 315                 320 aca act act ccc act cct ctt aat atc gcg tgc cca taa                   999
Thr Thr Thr Pro Thr Pro Leu Asn Ile Ala Cys Pro
                325                 330

<210> SEQ ID NO 24
<211> LENGTH: 332
<212> TYPE: PRT
<213> ORGANISM: Arabidopsis thaliana

<400> SEQUENCE: 24

Met Ala Glu Arg Lys Lys Arg Ser Ser Ile Gln Thr Asn Lys Pro Asn
1               5                   10                  15

Lys Lys Pro Met Lys Lys Pro Phe Gln Leu Asn His Leu Pro Gly
            20                  25                  30

Leu Ser Glu Asp Leu Lys Thr Met Arg Lys Leu Arg Phe Val Val Asn
        35                  40                  45

Asp Pro Tyr Ala Thr Asp Tyr Ser Ser Ser Glu Glu Glu Glu Arg Ser
```

```
            50                  55                  60
Gln Arg Arg Lys Arg Tyr Val Cys Glu Ile Asp Leu Pro Phe Ala Gln
 65                  70                  75                  80

Ala Ala Thr Gln Ala Glu Ser Glu Ser Ser Tyr Cys Gln Glu Ser Asn
                 85                  90                  95

Asn Asn Gly Val Ser Lys Thr Lys Ile Ser Ala Cys Ser Lys Lys Val
            100                 105                 110

Leu Arg Ser Lys Ala Ser Pro Val Val Gly Arg Ser Ser Thr Thr Val
            115                 120                 125

Ser Lys Pro Val Gly Val Arg Gln Arg Lys Trp Gly Lys Trp Ala Ala
            130                 135                 140

Glu Ile Arg His Pro Ile Thr Lys Val Arg Thr Trp Leu Gly Thr Tyr
145                 150                 155                 160

Glu Thr Leu Glu Gln Ala Ala Asp Ala Tyr Ala Thr Lys Lys Leu Glu
                165                 170                 175

Phe Asp Ala Leu Ala Ala Thr Ser Ala Ala Ser Ser Val Leu Ser
                180                 185                 190

Asn Glu Ser Gly Ser Met Ile Ser Ala Ser Gly Ser Ser Ile Asp Leu
            195                 200                 205

Asp Lys Lys Leu Val Asp Ser Thr Leu Asp Gln Gln Ala Gly Glu Ser
            210                 215                 220

Lys Lys Ala Ser Phe Asp Phe Asp Phe Ala Asp Leu Gln Ile Pro Glu
225                 230                 235                 240

Met Gly Cys Phe Ile Asp Asp Ser Phe Ile Pro Asn Ala Cys Glu Leu
                245                 250                 255

Asp Phe Leu Leu Thr Glu Glu Asn Asn Asn Gln Met Leu Asp Asp Tyr
            260                 265                 270

Cys Gly Ile Asp Asp Leu Asp Ile Ile Gly Leu Glu Cys Asp Gly Pro
            275                 280                 285

Ser Glu Leu Pro Asp Tyr Asp Phe Ser Asp Val Glu Ile Asp Leu Gly
            290                 295                 300

Leu Ile Gly Thr Thr Ile Asp Lys Tyr Ala Phe Val Asp His Ile Ala
305                 310                 315                 320

Thr Thr Thr Pro Thr Pro Leu Asn Ile Ala Cys Pro
                325                 330

<210> SEQ ID NO 25
<211> LENGTH: 1101
<212> TYPE: DNA
<213> ORGANISM: Arabidopsis thaliana
<220> FEATURE:
<221> NAME/KEY: CDS
<222> LOCATION: (1)..(1101)

<400> SEQUENCE: 25 atg ggg aga cat tct tgc tgt tac aaa caa aag ctg agg aaa ggg ctt      48
Met Gly Arg His Ser Cys Cys Tyr Lys Gln Lys Leu Arg Lys Gly Leu
 1               5                  10                  15 tgg tct cct gaa gaa gac gag aag ctt ctt act cac atc acc aat cac      96
Trp Ser Pro Glu Glu Asp Glu Lys Leu Leu Thr His Ile Thr Asn His
                20                  25                  30 ggc cat ggc tgc tgg agc tct gtc cct aaa ctc gct ggt ttg cag aga     144
Gly His Gly Cys Trp Ser Ser Val Pro Lys Leu Ala Gly Leu Gln Arg
            35                  40                  45 tgt ggg aag agt tgt cga cta aga tgg atc aat tac ttg aga cct gat     192
Cys Gly Lys Ser Cys Arg Leu Arg Trp Ile Asn Tyr Leu Arg Pro Asp
         50                  55                  60
```

```
tta aag aga gga gct ttt tct cct gaa gaa gag aat ctc atc gtc gaa      240
Leu Lys Arg Gly Ala Phe Ser Pro Glu Glu Glu Asn Leu Ile Val Glu
 65              70                  75                  80 ctt cat gcc gtc ctt gga aac aga tgg tca cag att gcg tca agg ctt      288
Leu His Ala Val Leu Gly Asn Arg Trp Ser Gln Ile Ala Ser Arg Leu
                 85                  90                  95 ccg ggt aga acc gac aac gag atc aag aat cta tgg aac tca agc atc      336
Pro Gly Arg Thr Asp Asn Glu Ile Lys Asn Leu Trp Asn Ser Ser Ile
            100                 105                 110 aag aag aaa ctg aaa caa aga ggc att gac cca aac aca cac aag ccc      384
Lys Lys Lys Leu Lys Gln Arg Gly Ile Asp Pro Asn Thr His Lys Pro
            115                 120                 125 atc tct gaa gtt gag agt ttt agc gac aaa gac aaa cca aca aca agc      432
Ile Ser Glu Val Glu Ser Phe Ser Asp Lys Asp Lys Pro Thr Thr Ser
130                 135                 140 aac aac aaa aga agc ggt aac gat cac aag tct cct agt tcc tct tct      480
Asn Asn Lys Arg Ser Gly Asn Asp His Lys Ser Pro Ser Ser Ser Ser
145                 150                 155                 160 gcg act aac caa gac ttc ttc ctc gaa agg cca tct gat tta tcc gac      528
Ala Thr Asn Gln Asp Phe Phe Leu Glu Arg Pro Ser Asp Leu Ser Asp
                165                 170                 175 tac ttc gga ttt cag aag ctt aac ttc aac tcc aat cta gga ctc tct      576
Tyr Phe Gly Phe Gln Lys Leu Asn Phe Asn Ser Asn Leu Gly Leu Ser
            180                 185                 190 gtt aca act gat tct tca ctc tgc tcg atg att ccg ccg cag ttt agc      624
Val Thr Thr Asp Ser Ser Leu Cys Ser Met Ile Pro Pro Gln Phe Ser
            195                 200                 205 ccc ggg aac atg gtt ggt tct gtc ctt cag aca cca gta tgc gta aag      672
Pro Gly Asn Met Val Gly Ser Val Leu Gln Thr Pro Val Cys Val Lys
210                 215                 220 ccc tcg att agt ctt cct ccc gac aac aac agt tcg agt cct atc tcc      720
Pro Ser Ile Ser Leu Pro Pro Asp Asn Asn Ser Ser Ser Pro Ile Ser
225                 230                 235                 240 gga gga gat cat gtg aaa ttg gct gca cca aac tgg gaa ttt cag aca      768
Gly Gly Asp His Val Lys Leu Ala Ala Pro Asn Trp Glu Phe Gln Thr
                245                 250                 255 aac aac aat aat acc tca aat ttc ttc gac aat ggc gga ttc tca tgg      816
Asn Asn Asn Asn Thr Ser Asn Phe Phe Asp Asn Gly Gly Phe Ser Trp
            260                 265                 270 tct atc cca aat tct tct act tct tct tca caa gtc aaa cca aat cat      864
Ser Ile Pro Asn Ser Ser Thr Ser Ser Ser Gln Val Lys Pro Asn His
            275                 280                 285 aac ttc gaa gaa ata aaa tgg tca gag tat ttg aac aca ccg ttc ttc      912
Asn Phe Glu Glu Ile Lys Trp Ser Glu Tyr Leu Asn Thr Pro Phe Phe
290                 295                 300 ata ggg agt act gta cag agt caa acc tct caa cca atc tac atc aaa      960
Ile Gly Ser Thr Val Gln Ser Gln Thr Ser Gln Pro Ile Tyr Ile Lys
305                 310                 315                 320 tca gaa aca gat tac tta gcc aat gtt tca aac atg aca gat cct tgg     1008
Ser Glu Thr Asp Tyr Leu Ala Asn Val Ser Asn Met Thr Asp Pro Trp
                325                 330                 335 agc caa aac gag aac ttg ggc aca act gaa act agt gac gtg ttc tcc     1056
Ser Gln Asn Glu Asn Leu Gly Thr Thr Glu Thr Ser Asp Val Phe Ser
            340                 345                 350 aag gat ctt cag aga atg gcc gtc tct ttt ggt cag tcc ctt tag         1101
Lys Asp Leu Gln Arg Met Ala Val Ser Phe Gly Gln Ser Leu
            355                 360                 365
```

<210> SEQ ID NO 26

<211> LENGTH: 366
<212> TYPE: PRT
<213> ORGANISM: Arabidopsis thaliana

<400> SEQUENCE: 26

Met Gly Arg His Ser Cys Cys Tyr Lys Gln Lys Leu Arg Lys Gly Leu
1               5                   10                  15

Trp Ser Pro Glu Glu Asp Lys Leu Leu Thr His Ile Thr Asn His
            20                  25                  30

Gly His Gly Cys Trp Ser Ser Val Pro Lys Leu Ala Gly Leu Gln Arg
        35                  40                  45

Cys Gly Lys Ser Cys Arg Leu Arg Trp Ile Asn Tyr Leu Arg Pro Asp
    50                  55                  60

Leu Lys Arg Gly Ala Phe Ser Pro Glu Glu Asn Leu Ile Val Glu
65              70                  75                  80

Leu His Ala Val Leu Gly Asn Arg Trp Ser Gln Ile Ala Ser Arg Leu
                85                  90                  95

Pro Gly Arg Thr Asp Asn Glu Ile Lys Asn Leu Trp Asn Ser Ser Ile
            100                 105                 110

Lys Lys Lys Leu Lys Gln Arg Gly Ile Asp Pro Asn Thr His Lys Pro
        115                 120                 125

Ile Ser Glu Val Glu Ser Phe Ser Asp Lys Asp Lys Pro Thr Thr Ser
    130                 135                 140

Asn Asn Lys Arg Ser Gly Asn Asp His Lys Ser Pro Ser Ser Ser Ser
145                 150                 155                 160

Ala Thr Asn Gln Asp Phe Phe Leu Glu Arg Pro Ser Asp Leu Ser Asp
                165                 170                 175

Tyr Phe Gly Phe Gln Lys Leu Asn Phe Asn Ser Asn Leu Gly Leu Ser
            180                 185                 190

Val Thr Thr Asp Ser Ser Leu Cys Ser Met Ile Pro Pro Gln Phe Ser
        195                 200                 205

Pro Gly Asn Met Val Gly Ser Val Leu Gln Thr Pro Val Cys Val Lys
    210                 215                 220

Pro Ser Ile Ser Leu Pro Pro Asp Asn Asn Ser Ser Ser Pro Ile Ser
225                 230                 235                 240

Gly Gly Asp His Val Lys Leu Ala Ala Pro Asn Trp Glu Phe Gln Thr
                245                 250                 255

Asn Asn Asn Asn Thr Ser Asn Phe Phe Asp Asn Gly Gly Phe Ser Trp
            260                 265                 270

Ser Ile Pro Asn Ser Ser Thr Ser Ser Ser Gln Val Lys Pro Asn His
        275                 280                 285

Asn Phe Glu Glu Ile Lys Trp Ser Glu Tyr Leu Asn Thr Pro Phe Phe
    290                 295                 300

Ile Gly Ser Thr Val Gln Ser Gln Thr Ser Gln Pro Ile Tyr Ile Lys
305                 310                 315                 320

Ser Glu Thr Asp Tyr Leu Ala Asn Val Ser Asn Met Thr Asp Pro Trp
                325                 330                 335

Ser Gln Asn Glu Asn Leu Gly Thr Thr Glu Thr Ser Asp Val Phe Ser
            340                 345                 350

Lys Asp Leu Gln Arg Met Ala Val Ser Phe Gly Gln Ser Leu
        355                 360                 365

<210> SEQ ID NO 27
<211> LENGTH: 708
<212> TYPE: DNA

<213> ORGANISM: Arabidopsis thaliana
<220> FEATURE:
<221> NAME/KEY: CDS
<222> LOCATION: (1)..(708)

<400> SEQUENCE: 27

```
atg gcc gat gag gtc aca atc ggg ttt cgc ttc tat ccc acg gaa gaa     48
Met Ala Asp Glu Val Thr Ile Gly Phe Arg Phe Tyr Pro Thr Glu Glu
1               5                   10                  15 gaa ctg gtt tcg ttc tac cta cga aac cag ctc gaa gga agg agt gat     96
Glu Leu Val Ser Phe Tyr Leu Arg Asn Gln Leu Glu Gly Arg Ser Asp
            20                  25                  30 gac tca atg cat cgt gtc att ccc gta ctt gac gtc ttt gag gtc gag    144
Asp Ser Met His Arg Val Ile Pro Val Leu Asp Val Phe Glu Val Glu
        35                  40                  45 cct agt cat ctt cca aat gtt gct gga gtg aga tgt cga gga gac gct    192
Pro Ser His Leu Pro Asn Val Ala Gly Val Arg Cys Arg Gly Asp Ala
    50                  55                  60 gag caa tgg ttc ttc ttc gtg cca cga caa gaa cgc gaa gca aga gga    240
Glu Gln Trp Phe Phe Phe Val Pro Arg Gln Glu Arg Glu Ala Arg Gly
65                  70                  75                  80 ggc aga ccg agt aga act act ggt tca gga tac tgg aaa gca act gga    288
Gly Arg Pro Ser Arg Thr Thr Gly Ser Gly Tyr Trp Lys Ala Thr Gly
                85                  90                  95 tca cct ggt cca gtc ttt tcc aaa gac aac aaa atg att gga gca aag    336
Ser Pro Gly Pro Val Phe Ser Lys Asp Asn Lys Met Ile Gly Ala Lys
            100                 105                 110 aaa act atg gtt ttc tac act gga aaa gca ccc aca gga aga aaa act    384
Lys Thr Met Val Phe Tyr Thr Gly Lys Ala Pro Thr Gly Arg Lys Thr
        115                 120                 125 aaa tgg aaa atg aat gag tac cac gcc gtt gac gaa aca gtc aac gct    432
Lys Trp Lys Met Asn Glu Tyr His Ala Val Asp Glu Thr Val Asn Ala
    130                 135                 140 tcc aca atc cct aag ctg aga cgt gag ttc agt tta tgt cga gtc tac    480
Ser Thr Ile Pro Lys Leu Arg Arg Glu Phe Ser Leu Cys Arg Val Tyr
145                 150                 155                 160 ata aca aca gga agc tcc aga gct ttt gat aga cgt cct gag gga gtt    528
Ile Thr Thr Gly Ser Ser Arg Ala Phe Asp Arg Arg Pro Glu Gly Val
                165                 170                 175 ttg cag aca gag aga atg cta aca agt gat gtt gca gta gct gag aca    576
Leu Gln Thr Glu Arg Met Leu Thr Ser Asp Val Ala Val Ala Glu Thr
            180                 185                 190 tcg ttc cgt gtg gaa agc tca ctg gaa act tcg att tca gga gga gaa    624
Ser Phe Arg Val Glu Ser Ser Leu Glu Thr Ser Ile Ser Gly Gly Glu
        195                 200                 205 cat att gat gtc tct atg aac aca gag ttt gtt gat gga cta tca gaa    672
His Ile Asp Val Ser Met Asn Thr Glu Phe Val Asp Gly Leu Ser Glu
    210                 215                 220 ccg atg tgg gac tgg gaa cag ctg act tgg cct tga                    708
Pro Met Trp Asp Trp Glu Gln Leu Thr Trp Pro
225                 230                 235
```

<210> SEQ ID NO 28
<211> LENGTH: 235
<212> TYPE: PRT
<213> ORGANISM: Arabidopsis thaliana

<400> SEQUENCE: 28

```
Met Ala Asp Glu Val Thr Ile Gly Phe Arg Phe Tyr Pro Thr Glu Glu
1               5                   10                  15

Glu Leu Val Ser Phe Tyr Leu Arg Asn Gln Leu Glu Gly Arg Ser Asp
```

```
                    20                  25                  30
Asp Ser Met His Arg Val Ile Pro Val Leu Asp Val Phe Glu Val Glu
                35                  40                  45
Pro Ser His Leu Pro Asn Val Ala Gly Val Arg Cys Arg Gly Asp Ala
    50                  55                  60
Glu Gln Trp Phe Phe Phe Val Pro Arg Gln Glu Arg Glu Ala Arg Gly
65                  70                  75                  80
Gly Arg Pro Ser Arg Thr Thr Gly Ser Gly Tyr Trp Lys Ala Thr Gly
                85                  90                  95
Ser Pro Gly Pro Val Phe Ser Lys Asp Asn Lys Met Ile Gly Ala Lys
            100                 105                 110
Lys Thr Met Val Phe Tyr Thr Gly Lys Ala Pro Thr Gly Arg Lys Thr
        115                 120                 125
Lys Trp Lys Met Asn Glu Tyr His Ala Val Asp Glu Thr Val Asn Ala
    130                 135                 140
Ser Thr Ile Pro Lys Leu Arg Arg Glu Phe Ser Leu Cys Arg Val Tyr
145                 150                 155                 160
Ile Thr Thr Gly Ser Ser Arg Ala Phe Asp Arg Arg Pro Glu Gly Val
                165                 170                 175
Leu Gln Thr Glu Arg Met Leu Thr Ser Asp Val Ala Val Ala Glu Thr
            180                 185                 190
Ser Phe Arg Val Glu Ser Ser Leu Glu Thr Ser Ile Ser Gly Gly Glu
        195                 200                 205
His Ile Asp Val Ser Met Asn Thr Glu Phe Val Asp Gly Leu Ser Glu
    210                 215                 220
Pro Met Trp Asp Trp Glu Gln Leu Thr Trp Pro
225                 230                 235

<210> SEQ ID NO 29
<211> LENGTH: 888
<212> TYPE: DNA
<213> ORGANISM: Arabidopsis thaliana
<220> FEATURE:
<221> NAME/KEY: CDS
<222> LOCATION: (1)..(888)

<400> SEQUENCE: 29 atg gca aga caa atc aac ata gag agt agt gtt tct caa gtt acc ttt      48
Met Ala Arg Gln Ile Asn Ile Glu Ser Ser Val Ser Gln Val Thr Phe
1               5                   10                  15 atc tcc tcc gcc atc ccc gcc gta tct tcc tcc tcc atc acc gct          96
Ile Ser Ser Ala Ile Pro Ala Val Ser Ser Ser Ser Ile Thr Ala
            20                  25                  30 tcc gcc tca ttg tcc tct tca cct act aca tct tcc tct tct tcg tca     144
Ser Ala Ser Leu Ser Ser Ser Pro Thr Thr Ser Ser Ser Ser Ser Ser
        35                  40                  45 tca aca aat tct aac ttc att gag gaa gac aac tct aaa aga aaa gca     192
Ser Thr Asn Ser Asn Phe Ile Glu Glu Asp Asn Ser Lys Arg Lys Ala
    50                  55                  60 tct cga aga tca ttg tca tcg tta gtc tcc gtt gaa gac gat gat gat     240
Ser Arg Arg Ser Leu Ser Ser Leu Val Ser Val Glu Asp Asp Asp Asp
65                  70                  75                  80 caa aac ggt gga ggt ggg aaa cgg cga aag acc aac ggt gga gat aaa     288
Gln Asn Gly Gly Gly Gly Lys Arg Arg Lys Thr Asn Gly Gly Asp Lys
                85                  90                  95 cat ccg acg tat aga gga gtg agg atg agg agt tgg gga aaa tgg gtg     336
His Pro Thr Tyr Arg Gly Val Arg Met Arg Ser Trp Gly Lys Trp Val
            100                 105                 110
```

```
tcg gag att aga gag ccg aga aag aaa tca aga atc tgg ctc ggg act      384
Ser Glu Ile Arg Glu Pro Arg Lys Lys Ser Arg Ile Trp Leu Gly Thr
        115                 120                 125 tat cca acg gct gag atg gca gct cga gct cat gac gta gcg gct tta      432
Tyr Pro Thr Ala Glu Met Ala Ala Arg Ala His Asp Val Ala Ala Leu
130                 135                 140 gcc att aaa ggt aca acg gct tac ctc aat ttt ccc aag tta gcc ggc      480
Ala Ile Lys Gly Thr Thr Ala Tyr Leu Asn Phe Pro Lys Leu Ala Gly
145                 150                 155                 160 gag ctt cct cgt cca gtc aca aat tct cct aaa gac att caa gcc gcc      528
Glu Leu Pro Arg Pro Val Thr Asn Ser Pro Lys Asp Ile Gln Ala Ala
                165                 170                 175 gcc tct tta gcg gcc gtt aac tgg caa gat tcg gtc aac gat gtg agt      576
Ala Ser Leu Ala Ala Val Asn Trp Gln Asp Ser Val Asn Asp Val Ser
            180                 185                 190 aat tct gaa gtg gct gaa ata gtt gaa gcc gag ccg agt cga gcc gtg      624
Asn Ser Glu Val Ala Glu Ile Val Glu Ala Glu Pro Ser Arg Ala Val
        195                 200                 205 gtg gct cag ttg ttt tct tcg gac aca agc acg acg acg acg act cag      672
Val Ala Gln Leu Phe Ser Ser Asp Thr Ser Thr Thr Thr Thr Thr Gln
210                 215                 220 agt caa gag tat tcg gaa gct tcg tgt gct tcg act tcg gcg tgt acg      720
Ser Gln Glu Tyr Ser Glu Ala Ser Cys Ala Ser Thr Ser Ala Cys Thr
225                 230                 235                 240 gac aaa gac agt gag gaa gag aag ctg ttt gat ttg ccg gat ttg ttt      768
Asp Lys Asp Ser Glu Glu Glu Lys Leu Phe Asp Leu Pro Asp Leu Phe
                245                 250                 255 acc gat gag aat gag atg atg ata cga aac gat gcg ttt tgc tac tac      816
Thr Asp Glu Asn Glu Met Met Ile Arg Asn Asp Ala Phe Cys Tyr Tyr
            260                 265                 270 tcg tcc acg tgg cag ctt tgt gga gcc gat gct ggg ttt cgg ctt gaa      864
Ser Ser Thr Trp Gln Leu Cys Gly Ala Asp Ala Gly Phe Arg Leu Glu
        275                 280                 285 gag ccg ttt ttt cta tct gaa tga                                      888
Glu Pro Phe Phe Leu Ser Glu
            290                 295

<210> SEQ ID NO 30
<211> LENGTH: 295
<212> TYPE: PRT
<213> ORGANISM: Arabidopsis thaliana

<400> SEQUENCE: 30

Met Ala Arg Gln Ile Asn Ile Glu Ser Ser Val Ser Gln Val Thr Phe
1               5                   10                  15

Ile Ser Ser Ala Ile Pro Ala Val Ser Ser Ser Ser Ile Thr Ala
            20                  25                  30

Ser Ala Ser Leu Ser Ser Ser Pro Thr Thr Ser Ser Ser Ser Ser
        35                  40                  45

Ser Thr Asn Ser Asn Phe Ile Glu Glu Asp Asn Ser Lys Arg Lys Ala
    50                  55                  60

Ser Arg Arg Ser Leu Ser Ser Leu Val Ser Val Glu Asp Asp Asp
65                  70                  75                  80

Gln Asn Gly Gly Gly Lys Arg Arg Lys Thr Asn Gly Gly Asp Lys
                85                  90                  95

His Pro Thr Tyr Arg Gly Val Arg Met Arg Ser Trp Gly Lys Trp Val
            100                 105                 110

Ser Glu Ile Arg Glu Pro Arg Lys Lys Ser Arg Ile Trp Leu Gly Thr
```

```
            115                 120                 125
Tyr Pro Thr Ala Glu Met Ala Ala Arg Ala His Asp Val Ala Ala Leu
    130                 135                 140

Ala Ile Lys Gly Thr Thr Ala Tyr Leu Asn Phe Pro Lys Leu Ala Gly
145                 150                 155                 160

Glu Leu Pro Arg Pro Val Thr Asn Ser Pro Lys Asp Ile Gln Ala Ala
                165                 170                 175

Ala Ser Leu Ala Ala Val Asn Trp Gln Asp Ser Val Asn Asp Val Ser
            180                 185                 190

Asn Ser Glu Val Ala Glu Ile Val Glu Ala Glu Pro Ser Arg Ala Val
        195                 200                 205

Val Ala Gln Leu Phe Ser Ser Asp Thr Ser Thr Thr Thr Thr Thr Gln
    210                 215                 220

Ser Gln Glu Tyr Ser Glu Ala Ser Cys Ala Ser Thr Ser Ala Cys Thr
225                 230                 235                 240

Asp Lys Asp Ser Glu Glu Glu Lys Leu Phe Asp Leu Pro Asp Leu Phe
                245                 250                 255

Thr Asp Glu Asn Glu Met Met Ile Arg Asn Asp Ala Phe Cys Tyr Tyr
            260                 265                 270

Ser Ser Thr Trp Gln Leu Cys Gly Ala Asp Ala Gly Phe Arg Leu Glu
        275                 280                 285

Glu Pro Phe Phe Leu Ser Glu
    290                 295

<210> SEQ ID NO 31
<211> LENGTH: 732
<212> TYPE: DNA
<213> ORGANISM: Arabidopsis thaliana
<220> FEATURE:
<221> NAME/KEY: CDS
<222> LOCATION: (1)..(732)

<400> SEQUENCE: 31 atg gtc atg gag ccc aag aag aac caa aat cta cca agt ttc tta aac      48
Met Val Met Glu Pro Lys Lys Asn Gln Asn Leu Pro Ser Phe Leu Asn
1               5                   10                  15 cca tca cga cag aat cag gac aac gac aag aag agg aaa caa aca gag      96
Pro Ser Arg Gln Asn Gln Asp Asn Asp Lys Lys Arg Lys Gln Thr Glu
            20                  25                  30 gtt aaa ggt ttc gac att gtg gtc ggc gaa aag agg aag aag aag gag     144
Val Lys Gly Phe Asp Ile Val Val Gly Glu Lys Arg Lys Lys Lys Glu
        35                  40                  45 aat gaa gag gaa gac caa gaa att cag att ctt tat gag aag gag aag     192
Asn Glu Glu Glu Asp Gln Glu Ile Gln Ile Leu Tyr Glu Lys Glu Lys
    50                  55                  60 aag aaa cca aac aaa gat cgt cac ctt aaa gtt gaa gga aga ggt cgt     240
Lys Lys Pro Asn Lys Asp Arg His Leu Lys Val Glu Gly Arg Gly Arg
65                  70                  75                  80 aga gtt agg tta cct cca ctc tgt gca gca agg att tat caa ttg act     288
Arg Val Arg Leu Pro Pro Leu Cys Ala Ala Arg Ile Tyr Gln Leu Thr
                85                  90                  95 aaa gaa tta ggt cac aaa tca gat ggt gag act ctt gaa tgg ttg ctt     336
Lys Glu Leu Gly His Lys Ser Asp Gly Glu Thr Leu Glu Trp Leu Leu
            100                 105                 110 caa cat gct gag cca tcg ata ctc tct gct act gta aat ggt atc aaa     384
Gln His Ala Glu Pro Ser Ile Leu Ser Ala Thr Val Asn Gly Ile Lys
        115                 120                 125 ccc act gag tct gtt gtt tct caa cct cct ctc acg gct gat ttg atg     432
```

```
                Pro Thr Glu Ser Val Val Ser Gln Pro Pro Leu Thr Ala Asp Leu Met
                    130                 135                 140 att tgt cat agc gtt gaa gaa gct tca agg act caa atg gag gca aat       480
Ile Cys His Ser Val Glu Glu Ala Ser Arg Thr Gln Met Glu Ala Asn
145                 150                 155                 160 ggg ttg tgg aga aat gaa aca gga cag acc att gga ggg ttt gat ctg       528
Gly Leu Trp Arg Asn Glu Thr Gly Gln Thr Ile Gly Gly Phe Asp Leu
                165                 170                 175 aat tac gga att ggg ttt gat ttc aat ggt gtt cca gag att ggt ttt       576
Asn Tyr Gly Ile Gly Phe Asp Phe Asn Gly Val Pro Glu Ile Gly Phe
            180                 185                 190 gga gat aat caa acg cct gga ctt gaa tta agg ctg tct caa gtt ggg       624
Gly Asp Asn Gln Thr Pro Gly Leu Glu Leu Arg Leu Ser Gln Val Gly
        195                 200                 205 gtt ttg aat cca cag gtt ttt caa caa atg ggt aaa gaa cag ttc agg       672
Val Leu Asn Pro Gln Val Phe Gln Gln Met Gly Lys Glu Gln Phe Arg
    210                 215                 220 gtt ctt cat cat cat tca cat gaa gat cag cag cag agt gca gag gaa       720
Val Leu His His His Ser His Glu Asp Gln Gln Gln Ser Ala Glu Glu
225                 230                 235                 240 aat ggt tca taa                                                       732
Asn Gly Ser <210> SEQ ID NO 32
<211> LENGTH: 243
<212> TYPE: PRT
<213> ORGANISM: Arabidopsis thaliana

<400> SEQUENCE: 32

Met Val Met Glu Pro Lys Lys Asn Gln Asn Leu Pro Ser Phe Leu Asn
1               5                   10                  15

Pro Ser Arg Gln Asn Gln Asp Asn Asp Lys Lys Arg Lys Gln Thr Glu
                20                  25                  30

Val Lys Gly Phe Asp Ile Val Val Gly Glu Lys Arg Lys Lys Lys Glu
            35                  40                  45

Asn Glu Glu Glu Asp Gln Glu Ile Gln Ile Leu Tyr Glu Lys Glu Lys
        50                  55                  60

Lys Lys Pro Asn Lys Asp Arg His Leu Lys Val Glu Gly Arg Gly Arg
65                  70                  75                  80

Arg Val Arg Leu Pro Pro Leu Cys Ala Ala Arg Ile Tyr Gln Leu Thr
                85                  90                  95

Lys Glu Leu Gly His Lys Ser Asp Gly Glu Thr Leu Glu Trp Leu Leu
                100                 105                 110

Gln His Ala Glu Pro Ser Ile Leu Ser Ala Thr Val Asn Gly Ile Lys
            115                 120                 125

Pro Thr Glu Ser Val Val Ser Gln Pro Pro Leu Thr Ala Asp Leu Met
        130                 135                 140

Ile Cys His Ser Val Glu Glu Ala Ser Arg Thr Gln Met Glu Ala Asn
145                 150                 155                 160

Gly Leu Trp Arg Asn Glu Thr Gly Gln Thr Ile Gly Gly Phe Asp Leu
                165                 170                 175

Asn Tyr Gly Ile Gly Phe Asp Phe Asn Gly Val Pro Glu Ile Gly Phe
            180                 185                 190

Gly Asp Asn Gln Thr Pro Gly Leu Glu Leu Arg Leu Ser Gln Val Gly
        195                 200                 205

Val Leu Asn Pro Gln Val Phe Gln Gln Met Gly Lys Glu Gln Phe Arg
    210                 215                 220
```

```
Val Leu His His His Ser His Glu Asp Gln Gln Gln Ser Ala Glu Glu
225                 230                 235                 240

Asn Gly Ser

<210> SEQ ID NO 33
<211> LENGTH: 1083
<212> TYPE: DNA
<213> ORGANISM: Arabidopsis thaliana
<220> FEATURE:
<221> NAME/KEY: CDS
<222> LOCATION: (1)..(1083)

<400> SEQUENCE: 33 atg aga tca gga gaa tgt gat gaa gag gag att caa gca aag caa gaa        48
Met Arg Ser Gly Glu Cys Asp Glu Glu Glu Ile Gln Ala Lys Gln Glu
1               5                   10                  15 aga gat caa aat caa aat cat caa gta aac tta aac cac atg ttg caa        96
Arg Asp Gln Asn Gln Asn His Gln Val Asn Leu Asn His Met Leu Gln
                20                  25                  30 caa caa cag ccg agt tcg gta tca tct tca agg caa tgg act tca gct       144
Gln Gln Gln Pro Ser Ser Val Ser Ser Ser Arg Gln Trp Thr Ser Ala
            35                  40                  45 ttt agg aat cca aga atc gtt cga gtc tca aga aca ttc ggt ggc aaa       192
Phe Arg Asn Pro Arg Ile Val Arg Val Ser Arg Thr Phe Gly Gly Lys
        50                  55                  60 gac aga cac agc aaa gta tgt aca gtc cgt ggt ctt cga gac cgg agg       240
Asp Arg His Ser Lys Val Cys Thr Val Arg Gly Leu Arg Asp Arg Arg
65                  70                  75                  80 ata agg ttg tcc gta cct aca gct att caa ctc tac gac ctt caa gat       288
Ile Arg Leu Ser Val Pro Thr Ala Ile Gln Leu Tyr Asp Leu Gln Asp
                85                  90                  95 cga tta ggg ctg agt cag cca agc aaa gtc att gat tgg tta ctc gaa       336
Arg Leu Gly Leu Ser Gln Pro Ser Lys Val Ile Asp Trp Leu Leu Glu
            100                 105                 110 gca gca aaa gat gac gta gac aag cta cct cct cta caa ttc cca cat       384
Ala Ala Lys Asp Asp Val Asp Lys Leu Pro Pro Leu Gln Phe Pro His
        115                 120                 125 gga ttt aac cag atg tat cca aat ctc atc ttc gga aac tcc ggg ttt       432
Gly Phe Asn Gln Met Tyr Pro Asn Leu Ile Phe Gly Asn Ser Gly Phe
    130                 135                 140 gga gaa tct cca tct tca act aca tca aca acg ttt cca gga acc aat       480
Gly Glu Ser Pro Ser Ser Thr Thr Ser Thr Thr Phe Pro Gly Thr Asn
145                 150                 155                 160 ctc ggg ttc ttg gaa aat tgg gat ctt ggt ggt tct tca aga aca aga       528
Leu Gly Phe Leu Glu Asn Trp Asp Leu Gly Gly Ser Ser Arg Thr Arg
                165                 170                 175 gca aga tta acc gat aca act acg acc caa aga gaa agt ttt gat ctt       576
Ala Arg Leu Thr Asp Thr Thr Thr Thr Gln Arg Glu Ser Phe Asp Leu
            180                 185                 190 gat aaa gga aaa tgg atc aaa aac gac gag aat agt aat caa gat cat       624
Asp Lys Gly Lys Trp Ile Lys Asn Asp Glu Asn Ser Asn Gln Asp His
        195                 200                 205 caa ggg ttt aac acc aat cat caa caa caa ttt cct ctg acc aat ccg       672
Gln Gly Phe Asn Thr Asn His Gln Gln Gln Phe Pro Leu Thr Asn Pro
    210                 215                 220 tac aac aac act tca gct tat tac aac ctt gga cat ctt caa caa tcg       720
Tyr Asn Asn Thr Ser Ala Tyr Tyr Asn Leu Gly His Leu Gln Gln Ser
225                 230                 235                 240 tta gac caa tct ggt aat aac gtt act gtc gca ata tct aat gtt gct       768
Leu Asp Gln Ser Gly Asn Asn Val Thr Val Ala Ile Ser Asn Val Ala
```

```
gct aat aat aac aat aat ctc aat ttg cat cct cct tcc tcg tct gcc      816
Ala Asn Asn Asn Asn Asn Leu Asn Leu His Pro Pro Ser Ser Ser Ala
            260                 265                 270 gga gat gga tct cag ctt ttt ttc ggt cct act cct ccg gca atg agc      864
Gly Asp Gly Ser Gln Leu Phe Phe Gly Pro Thr Pro Pro Ala Met Ser
        275                 280                 285 tct cta ttc ccg aca tac cct tcg ttt ctt gga gct tct cat cat cat      912
Ser Leu Phe Pro Thr Tyr Pro Ser Phe Leu Gly Ala Ser His His His
    290                 295                 300 cat gtc gtc gat gga gcc ggt cat ctt cag ctc ttt agc tcg aat tca      960
His Val Val Asp Gly Ala Gly His Leu Gln Leu Phe Ser Ser Asn Ser
305                 310                 315                 320 aat acc gca tcg cag caa cac atg atg ccg ggt aat acg agt ttg att     1008
Asn Thr Ala Ser Gln Gln His Met Met Pro Gly Asn Thr Ser Leu Ile
                325                 330                 335 aga cca ttt cat cat ttg atg agc tcg aat cat gat acg gat cat cat     1056
Arg Pro Phe His His Leu Met Ser Ser Asn His Asp Thr Asp His His
            340                 345                 350 agt agc gat aat gaa tca gat tct tga                                 1083
Ser Ser Asp Asn Glu Ser Asp Ser
        355                 360

<210> SEQ ID NO 34
<211> LENGTH: 360
<212> TYPE: PRT
<213> ORGANISM: Arabidopsis thaliana

<400> SEQUENCE: 34

Met Arg Ser Gly Glu Cys Asp Glu Glu Ile Gln Ala Lys Gln Glu
1               5                   10                  15

Arg Asp Gln Asn Gln Asn His Gln Val Asn Leu Asn His Met Leu Gln
                20                  25                  30

Gln Gln Gln Pro Ser Ser Val Ser Ser Arg Gln Trp Thr Ser Ala
            35                  40                  45

Phe Arg Asn Pro Arg Ile Val Arg Val Ser Arg Thr Phe Gly Gly Lys
 50                  55                  60

Asp Arg His Ser Lys Val Cys Thr Val Arg Gly Leu Arg Asp Arg Arg
65                  70                  75                  80

Ile Arg Leu Ser Val Pro Thr Ala Ile Gln Leu Tyr Asp Leu Gln Asp
                85                  90                  95

Arg Leu Gly Leu Ser Gln Pro Ser Lys Val Ile Asp Trp Leu Leu Glu
            100                 105                 110

Ala Ala Lys Asp Asp Val Asp Lys Leu Pro Pro Leu Gln Phe Pro His
        115                 120                 125

Gly Phe Asn Gln Met Tyr Pro Asn Leu Ile Phe Gly Asn Ser Gly Phe
    130                 135                 140

Gly Glu Ser Pro Ser Ser Thr Thr Ser Thr Thr Phe Pro Gly Thr Asn
145                 150                 155                 160

Leu Gly Phe Leu Glu Asn Trp Asp Leu Gly Gly Ser Ser Arg Thr Arg
                165                 170                 175

Ala Arg Leu Thr Asp Thr Thr Thr Thr Gln Arg Glu Ser Phe Asp Leu
            180                 185                 190

Asp Lys Gly Lys Trp Ile Lys Asn Asp Glu Asn Ser Asn Gln Asp His
        195                 200                 205

Gln Gly Phe Asn Thr Asn His Gln Gln Gln Phe Pro Leu Thr Asn Pro
    210                 215                 220
```

```
Tyr Asn Asn Thr Ser Ala Tyr Asn Leu Gly His Leu Gln Gln Ser
225                 230                 235                 240

Leu Asp Gln Ser Gly Asn Asn Val Thr Val Ala Ile Ser Asn Val Ala
            245                 250                 255

Ala Asn Asn Asn Asn Leu Asn Leu His Pro Pro Ser Ser Ser Ala
        260                 265                 270

Gly Asp Gly Ser Gln Leu Phe Phe Gly Pro Thr Pro Ala Met Ser
            275                 280                 285

Ser Leu Phe Pro Thr Tyr Pro Ser Phe Leu Gly Ala Ser His His His
    290                 295                 300

His Val Val Asp Gly Ala Gly His Leu Gln Leu Phe Ser Ser Asn Ser
305                 310                 315                 320

Asn Thr Ala Ser Gln Gln His Met Met Pro Gly Asn Thr Ser Leu Ile
                325                 330                 335

Arg Pro Phe His His Leu Met Ser Ser Asn His Asp Thr Asp His His
            340                 345                 350

Ser Ser Asp Asn Glu Ser Asp Ser
            355                 360

<210> SEQ ID NO 35
<211> LENGTH: 777
<212> TYPE: DNA
<213> ORGANISM: Arabidopsis thaliana
<220> FEATURE:
<221> NAME/KEY: CDS
<222> LOCATION: (1)..(777)

<400> SEQUENCE: 35 atg gga aag aga gca act act agt gtg agg aga gaa gag tta aac aga      48
Met Gly Lys Arg Ala Thr Thr Ser Val Arg Arg Glu Glu Leu Asn Arg
1               5                   10                  15 gga gct tgg act gat cat gaa gac aag atc ctt aga gat tac atc acc      96
Gly Ala Trp Thr Asp His Glu Asp Lys Ile Leu Arg Asp Tyr Ile Thr
            20                  25                  30 act cac ggc gaa ggc aaa tgg agc act ctc cct aac caa gct ggt ctc     144
Thr His Gly Glu Gly Lys Trp Ser Thr Leu Pro Asn Gln Ala Gly Leu
        35                  40                  45 aag agg tgt ggc aaa agc tgt aga ctt cgg tgg aag aac tac cta aga     192
Lys Arg Cys Gly Lys Ser Cys Arg Leu Arg Trp Lys Asn Tyr Leu Arg
    50                  55                  60 ccg ggg ata aag cgc ggt aac atc tca tct gat gaa gaa gaa ctc ata     240
Pro Gly Ile Lys Arg Gly Asn Ile Ser Ser Asp Glu Glu Glu Leu Ile
65                  70                  75                  80 atc cgt ctc cat aat ctt ctt gga aac aga tgg tcg ttg ata gct ggg     288
Ile Arg Leu His Asn Leu Leu Gly Asn Arg Trp Ser Leu Ile Ala Gly
                85                  90                  95 agg ctt cca ggc cga aca gac aat gaa ata aag aat cat tgg aac tca     336
Arg Leu Pro Gly Arg Thr Asp Asn Glu Ile Lys Asn His Trp Asn Ser
            100                 105                 110 aac ctc cgc aaa aga ctt ccc aaa act caa acc aag caa cca aaa cgt     384
Asn Leu Arg Lys Arg Leu Pro Lys Thr Gln Thr Lys Gln Pro Lys Arg
        115                 120                 125 ata aaa cat tcg acg aac aac gag aat aat gta tgt gtt ata cgt aca     432
Ile Lys His Ser Thr Asn Asn Glu Asn Asn Val Cys Val Ile Arg Thr
    130                 135                 140 aag gcg att agg tgc tca aag act ctt ctc ttc tcg gat ctc tct ctt     480
Lys Ala Ile Arg Cys Ser Lys Thr Leu Leu Phe Ser Asp Leu Ser Leu
145                 150                 155                 160
```

| | | | | | | | | | | | | | | | |
|---|---|---|---|---|---|---|---|---|---|---|---|---|---|---|---|
| cag | aag | aag | agt | agt | act | agt | cca | cta | cct | ctg | aaa | gaa | caa | gag | atg | 528 |
| Gln | Lys | Lys | Ser | Ser | Thr | Ser | Pro | Leu | Pro | Leu | Lys | Glu | Gln | Glu | Met | |
| | | | | 165 | | | | | 170 | | | | | 175 | | |
| gat | caa | ggt | gga | tct | tcg | ttg | atg | gga | gat | ctc | gaa | ttc | gat | ttc | gat | 576 |
| Asp | Gln | Gly | Gly | Ser | Ser | Leu | Met | Gly | Asp | Leu | Glu | Phe | Asp | Phe | Asp | |
| | | | 180 | | | | | 185 | | | | | 190 | | | |
| agg | atc | cat | tcg | gag | ttt | cac | ttc | ccg | gat | ttg | atg | gat | ttt | gat | ggt | 624 |
| Arg | Ile | His | Ser | Glu | Phe | His | Phe | Pro | Asp | Leu | Met | Asp | Phe | Asp | Gly | |
| | | | 195 | | | | | 200 | | | | | 205 | | | |
| ttg | gac | tgt | gga | aac | gtt | aca | tct | ctt | gtt | tca | tct | aac | gag | att | ttg | 672 |
| Leu | Asp | Cys | Gly | Asn | Val | Thr | Ser | Leu | Val | Ser | Ser | Asn | Glu | Ile | Leu | |
| | 210 | | | | | 215 | | | | | 220 | | | | | |
| gga | gag | ttg | gtt | cct | gct | caa | ggt | aat | ctc | gat | ctc | aat | aga | cct | ttc | 720 |
| Gly | Glu | Leu | Val | Pro | Ala | Gln | Gly | Asn | Leu | Asp | Leu | Asn | Arg | Pro | Phe | |
| 225 | | | | 230 | | | | | 235 | | | | | 240 | | |
| act | tct | tgt | cat | cat | cgt | ggc | gac | gat | gaa | gat | tgg | ctc | cga | gac | ttc | 768 |
| Thr | Ser | Cys | His | His | Arg | Gly | Asp | Asp | Glu | Asp | Trp | Leu | Arg | Asp | Phe | |
| | | | | 245 | | | | | 250 | | | | | 255 | | |
| act | tgt | tga | | | | | | | | | | | | | | 777 |
| Thr | Cys | | | | | | | | | | | | | | | |

<210> SEQ ID NO 36
<211> LENGTH: 258
<212> TYPE: PRT
<213> ORGANISM: Arabidopsis thaliana

<400> SEQUENCE: 36

Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
            20                  25                  30

Thr His Gly Glu Gly Lys Trp Ser Thr Leu Pro Asn Gln Ala Gly Leu
        35                  40                  45

Lys Arg Cys Gly Lys Ser Cys Arg Leu Arg Trp Lys Asn Tyr Leu Arg
    50                  55                  60

Pro Gly Ile Lys Arg Gly Asn Ile Ser Ser Asp Glu Glu Glu Leu Ile
65                  70                  75                  80

Ile Arg Leu His Asn Leu Leu Gly Asn Arg Trp Ser Leu Ile Ala Gly
                85                  90                  95

Arg Leu Pro Gly Arg Thr Asp Asn Glu Ile Lys Asn His Trp Asn Ser
            100                 105                 110

Asn Leu Arg Lys Arg Leu Pro Lys Thr Gln Thr Lys Gln Pro Lys Arg
        115                 120                 125

Ile Lys His Ser Thr Asn Asn Glu Asn Asn Val Cys Val Ile Arg Thr
    130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Leu Lys Glu Gln Glu Met
                165                 170                 175

Asp Gln Gly Gly Ser Ser Leu Met Gly Asp Leu Glu Phe Asp Phe Asp
            180                 185                 190

Arg Ile His Ser Glu Phe His Phe Pro Asp Leu Met Asp Phe Asp Gly
        195                 200                 205

Leu Asp Cys Gly Asn Val Thr Ser Leu Val Ser Ser Asn Glu Ile Leu
    210                 215                 220

Gly Glu Leu Val Pro Ala Gln Gly Asn Leu Asp Leu Asn Arg Pro Phe
225                 230                 235                 240

```
Thr Ser Cys His His Arg Gly Asp Asp Glu Asp Trp Leu Arg Asp Phe
            245                 250                 255

Thr Cys
```

<210> SEQ ID NO 37
<211> LENGTH: 528
<212> TYPE: DNA
<213> ORGANISM: Arabidopsis thaliana
<220> FEATURE:
<221> NAME/KEY: CDS
<222> LOCATION: (1)..(528)

<400> SEQUENCE: 37

```
atg atg aag tca aga cgt gaa caa tca atc gaa gaa gca atc gtc gca      48
Met Met Lys Ser Arg Arg Glu Gln Ser Ile Glu Glu Ala Ile Val Ala
1               5                   10                  15 aat tat ttg aag atg atg atc gat aac gta aac gtt tgg cct cgc cac      96
Asn Tyr Leu Lys Met Met Ile Asp Asn Val Asn Val Trp Pro Arg His
                20                  25                  30 ttc ctc cga agc gaa gac gtg tac tgc aag aat ccg tgg acg ctt ttc     144
Phe Leu Arg Ser Glu Asp Val Tyr Cys Lys Asn Pro Trp Thr Leu Phe
            35                  40                  45 gtt act aga gat cct ata atc cta cac ttc gga cga tac ttc ttc gtt     192
Val Thr Arg Asp Pro Ile Ile Leu His Phe Gly Arg Tyr Phe Phe Val
        50                  55                  60 aat cgg agt gtg aat tca ggt tta acc gat gga tgt gaa tac ggt tgt     240
Asn Arg Ser Val Asn Ser Gly Leu Thr Asp Gly Cys Glu Tyr Gly Cys
65                  70                  75                  80 tgg aga atc atc ggt cgt gat aga gtg atc aag tcg gtg acg acc ggg     288
Trp Arg Ile Ile Gly Arg Asp Arg Val Ile Lys Ser Val Thr Thr Gly
                85                  90                  95 aag att cta ggg tta aag aag gtt tat aag ttc tgt gaa act gat cgg     336
Lys Ile Leu Gly Leu Lys Lys Val Tyr Lys Phe Cys Glu Thr Asp Arg
            100                 105                 110 aaa ccg aaa tcg gtt ttt aag ttc ttg gaa aag gag aag aga aga gta     384
Lys Pro Lys Ser Val Phe Lys Phe Leu Glu Lys Glu Lys Arg Arg Val
        115                 120                 125 aga gat aga cga atc tgg gcg atg gaa gag tat agg ttt gca agt acg     432
Arg Asp Arg Arg Ile Trp Ala Met Glu Glu Tyr Arg Phe Ala Ser Thr
130                 135                 140 tgg aaa caa gat tac gtg atc tgc aag att cga cgt ctg tat cca caa     480
Trp Lys Gln Asp Tyr Val Ile Cys Lys Ile Arg Arg Leu Tyr Pro Gln
145                 150                 155                 160 cca ttt gac tac atg ttg gcc cag cac att cga ggt tac tat aaa tga     528
Pro Phe Asp Tyr Met Leu Ala Gln His Ile Arg Gly Tyr Tyr Lys
                165                 170                 175
```

<210> SEQ ID NO 38
<211> LENGTH: 175
<212> TYPE: PRT
<213> ORGANISM: Arabidopsis thaliana

<400> SEQUENCE: 38

```
Met Met Lys Ser Arg Arg Glu Gln Ser Ile Glu Glu Ala Ile Val Ala
1               5                   10                  15

Asn Tyr Leu Lys Met Met Ile Asp Asn Val Asn Val Trp Pro Arg His
                20                  25                  30

Phe Leu Arg Ser Glu Asp Val Tyr Cys Lys Asn Pro Trp Thr Leu Phe
            35                  40                  45

Val Thr Arg Asp Pro Ile Ile Leu His Phe Gly Arg Tyr Phe Phe Val
```

-continued

```
                50                  55                  60
Asn Arg Ser Val Asn Ser Gly Leu Thr Asp Gly Cys Glu Tyr Gly Cys
 65                  70                  75                  80

Trp Arg Ile Ile Gly Arg Asp Arg Val Ile Lys Ser Val Thr Thr Gly
                 85                  90                  95

Lys Ile Leu Gly Leu Lys Lys Val Tyr Lys Phe Cys Glu Thr Asp Arg
            100                 105                 110

Lys Pro Lys Ser Val Phe Lys Phe Leu Glu Lys Glu Lys Arg Arg Val
        115                 120                 125

Arg Asp Arg Arg Ile Trp Ala Met Glu Glu Tyr Arg Phe Ala Ser Thr
    130                 135                 140

Trp Lys Gln Asp Tyr Val Ile Cys Lys Ile Arg Arg Leu Tyr Pro Gln
145                 150                 155                 160

Pro Phe Asp Tyr Met Leu Ala Gln His Ile Arg Gly Tyr Tyr Lys
                165                 170                 175

<210> SEQ ID NO 39
<211> LENGTH: 930
<212> TYPE: DNA
<213> ORGANISM: Arabidopsis thaliana
<220> FEATURE:
<221> NAME/KEY: CDS
<222> LOCATION: (1)..(930)

<400> SEQUENCE: 39 atg tct ggt tcg acc cgg aaa gaa atg gat cgg atc aaa gga cca tgg      48
Met Ser Gly Ser Thr Arg Lys Glu Met Asp Arg Ile Lys Gly Pro Trp
 1               5                  10                  15 agt cct gaa gaa gac gat ctg tta caa tcg ttg gtt cag aag cac gga      96
Ser Pro Glu Glu Asp Asp Leu Leu Gln Ser Leu Val Gln Lys His Gly
                20                  25                  30 cca agg aac tgg tct ctg ata agc aaa tca atc cct gga cgt tcc ggt     144
Pro Arg Asn Trp Ser Leu Ile Ser Lys Ser Ile Pro Gly Arg Ser Gly
            35                  40                  45 aaa tct tgc cgt ctc cgt tgg tgt aat cag ctt tct ccg gag gta gag     192
Lys Ser Cys Arg Leu Arg Trp Cys Asn Gln Leu Ser Pro Glu Val Glu
        50                  55                  60 cac cgt gga ttc acg gcg gag gaa gat gat acg att ata cta gcg cac     240
His Arg Gly Phe Thr Ala Glu Glu Asp Asp Thr Ile Ile Leu Ala His
 65                  70                  75                  80 gct cgg ttt ggt aac aag tgg gcg acg att gca cgg ctt ctc aat ggt     288
Ala Arg Phe Gly Asn Lys Trp Ala Thr Ile Ala Arg Leu Leu Asn Gly
                85                  90                  95 cgc act gat aac gcg att aag aat cac tgg aac tca acg ctg aag cgg     336
Arg Thr Asp Asn Ala Ile Lys Asn His Trp Asn Ser Thr Leu Lys Arg
            100                 105                 110 aaa tgt agc ggc gga ggc ggc gga gag gaa ggg cag agt tgt gat         384
Lys Cys Ser Gly Gly Gly Gly Gly Glu Glu Gly Gln Ser Cys Asp
        115                 120                 125 ttc ggt ggt aat gga ggg tat gat ggt aat tta act gat gaa aaa ccg     432
Phe Gly Gly Asn Gly Gly Tyr Asp Gly Asn Leu Thr Asp Glu Lys Pro
    130                 135                 140 tta aaa cgg agg gcg agt ggt gga gga gga gtt gtt gtg gtg acg gcg     480
Leu Lys Arg Arg Ala Ser Gly Gly Gly Gly Val Val Val Val Thr Ala
145                 150                 155                 160 tta agt cca acg gga tct gac gtc agc gag caa tcg caa tct agt gga     528
Leu Ser Pro Thr Gly Ser Asp Val Ser Glu Gln Ser Gln Ser Ser Gly
                165                 170                 175 tct gtt tta ccg gtt tct tct tct tgt cat gtt ttt aaa ccg acg gcg     576
```

```
Ser Val Leu Pro Val Ser Ser Ser Cys His Val Phe Lys Pro Thr Ala
            180                 185                 190 aga gct ggt gga gtg gtg att gag tca tca tcg ccg gag gag gag gag       624
Arg Ala Gly Gly Val Val Ile Glu Ser Ser Ser Pro Glu Glu Glu Glu
        195                 200                 205 aaa gat ccg atg act tgt ttg agg ttg tct ttg cct tgg gtc aat gag       672
Lys Asp Pro Met Thr Cys Leu Arg Leu Ser Leu Pro Trp Val Asn Glu
210                 215                 220 tca aca act cca ccg gag ttg ttt ccg gtg aag aga gaa gaa gaa gaa       720
Ser Thr Thr Pro Pro Glu Leu Phe Pro Val Lys Arg Glu Glu Glu Glu
225                 230                 235                 240 gag aag gaa aga gag att tct gga ctt ggt gga gat ttt atg acg gtg       768
Glu Lys Glu Arg Glu Ile Ser Gly Leu Gly Gly Asp Phe Met Thr Val
                245                 250                 255 gtg cag gag atg att aag acg gag gtt agg agt tac atg gcg gat tta       816
Val Gln Glu Met Ile Lys Thr Glu Val Arg Ser Tyr Met Ala Asp Leu
            260                 265                 270 cag cta gga aac ggc gga gga gct gga gga gga gca agt tcg tgt atg       864
Gln Leu Gly Asn Gly Gly Gly Ala Gly Gly Gly Ala Ser Ser Cys Met
        275                 280                 285 gtg caa gga act aat ggt cgt aat gta ggg ttt aga gag ttt att gga       912
Val Gln Gly Thr Asn Gly Arg Asn Val Gly Phe Arg Glu Phe Ile Gly
290                 295                 300 tta ggt agg atc gag tag                                                930
Leu Gly Arg Ile Glu
305

<210> SEQ ID NO 40
<211> LENGTH: 309
<212> TYPE: PRT
<213> ORGANISM: Arabidopsis thaliana

<400> SEQUENCE: 40

Met Ser Gly Ser Thr Arg Lys Glu Met Asp Arg Ile Lys Gly Pro Trp
1               5                   10                  15

Ser Pro Glu Glu Asp Asp Leu Leu Gln Ser Leu Val Gln Lys His Gly
            20                  25                  30

Pro Arg Asn Trp Ser Leu Ile Ser Lys Ser Ile Pro Gly Arg Ser Gly
        35                  40                  45

Lys Ser Cys Arg Leu Arg Trp Cys Asn Gln Leu Ser Pro Glu Val Glu
    50                  55                  60

His Arg Gly Phe Thr Ala Glu Glu Asp Asp Thr Ile Ile Leu Ala His
65                  70                  75                  80

Ala Arg Phe Gly Asn Lys Trp Ala Thr Ile Ala Arg Leu Leu Asn Gly
                85                  90                  95

Arg Thr Asp Asn Ala Ile Lys Asn His Trp Asn Ser Thr Leu Lys Arg
            100                 105                 110

Lys Cys Ser Gly Gly Gly Gly Gly Glu Glu Gly Gln Ser Cys Asp
        115                 120                 125

Phe Gly Gly Asn Gly Gly Tyr Asp Gly Asn Leu Thr Asp Glu Lys Pro
    130                 135                 140

Leu Lys Arg Arg Ala Ser Gly Gly Gly Val Val Val Thr Ala
145                 150                 155                 160

Leu Ser Pro Thr Gly Ser Asp Val Ser Glu Gln Ser Gln Ser Ser Gly
                165                 170                 175

Ser Val Leu Pro Val Ser Ser Ser Cys His Val Phe Lys Pro Thr Ala
            180                 185                 190
```

```
Arg Ala Gly Gly Val Val Ile Glu Ser Ser Ser Pro Glu Glu Glu
            195                 200                 205

Lys Asp Pro Met Thr Cys Leu Arg Leu Ser Leu Pro Trp Val Asn Glu
    210                 215                 220

Ser Thr Thr Pro Pro Glu Leu Phe Pro Val Lys Arg Glu Glu Glu
225                 230                 235                 240

Glu Lys Glu Arg Glu Ile Ser Gly Leu Gly Gly Asp Phe Met Thr Val
                245                 250                 255

Val Gln Glu Met Ile Lys Thr Glu Val Arg Ser Tyr Met Ala Asp Leu
            260                 265                 270

Gln Leu Gly Asn Gly Gly Ala Gly Gly Ala Ser Ser Cys Met
            275                 280                 285

Val Gln Gly Thr Asn Gly Arg Asn Val Gly Phe Arg Glu Phe Ile Gly
        290                 295                 300

Leu Gly Arg Ile Glu
305
```

<210> SEQ ID NO 41
<211> LENGTH: 621
<212> TYPE: DNA
<213> ORGANISM: Arabidopsis thaliana
<220> FEATURE:
<221> NAME/KEY: CDS
<222> LOCATION: (1)..(621)

<400> SEQUENCE: 41

```
atg gag gtg gag aag agg att gta gtg aat gga gga atg aaa ttg cca    48
Met Glu Val Glu Lys Arg Ile Val Val Asn Gly Gly Met Lys Leu Pro
1               5                   10                  15 ata gga tac aga ttt cac cca acc gag caa gag ctt atc ctt cat tac    96
Ile Gly Tyr Arg Phe His Pro Thr Glu Gln Glu Leu Ile Leu His Tyr
                20                  25                  30 ttg ctc cca aag gcc ttt gct tct cct ttg cct tcc tcc atc atc cct   144
Leu Leu Pro Lys Ala Phe Ala Ser Pro Leu Pro Ser Ser Ile Ile Pro
            35                  40                  45 gtc ttt gac ctc ttc ttc tct cat cct ctt agt ttc cca ggg gac caa   192
Val Phe Asp Leu Phe Phe Ser His Pro Leu Ser Phe Pro Gly Asp Gln
        50                  55                  60 aag gag aag cag agg tac ttc ttt tgc aag aag aga gaa gtg tca agt   240
Lys Glu Lys Gln Arg Tyr Phe Phe Cys Lys Lys Arg Glu Val Ser Ser
65                  70                  75                  80 aat gag cat aga atc aag att tcc tct ggt gat ggt tat tgg aaa cct   288
Asn Glu His Arg Ile Lys Ile Ser Ser Gly Asp Gly Tyr Trp Lys Pro
                85                  90                  95 att ggt aaa gag aga cca atc att gcc tgt ggt aaa aca ttt ggg att   336
Ile Gly Lys Glu Arg Pro Ile Ile Ala Cys Gly Lys Thr Phe Gly Ile
                100                 105                 110 aga aga aca ctt gct ttc tat gaa aca aac aag tct tct tct tat tgc   384
Arg Arg Thr Leu Ala Phe Tyr Glu Thr Asn Lys Ser Ser Ser Tyr Cys
            115                 120                 125 aac aaa act aga tgg agc atg aca gag tat tgt ctt gcg gga ttt gcg   432
Asn Lys Thr Arg Trp Ser Met Thr Glu Tyr Cys Leu Ala Gly Phe Ala
        130                 135                 140 tcg gct aag gtg tct gga gaa tgg gca gtg tac aat gtt tat gag agg   480
Ser Ala Lys Val Ser Gly Glu Trp Ala Val Tyr Asn Val Tyr Glu Arg
145                 150                 155                 160 aaa ggc tca aaa gga aga aaa cag agg aaa tca aga gag gga gat gat   528
Lys Gly Ser Lys Gly Arg Lys Gln Arg Lys Ser Arg Glu Gly Asp Asp
                165                 170                 175
```

```
gaa gaa ttg aga tgc atc gac cat ttt acg gtt ggg tca aat cat gaa      576
Glu Glu Leu Arg Cys Ile Asp His Phe Thr Val Gly Ser Asn His Glu
            180                 185                 190 acc ggt cca cca ccg cct tct cct cct acc tca gct gat gag taa          621
Thr Gly Pro Pro Pro Pro Ser Pro Pro Thr Ser Ala Asp Glu
        195                 200                 205

<210> SEQ ID NO 42
<211> LENGTH: 206
<212> TYPE: PRT
<213> ORGANISM: Arabidopsis thaliana

<400> SEQUENCE: 42

Met Glu Val Glu Lys Arg Ile Val Val Asn Gly Gly Met Lys Leu Pro
1               5                   10                  15

Ile Gly Tyr Arg Phe His Pro Thr Glu Gln Glu Leu Ile Leu His Tyr
            20                  25                  30

Leu Leu Pro Lys Ala Phe Ala Ser Pro Leu Pro Ser Ser Ile Ile Pro
        35                  40                  45

Val Phe Asp Leu Phe Phe Ser His Pro Leu Ser Phe Pro Gly Asp Gln
    50                  55                  60

Lys Glu Lys Gln Arg Tyr Phe Phe Cys Lys Lys Arg Glu Val Ser Ser
65                  70                  75                  80

Asn Glu His Arg Ile Lys Ile Ser Ser Gly Asp Gly Tyr Trp Lys Pro
                85                  90                  95

Ile Gly Lys Glu Arg Pro Ile Ile Ala Cys Gly Lys Thr Phe Gly Ile
            100                 105                 110

Arg Arg Thr Leu Ala Phe Tyr Glu Thr Asn Lys Ser Ser Tyr Cys
        115                 120                 125

Asn Lys Thr Arg Trp Ser Met Thr Glu Tyr Cys Leu Ala Gly Phe Ala
    130                 135                 140

Ser Ala Lys Val Ser Gly Glu Trp Ala Val Tyr Asn Val Tyr Glu Arg
145                 150                 155                 160

Lys Gly Ser Lys Gly Arg Lys Gln Arg Lys Ser Arg Glu Gly Asp Asp
                165                 170                 175

Glu Glu Leu Arg Cys Ile Asp His Phe Thr Val Gly Ser Asn His Glu
            180                 185                 190

Thr Gly Pro Pro Pro Pro Ser Pro Pro Thr Ser Ala Asp Glu
        195                 200                 205

<210> SEQ ID NO 43
<211> LENGTH: 1416
<212> TYPE: DNA
<213> ORGANISM: Arabidopsis thaliana
<220> FEATURE:
<221> NAME/KEY: CDS
<222> LOCATION: (1)..(1416)

<400> SEQUENCE: 43 atg gag ttg gag cct ata tca tcg agt tgt tgc tcg tcg tct tct tct      48
Met Glu Leu Glu Pro Ile Ser Ser Ser Cys Cys Ser Ser Ser Ser Ser
1               5                   10                  15 tct tct ggg gag gag aat act gcg gcg gcg aac atg acg gag atg gag      96
Ser Ser Gly Glu Glu Asn Thr Ala Ala Ala Asn Met Thr Glu Met Glu
            20                  25                  30 gcg gca gaa gca ttg gcg gat tta gcg cag ctt gcg ata atg cga gag     144
Ala Ala Glu Ala Leu Ala Asp Leu Ala Gln Leu Ala Ile Met Arg Glu
        35                  40                  45 cag gtt ttc gaa tct gca gcg agt tgg gga agt aaa ggg aaa cgg gtg     192
```

```
                Gln Val Phe Glu Ser Ala Ala Ser Trp Gly Ser Lys Gly Lys Arg Val
                    50                  55                  60 agg aag cga gtc aag act gag tct cct cct tct gac tcg ctt ttg aaa        240
Arg Lys Arg Val Lys Thr Glu Ser Pro Pro Ser Asp Ser Leu Leu Lys
 65              70                  75                  80 cca cct gac tct gat acg tta cct act ccg gat cta gct gag gaa cga        288
Pro Pro Asp Ser Asp Thr Leu Pro Thr Pro Asp Leu Ala Glu Glu Arg
                 85                  90                  95 tta gtg aaa gaa gaa gag gaa gaa gaa gtt gaa cca ata act aaa            336
Leu Val Lys Glu Glu Glu Glu Glu Glu Val Glu Pro Ile Thr Lys
            100                 105                 110 gaa cta act aaa gct ccg gtt aaa tct gaa atc aat ggt gaa aca cct        384
Glu Leu Thr Lys Ala Pro Val Lys Ser Glu Ile Asn Gly Glu Thr Pro
        115                 120                 125 aaa cca att ctt gct tcg act cta ata agg tgt agt aga tca aat ggt        432
Lys Pro Ile Leu Ala Ser Thr Leu Ile Arg Cys Ser Arg Ser Asn Gly
    130                 135                 140 tgt ggc cga tca aga cag aat tta agt gag gct gaa aga gaa gaa cgt        480
Cys Gly Arg Ser Arg Gln Asn Leu Ser Glu Ala Glu Arg Glu Glu Arg
145                 150                 155                 160 aga atc aga agg ata tta gct aat aga gaa tct gcg agg cag aca att        528
Arg Ile Arg Arg Ile Leu Ala Asn Arg Glu Ser Ala Arg Gln Thr Ile
                165                 170                 175 cgg cga aga cag gca atg tgt gag gag ttg agt aaa aaa gca gct gat        576
Arg Arg Arg Gln Ala Met Cys Glu Glu Leu Ser Lys Lys Ala Ala Asp
            180                 185                 190 ctg aca tat gag aat gag aat ttg agg agg gaa aag gat tgg gct ttg        624
Leu Thr Tyr Glu Asn Glu Asn Leu Arg Arg Glu Lys Asp Trp Ala Leu
        195                 200                 205 aaa gag ttt cag tct ttg gag acg att aac aag cat tta aag gaa cag        672
Lys Glu Phe Gln Ser Leu Glu Thr Ile Asn Lys His Leu Lys Glu Gln
    210                 215                 220 gta ttg aag tca gta aaa ccc gat aca aaa gag cct gaa gaa tca ccc        720
Val Leu Lys Ser Val Lys Pro Asp Thr Lys Glu Pro Glu Glu Ser Pro
225                 230                 235                 240 aag cca tca caa gtt gag atg tct aca tca tct act ccg ttt tac ttc        768
Lys Pro Ser Gln Val Glu Met Ser Thr Ser Ser Thr Pro Phe Tyr Phe
                245                 250                 255 tac aac cag aat cca tat cag ctt ttc tgc tgg cct cat gtt act caa        816
Tyr Asn Gln Asn Pro Tyr Gln Leu Phe Cys Trp Pro His Val Thr Gln
            260                 265                 270 tca tca aat cca atg ata tcg cca ctt gaa ttc cct act tcg gga gga        864
Ser Ser Asn Pro Met Ile Ser Pro Leu Glu Phe Pro Thr Ser Gly Gly
        275                 280                 285 gct tct gct aaa act att acc acg cag gag cat gaa aat gct gca gat        912
Ala Ser Ala Lys Thr Ile Thr Thr Gln Glu His Glu Asn Ala Ala Asp
    290                 295                 300 gat aat ggg caa aaa act cac ttt tac gtt gta cct tgc cct tgg ttt        960
Asp Asn Gly Gln Lys Thr His Phe Tyr Val Val Pro Cys Pro Trp Phe
305                 310                 315                 320 ctc cct cct cct gat cac agc aat ggt gtt cct ttc ggg ctt caa gat       1008
Leu Pro Pro Pro Asp His Ser Asn Gly Val Pro Phe Gly Leu Gln Asp
                325                 330                 335 aca caa aga ggt act ttt tca aac ggg cac cat atc gat gat tct tct       1056
Thr Gln Arg Gly Thr Phe Ser Asn Gly His His Ile Asp Asp Ser Ser
            340                 345                 350 gca aga ccg atg gat gtc aca gaa act ccg cgg tcc cat cta cca act       1104
Ala Arg Pro Met Asp Val Thr Glu Thr Pro Arg Ser His Leu Pro Thr
        355                 360                 365
```

```
aga atc aaa gaa gag gac tct ggt tca ccc gaa acc aga cct tta tat    1152
Arg Ile Lys Glu Glu Asp Ser Gly Ser Pro Glu Thr Arg Pro Leu Tyr
    370                 375                 380 gat ctc aac gaa tct gct act gaa gtc ctc tca gaa gga gga gat gga    1200
Asp Leu Asn Glu Ser Ala Thr Glu Val Leu Ser Glu Gly Gly Asp Gly
385                 390                 395                 400 ttt cct gta acg cag caa gct tat agt tta aag cat gaa gat gtt tct    1248
Phe Pro Val Thr Gln Gln Ala Tyr Ser Leu Lys His Glu Asp Val Ser
                405                 410                 415 gag aca act aat gga gtt aca ctg atg ccg cct ggt cat cat gtt ttg    1296
Glu Thr Thr Asn Gly Val Thr Leu Met Pro Pro Gly His His Val Leu
            420                 425                 430 att tct cta ccg gag aaa aag cat gga tcg ttg gct gca gcg gaa gct    1344
Ile Ser Leu Pro Glu Lys Lys His Gly Ser Leu Ala Ala Ala Glu Ala
        435                 440                 445 aga aag aga cgg aaa gaa ctc aca agg ctc aag aac ctc cat ggc cgt    1392
Arg Lys Arg Arg Lys Glu Leu Thr Arg Leu Lys Asn Leu His Gly Arg
450                 455                 460 caa tgt cgg atg cag gtc gga taa                                    1416
Gln Cys Arg Met Gln Val Gly
465                 470

<210> SEQ ID NO 44
<211> LENGTH: 471
<212> TYPE: PRT
<213> ORGANISM: Arabidopsis thaliana

<400> SEQUENCE: 44

Met Glu Leu Glu Pro Ile Ser Ser Cys Cys Ser Ser Ser Ser
1               5                   10                  15

Ser Ser Gly Glu Glu Asn Thr Ala Ala Ala Asn Met Thr Glu Met Glu
            20                  25                  30

Ala Ala Glu Ala Leu Ala Asp Leu Ala Gln Leu Ala Ile Met Arg Glu
        35                  40                  45

Gln Val Phe Glu Ser Ala Ala Ser Trp Gly Ser Lys Gly Lys Arg Val
    50                  55                  60

Arg Lys Arg Val Lys Thr Glu Ser Pro Pro Ser Asp Ser Leu Leu Lys
65                  70                  75                  80

Pro Pro Asp Ser Asp Thr Leu Pro Thr Pro Asp Leu Ala Glu Glu Arg
                85                  90                  95

Leu Val Lys Glu Glu Glu Glu Glu Val Glu Pro Ile Thr Lys
            100                 105                 110

Glu Leu Thr Lys Ala Pro Val Lys Ser Glu Ile Asn Gly Glu Thr Pro
        115                 120                 125

Lys Pro Ile Leu Ala Ser Thr Leu Ile Arg Cys Ser Arg Ser Asn Gly
    130                 135                 140

Cys Gly Arg Ser Arg Gln Asn Leu Ser Glu Ala Glu Arg Glu Glu Arg
145                 150                 155                 160

Arg Ile Arg Arg Ile Leu Ala Asn Arg Glu Ser Ala Arg Gln Thr Ile
                165                 170                 175

Arg Arg Arg Gln Ala Met Cys Glu Glu Leu Ser Lys Lys Ala Ala Asp
            180                 185                 190

Leu Thr Tyr Glu Asn Glu Asn Leu Arg Arg Glu Lys Asp Trp Ala Leu
        195                 200                 205

Lys Glu Phe Gln Ser Leu Glu Thr Ile Asn Lys His Leu Lys Glu Gln
    210                 215                 220

Val Leu Lys Ser Val Lys Pro Asp Thr Lys Glu Pro Glu Glu Ser Pro
```

```
               225                 230                 235                 240
Lys Pro Ser Gln Val Glu Met Ser Thr Ser Thr Pro Phe Tyr Phe
                    245                 250                 255

Tyr Asn Gln Asn Pro Tyr Gln Leu Phe Cys Trp Pro His Val Thr Gln
                260                 265                 270

Ser Ser Asn Pro Met Ile Ser Pro Leu Glu Phe Pro Thr Ser Gly Gly
            275                 280                 285

Ala Ser Ala Lys Thr Ile Thr Thr Gln Glu His Glu Asn Ala Ala Asp
        290                 295                 300

Asp Asn Gly Gln Lys Thr His Phe Tyr Val Val Pro Cys Pro Trp Phe
305                 310                 315                 320

Leu Pro Pro Pro Asp His Ser Asn Gly Val Pro Phe Gly Leu Gln Asp
                    325                 330                 335

Thr Gln Arg Gly Thr Phe Ser Asn Gly His His Ile Asp Asp Ser Ser
                340                 345                 350

Ala Arg Pro Met Asp Val Thr Glu Thr Pro Arg Ser His Leu Pro Thr
            355                 360                 365

Arg Ile Lys Glu Glu Asp Ser Gly Ser Pro Glu Thr Arg Pro Leu Tyr
        370                 375                 380

Asp Leu Asn Glu Ser Ala Thr Glu Val Leu Ser Glu Gly Gly Asp Gly
385                 390                 395                 400

Phe Pro Val Thr Gln Gln Ala Tyr Ser Leu Lys His Glu Asp Val Ser
                    405                 410                 415

Glu Thr Thr Asn Gly Val Thr Leu Met Pro Gly His His Val Leu
                420                 425                 430

Ile Ser Leu Pro Glu Lys Lys His Gly Ser Leu Ala Ala Ala Glu Ala
            435                 440                 445

Arg Lys Arg Lys Glu Leu Thr Arg Leu Lys Asn Leu His Gly Arg
        450                 455                 460

Gln Cys Arg Met Gln Val Gly
465                 470

<210> SEQ ID NO 45
<211> LENGTH: 1077
<212> TYPE: DNA
<213> ORGANISM: Arabidopsis thaliana
<220> FEATURE:
<221> NAME/KEY: CDS
<222> LOCATION: (1)..(1077)

<400> SEQUENCE: 45 atg gct gat aat aag gtc aat ctt tcg att aat gga caa tca aaa gtg      48
Met Ala Asp Asn Lys Val Asn Leu Ser Ile Asn Gly Gln Ser Lys Val
1               5                   10                  15 cct cca ggt ttc aga ttc cat ccc acc gaa gaa gaa ctt ctc cat tac      96
Pro Pro Gly Phe Arg Phe His Pro Thr Glu Glu Glu Leu Leu His Tyr
            20                  25                  30 tat ctc cgt aag aaa gtt aac tct caa aag atc gat ctt gat gtc att     144
Tyr Leu Arg Lys Lys Val Asn Ser Gln Lys Ile Asp Leu Asp Val Ile
        35                  40                  45 cgt gaa gtt gat cta aac aag ctt gag cct tgg gat att caa gag gaa     192
Arg Glu Val Asp Leu Asn Lys Leu Glu Pro Trp Asp Ile Gln Glu Glu
    50                  55                  60 tgt aga atc ggt tca acg cca caa aac gac tgg tac ttc ttc agc cac     240
Cys Arg Ile Gly Ser Thr Pro Gln Asn Asp Trp Tyr Phe Phe Ser His
65                  70                  75                  80 aag gac aag aag tat cca acc ggg acc agg acg aac cgg gca aca gtc     288
```

|  |  |  |  |  |  |  |  |  |  |  |  |  |
|---|---|---|---|---|---|---|---|---|---|---|---|---|
| Lys | Asp | Lys | Lys | Tyr<br>85 | Pro | Thr | Gly | Thr<br>90 | Arg | Thr | Asn | Arg | Ala | Thr<br>95 | Val |

```
gct gga ttc tgg aaa gct acc gga cgt gac aaa atc atc tgc agt tgt      336
Ala Gly Phe Trp Lys Ala Thr Gly Arg Asp Lys Ile Ile Cys Ser Cys
        100                 105                 110 gtc cgg aga att gga ctg agg aag aca ctc gtg ttc tac aaa gga aga      384
Val Arg Arg Ile Gly Leu Arg Lys Thr Leu Val Phe Tyr Lys Gly Arg
            115                 120                 125 gct cct cac ggt cag aaa tcc gac tgg atc atg cat gag tat cgc ctc      432
Ala Pro His Gly Gln Lys Ser Asp Trp Ile Met His Glu Tyr Arg Leu
130                 135                 140 gac gat act cca atg tct aat ggc tat gct gat gtt gtt aca gaa gat      480
Asp Asp Thr Pro Met Ser Asn Gly Tyr Ala Asp Val Val Thr Glu Asp
145                 150                 155                 160 cca atg agc tat aac gaa gaa ggt tgg gtg gta tgt cga gtc ttc agg      528
Pro Met Ser Tyr Asn Glu Glu Gly Trp Val Val Cys Arg Val Phe Arg
                165                 170                 175 aag aag aac tat caa aag att gac gat tgt cct aaa atc act cta tct      576
Lys Lys Asn Tyr Gln Lys Ile Asp Asp Cys Pro Lys Ile Thr Leu Ser
            180                 185                 190 tct tta cct gat gac acg gag gaa gag aag ggg ccc acc ttt cac aac      624
Ser Leu Pro Asp Asp Thr Glu Glu Glu Lys Gly Pro Thr Phe His Asn
        195                 200                 205 act caa aac gtt acc ggt tta gac cat gtt ctt ctc tac atg gac cgt      672
Thr Gln Asn Val Thr Gly Leu Asp His Val Leu Leu Tyr Met Asp Arg
210                 215                 220 acc ggt tct aac att tgc atg ccc gag agc caa aca acg act caa cat      720
Thr Gly Ser Asn Ile Cys Met Pro Glu Ser Gln Thr Thr Thr Gln His
225                 230                 235                 240 caa gat gat gtc tta ttc atg caa ctc cca agt ctt gag aca cct aaa      768
Gln Asp Asp Val Leu Phe Met Gln Leu Pro Ser Leu Glu Thr Pro Lys
                245                 250                 255 tcc gag agc ccg gtc gac caa agt ttc ctg act cca agc aaa ctc gat      816
Ser Glu Ser Pro Val Asp Gln Ser Phe Leu Thr Pro Ser Lys Leu Asp
            260                 265                 270 ttc tct ccc gtt caa gag aag ata acc gaa aga ccg gtt tgc agc aac      864
Phe Ser Pro Val Gln Glu Lys Ile Thr Glu Arg Pro Val Cys Ser Asn
        275                 280                 285 tgg gct agt ctt gac cgg ctc gta gct tgg caa ttg aac aat ggt cat      912
Trp Ala Ser Leu Asp Arg Leu Val Ala Trp Gln Leu Asn Asn Gly His
290                 295                 300 cat aat ccg tgt cat cgt aag agt ttt gat gaa gaa gaa aat ggt          960
His Asn Pro Cys His Arg Lys Ser Phe Asp Glu Glu Glu Asn Gly
305                 310                 315                 320 gat act atg atg cag cga tgg gat ctt cat tgg aat aat gat gat aat     1008
Asp Thr Met Met Gln Arg Trp Asp Leu His Trp Asn Asn Asp Asp Asn
                325                 330                 335 gtt gat ctt tgg agt agt ttc act gag tct tct tcg tct tta gac cca     1056
Val Asp Leu Trp Ser Ser Phe Thr Glu Ser Ser Ser Ser Leu Asp Pro
            340                 345                 350 ctt ctt cat tta tct gta tga                                         1077
Leu Leu His Leu Ser Val
        355
```

<210> SEQ ID NO 46
<211> LENGTH: 358
<212> TYPE: PRT
<213> ORGANISM: Arabidopsis thaliana

<400> SEQUENCE: 46

```
Met Ala Asp Asn Lys Val Asn Leu Ser Ile Asn Gly Gln Ser Lys Val
1               5                   10                  15
Pro Pro Gly Phe Arg Phe His Pro Thr Glu Glu Leu Leu His Tyr
            20                  25                  30
Tyr Leu Arg Lys Lys Val Asn Ser Gln Lys Ile Asp Leu Asp Val Ile
            35                  40                  45
Arg Glu Val Asp Leu Asn Lys Leu Glu Pro Trp Asp Ile Gln Glu Glu
    50                  55                  60
Cys Arg Ile Gly Ser Thr Pro Gln Asn Asp Trp Tyr Phe Phe Ser His
65                  70                  75                  80
Lys Asp Lys Lys Tyr Pro Thr Gly Thr Arg Thr Asn Arg Ala Thr Val
                85                  90                  95
Ala Gly Phe Trp Lys Ala Thr Gly Arg Asp Lys Ile Ile Cys Ser Cys
            100                 105                 110
Val Arg Arg Ile Gly Leu Arg Lys Thr Leu Val Phe Tyr Lys Gly Arg
            115                 120                 125
Ala Pro His Gly Gln Lys Ser Asp Trp Ile Met His Glu Tyr Arg Leu
            130                 135                 140
Asp Asp Thr Pro Met Ser Asn Gly Tyr Ala Asp Val Val Thr Glu Asp
145                 150                 155                 160
Pro Met Ser Tyr Asn Glu Gly Trp Val Val Cys Arg Val Phe Arg
                165                 170                 175
Lys Lys Asn Tyr Gln Lys Ile Asp Asp Cys Pro Lys Ile Thr Leu Ser
            180                 185                 190
Ser Leu Pro Asp Asp Thr Glu Glu Lys Gly Pro Thr Phe His Asn
            195                 200                 205
Thr Gln Asn Val Thr Gly Leu Asp His Val Leu Leu Tyr Met Asp Arg
210                 215                 220
Thr Gly Ser Asn Ile Cys Met Pro Glu Ser Gln Thr Thr Gln His
225                 230                 235                 240
Gln Asp Asp Val Leu Phe Met Gln Leu Pro Ser Leu Glu Thr Pro Lys
            245                 250                 255
Ser Glu Ser Pro Val Asp Gln Ser Phe Leu Thr Pro Ser Lys Leu Asp
            260                 265                 270
Phe Ser Pro Val Gln Glu Lys Ile Thr Glu Arg Pro Val Cys Ser Asn
            275                 280                 285
Trp Ala Ser Leu Asp Arg Leu Val Ala Trp Gln Leu Asn Asn Gly His
            290                 295                 300
His Asn Pro Cys His Arg Lys Ser Phe Asp Glu Glu Glu Asn Gly
305                 310                 315                 320
Asp Thr Met Met Gln Arg Trp Asp Leu His Trp Asn Asp Asn
                325                 330                 335
Val Asp Leu Trp Ser Ser Phe Thr Glu Ser Ser Ser Leu Asp Pro
            340                 345                 350
Leu Leu His Leu Ser Val
            355

<210> SEQ ID NO 47
<211> LENGTH: 732
<212> TYPE: DNA
<213> ORGANISM: Arabidopsis thaliana
<220> FEATURE:
<221> NAME/KEY: CDS
<222> LOCATION: (1)..(732)

<400> SEQUENCE: 47
```

```
atg tac gga cag tgc aat ata gaa tcc gac tac gct ttg ttg gag tcg       48
Met Tyr Gly Gln Cys Asn Ile Glu Ser Asp Tyr Ala Leu Leu Glu Ser
1               5                   10                  15 ata aca cgt cac ttg cta gga gga gga gag aac gag ctg cga ctc           96
Ile Thr Arg His Leu Leu Gly Gly Gly Glu Asn Glu Leu Arg Leu
                20                  25                  30 aat gag tca aca ccg agt tcg tgt ttc aca gag agt tgg gga ggt ttg      144
Asn Glu Ser Thr Pro Ser Ser Cys Phe Thr Glu Ser Trp Gly Gly Leu
            35                  40                  45 cca ttg aaa gag aat gat tca gag gac atg ttg gtg tac gga ctc ctc      192
Pro Leu Lys Glu Asn Asp Ser Glu Asp Met Leu Val Tyr Gly Leu Leu
        50                  55                  60 aaa gat gcc ttc cat ttt gac acg tca tca tcg gac ttg agc tgt ctt      240
Lys Asp Ala Phe His Phe Asp Thr Ser Ser Ser Asp Leu Ser Cys Leu
65                  70                  75                  80 ttt gat ttt ccg gcg gtt aaa gtc gag cca act gag aac ttt acg gcg      288
Phe Asp Phe Pro Ala Val Lys Val Glu Pro Thr Glu Asn Phe Thr Ala
                85                  90                  95 atg gag gag aaa cca aag aaa gcg ata ccg gtt acg gag acg gca gtg      336
Met Glu Glu Lys Pro Lys Lys Ala Ile Pro Val Thr Glu Thr Ala Val
            100                 105                 110 aag gcg aag cat tac aga gga gtg agg cag aga ccg tgg ggg aaa ttc      384
Lys Ala Lys His Tyr Arg Gly Val Arg Gln Arg Pro Trp Gly Lys Phe
        115                 120                 125 gcg gcg gag ata cgt gat ccg gcg aag aat gga gct agg gtt tgg tta      432
Ala Ala Glu Ile Arg Asp Pro Ala Lys Asn Gly Ala Arg Val Trp Leu
130                 135                 140 ggg acg ttt gag acg gcg gaa gat gcg gct tta gct tac gat ata gct      480
Gly Thr Phe Glu Thr Ala Glu Asp Ala Ala Leu Ala Tyr Asp Ile Ala
145                 150                 155                 160 gct ttt agg atg cgt ggt tcc cgc gct tta ttg aat ttt ccg ttg agg      528
Ala Phe Arg Met Arg Gly Ser Arg Ala Leu Leu Asn Phe Pro Leu Arg
                165                 170                 175 gtt aat tcc ggt gaa cct gac ccg gtt cgg atc acg tct aag aga tct      576
Val Asn Ser Gly Glu Pro Asp Pro Val Arg Ile Thr Ser Lys Arg Ser
            180                 185                 190 tct tcg tcg tcg tcg tcg tcc tct tct acg tcg tcg tct gaa aac          624
Ser Ser Ser Ser Ser Ser Ser Ser Ser Thr Ser Ser Ser Glu Asn
        195                 200                 205 ggg aag ttg aaa cga agg aga aaa gca gag aat ctg acg tcg gag gtg      672
Gly Lys Leu Lys Arg Arg Arg Lys Ala Glu Asn Leu Thr Ser Glu Val
    210                 215                 220 gtg cag gtg aag tgt gag gtt ggt gat gag aca cgt gtt gat gag tta      720
Val Gln Val Lys Cys Glu Val Gly Asp Glu Thr Arg Val Asp Glu Leu
225                 230                 235                 240 ttg gtt tca taa                                                       732
Leu Val Ser <210> SEQ ID NO 48
<211> LENGTH: 243
<212> TYPE: PRT
<213> ORGANISM: Arabidopsis thaliana

<400> SEQUENCE: 48

Met Tyr Gly Gln Cys Asn Ile Glu Ser Asp Tyr Ala Leu Leu Glu Ser
1               5                   10                  15

Ile Thr Arg His Leu Leu Gly Gly Gly Glu Asn Glu Leu Arg Leu
                20                  25                  30

Asn Glu Ser Thr Pro Ser Ser Cys Phe Thr Glu Ser Trp Gly Gly Leu
```

```
                 35                  40                  45
Pro Leu Lys Glu Asn Asp Ser Glu Asp Met Leu Val Tyr Gly Leu Leu
     50                  55                  60

Lys Asp Ala Phe His Phe Asp Thr Ser Ser Asp Leu Ser Cys Leu
 65                  70                  75                  80

Phe Asp Phe Pro Ala Val Lys Val Glu Pro Thr Glu Asn Phe Thr Ala
                 85                  90                  95

Met Glu Glu Lys Pro Lys Lys Ala Ile Pro Val Thr Glu Thr Ala Val
                100                 105                 110

Lys Ala Lys His Tyr Arg Gly Val Arg Gln Arg Pro Trp Gly Lys Phe
                115                 120                 125

Ala Ala Glu Ile Arg Asp Pro Ala Lys Asn Gly Ala Arg Val Trp Leu
    130                 135                 140

Gly Thr Phe Glu Thr Ala Glu Asp Ala Ala Leu Ala Tyr Asp Ile Ala
145                 150                 155                 160

Ala Phe Arg Met Arg Gly Ser Arg Ala Leu Leu Asn Phe Pro Leu Arg
                165                 170                 175

Val Asn Ser Gly Glu Pro Asp Pro Val Arg Ile Thr Ser Lys Arg Ser
                180                 185                 190

Ser Ser Ser Ser Ser Ser Ser Ser Thr Ser Ser Ser Glu Asn
                195                 200                 205

Gly Lys Leu Lys Arg Arg Arg Lys Ala Glu Asn Leu Thr Ser Glu Val
    210                 215                 220

Val Gln Val Lys Cys Glu Val Gly Asp Glu Thr Arg Val Asp Glu Leu
225                 230                 235                 240

Leu Val Ser

<210> SEQ ID NO 49
<211> LENGTH: 747
<212> TYPE: DNA
<213> ORGANISM: Arabidopsis thaliana
<220> FEATURE:
<221> NAME/KEY: CDS
<222> LOCATION: (1)..(747)

<400> SEQUENCE: 49 atg gag ggt tcg tcc aaa ggg ctg cga aaa ggt gct tgg act act gaa      48
Met Glu Gly Ser Ser Lys Gly Leu Arg Lys Gly Ala Trp Thr Thr Glu
 1               5                  10                  15 gaa gat agt ctc ttg aga cag tgc att aat aag tat gga gaa ggc aaa      96
Glu Asp Ser Leu Leu Arg Gln Cys Ile Asn Lys Tyr Gly Glu Gly Lys
                 20                  25                  30 tgg cac caa gtt cct gta aga gct ggg cta aac cgg tgc agg aaa agt     144
Trp His Gln Val Pro Val Arg Ala Gly Leu Asn Arg Cys Arg Lys Ser
             35                  40                  45 tgt aga tta aga tgg ttg aac tat ttg aag cca agt atc aag aga gga     192
Cys Arg Leu Arg Trp Leu Asn Tyr Leu Lys Pro Ser Ile Lys Arg Gly
     50                  55                  60 aaa ctt agc tct gat gaa gtc gat ctt ctt ctt cgc ctt cat agg ctt     240
Lys Leu Ser Ser Asp Glu Val Asp Leu Leu Leu Arg Leu His Arg Leu
 65                  70                  75                  80 cta ggg aat agg tgg tct tta att gct gga aga tta cct ggt cgg acc     288
Leu Gly Asn Arg Trp Ser Leu Ile Ala Gly Arg Leu Pro Gly Arg Thr
                 85                  90                  95 gca aat gac gtc aag aat tac tgg aac act cat ctg agt aag aaa cat     336
Ala Asn Asp Val Lys Asn Tyr Trp Asn Thr His Leu Ser Lys Lys His
                100                 105                 110
```

```
gaa ccg tgt tgt aag ata aag atg aaa aag aga gac att acg ccc att       384
Glu Pro Cys Cys Lys Ile Lys Met Lys Lys Arg Asp Ile Thr Pro Ile
        115                 120                 125 cct aca aca ccg gca cta aaa aac aat gtt tat aag cct cga cct cga       432
Pro Thr Thr Pro Ala Leu Lys Asn Asn Val Tyr Lys Pro Arg Pro Arg
130                 135                 140 tcc ttc aca gtt aac aac gac tgc aac cat ctc aat gcc cca cca aaa       480
Ser Phe Thr Val Asn Asn Asp Cys Asn His Leu Asn Ala Pro Pro Lys
145                 150                 155                 160 gtt gac gtt aat cct cca tgc ctt gga ctt aac atc aat aat gtt tgt       528
Val Asp Val Asn Pro Pro Cys Leu Gly Leu Asn Ile Asn Asn Val Cys
                165                 170                 175 gac aat agt atc ata tac aac aaa gat aag aag aaa gac caa cta gtg       576
Asp Asn Ser Ile Ile Tyr Asn Lys Asp Lys Lys Lys Asp Gln Leu Val
            180                 185                 190 aat aat ttg att gat gga gat aat atg tgg tta gag aaa ttc cta gag       624
Asn Asn Leu Ile Asp Gly Asp Asn Met Trp Leu Glu Lys Phe Leu Glu
        195                 200                 205 gaa agc caa gag gta gat att ttg gtt cct gaa gcg acg aca aca gaa       672
Glu Ser Gln Glu Val Asp Ile Leu Val Pro Glu Ala Thr Thr Thr Glu
210                 215                 220 aag ggg gac acc ttg gct ttt gac gtt gat caa ctt tgg agt ctt ttc       720
Lys Gly Asp Thr Leu Ala Phe Asp Val Asp Gln Leu Trp Ser Leu Phe
225                 230                 235                 240 gat gga gag act gtg aaa ttt gat tag                                   747
Asp Gly Glu Thr Val Lys Phe Asp
                245

<210> SEQ ID NO 50
<211> LENGTH: 248
<212> TYPE: PRT
<213> ORGANISM: Arabidopsis thaliana

<400> SEQUENCE: 50

Met Glu Gly Ser Ser Lys Gly Leu Arg Lys Gly Ala Trp Thr Thr Glu
1               5                   10                  15

Glu Asp Ser Leu Leu Arg Gln Cys Ile Asn Lys Tyr Gly Glu Gly Lys
            20                  25                  30

Trp His Gln Val Pro Val Arg Ala Gly Leu Asn Arg Cys Arg Lys Ser
        35                  40                  45

Cys Arg Leu Arg Trp Leu Asn Tyr Leu Lys Pro Ser Ile Lys Arg Gly
    50                  55                  60

Lys Leu Ser Ser Asp Glu Val Asp Leu Leu Arg Leu His Arg Leu
65                  70                  75                  80

Leu Gly Asn Arg Trp Ser Leu Ile Ala Gly Arg Leu Pro Gly Arg Thr
                85                  90                  95

Ala Asn Asp Val Lys Asn Tyr Trp Asn Thr His Leu Ser Lys Lys His
            100                 105                 110

Glu Pro Cys Cys Lys Ile Lys Met Lys Lys Arg Asp Ile Thr Pro Ile
        115                 120                 125

Pro Thr Thr Pro Ala Leu Lys Asn Asn Val Tyr Lys Pro Arg Pro Arg
    130                 135                 140

Ser Phe Thr Val Asn Asn Asp Cys Asn His Leu Asn Ala Pro Pro Lys
145                 150                 155                 160

Val Asp Val Asn Pro Pro Cys Leu Gly Leu Asn Ile Asn Asn Val Cys
                165                 170                 175

Asp Asn Ser Ile Ile Tyr Asn Lys Asp Lys Lys Lys Asp Gln Leu Val
            180                 185                 190
```

-continued

```
Asn Asn Leu Ile Asp Gly Asp Asn Met Trp Leu Glu Lys Phe Leu Glu
        195                 200                 205

Glu Ser Gln Glu Val Asp Ile Leu Val Pro Glu Ala Thr Thr Thr Glu
    210                 215                 220

Lys Gly Asp Thr Leu Ala Phe Asp Val Asp Gln Leu Trp Ser Leu Phe
225                 230                 235                 240

Asp Gly Glu Thr Val Lys Phe Asp
                245
```

<210> SEQ ID NO 51
<211> LENGTH: 1113
<212> TYPE: DNA
<213> ORGANISM: Arabidopsis thaliana
<220> FEATURE:
<221> NAME/KEY: CDS
<222> LOCATION: (1)..(1113)

<400> SEQUENCE: 51

```
atg ggt cat cac tca tgc tgc aac cag caa aag gtg aag aga ggg ctt      48
Met Gly His His Ser Cys Cys Asn Gln Gln Lys Val Lys Arg Gly Leu
1               5                   10                  15 tgg tca ccg gaa gaa gat gag aag ctt att aga tat atc aca act cat      96
Trp Ser Pro Glu Glu Asp Glu Lys Leu Ile Arg Tyr Ile Thr Thr His
                20                  25                  30 ggc tat gga tgt tgg agt gaa gtc cct gaa aaa gca ggg ctt caa aga     144
Gly Tyr Gly Cys Trp Ser Glu Val Pro Glu Lys Ala Gly Leu Gln Arg
            35                  40                  45 tgt gga aaa agt tgt aga ttg cga tgg ata aac tat ctt cga cct gat     192
Cys Gly Lys Ser Cys Arg Leu Arg Trp Ile Asn Tyr Leu Arg Pro Asp
        50                  55                  60 atc agg aga gga agg ttc tct cca gaa gaa gag aaa ttg atc ata agc     240
Ile Arg Arg Gly Arg Phe Ser Pro Glu Glu Glu Lys Leu Ile Ile Ser
65                  70                  75                  80 ctt cat gga gtt gtg gga aac agg tgg gct cat ata gct agt cat tta     288
Leu His Gly Val Val Gly Asn Arg Trp Ala His Ile Ala Ser His Leu
                85                  90                  95 ccg gga aga aca gat aac gag att aaa aac tat tgg aat tca tgg att     336
Pro Gly Arg Thr Asp Asn Glu Ile Lys Asn Tyr Trp Asn Ser Trp Ile
                100                 105                 110 aag aaa aag ata cga aaa ccg cac cat cat tac agt cgt cat caa ccg     384
Lys Lys Lys Ile Arg Lys Pro His His His Tyr Ser Arg His Gln Pro
            115                 120                 125 tca gta act act gtg aca ttg aat gcg gac act aca tcg att gcc act     432
Ser Val Thr Thr Val Thr Leu Asn Ala Asp Thr Thr Ser Ile Ala Thr
        130                 135                 140 acc atc gag gcc tct acc acc aca aca tcg act atc gat aac tta cat     480
Thr Ile Glu Ala Ser Thr Thr Thr Thr Ser Thr Ile Asp Asn Leu His
145                 150                 155                 160 ttt gac ggt ttc act gat tct cct aac caa tta aat ttc acc aat gat     528
Phe Asp Gly Phe Thr Asp Ser Pro Asn Gln Leu Asn Phe Thr Asn Asp
                165                 170                 175 caa gaa act aat ata aag att caa gaa act ttt ttc tcc cat aaa cct     576
Gln Glu Thr Asn Ile Lys Ile Gln Glu Thr Phe Phe Ser His Lys Pro
                180                 185                 190 cct ctc ttc atg gta gac aca aca ctt cct atc cta gaa gga atg ttc     624
Pro Leu Phe Met Val Asp Thr Thr Leu Pro Ile Leu Glu Gly Met Phe
            195                 200                 205 tct gaa aac atc atc aca aac aat aac aag aac aat gat cat gat gac     672
Ser Glu Asn Ile Ile Thr Asn Asn Asn Lys Asn Asn Asp His Asp Asp
        210                 215                 220
```

-continued

```
acg caa aga gga gga aga gaa aat gtt tgt gaa caa gca ttt cta aca      720
Thr Gln Arg Gly Gly Arg Glu Asn Val Cys Glu Gln Ala Phe Leu Thr
225                 230                 235                 240 act aac acg gaa gaa tgg gat atg aat ctt cgt cag caa gag ccg ttt      768
Thr Asn Thr Glu Glu Trp Asp Met Asn Leu Arg Gln Gln Glu Pro Phe
            245                 250                 255 caa gtt cct aca ctg gcg tca cat gtg ttc aac aac tct tcc aat tca      816
Gln Val Pro Thr Leu Ala Ser His Val Phe Asn Asn Ser Ser Asn Ser
        260                 265                 270 aat att gac acg gtt ata agt tat aat cta ccg gcg cta ata gag gga      864
Asn Ile Asp Thr Val Ile Ser Tyr Asn Leu Pro Ala Leu Ile Glu Gly
    275                 280                 285 aat gtc gat aac atc gtc cat aat gaa aac agc aat gtc caa gat gga      912
Asn Val Asp Asn Ile Val His Asn Glu Asn Ser Asn Val Gln Asp Gly
290                 295                 300 gaa atg gcg tcc aca ttc gaa tgt tta aag agg caa gaa cta agc tat      960
Glu Met Ala Ser Thr Phe Glu Cys Leu Lys Arg Gln Glu Leu Ser Tyr
305                 310                 315                 320 gat caa tgg gac gat tca caa caa tgc tct aac ttt ttc ttt tgg gac     1008
Asp Gln Trp Asp Asp Ser Gln Gln Cys Ser Asn Phe Phe Phe Trp Asp
            325                 330                 335 aac ctt aat ata aac gtg gaa ggt tca tct ctt gtt gga aac caa gac     1056
Asn Leu Asn Ile Asn Val Glu Gly Ser Ser Leu Val Gly Asn Gln Asp
        340                 345                 350 cca tca atg aat ttg gga tca tct gcc tta tct tct tct ttc cct tct     1104
Pro Ser Met Asn Leu Gly Ser Ser Ala Leu Ser Ser Ser Phe Pro Ser
    355                 360                 365 tcg ttt taa                                                          1113
Ser Phe
    370

<210> SEQ ID NO 52
<211> LENGTH: 370
<212> TYPE: PRT
<213> ORGANISM: Arabidopsis thaliana

<400> SEQUENCE: 52

Met Gly His His Ser Cys Cys Asn Gln Gln Lys Val Lys Arg Gly Leu
1               5                   10                  15

Trp Ser Pro Glu Glu Asp Glu Lys Leu Ile Arg Tyr Ile Thr Thr His
            20                  25                  30

Gly Tyr Gly Cys Trp Ser Glu Val Pro Glu Lys Ala Gly Leu Gln Arg
        35                  40                  45

Cys Gly Lys Ser Cys Arg Leu Arg Trp Ile Asn Tyr Leu Arg Pro Asp
    50                  55                  60

Ile Arg Arg Gly Arg Phe Ser Pro Glu Glu Lys Leu Ile Ile Ser
65                  70                  75                  80

Leu His Gly Val Val Gly Asn Arg Trp Ala His Ile Ala Ser His Leu
                85                  90                  95

Pro Gly Arg Thr Asp Asn Glu Ile Lys Asn Tyr Trp Asn Ser Trp Ile
            100                 105                 110

Lys Lys Lys Ile Arg Lys Pro His His Tyr Ser Arg His Gln Pro
        115                 120                 125

Ser Val Thr Thr Val Thr Leu Asn Ala Asp Thr Thr Ser Ile Ala Thr
    130                 135                 140

Thr Ile Glu Ala Ser Thr Thr Thr Thr Ser Thr Ile Asp Asn Leu His
145                 150                 155                 160
```

```
Phe Asp Gly Phe Thr Asp Ser Pro Asn Gln Leu Asn Phe Thr Asn Asp
                165                 170                 175

Gln Glu Thr Asn Ile Lys Ile Gln Glu Thr Phe Phe Ser His Lys Pro
            180                 185                 190

Pro Leu Phe Met Val Asp Thr Thr Leu Pro Ile Leu Glu Gly Met Phe
        195                 200                 205

Ser Glu Asn Ile Ile Thr Asn Asn Lys Asn Asn Asp His Asp Asp
    210                 215                 220

Thr Gln Arg Gly Gly Arg Glu Asn Val Cys Glu Gln Ala Phe Leu Thr
225                 230                 235                 240

Thr Asn Thr Glu Glu Trp Asp Met Asn Leu Arg Gln Gln Glu Pro Phe
                245                 250                 255

Gln Val Pro Thr Leu Ala Ser His Val Phe Asn Asn Ser Ser Asn Ser
            260                 265                 270

Asn Ile Asp Thr Val Ile Ser Tyr Asn Leu Pro Ala Leu Ile Glu Gly
        275                 280                 285

Asn Val Asp Asn Ile Val His Asn Glu Asn Ser Asn Val Gln Asp Gly
    290                 295                 300

Glu Met Ala Ser Thr Phe Glu Cys Leu Lys Arg Gln Glu Leu Ser Tyr
305                 310                 315                 320

Asp Gln Trp Asp Asp Ser Gln Gln Cys Ser Asn Phe Phe Trp Asp
                325                 330                 335

Asn Leu Asn Ile Asn Val Glu Gly Ser Ser Leu Val Gly Asn Gln Asp
                340                 345                 350

Pro Ser Met Asn Leu Gly Ser Ser Ala Leu Ser Ser Ser Phe Pro Ser
            355                 360                 365

Ser Phe
    370

<210> SEQ ID NO 53
<211> LENGTH: 1095
<212> TYPE: DNA
<213> ORGANISM: Arabidopsis thaliana
<220> FEATURE:
<221> NAME/KEY: CDS
<222> LOCATION: (1)..(1095)

<400> SEQUENCE: 53 atg gag agc acc gat tct tcc ggt ggt cca cca ccg cca caa cct aac      48
Met Glu Ser Thr Asp Ser Ser Gly Gly Pro Pro Pro Pro Gln Pro Asn
1               5                   10                  15 ctt cct cca ggc ttc cgg ttt cac cct acc gac gaa gag ctt gtt gtt      96
Leu Pro Pro Gly Phe Arg Phe His Pro Thr Asp Glu Glu Leu Val Val
            20                  25                  30 cac tac ctc aaa cgc aaa gca gcc tct gct cct tta cct gtc gcc atc     144
His Tyr Leu Lys Arg Lys Ala Ala Ser Ala Pro Leu Pro Val Ala Ile
        35                  40                  45 atc gcc gaa gtc gat ctc tat aaa ttt gat cca tgg gaa ctt ccc gct     192
Ile Ala Glu Val Asp Leu Tyr Lys Phe Asp Pro Trp Glu Leu Pro Ala
    50                  55                  60 aaa gca tcg ttt gga gaa caa gaa tgg tac ttc ttt agt cca cga gat     240
Lys Ala Ser Phe Gly Glu Gln Glu Trp Tyr Phe Phe Ser Pro Arg Asp
65                  70                  75                  80 cgg aag tat cca aac gga gca aga cca aac aga gcg gcg act tca ggt     288
Arg Lys Tyr Pro Asn Gly Ala Arg Pro Asn Arg Ala Ala Thr Ser Gly
                85                  90                  95 tat tgg aaa gcg acc ggt aca gat aaa ccg gta ctt gct tcc gac ggt     336
Tyr Trp Lys Ala Thr Gly Thr Asp Lys Pro Val Leu Ala Ser Asp Gly
```

```
aac caa aag gtg ggc gtg aag aag gca cta gtc ttc tac agt ggt aaa    384
Asn Gln Lys Val Gly Val Lys Lys Ala Leu Val Phe Tyr Ser Gly Lys
        115                 120                 125 cca cca aaa ggc gtt aaa agt gat tgg atc atg cat gag tat cgt ctc    432
Pro Pro Lys Gly Val Lys Ser Asp Trp Ile Met His Glu Tyr Arg Leu
130                 135                 140 atc gaa aac aaa cca aac aat cga cct cct ggc tgt gat ttc ggc aac    480
Ile Glu Asn Lys Pro Asn Asn Arg Pro Pro Gly Cys Asp Phe Gly Asn
145                 150                 155                 160 aaa aaa aac tca ctc aga ctt gat gat tgg gtg tta tgt aga atc tac    528
Lys Lys Asn Ser Leu Arg Leu Asp Asp Trp Val Leu Cys Arg Ile Tyr
            165                 170                 175 aag aag aac aac gca agt cga cat gtt gat aac gat aag gat cat gat    576
Lys Lys Asn Asn Ala Ser Arg His Val Asp Asn Asp Lys Asp His Asp
        180                 185                 190 atg atc gat tac att ttc agg aag att cct ccg tct tta tca atg gcg    624
Met Ile Asp Tyr Ile Phe Arg Lys Ile Pro Pro Ser Leu Ser Met Ala
    195                 200                 205 gct gct tct aca gga ctt cac caa cat cat cat aat gtc tca aga tca    672
Ala Ala Ser Thr Gly Leu His Gln His His His Asn Val Ser Arg Ser
210                 215                 220 atg aat ttc ttc cct ggc aaa ttc tcc ggt ggt ggt tac ggg att ttc    720
Met Asn Phe Phe Pro Gly Lys Phe Ser Gly Gly Gly Tyr Gly Ile Phe
225                 230                 235                 240 tct gac ggt ggt aac acg agt ata tac gac ggc ggt ggc atg atc aac    768
Ser Asp Gly Gly Asn Thr Ser Ile Tyr Asp Gly Gly Gly Met Ile Asn
            245                 250                 255 aat att ggt act gac tca gta gat cac gac aat aac gct gac gtc gtt    816
Asn Ile Gly Thr Asp Ser Val Asp His Asp Asn Asn Ala Asp Val Val
        260                 265                 270 ggt tta aat cat gct tcg tcg tca ggt cct atg atg atg gcg aat ttg    864
Gly Leu Asn His Ala Ser Ser Ser Gly Pro Met Met Met Ala Asn Leu
    275                 280                 285 aaa cga act ctc ccg gtg ccg tat tgg cct gta gca gat gag gag caa    912
Lys Arg Thr Leu Pro Val Pro Tyr Trp Pro Val Ala Asp Glu Glu Gln
290                 295                 300 gat gca tct ccg agc aaa cgg ttt cac ggt gta gga gga gga gga          960
Asp Ala Ser Pro Ser Lys Arg Phe His Gly Val Gly Gly Gly Gly Gly
305                 310                 315                 320 gat tgt tcg aac atg tct tcc tcc atg atg gaa gag act cca cca ttg    1008
Asp Cys Ser Asn Met Ser Ser Ser Met Met Glu Glu Thr Pro Pro Leu
            325                 330                 335 atg caa caa caa ggt ggt gtg tta gga gat gga tta ttc aga acg aca    1056
Met Gln Gln Gln Gly Gly Val Leu Gly Asp Gly Leu Phe Arg Thr Thr
        340                 345                 350 tcg tac caa tta ccc ggt tta aat tgg tac tct tct taa                1095
Ser Tyr Gln Leu Pro Gly Leu Asn Trp Tyr Ser Ser
    355                 360

<210> SEQ ID NO 54
<211> LENGTH: 364
<212> TYPE: PRT
<213> ORGANISM: Arabidopsis thaliana

<400> SEQUENCE: 54

Met Glu Ser Thr Asp Ser Ser Gly Gly Pro Pro Pro Gln Pro Asn
1               5                   10                  15

Leu Pro Pro Gly Phe Arg Phe His Pro Thr Asp Glu Glu Leu Val Val
            20                  25                  30
```

His Tyr Leu Lys Arg Lys Ala Ala Ser Ala Pro Leu Pro Val Ala Ile
            35                  40                  45

Ile Ala Glu Val Asp Leu Tyr Lys Phe Asp Pro Trp Glu Leu Pro Ala
 50                  55                  60

Lys Ala Ser Phe Gly Glu Gln Glu Trp Tyr Phe Phe Ser Pro Arg Asp
 65                  70                  75                  80

Arg Lys Tyr Pro Asn Gly Ala Arg Pro Asn Arg Ala Ala Thr Ser Gly
                85                  90                  95

Tyr Trp Lys Ala Thr Gly Thr Asp Lys Pro Val Leu Ala Ser Asp Gly
                100                 105                 110

Asn Gln Lys Val Gly Val Lys Lys Ala Leu Val Phe Tyr Ser Gly Lys
                115                 120                 125

Pro Pro Lys Gly Val Lys Ser Asp Trp Ile Met His Glu Tyr Arg Leu
                130                 135                 140

Ile Glu Asn Lys Pro Asn Asn Arg Pro Pro Gly Cys Asp Phe Gly Asn
145                 150                 155                 160

Lys Lys Asn Ser Leu Arg Leu Asp Asp Trp Val Leu Cys Arg Ile Tyr
                165                 170                 175

Lys Lys Asn Asn Ala Ser Arg His Val Asp Asn Asp Lys Asp His Asp
                180                 185                 190

Met Ile Asp Tyr Ile Phe Arg Lys Ile Pro Pro Ser Leu Ser Met Ala
                195                 200                 205

Ala Ala Ser Thr Gly Leu His Gln His His Asn Val Ser Arg Ser
                210                 215                 220

Met Asn Phe Phe Pro Gly Lys Phe Ser Gly Gly Tyr Gly Ile Phe
225                 230                 235                 240

Ser Asp Gly Gly Asn Thr Ser Ile Tyr Asp Gly Gly Met Ile Asn
                245                 250                 255

Asn Ile Gly Thr Asp Ser Val Asp His Asp Asn Asn Ala Asp Val Val
                260                 265                 270

Gly Leu Asn His Ala Ser Ser Ser Gly Pro Met Met Met Ala Asn Leu
                275                 280                 285

Lys Arg Thr Leu Pro Val Pro Tyr Trp Pro Val Ala Asp Glu Glu Gln
290                 295                 300

Asp Ala Ser Pro Ser Lys Arg Phe His Gly Val Gly Gly Gly Gly
305                 310                 315                 320

Asp Cys Ser Asn Met Ser Ser Ser Met Met Glu Glu Thr Pro Pro Leu
                325                 330                 335

Met Gln Gln Gln Gly Gly Val Leu Gly Asp Gly Leu Phe Arg Thr Thr
                340                 345                 350

Ser Tyr Gln Leu Pro Gly Leu Asn Trp Tyr Ser Ser
                355                 360

<210> SEQ ID NO 55
<211> LENGTH: 1071
<212> TYPE: DNA
<213> ORGANISM: Arabidopsis thaliana
<220> FEATURE:
<221> NAME/KEY: CDS
<222> LOCATION: (1)..(1071)

<400> SEQUENCE: 55 atg gcg aca att cag aag ctt gaa gaa gtt gca ggc aaa gat caa act         48
Met Ala Thr Ile Gln Lys Leu Glu Glu Val Ala Gly Lys Asp Gln Thr
1               5                   10                  15

| | |
|---|---|
| cta aga gcc gtt gat cta acc atc atc aac ggc gtc aga aac gtc gaa<br>Leu Arg Ala Val Asp Leu Thr Ile Ile Asn Gly Val Arg Asn Val Glu<br>     20                     25                   30 | 96 |
| act tca aga cct ttc caa gta aat ccc aca gtg agt ctc gag ccc aag<br>Thr Ser Arg Pro Phe Gln Val Asn Pro Thr Val Ser Leu Glu Pro Lys<br>        35                   40                   45 | 144 |
| gcg gag ccg gtg atg ccg tcg ttt tca atg tct tta gct cca ccg tct<br>Ala Glu Pro Val Met Pro Ser Phe Ser Met Ser Leu Ala Pro Pro Ser<br>50                    55                   60 | 192 |
| tcg aca gga cca cca ttg aag aga gct tcg act aaa gac cgt cac acg<br>Ser Thr Gly Pro Pro Leu Lys Arg Ala Ser Thr Lys Asp Arg His Thr<br>65                    70                   75                   80 | 240 |
| aag gtt gaa gga aga ggg aga agg ata cgg atg cct gcc acg tgt gcg<br>Lys Val Glu Gly Arg Gly Arg Arg Ile Arg Met Pro Ala Thr Cys Ala<br>               85                   90                   95 | 288 |
| gct agg att ttt caa tta act cga gag tta ggt cac aaa tcc gac ggc<br>Ala Arg Ile Phe Gln Leu Thr Arg Glu Leu Gly His Lys Ser Asp Gly<br>              100                  105                  110 | 336 |
| gaa acg att cgg tgg ttg ttg gag aac gct gag ccg gcg att ata gcc<br>Glu Thr Ile Arg Trp Leu Leu Glu Asn Ala Glu Pro Ala Ile Ile Ala<br>        115                  120                  125 | 384 |
| gcc acg ggt acg gga acg gtt ccc gcc atc gcc atg tcg gtt aac gga<br>Ala Thr Gly Thr Gly Thr Val Pro Ala Ile Ala Met Ser Val Asn Gly<br>130                     135                  140 | 432 |
| acc tta aaa atc ccg acg acg acg aac gct gat tct gat atg ggt gaa<br>Thr Leu Lys Ile Pro Thr Thr Thr Asn Ala Asp Ser Asp Met Gly Glu<br>145                     150                  155                  160 | 480 |
| aat ctg atg aag aag aaa cgt aaa cga cct tct aac agt gag tat ata<br>Asn Leu Met Lys Lys Lys Arg Lys Arg Pro Ser Asn Ser Glu Tyr Ile<br>              165                  170                  175 | 528 |
| gac ata agc gac gcc gtt tca gct tcc tcc ggt tta gct cca att gcc<br>Asp Ile Ser Asp Ala Val Ser Ala Ser Ser Gly Leu Ala Pro Ile Ala<br>            180                  185                  190 | 576 |
| acg acg aca acg atc caa cct ccg caa gct ctg gca tca tcc act gtg<br>Thr Thr Thr Thr Ile Gln Pro Pro Gln Ala Leu Ala Ser Ser Thr Val<br>        195                  200                  205 | 624 |
| gct cag caa ctt ctg ccg caa gga atg tat ccg atg tgg gct att cca<br>Ala Gln Gln Leu Leu Pro Gln Gly Met Tyr Pro Met Trp Ala Ile Pro<br>210                     215                  220 | 672 |
| tca aac gca atg att ccg acg gtc gga gct ttc ttc ttg att cca caa<br>Ser Asn Ala Met Ile Pro Thr Val Gly Ala Phe Phe Leu Ile Pro Gln<br>225                   230                  235                  240 | 720 |
| atc gct ggt ccg tcg aat cag cct cag tta tta gct ttt ccc gcc gcc<br>Ile Ala Gly Pro Ser Asn Gln Pro Gln Leu Leu Ala Phe Pro Ala Ala<br>              245                  250                  255 | 768 |
| gct gct tcg ccg tcg tct tac gtc gcc gct gtt caa cag gct tcc acg<br>Ala Ala Ser Pro Ser Ser Tyr Val Ala Ala Val Gln Gln Ala Ser Thr<br>            260                  265                  270 | 816 |
| atg gct aga cca cct cct tta caa gtt gtt cca agc agc ggc ttt gta<br>Met Ala Arg Pro Pro Pro Leu Gln Val Val Pro Ser Ser Gly Phe Val<br>        275                  280                  285 | 864 |
| tcc gtt tca gac gtt agc ggt tcg aat tta tca aga gcg acg tcg gtt<br>Ser Val Ser Asp Val Ser Gly Ser Asn Leu Ser Arg Ala Thr Ser Val<br>290                     295                  300 | 912 |
| atg gct ccg agc tca agc tca ggc gta aca acc ggt agt tca tcg tca<br>Met Ala Pro Ser Ser Ser Ser Gly Val Thr Thr Gly Ser Ser Ser Ser<br>305                     310                  315                  320 | 960 |
| att gca aca aca acg acg cac acg ctg aga gac ttc tcc cta gag ata<br>Ile Ala Thr Thr Thr Thr His Thr Leu Arg Asp Phe Ser Leu Glu Ile<br>              325                  330                  335 | 1008 |

```
tac gag aaa caa gag ctt cac cag ttc atg agc acc aca aca gca cgg    1056
Tyr Glu Lys Gln Glu Leu His Gln Phe Met Ser Thr Thr Thr Ala Arg
            340                 345                 350 tca tcg aac cac tga                                                1071
Ser Ser Asn His
            355

<210> SEQ ID NO 56
<211> LENGTH: 356
<212> TYPE: PRT
<213> ORGANISM: Arabidopsis thaliana

<400> SEQUENCE: 56

Met Ala Thr Ile Gln Lys Leu Glu Glu Val Ala Gly Lys Asp Gln Thr
1               5                   10                  15

Leu Arg Ala Val Asp Leu Thr Ile Ile Asn Gly Val Arg Asn Val Glu
            20                  25                  30

Thr Ser Arg Pro Phe Gln Val Asn Pro Thr Val Ser Leu Glu Pro Lys
        35                  40                  45

Ala Glu Pro Val Met Pro Ser Phe Ser Met Ser Leu Ala Pro Pro Ser
    50                  55                  60

Ser Thr Gly Pro Pro Leu Lys Arg Ala Ser Thr Lys Asp Arg His Thr
65                  70                  75                  80

Lys Val Glu Gly Arg Gly Arg Arg Ile Arg Met Pro Ala Thr Cys Ala
                85                  90                  95

Ala Arg Ile Phe Gln Leu Thr Arg Glu Leu Gly His Lys Ser Asp Gly
            100                 105                 110

Glu Thr Ile Arg Trp Leu Leu Glu Asn Ala Glu Pro Ala Ile Ile Ala
        115                 120                 125

Ala Thr Gly Thr Gly Thr Val Pro Ala Ile Ala Met Ser Val Asn Gly
    130                 135                 140

Thr Leu Lys Ile Pro Thr Thr Asn Ala Asp Ser Asp Met Gly Glu
145                 150                 155                 160

Asn Leu Met Lys Lys Lys Arg Lys Arg Pro Ser Asn Ser Glu Tyr Ile
                165                 170                 175

Asp Ile Ser Asp Ala Val Ser Ala Ser Ser Gly Leu Ala Pro Ile Ala
            180                 185                 190

Thr Thr Thr Thr Ile Gln Pro Pro Gln Ala Leu Ala Ser Ser Thr Val
        195                 200                 205

Ala Gln Gln Leu Leu Pro Gln Gly Met Tyr Pro Met Trp Ala Ile Pro
    210                 215                 220

Ser Asn Ala Met Ile Pro Thr Val Gly Ala Phe Phe Leu Ile Pro Gln
225                 230                 235                 240

Ile Ala Gly Pro Ser Asn Gln Pro Gln Leu Leu Ala Phe Pro Ala Ala
                245                 250                 255

Ala Ala Ser Pro Ser Ser Tyr Val Ala Ala Val Gln Gln Ala Ser Thr
            260                 265                 270

Met Ala Arg Pro Pro Leu Gln Val Val Pro Ser Ser Gly Phe Val
        275                 280                 285

Ser Val Ser Asp Val Ser Gly Ser Asn Leu Ser Arg Ala Thr Ser Val
    290                 295                 300

Met Ala Pro Ser Ser Ser Ser Gly Val Thr Thr Gly Ser Ser Ser Ser
305                 310                 315                 320

Ile Ala Thr Thr Thr Thr His Thr Leu Arg Asp Phe Ser Leu Glu Ile
                325                 330                 335
```

```
                    Tyr Glu Lys Gln Glu Leu His Gln Phe Met Ser Thr Thr Thr Ala Arg
                                    340                 345                 350

Ser Ser Asn His
                            355

<210> SEQ ID NO 57
<211> LENGTH: 732
<212> TYPE: DNA
<213> ORGANISM: Arabidopsis thaliana
<220> FEATURE:
<221> NAME/KEY: CDS
<222> LOCATION: (1)..(732)

<400> SEQUENCE: 57 atg gaa tat tcc caa tct tcc atg tat tca tct cca agt tct tgg agc        48
Met Glu Tyr Ser Gln Ser Ser Met Tyr Ser Ser Pro Ser Ser Trp Ser
1               5                   10                  15 tca tca caa gaa tca ctc tta tgg aac gag agc tgt ttc ttg gat caa        96
Ser Ser Gln Glu Ser Leu Leu Trp Asn Glu Ser Cys Phe Leu Asp Gln
                20                  25                  30 tca tct gaa cct caa gcc ttc ttt tgc cct aat tat gat tac tcc gat       144
Ser Ser Glu Pro Gln Ala Phe Phe Cys Pro Asn Tyr Asp Tyr Ser Asp
            35                  40                  45 gac ttt ttc tca ttt gag tca ccg gag atg atg att aag gaa gaa att       192
Asp Phe Phe Ser Phe Glu Ser Pro Glu Met Met Ile Lys Glu Glu Ile
        50                  55                  60 caa aac ggc gac gtt tct aac tcc gaa gaa gaa aag gtt gga att           240
Gln Asn Gly Asp Val Ser Asn Ser Glu Glu Glu Lys Val Gly Ile
65                  70                  75                  80 gat gaa gaa aga tca tac aga gga gtg agg aaa agg ccg tgg ggg aaa       288
Asp Glu Glu Arg Ser Tyr Arg Gly Val Arg Lys Arg Pro Trp Gly Lys
                85                  90                  95 ttt gca gcg gag ata aga gat tca acg agg aat gga att agg gtt tgg       336
Phe Ala Ala Glu Ile Arg Asp Ser Thr Arg Asn Gly Ile Arg Val Trp
            100                 105                 110 ctc ggg aca ttt gac aaa gcc gag gaa gcc gct ctt gct tat gat caa       384
Leu Gly Thr Phe Asp Lys Ala Glu Glu Ala Ala Leu Ala Tyr Asp Gln
        115                 120                 125 gcg gct ttc gcc aca aaa gga tct ctt gca aca ctt aat ttc ccg gtg       432
Ala Ala Phe Ala Thr Lys Gly Ser Leu Ala Thr Leu Asn Phe Pro Val
    130                 135                 140 gaa gtg gtt aga gag tcg cta aag aaa atg gag aat gtg aat ctt cat       480
Glu Val Val Arg Glu Ser Leu Lys Lys Met Glu Asn Val Asn Leu His
145                 150                 155                 160 gat gga gga tct ccg gtt atg gcc ttg aag aga aaa cat tct ctt cga       528
Asp Gly Gly Ser Pro Val Met Ala Leu Lys Arg Lys His Ser Leu Arg
                165                 170                 175 aac cgg cct aga ggg aaa aag cga tcc tct tct tct tct tct tct tct       576
Asn Arg Pro Arg Gly Lys Lys Arg Ser Ser Ser Ser Ser Ser Ser Ser
            180                 185                 190 tct aat tct tct tct tgc tct tct tct tcg tct act tct tca aca tca       624
Ser Asn Ser Ser Ser Cys Ser Ser Ser Ser Thr Ser Ser Thr Ser
        195                 200                 205 aga agt agt agt aag cag agt gtt gtg aag caa gaa agt ggt aca ctt       672
Arg Ser Ser Ser Lys Gln Ser Val Val Lys Gln Glu Ser Gly Thr Leu
    210                 215                 220 gtg gtt ttt gaa gat tta ggt gct gag tat tta gaa caa ctt ctt atg       720
Val Val Phe Glu Asp Leu Gly Ala Glu Tyr Leu Glu Gln Leu Leu Met
225                 230                 235                 240 agc tca tgt tga                                                       732
```

Ser Ser Cys

<210> SEQ ID NO 58
<211> LENGTH: 243
<212> TYPE: PRT
<213> ORGANISM: Arabidopsis thaliana

<400> SEQUENCE: 58

```
Met Glu Tyr Ser Gln Ser Ser Met Tyr Ser Ser Pro Ser Ser Trp Ser
1               5                   10                  15

Ser Ser Gln Glu Ser Leu Leu Trp Asn Glu Ser Cys Phe Leu Asp Gln
            20                  25                  30

Ser Ser Glu Pro Gln Ala Phe Phe Cys Pro Asn Tyr Asp Tyr Ser Asp
        35                  40                  45

Asp Phe Phe Ser Phe Glu Ser Pro Glu Met Met Ile Lys Glu Glu Ile
    50                  55                  60

Gln Asn Gly Asp Val Ser Asn Ser Glu Glu Glu Lys Val Gly Ile
65                  70                  75                  80

Asp Glu Glu Arg Ser Tyr Arg Gly Val Arg Lys Arg Pro Trp Gly Lys
                85                  90                  95

Phe Ala Ala Glu Ile Arg Asp Ser Thr Arg Asn Gly Ile Arg Val Trp
            100                 105                 110

Leu Gly Thr Phe Asp Lys Ala Glu Glu Ala Ala Leu Ala Tyr Asp Gln
        115                 120                 125

Ala Ala Phe Ala Thr Lys Gly Ser Leu Ala Thr Leu Asn Phe Pro Val
    130                 135                 140

Glu Val Val Arg Glu Ser Leu Lys Lys Met Glu Asn Val Asn Leu His
145                 150                 155                 160

Asp Gly Gly Ser Pro Val Met Ala Leu Lys Arg Lys His Ser Leu Arg
                165                 170                 175

Asn Arg Pro Arg Gly Lys Lys Arg Ser Ser Ser Ser Ser Ser Ser Ser
            180                 185                 190

Ser Asn Ser Ser Ser Cys Ser Ser Ser Ser Thr Ser Ser Thr Ser
        195                 200                 205

Arg Ser Ser Lys Gln Ser Val Val Lys Gln Glu Ser Gly Thr Leu
    210                 215                 220

Val Val Phe Glu Asp Leu Gly Ala Glu Tyr Leu Glu Gln Leu Leu Met
225                 230                 235                 240

Ser Ser Cys
```

<210> SEQ ID NO 59
<211> LENGTH: 1188
<212> TYPE: DNA
<213> ORGANISM: Arabidopsis thaliana
<220> FEATURE:
<221> NAME/KEY: CDS
<222> LOCATION: (1)..(1188)

<400> SEQUENCE: 59

```
atg aat tca ttt tcc cac gtc cct ccg ggt ttt aga ttt cac ccg aca      48
Met Asn Ser Phe Ser His Val Pro Pro Gly Phe Arg Phe His Pro Thr
1               5                   10                  15 gat gaa gaa ctt gta gac tac tac ctg agg aaa aaa gtc gca tcg aag      96
Asp Glu Glu Leu Val Asp Tyr Tyr Leu Arg Lys Lys Val Ala Ser Lys
                20                  25                  30 aga ata gaa att gat ttc ata aag gac att gat ctt tac aag att gag     144
Arg Ile Glu Ile Asp Phe Ile Lys Asp Ile Asp Leu Tyr Lys Ile Glu
            35                  40                  45
```

```
cca tgg gac ctt caa gag ttg tgc aaa att ggg cat gaa gag cag agt     192
Pro Trp Asp Leu Gln Glu Leu Cys Lys Ile Gly His Glu Glu Gln Ser
        50                  55                  60 gat tgg tac ttc ttt agc cat aaa gac aag aag tat ccc aca ggg act     240
Asp Trp Tyr Phe Phe Ser His Lys Asp Lys Lys Tyr Pro Thr Gly Thr
 65                  70                  75                  80 cga acc aat aga gca aca aaa gca ggg ttt tgg aaa gcc acc gga aga     288
Arg Thr Asn Arg Ala Thr Lys Ala Gly Phe Trp Lys Ala Thr Gly Arg
                 85                  90                  95 gat aag gct atc tat ttg agg cat agt cta att ggc atg agg aaa aca     336
Asp Lys Ala Ile Tyr Leu Arg His Ser Leu Ile Gly Met Arg Lys Thr
            100                 105                 110 ctt gtg ttt tac aag gga aga gcc cca aat gga caa aag tct gat tgg     384
Leu Val Phe Tyr Lys Gly Arg Ala Pro Asn Gly Gln Lys Ser Asp Trp
        115                 120                 125 atc atg cac gaa tac cgc tta gaa acc gat gaa aac gga act cct cag     432
Ile Met His Glu Tyr Arg Leu Glu Thr Asp Glu Asn Gly Thr Pro Gln
130                 135                 140 gaa gaa gga tgg gtt gtg tgt agg gtt ttc aag aag aga ttg gct gca     480
Glu Glu Gly Trp Val Val Cys Arg Val Phe Lys Lys Arg Leu Ala Ala
145                 150                 155                 160 gtt aga cga atg gga gat tac gac tca tcc cct tca cat tgg tac gat     528
Val Arg Arg Met Gly Asp Tyr Asp Ser Ser Pro Ser His Trp Tyr Asp
                165                 170                 175 gat caa ctt tct ttt atg gcc tcc gag ctc gag aca aac ggt caa cga     576
Asp Gln Leu Ser Phe Met Ala Ser Glu Leu Glu Thr Asn Gly Gln Arg
            180                 185                 190 cgg att ctc ccc aat cat cat cag cag cag cag cac gag cac caa caa     624
Arg Ile Leu Pro Asn His His Gln Gln Gln Gln His Glu His Gln Gln
        195                 200                 205 cat atg cca tat ggc ctc aat gca tct gct tac gct ctc aac aac cct     672
His Met Pro Tyr Gly Leu Asn Ala Ser Ala Tyr Ala Leu Asn Asn Pro
210                 215                 220 aac ttg caa tgc aag caa gag cta gaa cta cac tac aac cac ctg gta     720
Asn Leu Gln Cys Lys Gln Glu Leu Glu Leu His Tyr Asn His Leu Val
225                 230                 235                 240 caa cga aat cat ctt ctt gat gaa tct cat tta tcg ttc ctc caa ctt     768
Gln Arg Asn His Leu Leu Asp Glu Ser His Leu Ser Phe Leu Gln Leu
                245                 250                 255 cct caa cta gaa agc cct aag att caa caa gat aac agt aat tgc aac     816
Pro Gln Leu Glu Ser Pro Lys Ile Gln Gln Asp Asn Ser Asn Cys Asn
            260                 265                 270 tct ctt cct tat gga aca agc aac atc gat aat aac tcg agc cat aat     864
Ser Leu Pro Tyr Gly Thr Ser Asn Ile Asp Asn Asn Ser Ser His Asn
        275                 280                 285 gct aac ttg cag caa tca aat atc gcg cat gag gaa caa ttg aat caa     912
Ala Asn Leu Gln Gln Ser Asn Ile Ala His Glu Glu Gln Leu Asn Gln
290                 295                 300 gga aat cag aac ttc agc tct cta tac atg aac agc ggc aac gag caa     960
Gly Asn Gln Asn Phe Ser Ser Leu Tyr Met Asn Ser Gly Asn Glu Gln
305                 310                 315                 320 gtg atg gac caa gtc aca gac tgg aga gtt ctc gat aaa ttt gtt gct    1008
Val Met Asp Gln Val Thr Asp Trp Arg Val Leu Asp Lys Phe Val Ala
                325                 330                 335 tct cag cta agc aac gag gag gct gcc aca gct tct gca tct ata cag    1056
Ser Gln Leu Ser Asn Glu Glu Ala Ala Thr Ala Ser Ala Ser Ile Gln
            340                 345                 350 aat aat gcc aag gac aca agc aat gct gag tac caa gtt gat gaa gaa    1104
Asn Asn Ala Lys Asp Thr Ser Asn Ala Glu Tyr Gln Val Asp Glu Glu
```

```
               355                 360                 365
aaa gat ccg aaa agg gct tca gac atg gga gaa gaa tat act gct tct    1152
Lys Asp Pro Lys Arg Ala Ser Asp Met Gly Glu Glu Tyr Thr Ala Ser
370                 375                 380 act tct tcg agt tgt cag att gat cta tgg aag tga                    1188
Thr Ser Ser Ser Cys Gln Ile Asp Leu Trp Lys
385                 390                 395

<210> SEQ ID NO 60
<211> LENGTH: 395
<212> TYPE: PRT
<213> ORGANISM: Arabidopsis thaliana

<400> SEQUENCE: 60

Met Asn Ser Phe Ser His Val Pro Pro Gly Phe Arg Phe His Pro Thr
1               5                   10                  15

Asp Glu Glu Leu Val Asp Tyr Tyr Leu Arg Lys Val Ala Ser Lys
                20                  25                  30

Arg Ile Glu Ile Asp Phe Ile Lys Asp Ile Asp Leu Tyr Lys Ile Glu
                35                  40                  45

Pro Trp Asp Leu Gln Glu Leu Cys Lys Ile Gly His Glu Glu Gln Ser
50                  55                  60

Asp Trp Tyr Phe Phe Ser His Lys Asp Lys Lys Tyr Pro Thr Gly Thr
65                  70                  75                  80

Arg Thr Asn Arg Ala Thr Lys Ala Gly Phe Trp Lys Ala Thr Gly Arg
                85                  90                  95

Asp Lys Ala Ile Tyr Leu Arg His Ser Leu Ile Gly Met Arg Lys Thr
                100                 105                 110

Leu Val Phe Tyr Lys Gly Arg Ala Pro Asn Gly Gln Lys Ser Asp Trp
                115                 120                 125

Ile Met His Glu Tyr Arg Leu Glu Thr Asp Glu Asn Gly Thr Pro Gln
130                 135                 140

Glu Glu Gly Trp Val Val Cys Arg Val Phe Lys Lys Arg Leu Ala Ala
145                 150                 155                 160

Val Arg Arg Met Gly Asp Tyr Asp Ser Ser Pro Ser His Trp Tyr Asp
                165                 170                 175

Asp Gln Leu Ser Phe Met Ala Ser Glu Leu Glu Thr Asn Gly Gln Arg
                180                 185                 190

Arg Ile Leu Pro Asn His His Gln Gln Gln His Glu His Gln Gln
                195                 200                 205

His Met Pro Tyr Gly Leu Asn Ala Ser Ala Tyr Ala Leu Asn Asn Pro
210                 215                 220

Asn Leu Gln Cys Lys Gln Glu Leu Glu Leu His Tyr Asn His Leu Val
225                 230                 235                 240

Gln Arg Asn His Leu Leu Asp Glu Ser His Leu Ser Phe Leu Gln Leu
                245                 250                 255

Pro Gln Leu Glu Ser Pro Lys Ile Gln Gln Asp Asn Ser Asn Cys Asn
                260                 265                 270

Ser Leu Pro Tyr Gly Thr Ser Asn Ile Asp Asn Asn Ser Ser His Asn
                275                 280                 285

Ala Asn Leu Gln Gln Ser Asn Ile Ala His Glu Glu Gln Leu Asn Gln
                290                 295                 300

Gly Asn Gln Asn Phe Ser Ser Leu Tyr Met Asn Ser Gly Asn Glu Gln
305                 310                 315                 320

Val Met Asp Gln Val Thr Asp Trp Arg Val Leu Asp Lys Phe Val Ala
```

```
                   325                 330                 335
Ser Gln Leu Ser Asn Glu Glu Ala Ala Thr Ala Ser Ala Ser Ile Gln
            340                 345                 350

Asn Asn Ala Lys Asp Thr Ser Asn Ala Glu Tyr Gln Val Asp Glu Glu
        355                 360                 365

Lys Asp Pro Lys Arg Ala Ser Asp Met Gly Glu Glu Tyr Thr Ala Ser
    370                 375                 380

Thr Ser Ser Ser Cys Gln Ile Asp Leu Trp Lys
385                 390                 395

<210> SEQ ID NO 61
<211> LENGTH: 1005
<212> TYPE: DNA
<213> ORGANISM: Arabidopsis thaliana
<220> FEATURE:
<221> NAME/KEY: CDS
<222> LOCATION: (1)..(1005)

<400> SEQUENCE: 61 atg aac ata tca gta aac gga cag tca caa gta cct cct ggc ttt agg       48
Met Asn Ile Ser Val Asn Gly Gln Ser Gln Val Pro Pro Gly Phe Arg
1               5                   10                  15 ttt cac cca acc gag gaa gag ctc ttg aag tat tac ctc cgc aag aaa       96
Phe His Pro Thr Glu Glu Glu Leu Leu Lys Tyr Tyr Leu Arg Lys Lys
                20                  25                  30 atc tct aac atc aag atc gat ctc gat gtt att cct gac att gat ctc      144
Ile Ser Asn Ile Lys Ile Asp Leu Asp Val Ile Pro Asp Ile Asp Leu
            35                  40                  45 aac aag ctc gag cct tgg gat att caa gag atg tgt aag att gga acg      192
Asn Lys Leu Glu Pro Trp Asp Ile Gln Glu Met Cys Lys Ile Gly Thr
        50                  55                  60 acg ccg caa aac gat tgg tac ttt tat agc cat aag gac aag aag tat      240
Thr Pro Gln Asn Asp Trp Tyr Phe Tyr Ser His Lys Asp Lys Lys Tyr
65                  70                  75                  80 ccc acc ggg act aga acc aac aga gcc acc acg gtc gga ttt tgg aaa      288
Pro Thr Gly Thr Arg Thr Asn Arg Ala Thr Thr Val Gly Phe Trp Lys
                85                  90                  95 gcg acg gga cgt gac aag acc ata tat acc aat ggt gat aga atc ggg      336
Ala Thr Gly Arg Asp Lys Thr Ile Tyr Thr Asn Gly Asp Arg Ile Gly
            100                 105                 110 atg cga aag acg ctt gtc ttc tac aaa ggt cga gcc cct cat ggt cag      384
Met Arg Lys Thr Leu Val Phe Tyr Lys Gly Arg Ala Pro His Gly Gln
        115                 120                 125 aaa tcc gat tgg atc atg cac gaa tat aga ctc gac gag agt gta tta      432
Lys Ser Asp Trp Ile Met His Glu Tyr Arg Leu Asp Glu Ser Val Leu
    130                 135                 140 atc tcc tcg tgt ggc gat cat gac gtc aac gta gaa acg tgt gat gtc      480
Ile Ser Ser Cys Gly Asp His Asp Val Asn Val Glu Thr Cys Asp Val
145                 150                 155                 160 ata gga agt gac gaa gga tgg gtg gtg tgt cgt gtt ttc aag aaa aat      528
Ile Gly Ser Asp Glu Gly Trp Val Val Cys Arg Val Phe Lys Lys Asn
                165                 170                 175 aac ctt tgc aaa aac atg att agt agt agc ccg gcg agt tcg gtg aaa      576
Asn Leu Cys Lys Asn Met Ile Ser Ser Ser Pro Ala Ser Ser Val Lys
            180                 185                 190 acg ccg tcg ttc aat gag gag act atc gag caa ctt ctc gaa gtt atg      624
Thr Pro Ser Phe Asn Glu Glu Thr Ile Glu Gln Leu Leu Glu Val Met
        195                 200                 205 ggg caa tct tgt aaa gga gag ata gtt tta gac cct ttc tta aaa ctc      672
Gly Gln Ser Cys Lys Gly Glu Ile Val Leu Asp Pro Phe Leu Lys Leu
```

```
                    210                 215                 220
cct aac ctc gaa tgc cat aac aac acc acc atc acg agt tat cag tgg     720
Pro Asn Leu Glu Cys His Asn Asn Thr Thr Ile Thr Ser Tyr Gln Trp
225                 230                 235                 240 tta atc gac gac caa gtc aac aac tgc cac gtc agc aaa gtt atg gat     768
Leu Ile Asp Asp Gln Val Asn Asn Cys His Val Ser Lys Val Met Asp
                245                 250                 255 ccc agc ttc atc act agc tgg gcc gct ttg gat cgg ctc gtt gcc tca     816
Pro Ser Phe Ile Thr Ser Trp Ala Ala Leu Asp Arg Leu Val Ala Ser
            260                 265                 270 cag tta aat ggg ccc aac tcg tat tca ata cca gcc gtt aat gag act     864
Gln Leu Asn Gly Pro Asn Ser Tyr Ser Ile Pro Ala Val Asn Glu Thr
        275                 280                 285 tca caa tca ccg tat cat gga ctg aac cgg tcc ggt tgt aat acc ggt     912
Ser Gln Ser Pro Tyr His Gly Leu Asn Arg Ser Gly Cys Asn Thr Gly
    290                 295                 300 tta aca cca gat tac tat ata ccg gag att gat tta tgg aac gag gca     960
Leu Thr Pro Asp Tyr Tyr Ile Pro Glu Ile Asp Leu Trp Asn Glu Ala
305                 310                 315                 320 gat ttc gcg aga acg aca tgc cac ttg ttg aac ggt agt gga taa        1005
Asp Phe Ala Arg Thr Thr Cys His Leu Leu Asn Gly Ser Gly
                325                 330

<210> SEQ ID NO 62
<211> LENGTH: 334
<212> TYPE: PRT
<213> ORGANISM: Arabidopsis thaliana

<400> SEQUENCE: 62

Met Asn Ile Ser Val Asn Gly Gln Ser Gln Val Pro Pro Gly Phe Arg
1               5                   10                  15

Phe His Pro Thr Glu Glu Glu Leu Leu Lys Tyr Tyr Leu Arg Lys Lys
                20                  25                  30

Ile Ser Asn Ile Lys Ile Asp Leu Asp Val Ile Pro Asp Ile Asp Leu
            35                  40                  45

Asn Lys Leu Glu Pro Trp Asp Ile Gln Glu Met Cys Lys Ile Gly Thr
        50                  55                  60

Thr Pro Gln Asn Asp Trp Tyr Phe Tyr Ser His Lys Asp Lys Lys Tyr
65                  70                  75                  80

Pro Thr Gly Thr Arg Thr Asn Arg Ala Thr Thr Val Gly Phe Trp Lys
                85                  90                  95

Ala Thr Gly Arg Asp Lys Thr Ile Tyr Thr Asn Gly Asp Arg Ile Gly
            100                 105                 110

Met Arg Lys Thr Leu Val Phe Tyr Lys Gly Arg Ala Pro His Gly Gln
        115                 120                 125

Lys Ser Asp Trp Ile Met His Glu Tyr Arg Leu Asp Glu Ser Val Leu
    130                 135                 140

Ile Ser Ser Cys Gly Asp His Asp Val Asn Val Glu Thr Cys Asp Val
145                 150                 155                 160

Ile Gly Ser Asp Glu Gly Trp Val Val Cys Arg Val Phe Lys Lys Asn
                165                 170                 175

Asn Leu Cys Lys Asn Met Ile Ser Ser Pro Ala Ser Ser Val Lys
            180                 185                 190

Thr Pro Ser Phe Asn Glu Glu Thr Ile Glu Gln Leu Leu Glu Val Met
        195                 200                 205

Gly Gln Ser Cys Lys Gly Glu Ile Val Leu Asp Pro Phe Leu Lys Leu
    210                 215                 220
```

```
Pro Asn Leu Glu Cys His Asn Thr Thr Ile Thr Ser Tyr Gln Trp
225                 230                 235                 240

Leu Ile Asp Asp Gln Val Asn Asn Cys His Val Ser Lys Val Met Asp
            245                 250                 255

Pro Ser Phe Ile Thr Ser Trp Ala Ala Leu Asp Arg Leu Val Ala Ser
            260                 265                 270

Gln Leu Asn Gly Pro Asn Ser Tyr Ser Ile Pro Ala Val Asn Glu Thr
                275                 280                 285

Ser Gln Ser Pro Tyr His Gly Leu Asn Arg Ser Gly Cys Asn Thr Gly
            290                 295                 300

Leu Thr Pro Asp Tyr Tyr Ile Pro Glu Ile Asp Leu Trp Asn Glu Ala
305                 310                 315                 320

Asp Phe Ala Arg Thr Thr Cys His Leu Leu Asn Gly Ser Gly
                325                 330

<210> SEQ ID NO 63
<211> LENGTH: 792
<212> TYPE: DNA
<213> ORGANISM: Arabidopsis thaliana
<220> FEATURE:
<221> NAME/KEY: CDS
<222> LOCATION: (1)..(792)

<400> SEQUENCE: 63 atg gcg aat tca gga aat tat gga aag agg ccc ttt cga ggc gat gaa      48
Met Ala Asn Ser Gly Asn Tyr Gly Lys Arg Pro Phe Arg Gly Asp Glu
1               5                   10                  15 tcg gat gaa aag aaa gaa gcc gat gat gat gag aac ata ttc cct ttc      96
Ser Asp Glu Lys Lys Glu Ala Asp Asp Asp Glu Asn Ile Phe Pro Phe
            20                  25                  30 ttc tct gcc cga tcc caa tat gac atg cgt gcc atg gtc tca gcc ttg     144
Phe Ser Ala Arg Ser Gln Tyr Asp Met Arg Ala Met Val Ser Ala Leu
        35                  40                  45 act caa gtc att gga aac caa agc agc tct cat gat aat aac caa cat     192
Thr Gln Val Ile Gly Asn Gln Ser Ser Ser His Asp Asn Asn Gln His
    50                  55                  60 caa cct gtt gtg tat aat caa caa gat cct aac cca ccg gct cct cca     240
Gln Pro Val Val Tyr Asn Gln Gln Asp Pro Asn Pro Pro Ala Pro Pro
65                  70                  75                  80 act caa gat caa ggg cta ttg agg aag agg cac tat aga ggg gta aga     288
Thr Gln Asp Gln Gly Leu Leu Arg Lys Arg His Tyr Arg Gly Val Arg
                85                  90                  95 caa cga cca tgg gga aag tgg gca gct gaa att cgg gat ccg caa aag     336
Gln Arg Pro Trp Gly Lys Trp Ala Ala Glu Ile Arg Asp Pro Gln Lys
            100                 105                 110 gca gca cgg gtg tgg ctc ggg aca ttt gag act gct gaa gct gcg gct     384
Ala Ala Arg Val Trp Leu Gly Thr Phe Glu Thr Ala Glu Ala Ala Ala
        115                 120                 125 tta gct tat gat aac gca gct ctt aag ttc aaa gga agc aaa gcc aaa     432
Leu Ala Tyr Asp Asn Ala Ala Leu Lys Phe Lys Gly Ser Lys Ala Lys
    130                 135                 140 ctc aat ttc cct gag aga gct caa cta gca agt aac act agt aca act     480
Leu Asn Phe Pro Glu Arg Ala Gln Leu Ala Ser Asn Thr Ser Thr Thr
145                 150                 155                 160 acc ggt cca cca aac tat tat tct tct aat aat caa att tac tac tca     528
Thr Gly Pro Pro Asn Tyr Tyr Ser Ser Asn Asn Gln Ile Tyr Tyr Ser
                165                 170                 175 aat ccg cag act aat ccg caa acc ata cct tat ttt aac caa tac tac     576
Asn Pro Gln Thr Asn Pro Gln Thr Ile Pro Tyr Phe Asn Gln Tyr Tyr
```

```
                    180                 185                 190
tat aac caa tat ctt cat caa ggg ggg aat agt aac gat gca tta agt      624
Tyr Asn Gln Tyr Leu His Gln Gly Gly Asn Ser Asn Asp Ala Leu Ser
            195                 200                 205 tat agc ttg gcc ggt gga gaa acc gga ggc tca atg tat aat cat cag      672
Tyr Ser Leu Ala Gly Gly Glu Thr Gly Gly Ser Met Tyr Asn His Gln
        210                 215                 220 acg tta tct act aca aat tct tca tct tct ggt gga tct tca agg caa      720
Thr Leu Ser Thr Thr Asn Ser Ser Ser Ser Gly Gly Ser Ser Arg Gln
225                 230                 235                 240 caa gat gat gaa caa gat tac gcc aga tat ttg cgt ttt ggg gat tct      768
Gln Asp Asp Glu Gln Asp Tyr Ala Arg Tyr Leu Arg Phe Gly Asp Ser
                245                 250                 255 tca cct cct aat tct ggt ttt tga                                      792
Ser Pro Pro Asn Ser Gly Phe
            260
```

<210> SEQ ID NO 64
<211> LENGTH: 263
<212> TYPE: PRT
<213> ORGANISM: Arabidopsis thaliana

<400> SEQUENCE: 64

```
Met Ala Asn Ser Gly Asn Tyr Gly Lys Arg Pro Phe Arg Gly Asp Glu
1               5                   10                  15

Ser Asp Glu Lys Lys Glu Ala Asp Asp Glu Asn Ile Phe Pro Phe
            20                  25                  30

Phe Ser Ala Arg Ser Gln Tyr Asp Met Arg Ala Met Val Ser Ala Leu
        35                  40                  45

Thr Gln Val Ile Gly Asn Gln Ser Ser His Asp Asn Asn Gln His
    50                  55                  60

Gln Pro Val Val Tyr Asn Gln Asp Pro Asn Pro Ala Pro Pro
65                  70                  75                  80

Thr Gln Asp Gln Gly Leu Leu Arg Lys Arg His Tyr Arg Gly Val Arg
                85                  90                  95

Gln Arg Pro Trp Gly Lys Trp Ala Ala Glu Ile Arg Asp Pro Gln Lys
            100                 105                 110

Ala Ala Arg Val Trp Leu Gly Thr Phe Glu Thr Ala Glu Ala Ala
        115                 120                 125

Leu Ala Tyr Asp Asn Ala Ala Leu Lys Phe Lys Gly Ser Lys Ala Lys
    130                 135                 140

Leu Asn Phe Pro Glu Arg Ala Gln Leu Ala Ser Asn Thr Ser Thr Thr
145                 150                 155                 160

Thr Gly Pro Pro Asn Tyr Tyr Ser Ser Asn Asn Gln Ile Tyr Tyr Ser
                165                 170                 175

Asn Pro Gln Thr Asn Pro Gln Thr Ile Pro Tyr Phe Asn Gln Tyr Tyr
            180                 185                 190

Tyr Asn Gln Tyr Leu His Gln Gly Gly Asn Ser Asn Asp Ala Leu Ser
        195                 200                 205

Tyr Ser Leu Ala Gly Gly Glu Thr Gly Gly Ser Met Tyr Asn His Gln
    210                 215                 220

Thr Leu Ser Thr Thr Asn Ser Ser Ser Ser Gly Gly Ser Ser Arg Gln
225                 230                 235                 240

Gln Asp Asp Glu Gln Asp Tyr Ala Arg Tyr Leu Arg Phe Gly Asp Ser
                245                 250                 255

Ser Pro Pro Asn Ser Gly Phe
            260
```

<210> SEQ ID NO 65
<211> LENGTH: 1140
<212> TYPE: DNA
<213> ORGANISM: Arabidopsis thaliana
<220> FEATURE:
<221> NAME/KEY: CDS
<222> LOCATION: (1)..(1140)

<400> SEQUENCE: 65

| | | | | | | | | | | | | | | | | |
|---|---|---|---|---|---|---|---|---|---|---|---|---|---|---|---|---|
| atg | tgt | gga | gga | gct | ata | atc | tcc | gat | ttc | ata | cct | ccg | ccg | agg | tcc | 48 |
| Met | Cys | Gly | Gly | Ala | Ile | Ile | Ser | Asp | Phe | Ile | Pro | Pro | Pro | Arg | Ser | |
| 1 | | | | 5 | | | | | 10 | | | | | 15 | | |
| ctc | cgc | gtc | act | aac | gag | ttt | atc | tgg | ccg | gat | ctg | aaa | aac | aaa | gtg | 96 |
| Leu | Arg | Val | Thr | Asn | Glu | Phe | Ile | Trp | Pro | Asp | Leu | Lys | Asn | Lys | Val | |
| | | | 20 | | | | | 25 | | | | | 30 | | | |
| aaa | gct | tca | aag | aag | aga | tcg | aat | aag | cga | tcc | gat | ttc | ttc | gat | ctt | 144 |
| Lys | Ala | Ser | Lys | Lys | Arg | Ser | Asn | Lys | Arg | Ser | Asp | Phe | Phe | Asp | Leu | |
| | | | | 35 | | | | | 40 | | | | | 45 | | |
| gac | gat | gat | ttc | gaa | gct | gat | ttc | caa | ggg | ttt | aag | gat | gac | tcg | gct | 192 |
| Asp | Asp | Asp | Phe | Glu | Ala | Asp | Phe | Gln | Gly | Phe | Lys | Asp | Asp | Ser | Ala | |
| 50 | | | | | 55 | | | | | 60 | | | | | | |
| ttt | gac | tgc | gaa | gac | gat | gat | gat | gtc | ttc | gtc | aat | gtt | aag | cct | ttc | 240 |
| Phe | Asp | Cys | Glu | Asp | Asp | Asp | Asp | Val | Phe | Val | Asn | Val | Lys | Pro | Phe | |
| 65 | | | | | 70 | | | | | 75 | | | | | 80 | |
| gtc | ttc | acc | gca | act | act | aag | ccc | gta | gct | tcc | gct | ttc | gtc | tcc | act | 288 |
| Val | Phe | Thr | Ala | Thr | Thr | Lys | Pro | Val | Ala | Ser | Ala | Phe | Val | Ser | Thr | |
| | | | | 85 | | | | | 90 | | | | | 95 | | |
| ggt | ata | tat | ttg | gta | ggt | tca | gca | tat | gcc | aag | aaa | act | gta | gag | tcc | 336 |
| Gly | Ile | Tyr | Leu | Val | Gly | Ser | Ala | Tyr | Ala | Lys | Lys | Thr | Val | Glu | Ser | |
| | | | | | 100 | | | | | 105 | | | | | 110 | |
| gct | gag | caa | gct | gag | aaa | tct | tct | aag | agg | aag | agg | aag | aat | caa | tac | 384 |
| Ala | Glu | Gln | Ala | Glu | Lys | Ser | Ser | Lys | Arg | Lys | Arg | Lys | Asn | Gln | Tyr | |
| | | | | 115 | | | | | 120 | | | | | 125 | | |
| cga | ggg | att | agg | cag | cgt | cct | tgg | gga | aaa | tgg | gct | gcg | gag | atc | cgt | 432 |
| Arg | Gly | Ile | Arg | Gln | Arg | Pro | Trp | Gly | Lys | Trp | Ala | Ala | Glu | Ile | Arg | |
| | 130 | | | | | 135 | | | | | 140 | | | | | |
| gat | ccg | aga | aaa | ggc | tcc | cga | gaa | tgg | ctt | gga | aca | ttc | gac | act | gct | 480 |
| Asp | Pro | Arg | Lys | Gly | Ser | Arg | Glu | Trp | Leu | Gly | Thr | Phe | Asp | Thr | Ala | |
| 145 | | | | | 150 | | | | | 155 | | | | | 160 | |
| gag | gaa | gca | gca | aga | gct | tat | gat | gct | gca | gca | cgc | aga | atc | cgt | ggc | 528 |
| Glu | Glu | Ala | Ala | Arg | Ala | Tyr | Asp | Ala | Ala | Ala | Arg | Arg | Ile | Arg | Gly | |
| | | | | 165 | | | | | 170 | | | | | 175 | | |
| acg | aaa | gct | aag | gtg | aat | ttt | ccc | gag | gag | aag | aac | cct | agc | gtc | gta | 576 |
| Thr | Lys | Ala | Lys | Val | Asn | Phe | Pro | Glu | Glu | Lys | Asn | Pro | Ser | Val | Val | |
| | | | | 180 | | | | | 185 | | | | | 190 | | |
| tcc | cag | aaa | cgt | cct | agt | gct | aag | act | aat | aat | ctt | cag | aaa | tca | gtg | 624 |
| Ser | Gln | Lys | Arg | Pro | Ser | Ala | Lys | Thr | Asn | Asn | Leu | Gln | Lys | Ser | Val | |
| | | | 195 | | | | | 200 | | | | | 205 | | | |
| gct | aaa | cca | aac | aaa | agc | gta | act | ttg | gtt | cag | cag | cca | aca | cat | ctg | 672 |
| Ala | Lys | Pro | Asn | Lys | Ser | Val | Thr | Leu | Val | Gln | Gln | Pro | Thr | His | Leu | |
| | 210 | | | | | 215 | | | | | 220 | | | | | |
| agt | cag | cag | tac | tgc | aac | aac | tcc | ttt | gac | aac | tct | ttt | ggt | gat | atg | 720 |
| Ser | Gln | Gln | Tyr | Cys | Asn | Asn | Ser | Phe | Asp | Asn | Ser | Phe | Gly | Asp | Met | |
| 225 | | | | | 230 | | | | | 235 | | | | | 240 | |
| agt | ttc | atg | gaa | gag | aag | cct | cag | atg | tac | aac | aat | cag | ttt | ggg | tta | 768 |
| Ser | Phe | Met | Glu | Glu | Lys | Pro | Gln | Met | Tyr | Asn | Asn | Gln | Phe | Gly | Leu | |
| | | | | 245 | | | | | 250 | | | | | 255 | | |
| aca | aac | tcg | ttc | gat | gct | gga | ggt | aac | aat | gga | tac | cag | tat | ttc | agt | 816 |
| Thr | Asn | Ser | Phe | Asp | Ala | Gly | Gly | Asn | Asn | Gly | Tyr | Gln | Tyr | Phe | Ser | |

```
              260                 265                 270
tcc gat cag ggc agt aac tcc ttc gac tgt tct gag ttc ggg tgg agt         864
Ser Asp Gln Gly Ser Asn Ser Phe Asp Cys Ser Glu Phe Gly Trp Ser
    275                 280                 285 gat cac ggc cct aaa aca ccc gag atc tct tca atg ctt gtc aat aac         912
Asp His Gly Pro Lys Thr Pro Glu Ile Ser Ser Met Leu Val Asn Asn
290                 295                 300 aac gaa gca tca ttt gtt gaa gaa acc aat gca gcc aag aag ctc aaa         960
Asn Glu Ala Ser Phe Val Glu Glu Thr Asn Ala Ala Lys Lys Leu Lys
305                 310                 315                 320 cca aac tct gat gag tca gac gat ctg atg gca tac ctt gac aac gcc        1008
Pro Asn Ser Asp Glu Ser Asp Asp Leu Met Ala Tyr Leu Asp Asn Ala
            325                 330                 335 ttg tgg gac acc cca cta gaa gtg gaa gcc atg ctt ggc gca gat gct        1056
Leu Trp Asp Thr Pro Leu Glu Val Glu Ala Met Leu Gly Ala Asp Ala
                340                 345                 350 ggt gct gtg act cag gaa gag gaa aac cca gtg gag cta tgg agc tta        1104
Gly Ala Val Thr Gln Glu Glu Glu Asn Pro Val Glu Leu Trp Ser Leu
        355                 360                 365 gat gag atc aat ttc atg ctg gaa gga gac ttt tga                        1140
Asp Glu Ile Asn Phe Met Leu Glu Gly Asp Phe
    370                 375

<210> SEQ ID NO 66
<211> LENGTH: 379
<212> TYPE: PRT
<213> ORGANISM: Arabidopsis thaliana

<400> SEQUENCE: 66

Met Cys Gly Gly Ala Ile Ile Ser Asp Phe Ile Pro Pro Arg Ser
1               5                   10                  15

Leu Arg Val Thr Asn Glu Phe Ile Trp Pro Asp Leu Lys Asn Lys Val
                20                  25                  30

Lys Ala Ser Lys Lys Arg Ser Asn Lys Arg Ser Asp Phe Phe Asp Leu
            35                  40                  45

Asp Asp Asp Phe Glu Ala Asp Phe Gln Gly Phe Lys Asp Asp Ser Ala
        50                  55                  60

Phe Asp Cys Glu Asp Asp Asp Val Phe Val Asn Val Lys Pro Phe
65                  70                  75                  80

Val Phe Thr Ala Thr Thr Lys Pro Val Ala Ser Ala Phe Val Ser Thr
                85                  90                  95

Gly Ile Tyr Leu Val Gly Ser Ala Tyr Ala Lys Lys Thr Val Glu Ser
            100                 105                 110

Ala Glu Gln Ala Glu Lys Ser Ser Lys Arg Lys Arg Lys Asn Gln Tyr
        115                 120                 125

Arg Gly Ile Arg Gln Arg Pro Trp Gly Lys Trp Ala Ala Glu Ile Arg
    130                 135                 140

Asp Pro Arg Lys Gly Ser Arg Glu Trp Leu Gly Thr Phe Asp Thr Ala
145                 150                 155                 160

Glu Glu Ala Ala Arg Ala Tyr Asp Ala Ala Ala Arg Ile Arg Gly
                165                 170                 175

Thr Lys Ala Lys Val Asn Phe Pro Glu Glu Lys Asn Pro Ser Val Val
            180                 185                 190

Ser Gln Lys Arg Pro Ser Ala Lys Thr Asn Asn Leu Gln Lys Ser Val
        195                 200                 205

Ala Lys Pro Asn Lys Ser Val Thr Leu Val Gln Gln Pro Thr His Leu
    210                 215                 220
```

```
Ser Gln Gln Tyr Cys Asn Asn Ser Phe Asp Asn Ser Phe Gly Asp Met
225                 230                 235                 240

Ser Phe Met Glu Glu Lys Pro Gln Met Tyr Asn Asn Gln Phe Gly Leu
            245                 250                 255

Thr Asn Ser Phe Asp Ala Gly Gly Asn Asn Gly Tyr Gln Tyr Phe Ser
        260                 265                 270

Ser Asp Gln Gly Ser Asn Ser Phe Asp Cys Ser Glu Phe Gly Trp Ser
    275                 280                 285

Asp His Gly Pro Lys Thr Pro Glu Ile Ser Ser Met Leu Val Asn Asn
290                 295                 300

Asn Glu Ala Ser Phe Val Glu Glu Thr Asn Ala Ala Lys Lys Leu Lys
305                 310                 315                 320

Pro Asn Ser Asp Glu Ser Asp Asp Leu Met Ala Tyr Leu Asp Asn Ala
            325                 330                 335

Leu Trp Asp Thr Pro Leu Glu Val Glu Ala Met Leu Gly Ala Asp Ala
        340                 345                 350

Gly Ala Val Thr Gln Glu Glu Asn Pro Val Glu Leu Trp Ser Leu
    355                 360                 365

Asp Glu Ile Asn Phe Met Leu Glu Gly Asp Phe
    370                 375

<210> SEQ ID NO 67
<211> LENGTH: 738
<212> TYPE: DNA
<213> ORGANISM: Arabidopsis thaliana
<220> FEATURE:
<221> NAME/KEY: CDS
<222> LOCATION: (1)..(738)

<400> SEQUENCE: 67 atg gag ttc aat ggt aat ttg aat gcc ggt tct tgc tct aga tca aaa        48
Met Glu Phe Asn Gly Asn Leu Asn Ala Gly Ser Cys Ser Arg Ser Lys
1               5                   10                  15 aag agt cat agg caa aag cag caa caa ccg cag cca cag cca caa caa        96
Lys Ser His Arg Gln Lys Gln Gln Gln Pro Gln Pro Gln Pro Gln Gln
            20                  25                  30 cat att gaa gaa ata aag tat gta gga gtg agg agg agg cca tgg gga       144
His Ile Glu Glu Ile Lys Tyr Val Gly Val Arg Arg Arg Pro Trp Gly
        35                  40                  45 aga tat gca gct gag ata aga aac ccg acg acg aaa gag agg tat tgg       192
Arg Tyr Ala Ala Glu Ile Arg Asn Pro Thr Thr Lys Glu Arg Tyr Trp
    50                  55                  60 cta ggt act ttt gac acg gcc gag gag gct gca ttg gct tat gat aga       240
Leu Gly Thr Phe Asp Thr Ala Glu Glu Ala Ala Leu Ala Tyr Asp Arg
65                  70                  75                  80 gcc gca cgg tcc ata aga ggc ttg act gct cga acc aac ttt gtc tac       288
Ala Ala Arg Ser Ile Arg Gly Leu Thr Ala Arg Thr Asn Phe Val Tyr
                85                  90                  95 tcc gat atg cct cgt ggc tcc tca gta act tcc ttt gtg tct cct gat       336
Ser Asp Met Pro Arg Gly Ser Ser Val Thr Ser Phe Val Ser Pro Asp
            100                 105                 110 gaa tcc caa cgt ttc att tcc gag tta ttc aac cct cca agc caa cta       384
Glu Ser Gln Arg Phe Ile Ser Glu Leu Phe Asn Pro Pro Ser Gln Leu
        115                 120                 125 gaa gct act aac agc aac aat aac aat aac aat ctc tac tca tcg           432
Glu Ala Thr Asn Ser Asn Asn Asn Asn Asn Asn Leu Tyr Ser Ser
    130                 135                 140 acc aac aac caa aac cag aac tct att gag ttc tca tac aat ggg tgg       480
```

```
Thr Asn Asn Gln Asn Gln Asn Ser Ile Glu Phe Ser Tyr Asn Gly Trp
145                 150                 155                 160 cct cag gag gct gaa tgt ggt tat caa tct ata acc agt aat gct gag    528
Pro Gln Glu Ala Glu Cys Gly Tyr Gln Ser Ile Thr Ser Asn Ala Glu
                165                 170                 175 cat tgt gat cat gag ctt cca cct ctt cct ccc agt act tgt ttt gga    576
His Cys Asp His Glu Leu Pro Pro Leu Pro Pro Ser Thr Cys Phe Gly
            180                 185                 190 gct gaa ctg agg att ccg gag acg gat agc tat tgg aat gtt gcg cat    624
Ala Glu Leu Arg Ile Pro Glu Thr Asp Ser Tyr Trp Asn Val Ala His
        195                 200                 205 gca agc ata gac acg ttt gcc ttc gag ctt gat ggc ttt gtg gat caa    672
Ala Ser Ile Asp Thr Phe Ala Phe Glu Leu Asp Gly Phe Val Asp Gln
    210                 215                 220 aac agt ctt ggt cag agt gga aca gaa ggg ttt aat tct tta ccc tcc    720
Asn Ser Leu Gly Gln Ser Gly Thr Glu Gly Phe Asn Ser Leu Pro Ser
225                 230                 235                 240 aca ttc ttc tac caa taa                                            738
Thr Phe Phe Tyr Gln
                245

<210> SEQ ID NO 68
<211> LENGTH: 245
<212> TYPE: PRT
<213> ORGANISM: Arabidopsis thaliana

<400> SEQUENCE: 68

Met Glu Phe Asn Gly Asn Leu Asn Ala Gly Ser Cys Ser Arg Ser Lys
1               5                   10                  15

Lys Ser His Arg Gln Lys Gln Gln Pro Gln Pro Gln Pro Gln Gln
            20                  25                  30

His Ile Glu Glu Ile Lys Tyr Val Gly Val Arg Arg Pro Trp Gly
        35                  40                  45

Arg Tyr Ala Ala Glu Ile Arg Asn Pro Thr Thr Lys Glu Arg Tyr Trp
50                  55                  60

Leu Gly Thr Phe Asp Thr Ala Glu Glu Ala Ala Leu Ala Tyr Asp Arg
65                  70                  75                  80

Ala Ala Arg Ser Ile Arg Gly Leu Thr Ala Arg Thr Asn Phe Val Tyr
                85                  90                  95

Ser Asp Met Pro Arg Gly Ser Ser Val Thr Ser Phe Val Ser Pro Asp
            100                 105                 110

Glu Ser Gln Arg Phe Ile Ser Glu Leu Phe Asn Pro Pro Ser Gln Leu
        115                 120                 125

Glu Ala Thr Asn Ser Asn Asn Asn Asn Asn Asn Leu Tyr Ser Ser
    130                 135                 140

Thr Asn Asn Gln Asn Gln Asn Ser Ile Glu Phe Ser Tyr Asn Gly Trp
145                 150                 155                 160

Pro Gln Glu Ala Glu Cys Gly Tyr Gln Ser Ile Thr Ser Asn Ala Glu
                165                 170                 175

His Cys Asp His Glu Leu Pro Pro Leu Pro Pro Ser Thr Cys Phe Gly
            180                 185                 190

Ala Glu Leu Arg Ile Pro Glu Thr Asp Ser Tyr Trp Asn Val Ala His
        195                 200                 205

Ala Ser Ile Asp Thr Phe Ala Phe Glu Leu Asp Gly Phe Val Asp Gln
    210                 215                 220

Asn Ser Leu Gly Gln Ser Gly Thr Glu Gly Phe Asn Ser Leu Pro Ser
225                 230                 235                 240
```

```
Thr Phe Phe Tyr Gln
            245

<210> SEQ ID NO 69
<211> LENGTH: 771
<212> TYPE: DNA
<213> ORGANISM: Arabidopsis thaliana
<220> FEATURE:
<221> NAME/KEY: CDS
<222> LOCATION: (1)..(771)

<400> SEQUENCE: 69 atg gga agg ggt agg gtt caa ttg aag agg ata gag aac aag atc aat         48
Met Gly Arg Gly Arg Val Gln Leu Lys Arg Ile Glu Asn Lys Ile Asn
1               5                   10                  15 aga caa gtg aca ttc tcg aaa aga aga gct ggt ctt ttg aag aaa gct         96
Arg Gln Val Thr Phe Ser Lys Arg Arg Ala Gly Leu Leu Lys Lys Ala
                20                  25                  30 cat gag atc tct gtt ctc tgt gat gct gaa gtt gct ctt gtt gtc ttc        144
His Glu Ile Ser Val Leu Cys Asp Ala Glu Val Ala Leu Val Val Phe
            35                  40                  45 tcc cat aag gga aaa ctc ttc gaa tac tcc act gat tct tgt atg gag        192
Ser His Lys Gly Lys Leu Phe Glu Tyr Ser Thr Asp Ser Cys Met Glu
        50                  55                  60 aag ata ctt gaa cgc tat gag agg tac tct tac gcc gaa aga cag ctt        240
Lys Ile Leu Glu Arg Tyr Glu Arg Tyr Ser Tyr Ala Glu Arg Gln Leu
65                  70                  75                  80 att gca cct gag tcc gac gtc aat aca aac tgg tcg atg gag tat aac        288
Ile Ala Pro Glu Ser Asp Val Asn Thr Asn Trp Ser Met Glu Tyr Asn
                85                  90                  95 agg ctt aag gct aag att gag ctt ttg gag aga aac cag agg cat tat        336
Arg Leu Lys Ala Lys Ile Glu Leu Leu Glu Arg Asn Gln Arg His Tyr
                100                 105                 110 ctt ggg gaa gac ttg caa gca atg agc cct aaa gag ctt cag aat ctg        384
Leu Gly Glu Asp Leu Gln Ala Met Ser Pro Lys Glu Leu Gln Asn Leu
            115                 120                 125 gag cag cag ctt gac act gct ctt aag cac atc cgc act aga aaa aac        432
Glu Gln Gln Leu Asp Thr Ala Leu Lys His Ile Arg Thr Arg Lys Asn
        130                 135                 140 caa ctt atg tac gag tcc atc aat gag ctc caa aaa aag gag aag gcc        480
Gln Leu Met Tyr Glu Ser Ile Asn Glu Leu Gln Lys Lys Glu Lys Ala
145                 150                 155                 160 ata cag gag caa aac agc atg ctt tct aaa cag atc aag gag agg gaa        528
Ile Gln Glu Gln Asn Ser Met Leu Ser Lys Gln Ile Lys Glu Arg Glu
                165                 170                 175 aaa att ctt agg gct caa cag gag cag tgg gat cag cag aac caa ggc        576
Lys Ile Leu Arg Ala Gln Gln Glu Gln Trp Asp Gln Gln Asn Gln Gly
                180                 185                 190 cac aat atg cct ccc cct ctg cca ccg cag cag cac caa atc cag cat        624
His Asn Met Pro Pro Pro Leu Pro Pro Gln Gln His Gln Ile Gln His
            195                 200                 205 cct tac atg ctc tct cat cag cca tct cct ttt ctc aac atg ggt ggt        672
Pro Tyr Met Leu Ser His Gln Pro Ser Pro Phe Leu Asn Met Gly Gly
        210                 215                 220 ctg tat caa gaa gat gat cct atg gca atg agg agg aat gat ctc gaa        720
Leu Tyr Gln Glu Asp Asp Pro Met Ala Met Arg Arg Asn Asp Leu Glu
225                 230                 235                 240 ctg act ctt gaa ccc gtt tac aac tgc aac ctt ggc tgc ttc gcc gca        768
Leu Thr Leu Glu Pro Val Tyr Asn Cys Asn Leu Gly Cys Phe Ala Ala
                245                 250                 255
``` tga                                                          771

<210> SEQ ID NO 70
<211> LENGTH: 256
<212> TYPE: PRT
<213> ORGANISM: Arabidopsis thaliana

<400> SEQUENCE: 70

Met Gly Arg Gly Arg Val Gln Leu Lys Arg Ile Glu Asn Lys Ile Asn
1               5                   10                  15

Arg Gln Val Thr Phe Ser Lys Arg Arg Ala Gly Leu Leu Lys Lys Ala
            20                  25                  30

His Glu Ile Ser Val Leu Cys Asp Ala Glu Val Ala Leu Val Val Phe
        35                  40                  45

Ser His Lys Gly Lys Leu Phe Glu Tyr Ser Thr Asp Ser Cys Met Glu
    50                  55                  60

Lys Ile Leu Glu Arg Tyr Glu Arg Tyr Ser Tyr Ala Glu Arg Gln Leu
65                  70                  75                  80

Ile Ala Pro Glu Ser Asp Val Asn Thr Asn Trp Ser Met Glu Tyr Asn
                85                  90                  95

Arg Leu Lys Ala Lys Ile Glu Leu Leu Glu Arg Asn Gln Arg His Tyr
            100                 105                 110

Leu Gly Glu Asp Leu Gln Ala Met Ser Pro Lys Glu Leu Gln Asn Leu
        115                 120                 125

Glu Gln Gln Leu Asp Thr Ala Leu Lys His Ile Arg Thr Arg Lys Asn
    130                 135                 140

Gln Leu Met Tyr Glu Ser Ile Asn Glu Leu Gln Lys Lys Glu Lys Ala
145                 150                 155                 160

Ile Gln Glu Gln Asn Ser Met Leu Ser Lys Gln Ile Lys Glu Arg Glu
                165                 170                 175

Lys Ile Leu Arg Ala Gln Gln Glu Gln Trp Asp Gln Asn Gln Gly
            180                 185                 190

His Asn Met Pro Pro Leu Pro Pro Gln Gln His Gln Ile Gln His
        195                 200                 205

Pro Tyr Met Leu Ser His Gln Pro Ser Pro Phe Leu Asn Met Gly Gly
    210                 215                 220

Leu Tyr Gln Glu Asp Asp Pro Met Ala Met Arg Arg Asn Asp Leu Glu
225                 230                 235                 240

Leu Thr Leu Glu Pro Val Tyr Asn Cys Asn Leu Gly Cys Phe Ala Ala
                245                 250                 255

<210> SEQ ID NO 71
<211> LENGTH: 1356
<212> TYPE: DNA
<213> ORGANISM: Arabidopsis thaliana
<220> FEATURE:
<221> NAME/KEY: CDS
<222> LOCATION: (1)..(1356)

<400> SEQUENCE: 71 atg ggt cgc gaa tct gtg gct gtt gtg act gcg ccg ccc tcg gcg act        48
Met Gly Arg Glu Ser Val Ala Val Val Thr Ala Pro Pro Ser Ala Thr
1               5                   10                  15 gct ccg ggt act gct tcg gtg gcg acc tcg ctt gct cct ggc ttc cga        96
Ala Pro Gly Thr Ala Ser Val Ala Thr Ser Leu Ala Pro Gly Phe Arg
            20                  25                  30 ttt cat ccg act gat gag gaa ctc gtg agc tat tac ttg aag agg aag      144
Phe His Pro Thr Asp Glu Glu Leu Val Ser Tyr Tyr Leu Lys Arg Lys -continued

```
                 35                  40                  45
gtt ctg ggc caa cct gta cgc ttc gat gcg att gga gag gtc gat ata        192
Val Leu Gly Gln Pro Val Arg Phe Asp Ala Ile Gly Glu Val Asp Ile
    50                  55                  60 tac aag cat gag ccc tgg gat tta gca gtg ttt tcg aga ttg aag aca        240
Tyr Lys His Glu Pro Trp Asp Leu Ala Val Phe Ser Arg Leu Lys Thr
 65                  70                  75                  80 agg gac caa gaa tgg tac ttc tac agt gca tta gat aag aag tat gga        288
Arg Asp Gln Glu Trp Tyr Phe Tyr Ser Ala Leu Asp Lys Lys Tyr Gly
                 85                  90                  95 aac ggt gct agg atg aac cga gca act aac aga ggg tac tgg aaa gct        336
Asn Gly Ala Arg Met Asn Arg Ala Thr Asn Arg Gly Tyr Trp Lys Ala
            100                 105                 110 act gga aaa gac aga gaa atc cgc cgt gac att ctg ctt ctc ggt atg        384
Thr Gly Lys Asp Arg Glu Ile Arg Arg Asp Ile Leu Leu Leu Gly Met
        115                 120                 125 aaa aag aca ctt gtt ttc cac agt ggg cgt gca cca gac ggg ctt cgg        432
Lys Lys Thr Leu Val Phe His Ser Gly Arg Ala Pro Asp Gly Leu Arg
    130                 135                 140 act aat tgg gtt atg cat gag tat cgc ctt gtg gaa tat gaa acc gag        480
Thr Asn Trp Val Met His Glu Tyr Arg Leu Val Glu Tyr Glu Thr Glu
145                 150                 155                 160 aaa aac gga aac ctg gtg caa gat gca tat gtg ttg tgt aga gtc ttc        528
Lys Asn Gly Asn Leu Val Gln Asp Ala Tyr Val Leu Cys Arg Val Phe
                165                 170                 175 cac aag aat aac att ggg cca cca agt ggg aac aga tat gct ccg ttc        576
His Lys Asn Asn Ile Gly Pro Pro Ser Gly Asn Arg Tyr Ala Pro Phe
            180                 185                 190 atg gaa gag gaa tgg gct gat gat gaa gga gct ctg att cca gga ata        624
Met Glu Glu Glu Trp Ala Asp Asp Glu Gly Ala Leu Ile Pro Gly Ile
        195                 200                 205 gac gtt aag ctc agg cta gag ccg ccg cca gta gcc aat gga aac gac        672
Asp Val Lys Leu Arg Leu Glu Pro Pro Pro Val Ala Asn Gly Asn Asp
    210                 215                 220 cag atg gac cag gaa atc cag tca gcc agc aag agt ctc atc aac atc        720
Gln Met Asp Gln Glu Ile Gln Ser Ala Ser Lys Ser Leu Ile Asn Ile
225                 230                 235                 240 aat gag cca ccg aga gag aca gct cca ctg gat atc gaa tcg gac caa        768
Asn Glu Pro Pro Arg Glu Thr Ala Pro Leu Asp Ile Glu Ser Asp Gln
                245                 250                 255 cag aat cat cat gag aat gac ctc aag ccg gag gag cat aac aac aat        816
Gln Asn His His Glu Asn Asp Leu Lys Pro Glu Glu His Asn Asn Asn
            260                 265                 270 aat aat tat gat gaa aac gag gaa aca ctc aaa cgc gag cag atg gaa        864
Asn Asn Tyr Asp Glu Asn Glu Glu Thr Leu Lys Arg Glu Gln Met Glu
        275                 280                 285 gaa gag gag cgt cct cct cga cct gta tgc gtt ctc aac aaa gaa gct        912
Glu Glu Glu Arg Pro Pro Arg Pro Val Cys Val Leu Asn Lys Glu Ala
    290                 295                 300 cca tta cct ctt ctg caa tac aaa cgt aga cgc caa agc gag tcc aac        960
Pro Leu Pro Leu Leu Gln Tyr Lys Arg Arg Arg Gln Ser Glu Ser Asn
305                 310                 315                 320 aac aac tca agc agg aac aca cag gac cat tgt tcg tcc aca aca aca       1008
Asn Asn Ser Ser Arg Asn Thr Gln Asp His Cys Ser Ser Thr Thr Thr
                325                 330                 335 act gtc gac aat aca acc act tta atc tca tca tct gcc gct gcc acc       1056
Thr Val Asp Asn Thr Thr Thr Leu Ile Ser Ser Ser Ala Ala Ala Thr
            340                 345                 350 aac act gcc atc tct gca ttg ctt gag ttc tca ctc atg ggt atc tcc       1104
```

```
                Asn Thr Ala Ile Ser Ala Leu Leu Glu Phe Ser Leu Met Gly Ile Ser
                            355                 360                 365 gac aag aaa gaa aag ccg cag caa ccg cta cgt cct cac aag gaa cct         1152
Asp Lys Lys Glu Lys Pro Gln Gln Pro Leu Arg Pro His Lys Glu Pro
        370                 375                 380 ttg cct cct caa act cca ctt gca tct cct gaa gag aag gtt aat gat         1200
Leu Pro Pro Gln Thr Pro Leu Ala Ser Pro Glu Glu Lys Val Asn Asp
385                 390                 395                 400 ctc cag aag gag att cac cag atg tct gtt gaa aga gaa act ttc aag         1248
Leu Gln Lys Glu Ile His Gln Met Ser Val Glu Arg Glu Thr Phe Lys
                405                 410                 415 ctt gaa atg atg agt gca gaa gct atg atc agt att ctc cag tca agg         1296
Leu Glu Met Met Ser Ala Glu Ala Met Ile Ser Ile Leu Gln Ser Arg
            420                 425                 430 atc gat gcg ctg cgt cag gag aac gag gaa ctc aag aag aac aat gct         1344
Ile Asp Ala Leu Arg Gln Glu Asn Glu Glu Leu Lys Lys Asn Asn Ala
        435                 440                 445 aat gga caa taa                                                         1356
Asn Gly Gln
    450

<210> SEQ ID NO 72
<211> LENGTH: 451
<212> TYPE: PRT
<213> ORGANISM: Arabidopsis thaliana

<400> SEQUENCE: 72

Met Gly Arg Glu Ser Val Ala Val Val Thr Ala Pro Pro Ser Ala Thr
1               5                   10                  15

Ala Pro Gly Thr Ala Ser Val Ala Thr Ser Leu Ala Pro Gly Phe Arg
            20                  25                  30

Phe His Pro Thr Asp Glu Glu Leu Val Ser Tyr Tyr Leu Lys Arg Lys
        35                  40                  45

Val Leu Gly Gln Pro Val Arg Phe Asp Ala Ile Gly Glu Val Asp Ile
    50                  55                  60

Tyr Lys His Glu Pro Trp Asp Leu Ala Val Phe Ser Arg Leu Lys Thr
65                  70                  75                  80

Arg Asp Gln Glu Trp Tyr Phe Tyr Ser Ala Leu Asp Lys Lys Tyr Gly
                85                  90                  95

Asn Gly Ala Arg Met Asn Arg Ala Thr Asn Arg Gly Tyr Trp Lys Ala
            100                 105                 110

Thr Gly Lys Asp Arg Glu Ile Arg Arg Asp Ile Leu Leu Leu Gly Met
        115                 120                 125

Lys Lys Thr Leu Val Phe His Ser Gly Arg Ala Pro Asp Gly Leu Arg
    130                 135                 140

Thr Asn Trp Val Met His Glu Tyr Arg Leu Val Glu Tyr Glu Thr Glu
145                 150                 155                 160

Lys Asn Gly Asn Leu Val Gln Asp Ala Tyr Val Leu Cys Arg Val Phe
                165                 170                 175

His Lys Asn Asn Ile Gly Pro Pro Ser Gly Asn Arg Tyr Ala Pro Phe
            180                 185                 190

Met Glu Glu Glu Trp Ala Asp Asp Glu Gly Ala Leu Ile Pro Gly Ile
        195                 200                 205

Asp Val Lys Leu Arg Leu Glu Pro Pro Val Ala Asn Gly Asn Asp
    210                 215                 220

Gln Met Asp Gln Glu Ile Gln Ser Ala Ser Lys Ser Leu Ile Asn Ile
225                 230                 235                 240
```

```
Asn Glu Pro Pro Arg Glu Thr Ala Pro Leu Asp Ile Glu Ser Asp Gln
            245                 250                 255

Gln Asn His His Glu Asn Asp Leu Lys Pro Glu His Asn Asn Asn
        260                 265                 270

Asn Asn Tyr Asp Glu Asn Glu Glu Thr Leu Lys Arg Glu Gln Met Glu
            275                 280                 285

Glu Glu Glu Arg Pro Pro Arg Pro Val Cys Val Leu Asn Lys Glu Ala
        290                 295                 300

Pro Leu Pro Leu Leu Gln Tyr Lys Arg Arg Gln Ser Glu Ser Asn
305                 310                 315                 320

Asn Asn Ser Ser Arg Asn Thr Gln Asp His Cys Ser Ser Thr Thr Thr
            325                 330                 335

Thr Val Asp Asn Thr Thr Thr Leu Ile Ser Ser Ser Ala Ala Ala Thr
            340                 345                 350

Asn Thr Ala Ile Ser Ala Leu Leu Glu Phe Ser Leu Met Gly Ile Ser
            355                 360                 365

Asp Lys Lys Glu Lys Pro Gln Gln Pro Leu Arg Pro His Lys Glu Pro
    370                 375                 380

Leu Pro Pro Gln Thr Pro Leu Ala Ser Pro Glu Glu Lys Val Asn Asp
385                 390                 395                 400

Leu Gln Lys Glu Ile His Gln Met Ser Val Glu Arg Glu Thr Phe Lys
                405                 410                 415

Leu Glu Met Met Ser Ala Glu Ala Met Ile Ser Ile Leu Gln Ser Arg
            420                 425                 430

Ile Asp Ala Leu Arg Gln Glu Asn Glu Glu Leu Lys Lys Asn Asn Ala
                435                 440                 445

Asn Gly Gln
    450

<210> SEQ ID NO 73
<211> LENGTH: 726
<212> TYPE: DNA
<213> ORGANISM: Arabidopsis thaliana
<220> FEATURE:
<221> NAME/KEY: CDS
<222> LOCATION: (1)..(726)

<400> SEQUENCE: 73 atg gca act aaa caa gaa gct tta gcc atc gat ttc ata agc caa cac      48
Met Ala Thr Lys Gln Glu Ala Leu Ala Ile Asp Phe Ile Ser Gln His
1               5                   10                  15 ctt ctc aca gac ttt gtt tcc atg gaa act gat cac cca tct ctt ttt      96
Leu Leu Thr Asp Phe Val Ser Met Glu Thr Asp His Pro Ser Leu Phe
            20                  25                  30 acc aac caa ctt cac aac ttt cac tca gaa aca ggc cct aga acc atc     144
Thr Asn Gln Leu His Asn Phe His Ser Glu Thr Gly Pro Arg Thr Ile
        35                  40                  45 acc aac caa tcc cct aaa ccg aat tcg act ctt aac cag cgt aaa ccg     192
Thr Asn Gln Ser Pro Lys Pro Asn Ser Thr Leu Asn Gln Arg Lys Pro
    50                  55                  60 ccc tta ccg aat cta tcc gtc tcg aga acg gtt tca aca aag aca gag     240
Pro Leu Pro Asn Leu Ser Val Ser Arg Thr Val Ser Thr Lys Thr Glu
65                  70                  75                  80 aaa gag gaa gaa gag agg cac tac agg gga gtg aga cga aga ccg tgg     288
Lys Glu Glu Glu Glu Arg His Tyr Arg Gly Val Arg Arg Pro Trp
                85                  90                  95 gga aaa tac gcg gcg gag att agg gat ccg aac aaa aag ggt tgt agg     336
```

```
                Gly Lys Tyr Ala Ala Glu Ile Arg Asp Pro Asn Lys Lys Gly Cys Arg
                                100                 105                 110 atc tgg ctt ggg act tac gac act gcc gtg gaa gct gga aga gct tat       384
Ile Trp Leu Gly Thr Tyr Asp Thr Ala Val Glu Ala Gly Arg Ala Tyr
        115                 120                 125 gac caa gcg gcg ttt caa tta cgt gga aga aaa gca atc ttg aat ttc       432
Asp Gln Ala Ala Phe Gln Leu Arg Gly Arg Lys Ala Ile Leu Asn Phe
130                 135                 140 cct ctc gat gtt agg gtt acg tca gaa act tgt tct ggg gaa gga gtt       480
Pro Leu Asp Val Arg Val Thr Ser Glu Thr Cys Ser Gly Glu Gly Val
145                 150                 155                 160 atc gga tta ggg aaa cga aag cga gat aag ggt tct ccg ccg gaa gag       528
Ile Gly Leu Gly Lys Arg Lys Arg Asp Lys Gly Ser Pro Pro Glu Glu
                165                 170                 175 gag aag gcg gct agg gtt aaa gtg gag gaa gaa gag agt aat acg tcg       576
Glu Lys Ala Ala Arg Val Lys Val Glu Glu Glu Glu Ser Asn Thr Ser
            180                 185                 190 gag acg acg gag gct gag gtt gag ccg gtg gta cca ttg acg ccg tca       624
Glu Thr Thr Glu Ala Glu Val Glu Pro Val Val Pro Leu Thr Pro Ser
        195                 200                 205 agt tgg atg ggg ttt tgg gat gtg gga gca gga gat ggt att ttc agt       672
Ser Trp Met Gly Phe Trp Asp Val Gly Ala Gly Asp Gly Ile Phe Ser
210                 215                 220 att cct ccg tta tct ccg acg tct ccc aac ttt tcc gtt atc tcc gtc       720
Ile Pro Pro Leu Ser Pro Thr Ser Pro Asn Phe Ser Val Ile Ser Val
225                 230                 235                 240 act taa                                                                726
Thr

<210> SEQ ID NO 74
<211> LENGTH: 241
<212> TYPE: PRT
<213> ORGANISM: Arabidopsis thaliana

<400> SEQUENCE: 74

Met Ala Thr Lys Gln Glu Ala Leu Ala Ile Asp Phe Ile Ser Gln His
1               5                   10                  15

Leu Leu Thr Asp Phe Val Ser Met Glu Thr Asp His Pro Ser Leu Phe
            20                  25                  30

Thr Asn Gln Leu His Asn Phe His Ser Glu Thr Gly Pro Arg Thr Ile
        35                  40                  45

Thr Asn Gln Ser Pro Lys Pro Asn Ser Thr Leu Asn Gln Arg Lys Pro
    50                  55                  60

Pro Leu Pro Asn Leu Ser Val Ser Arg Thr Val Ser Thr Lys Thr Glu
65                  70                  75                  80

Lys Glu Glu Glu Arg His Tyr Arg Gly Val Arg Arg Pro Trp
                85                  90                  95

Gly Lys Tyr Ala Ala Glu Ile Arg Asp Pro Asn Lys Lys Gly Cys Arg
                100                 105                 110

Ile Trp Leu Gly Thr Tyr Asp Thr Ala Val Glu Ala Gly Arg Ala Tyr
        115                 120                 125

Asp Gln Ala Ala Phe Gln Leu Arg Gly Arg Lys Ala Ile Leu Asn Phe
130                 135                 140

Pro Leu Asp Val Arg Val Thr Ser Glu Thr Cys Ser Gly Glu Gly Val
145                 150                 155                 160

Ile Gly Leu Gly Lys Arg Lys Arg Asp Lys Gly Ser Pro Pro Glu Glu
                165                 170                 175
```

```
Glu Lys Ala Ala Arg Val Lys Val Glu Glu Glu Ser Asn Thr Ser
            180                 185                 190

Glu Thr Thr Glu Ala Glu Val Glu Pro Val Val Pro Leu Thr Pro Ser
        195                 200                 205

Ser Trp Met Gly Phe Trp Asp Val Gly Ala Gly Asp Gly Ile Phe Ser
    210                 215                 220

Ile Pro Pro Leu Ser Pro Thr Ser Pro Asn Phe Ser Val Ile Ser Val
225                 230                 235                 240

Thr

<210> SEQ ID NO 75
<211> LENGTH: 579
<212> TYPE: DNA
<213> ORGANISM: Arabidopsis thaliana
<220> FEATURE:
<221> NAME/KEY: CDS
<222> LOCATION: (1)..(579)

<400> SEQUENCE: 75 atg gtg tct atg ctg act aat gtt gtc tct ggt gag acc gaa ccc tcg        48
Met Val Ser Met Leu Thr Asn Val Val Ser Gly Glu Thr Glu Pro Ser
1               5                   10                  15 gca tct gcg aca tgg acg atg ggt cat aag aga gaa aga gaa gag ttt        96
Ala Ser Ala Thr Trp Thr Met Gly His Lys Arg Glu Arg Glu Glu Phe
            20                  25                  30 tct ttg cct cct caa cca ttg att acc ggt tca gct gtg act aaa gaa       144
Ser Leu Pro Pro Gln Pro Leu Ile Thr Gly Ser Ala Val Thr Lys Glu
        35                  40                  45 tgt gaa agc tca atg tcc ttg gag agg cca aaa aaa tat aga gga gta       192
Cys Glu Ser Ser Met Ser Leu Glu Arg Pro Lys Lys Tyr Arg Gly Val
    50                  55                  60 agg caa cga cca tgg gga aaa tgg gcg gcg gag att cga gac cca cac       240
Arg Gln Arg Pro Trp Gly Lys Trp Ala Ala Glu Ile Arg Asp Pro His
65                  70                  75                  80 aag gcg aca cgt gta tgg ctt ggg aca ttc gag aca gcc gag gcc gcc       288
Lys Ala Thr Arg Val Trp Leu Gly Thr Phe Glu Thr Ala Glu Ala Ala
                85                  90                  95 gca aga gcc tat gat gcg gca gca ctt cgc ttt aga gga agc aaa gca       336
Ala Arg Ala Tyr Asp Ala Ala Ala Leu Arg Phe Arg Gly Ser Lys Ala
            100                 105                 110 aag ctt aat ttc ccc gaa aat gtt gga act cag acg att caa cga aat       384
Lys Leu Asn Phe Pro Glu Asn Val Gly Thr Gln Thr Ile Gln Arg Asn
        115                 120                 125 tct cat ttc ttg caa aac tct atg caa cct tct ctg aca tac atc gat       432
Ser His Phe Leu Gln Asn Ser Met Gln Pro Ser Leu Thr Tyr Ile Asp
    130                 135                 140 caa tgt cca act cta tta tct tac tct cga tgt atg gag caa caa caa       480
Gln Cys Pro Thr Leu Leu Ser Tyr Ser Arg Cys Met Glu Gln Gln Gln
145                 150                 155                 160 cca tta gta ggc atg ttg cag cca aca gag gag gaa aat cac ttt ttc       528
Pro Leu Val Gly Met Leu Gln Pro Thr Glu Glu Glu Asn His Phe Phe
                165                 170                 175 gaa aaa cca tgg acc gaa tat gat caa tac aat tac tcc tct ttt ggt       576
Glu Lys Pro Trp Thr Glu Tyr Asp Gln Tyr Asn Tyr Ser Ser Phe Gly
            180                 185                 190 taa                                                                   579

<210> SEQ ID NO 76
<211> LENGTH: 192
<212> TYPE: PRT
```

<213> ORGANISM: Arabidopsis thaliana

<400> SEQUENCE: 76

```
Met Val Ser Met Leu Thr Asn Val Val Ser Gly Glu Thr Glu Pro Ser
1               5                   10                  15

Ala Ser Ala Thr Trp Thr Met Gly His Lys Arg Glu Arg Glu Phe
            20                  25                  30

Ser Leu Pro Pro Gln Pro Leu Ile Thr Gly Ser Ala Val Thr Lys Glu
        35                  40                  45

Cys Glu Ser Ser Met Ser Leu Glu Arg Pro Lys Lys Tyr Arg Gly Val
    50                  55                  60

Arg Gln Arg Pro Trp Gly Lys Trp Ala Ala Glu Ile Arg Asp Pro His
65                  70                  75                  80

Lys Ala Thr Arg Val Trp Leu Gly Thr Phe Glu Thr Ala Glu Ala Ala
                85                  90                  95

Ala Arg Ala Tyr Asp Ala Ala Ala Leu Arg Phe Arg Gly Ser Lys Ala
            100                 105                 110

Lys Leu Asn Phe Pro Glu Asn Val Gly Thr Gln Thr Ile Gln Arg Asn
        115                 120                 125

Ser His Phe Leu Gln Asn Ser Met Gln Pro Ser Leu Thr Tyr Ile Asp
    130                 135                 140

Gln Cys Pro Thr Leu Leu Ser Tyr Ser Arg Cys Met Glu Gln Gln
145                 150                 155                 160

Pro Leu Val Gly Met Leu Gln Pro Thr Glu Glu Asn His Phe Phe
                165                 170                 175

Glu Lys Pro Trp Thr Glu Tyr Asp Gln Tyr Asn Tyr Ser Ser Phe Gly
            180                 185                 190
```

<210> SEQ ID NO 77
<211> LENGTH: 1080
<212> TYPE: DNA
<213> ORGANISM: Arabidopsis thaliana
<220> FEATURE:
<221> NAME/KEY: CDS
<222> LOCATION: (1)..(1080)

<400> SEQUENCE: 77

```
atg ata agc aag gat cca aga tcg agt tta cct cca ggg ttt cga ttt    48
Met Ile Ser Lys Asp Pro Arg Ser Ser Leu Pro Pro Gly Phe Arg Phe
1               5                   10                  15 cat cca aca gat gaa gaa ctc att ctc cat tac cta agg aag aaa gtt    96
His Pro Thr Asp Glu Glu Leu Ile Leu His Tyr Leu Arg Lys Lys Val
            20                  25                  30 tcc tct tcc cca gtc ccg ctt tcg att atc gcc gat gtc gat atc tac   144
Ser Ser Ser Pro Val Pro Leu Ser Ile Ile Ala Asp Val Asp Ile Tyr
        35                  40                  45 aaa tcc gat cca tgg gat tta cca gct aag gct cca ttt ggg gag aaa   192
Lys Ser Asp Pro Trp Asp Leu Pro Ala Lys Ala Pro Phe Gly Glu Lys
    50                  55                  60 gag tgg tat ttt ttc agt ccg agg gat agg aaa tat cca aac gga gca   240
Glu Trp Tyr Phe Phe Ser Pro Arg Asp Arg Lys Tyr Pro Asn Gly Ala
65                  70                  75                  80 aga cca aac aga gca gct gcg tct gga tat tgg aaa gca acc gga aca   288
Arg Pro Asn Arg Ala Ala Ala Ser Gly Tyr Trp Lys Ala Thr Gly Thr
                85                  90                  95 gat aaa ttg att gcg gta cca aat ggt gaa ggg ttt cat gaa aac att   336
Asp Lys Leu Ile Ala Val Pro Asn Gly Glu Gly Phe His Glu Asn Ile
            100                 105                 110
```

```
ggt ata aaa aaa gct ctt gtg ttt tat aga gga aag cct cca aaa ggt    384
Gly Ile Lys Lys Ala Leu Val Phe Tyr Arg Gly Lys Pro Pro Lys Gly
        115                 120                 125 gtt aaa acc aat tgg atc atg cat gaa tat cgt ctt gcc gat tca tta    432
Val Lys Thr Asn Trp Ile Met His Glu Tyr Arg Leu Ala Asp Ser Leu
130                 135                 140 tct ccc aaa aga att aac tct tct agg agc ggt ggt agc gaa gtt aat    480
Ser Pro Lys Arg Ile Asn Ser Ser Arg Ser Gly Gly Ser Glu Val Asn
145                 150                 155                 160 aat aat ttt gga gat agg aat tct aaa gaa tat tcg atg aga ctg gat    528
Asn Asn Phe Gly Asp Arg Asn Ser Lys Glu Tyr Ser Met Arg Leu Asp
                165                 170                 175 gat tgg gtt ctt tgc cgg att tac aag aaa tca cac gct tca ttg tca    576
Asp Trp Val Leu Cys Arg Ile Tyr Lys Lys Ser His Ala Ser Leu Ser
            180                 185                 190 tca cct gat gtt gct ttg gtc aca agc aat caa gag cat gag gaa aat    624
Ser Pro Asp Val Ala Leu Val Thr Ser Asn Gln Glu His Glu Glu Asn
        195                 200                 205 gac aac gaa cca ttc gta gac cgc gga acc ttt ttg cca aat ttg caa    672
Asp Asn Glu Pro Phe Val Asp Arg Gly Thr Phe Leu Pro Asn Leu Gln
    210                 215                 220 aat gat caa ccc ctt aaa cgc cag aag tct tct tgt tcg ttc tca aac    720
Asn Asp Gln Pro Leu Lys Arg Gln Lys Ser Ser Cys Ser Phe Ser Asn
225                 230                 235                 240 tta cta gac gct aca gat ttg acg ttt ctc gca aat ttt cta aac gaa    768
Leu Leu Asp Ala Thr Asp Leu Thr Phe Leu Ala Asn Phe Leu Asn Glu
                245                 250                 255 acc ccg gaa aat cgt tct gaa tca gat ttt tct ttc atg att ggc aat    816
Thr Pro Glu Asn Arg Ser Glu Ser Asp Phe Ser Phe Met Ile Gly Asn
            260                 265                 270 ttc tct aat cct gac att tac gga aac cat tac ttg gat cag aag tta    864
Phe Ser Asn Pro Asp Ile Tyr Gly Asn His Tyr Leu Asp Gln Lys Leu
        275                 280                 285 ccg cag ttg agc tct ccc act tca gag aca agc ggc atc gga agc aaa    912
Pro Gln Leu Ser Ser Pro Thr Ser Glu Thr Ser Gly Ile Gly Ser Lys
    290                 295                 300 aga gag aga gtg gat ttt gcg gaa gaa acg ata aac gct tcg aag aag    960
Arg Glu Arg Val Asp Phe Ala Glu Glu Thr Ile Asn Ala Ser Lys Lys
305                 310                 315                 320 atg atg aac aca tat agt tac aat aat agt ata gat caa atg gat cat   1008
Met Met Asn Thr Tyr Ser Tyr Asn Asn Ser Ile Asp Gln Met Asp His
                325                 330                 335 agt atg atg caa caa cct agt ttc ctg aac cag gaa ctc atg atg agt   1056
Ser Met Met Gln Gln Pro Ser Phe Leu Asn Gln Glu Leu Met Met Ser
            340                 345                 350 tct cac ctt caa tat caa ggc tag                                   1080
Ser His Leu Gln Tyr Gln Gly
        355
```

<210> SEQ ID NO 78
<211> LENGTH: 359
<212> TYPE: PRT
<213> ORGANISM: Arabidopsis thaliana

<400> SEQUENCE: 78

```
Met Ile Ser Lys Asp Pro Arg Ser Ser Leu Pro Gly Phe Arg Phe
1               5                   10                  15

His Pro Thr Asp Glu Glu Leu Ile Leu His Tyr Leu Arg Lys Lys Val
                20                  25                  30

Ser Ser Ser Pro Val Pro Leu Ser Ile Ile Ala Asp Val Asp Ile Tyr
```

```
                    35                  40                  45
Lys Ser Asp Pro Trp Asp Leu Pro Ala Lys Ala Pro Phe Gly Glu Lys
 50                  55                  60

Glu Trp Tyr Phe Phe Ser Pro Arg Asp Arg Lys Tyr Pro Asn Gly Ala
 65                  70                  75                  80

Arg Pro Asn Arg Ala Ala Ala Ser Gly Tyr Trp Lys Ala Thr Gly Thr
                 85                  90                  95

Asp Lys Leu Ile Ala Val Pro Asn Gly Glu Gly Phe His Glu Asn Ile
                100                 105                 110

Gly Ile Lys Lys Ala Leu Val Phe Tyr Arg Gly Lys Pro Pro Lys Gly
                115                 120                 125

Val Lys Thr Asn Trp Ile Met His Glu Tyr Arg Leu Ala Asp Ser Leu
130                 135                 140

Ser Pro Lys Arg Ile Asn Ser Arg Ser Gly Gly Ser Glu Val Asn
145                 150                 155                 160

Asn Asn Phe Gly Asp Arg Asn Ser Lys Glu Tyr Ser Met Arg Leu Asp
                165                 170                 175

Asp Trp Val Leu Cys Arg Ile Tyr Lys Lys Ser His Ala Ser Leu Ser
                180                 185                 190

Ser Pro Asp Val Ala Leu Val Thr Ser Asn Gln Glu His Glu Asn
                195                 200                 205

Asp Asn Glu Pro Phe Val Asp Arg Gly Thr Phe Leu Pro Asn Leu Gln
210                 215                 220

Asn Asp Gln Pro Leu Lys Arg Gln Lys Ser Ser Cys Ser Phe Ser Asn
225                 230                 235                 240

Leu Leu Asp Ala Thr Asp Leu Thr Phe Leu Ala Asn Phe Leu Asn Glu
                245                 250                 255

Thr Pro Glu Asn Arg Ser Glu Ser Asp Phe Ser Phe Met Ile Gly Asn
                260                 265                 270

Phe Ser Asn Pro Asp Ile Tyr Gly Asn His Tyr Leu Asp Gln Lys Leu
                275                 280                 285

Pro Gln Leu Ser Ser Pro Thr Ser Glu Thr Ser Gly Ile Gly Ser Lys
                290                 295                 300

Arg Glu Arg Val Asp Phe Ala Glu Glu Thr Ile Asn Ala Ser Lys Lys
305                 310                 315                 320

Met Met Asn Thr Tyr Ser Tyr Asn Asn Ser Ile Asp Gln Met Asp His
                325                 330                 335

Ser Met Met Gln Gln Pro Ser Phe Leu Asn Gln Glu Leu Met Met Ser
                340                 345                 350

Ser His Leu Gln Tyr Gln Gly
                355

<210> SEQ ID NO 79
<211> LENGTH: 1098
<212> TYPE: DNA
<213> ORGANISM: Arabidopsis thaliana
<220> FEATURE:
<221> NAME/KEY: CDS
<222> LOCATION: (1)..(1098)

<400> SEQUENCE: 79 atg atg tca aaa tct atg agc ata tca gtg aac gga caa tct caa gtg      48
Met Met Ser Lys Ser Met Ser Ile Ser Val Asn Gly Gln Ser Gln Val
  1               5                  10                  15 cct cct ggg ttt agg ttt cat ccg acc gag gaa gag ctg ttg cag tat      96
Pro Pro Gly Phe Arg Phe His Pro Thr Glu Glu Glu Leu Leu Gln Tyr
```

```
                      20                  25                   30
tat ctc cgg aag aaa gtt aat agc atc gag atc gat ctt gat gtc att        144
Tyr Leu Arg Lys Lys Val Asn Ser Ile Glu Ile Asp Leu Asp Val Ile
         35                  40                  45 cgc gac gtt gat ctc aac aag ctc gag cct tgg gac att caa gag atg        192
Arg Asp Val Asp Leu Asn Lys Leu Glu Pro Trp Asp Ile Gln Glu Met
 50                  55                  60 tgt aaa ata gga aca acg cca caa aac gac tgg tat ttc ttt agc cac        240
Cys Lys Ile Gly Thr Thr Pro Gln Asn Asp Trp Tyr Phe Phe Ser His
 65                  70                  75                  80 aag gac aaa aaa tat ccg acg gga acg aga act aac aga gcc act gcg        288
Lys Asp Lys Lys Tyr Pro Thr Gly Thr Arg Thr Asn Arg Ala Thr Ala
                 85                  90                  95 gct gga ttt tgg aaa gca act ggc cgc gac aag atc ata tat agc aat        336
Ala Gly Phe Trp Lys Ala Thr Gly Arg Asp Lys Ile Ile Tyr Ser Asn
            100                 105                 110 ggc cgt aga att ggg atg aga aag act ctt gtt ttc tac aaa ggc cga        384
Gly Arg Arg Ile Gly Met Arg Lys Thr Leu Val Phe Tyr Lys Gly Arg
        115                 120                 125 gct cct cac ggc caa aaa tct gat tgg atc atg cat gaa tat aga ctc        432
Ala Pro His Gly Gln Lys Ser Asp Trp Ile Met His Glu Tyr Arg Leu
130                 135                 140 gat gac aac att att tcc ccc gag gat gtc acc gtt cat gag gtc gtg        480
Asp Asp Asn Ile Ile Ser Pro Glu Asp Val Thr Val His Glu Val Val
145                 150                 155                 160 agt att ata ggg gaa gca tca caa gac gaa gga tgg gtg gtg tgt cgt        528
Ser Ile Ile Gly Glu Ala Ser Gln Asp Glu Gly Trp Val Val Cys Arg
                165                 170                 175 att ttc aag aag aag aat ctt cac aaa acc cta aac agt ccc gtc gga        576
Ile Phe Lys Lys Lys Asn Leu His Lys Thr Leu Asn Ser Pro Val Gly
            180                 185                 190 gga gct tcc ctg agc ggc ggc gga gat acg ccg aag acg aca tca tct        624
Gly Ala Ser Leu Ser Gly Gly Gly Asp Thr Pro Lys Thr Thr Ser Ser
        195                 200                 205 cag atc ttc aac gag gat act ctc gac caa ttt ctt gaa ctt atg ggg        672
Gln Ile Phe Asn Glu Asp Thr Leu Asp Gln Phe Leu Glu Leu Met Gly
    210                 215                 220 aga tct tgt aaa gaa gag cta aat ctt gac cct ttc atg aaa ctc cca        720
Arg Ser Cys Lys Glu Glu Leu Asn Leu Asp Pro Phe Met Lys Leu Pro
225                 230                 235                 240 aac ctc gaa agc cct aac agt cag gca atc aac aac tgc cac gta agc        768
Asn Leu Glu Ser Pro Asn Ser Gln Ala Ile Asn Asn Cys His Val Ser
                245                 250                 255 tct ccc gac act aat cat aat atc cac gtc agc aac gtg gtc gac act        816
Ser Pro Asp Thr Asn His Asn Ile His Val Ser Asn Val Val Asp Thr
            260                 265                 270 agc ttt gtt act agc tgg gcg gct tta gac cgc ctc gtg gcc tcg cag        864
Ser Phe Val Thr Ser Trp Ala Ala Leu Asp Arg Leu Val Ala Ser Gln
        275                 280                 285 ctt aac gga ccc aca tca tat tca att aca gcc gtc aat gag agc cac        912
Leu Asn Gly Pro Thr Ser Tyr Ser Ile Thr Ala Val Asn Glu Ser His
    290                 295                 300 gtg ggc cat gat cat ctc gct ttg cct tcc gtc cga tct ccg tac ccc        960
Val Gly His Asp His Leu Ala Leu Pro Ser Val Arg Ser Pro Tyr Pro
305                 310                 315                 320 agc cta aac cgg tcc gct tcg tac cac gcc ggt tta aca cag gaa tat       1008
Ser Leu Asn Arg Ser Ala Ser Tyr His Ala Gly Leu Thr Gln Glu Tyr
                325                 330                 335 aca ccg gag atg gag cta tgg aat acg acg acg tcg tct cta tcg tca       1056
```

```
Thr Pro Glu Met Glu Leu Trp Asn Thr Thr Ser Ser Leu Ser Ser
            340                 345                 350 tcg cct ggc cca ttt tgt cac gtg tcg aat ggt agt gga taa          1098
Ser Pro Gly Pro Phe Cys His Val Ser Asn Gly Ser Gly
            355                 360                 365

<210> SEQ ID NO 80
<211> LENGTH: 365
<212> TYPE: PRT
<213> ORGANISM: Arabidopsis thaliana

<400> SEQUENCE: 80

Met Met Ser Lys Ser Met Ser Ile Ser Val Asn Gly Gln Ser Gln Val
1               5                   10                  15

Pro Pro Gly Phe Arg Phe His Pro Thr Glu Glu Leu Leu Gln Tyr
            20                  25                  30

Tyr Leu Arg Lys Lys Val Asn Ser Ile Glu Ile Asp Leu Asp Val Ile
            35                  40                  45

Arg Asp Val Asp Leu Asn Lys Leu Glu Pro Trp Asp Ile Gln Glu Met
50                  55                  60

Cys Lys Ile Gly Thr Thr Pro Gln Asn Asp Trp Tyr Phe Phe Ser His
65                  70                  75                  80

Lys Asp Lys Lys Tyr Pro Thr Gly Thr Arg Thr Asn Arg Ala Thr Ala
                85                  90                  95

Ala Gly Phe Trp Lys Ala Thr Gly Arg Asp Lys Ile Ile Tyr Ser Asn
            100                 105                 110

Gly Arg Arg Ile Gly Met Arg Lys Thr Leu Val Phe Tyr Lys Gly Arg
            115                 120                 125

Ala Pro His Gly Gln Lys Ser Asp Trp Ile Met His Glu Tyr Arg Leu
            130                 135                 140

Asp Asp Asn Ile Ile Ser Pro Glu Asp Val Thr Val His Glu Val Val
145                 150                 155                 160

Ser Ile Ile Gly Glu Ala Ser Gln Asp Glu Gly Trp Val Val Cys Arg
                165                 170                 175

Ile Phe Lys Lys Lys Asn Leu His Lys Thr Leu Asn Ser Pro Val Gly
            180                 185                 190

Gly Ala Ser Leu Ser Gly Gly Gly Asp Thr Pro Lys Thr Thr Ser Ser
            195                 200                 205

Gln Ile Phe Asn Glu Asp Thr Leu Asp Gln Phe Leu Glu Leu Met Gly
            210                 215                 220

Arg Ser Cys Lys Glu Glu Leu Asn Leu Asp Pro Phe Met Lys Leu Pro
225                 230                 235                 240

Asn Leu Glu Ser Pro Asn Ser Gln Ala Ile Asn Asn Cys His Val Ser
                245                 250                 255

Ser Pro Asp Thr Asn His Asn Ile His Val Ser Asn Val Val Asp Thr
            260                 265                 270

Ser Phe Val Thr Ser Trp Ala Ala Leu Asp Arg Leu Val Ala Ser Gln
            275                 280                 285

Leu Asn Gly Pro Thr Ser Tyr Ser Ile Thr Ala Val Asn Glu Ser His
            290                 295                 300

Val Gly His Asp His Leu Ala Leu Pro Ser Val Arg Ser Pro Tyr Pro
305                 310                 315                 320

Ser Leu Asn Arg Ser Ala Ser Tyr His Ala Gly Leu Thr Gln Glu Tyr
                325                 330                 335

Thr Pro Glu Met Glu Leu Trp Asn Thr Thr Ser Ser Leu Ser Ser
```

```
            340                 345                 350
Ser Pro Gly Pro Phe Cys His Val Ser Asn Gly Ser Gly
        355                 360                 365

<210> SEQ ID NO 81
<211> LENGTH: 777
<212> TYPE: DNA
<213> ORGANISM: Arabidopsis thaliana
<220> FEATURE:
<221> NAME/KEY: CDS
<222> LOCATION: (1)..(777)

<400> SEQUENCE: 81 atg gga aag aga gca act act agt gtg agg aga gaa gag tta aac aga        48
Met Gly Lys Arg Ala Thr Thr Ser Val Arg Arg Glu Glu Leu Asn Arg
1               5                   10                  15 gga gct tgg act gat cat gaa gac aag atc ctt aga gat tac atc acc        96
Gly Ala Trp Thr Asp His Glu Asp Lys Ile Leu Arg Asp Tyr Ile Thr
                20                  25                  30 act cac ggc gaa ggc aaa tgg agc act ctc cct aac caa gct ggt ctc       144
Thr His Gly Glu Gly Lys Trp Ser Thr Leu Pro Asn Gln Ala Gly Leu
            35                  40                  45 aag agg tgt ggc aaa agc tgt aga ctt cgg tgg aag aac tac cta aga       192
Lys Arg Cys Gly Lys Ser Cys Arg Leu Arg Trp Lys Asn Tyr Leu Arg
        50                  55                  60 ccg ggg ata aag cgc ggt aac atc tca tct gat gaa gaa gaa ctc ata       240
Pro Gly Ile Lys Arg Gly Asn Ile Ser Ser Asp Glu Glu Glu Leu Ile
65                  70                  75                  80 atc cgt ctc cat aat ctt ctt gga aac aga tgg tcg ttg ata gct ggg       288
Ile Arg Leu His Asn Leu Leu Gly Asn Arg Trp Ser Leu Ile Ala Gly
                85                  90                  95 agg ctt cca ggc cga aca gac aat gaa ata aag aat cat tgg aac tca       336
Arg Leu Pro Gly Arg Thr Asp Asn Glu Ile Lys Asn His Trp Asn Ser
            100                 105                 110 aac ctc cgc aaa aga ctt ccc aaa act caa acc aag caa cca aaa cgt       384
Asn Leu Arg Lys Arg Leu Pro Lys Thr Gln Thr Lys Gln Pro Lys Arg
        115                 120                 125 ata aaa cat tcg acg aac aac gag aat aat gta tgt gtt ata cgt aca       432
Ile Lys His Ser Thr Asn Asn Glu Asn Asn Val Cys Val Ile Arg Thr
    130                 135                 140 aag gcg att agg tgc tca aag act ctt ctc ttc tcg gat ctc tct ctt       480
Lys Ala Ile Arg Cys Ser Lys Thr Leu Leu Phe Ser Asp Leu Ser Leu
145                 150                 155                 160 cag aag aag agt agt act agt cca cta cct ctg aaa gaa caa gag atg       528
Gln Lys Lys Ser Ser Thr Ser Pro Leu Pro Leu Lys Glu Gln Glu Met
                165                 170                 175 gat caa ggt gga tct tcg ttg atg gga gat ctc gaa ttc gat ttc gat       576
Asp Gln Gly Gly Ser Ser Leu Met Gly Asp Leu Glu Phe Asp Phe Asp
            180                 185                 190 agg atc cat tcg gag ttt cac ttc ccg gat ttg atg gat ttt gat ggt       624
Arg Ile His Ser Glu Phe His Phe Pro Asp Leu Met Asp Phe Asp Gly
        195                 200                 205 ttg gac tgt gga aac gtt aca tct ctt gtt tca tct aac gag att ttg       672
Leu Asp Cys Gly Asn Val Thr Ser Leu Val Ser Ser Asn Glu Ile Leu
    210                 215                 220 gga gag ttg gtt cct gct caa ggt aat ctc gat ctc aat aga cct ttc       720
Gly Glu Leu Val Pro Ala Gln Gly Asn Leu Asp Leu Asn Arg Pro Phe
225                 230                 235                 240 act tct tgt cat cat cgt ggc gac gat gaa gat tgg ctc cga gac ttc       768
Thr Ser Cys His His Arg Gly Asp Asp Glu Asp Trp Leu Arg Asp Phe
                245                 250                 255
```

```
act tgt tga                                                          777
Thr Cys <210> SEQ ID NO 82
<211> LENGTH: 258
<212> TYPE: PRT
<213> ORGANISM: Arabidopsis thaliana

<400> SEQUENCE: 82

Met Gly Lys Arg Ala Thr Thr Ser Val Arg Arg Glu Glu Leu Asn Arg
1               5                   10                  15

Gly Ala Trp Thr Asp His Glu Asp Lys Ile Leu Arg Asp Tyr Ile Thr
            20                  25                  30

Thr His Gly Glu Gly Lys Trp Ser Thr Leu Pro Asn Gln Ala Gly Leu
        35                  40                  45

Lys Arg Cys Gly Lys Ser Cys Arg Leu Arg Trp Lys Asn Tyr Leu Arg
    50                  55                  60

Pro Gly Ile Lys Arg Gly Asn Ile Ser Ser Asp Glu Glu Leu Ile
65                  70                  75                  80

Ile Arg Leu His Asn Leu Leu Gly Asn Arg Trp Ser Leu Ile Ala Gly
                85                  90                  95

Arg Leu Pro Gly Arg Thr Asp Asn Glu Ile Lys Asn His Trp Asn Ser
            100                 105                 110

Asn Leu Arg Lys Arg Leu Pro Lys Thr Gln Thr Lys Gln Pro Lys Arg
        115                 120                 125

Ile Lys His Ser Thr Asn Asn Glu Asn Asn Val Cys Val Ile Arg Thr
    130                 135                 140

Lys Ala Ile Arg Cys Ser Lys Thr Leu Leu Phe Ser Asp Leu Ser Leu
145                 150                 155                 160

Gln Lys Lys Ser Ser Thr Ser Pro Leu Pro Leu Lys Glu Gln Glu Met
                165                 170                 175

Asp Gln Gly Gly Ser Ser Leu Met Gly Asp Leu Glu Phe Asp Phe Asp
            180                 185                 190

Arg Ile His Ser Glu Phe His Phe Pro Asp Leu Met Asp Phe Asp Gly
        195                 200                 205

Leu Asp Cys Gly Asn Val Thr Ser Leu Val Ser Ser Asn Glu Ile Leu
    210                 215                 220

Gly Glu Leu Val Pro Ala Gln Gly Asn Leu Asp Leu Asn Arg Pro Phe
225                 230                 235                 240

Thr Ser Cys His His Arg Gly Asp Asp Glu Asp Trp Leu Arg Asp Phe
                245                 250                 255

Thr Cys

<210> SEQ ID NO 83
<211> LENGTH: 573
<212> TYPE: DNA
<213> ORGANISM: Arabidopsis thaliana
<220> FEATURE:
<221> NAME/KEY: CDS
<222> LOCATION: (1)..(573)

<400> SEQUENCE: 83 atg gcg ttc gca gga aca acc cag aaa tgc atg gca tgt gac aaa aca    48
Met Ala Phe Ala Gly Thr Thr Gln Lys Cys Met Ala Cys Asp Lys Thr
1               5                   10                  15 gtt tat ctt gtc gac aag tta acc gcc gat aac cgg gtc tac cac aaa    96
Val Tyr Leu Val Asp Lys Leu Thr Ala Asp Asn Arg Val Tyr His Lys
```

|  |  |  |  |  |  |  |  |  |  |  |  |  |  |  |  |
|---|---|---|---|---|---|---|---|---|---|---|---|---|---|---|---|
| gct | tgt | ttc | cga | tgt | cac | cat | tgc | aaa | gga | act | ctc | aag | ctt | agc | aat | 144
| Ala | Cys | Phe | Arg | Cys | His | His | Cys | Lys | Gly | Thr | Leu | Lys | Leu | Ser | Asn |

```
              20                  25                  30
gct tgt ttc cga tgt cac cat tgc aaa gga act ctc aag ctt agc aat    144
Ala Cys Phe Arg Cys His His Cys Lys Gly Thr Leu Lys Leu Ser Asn
         35                  40                  45 tac aac tcc ttt gaa gga gtt ctc tac tgc aga cca cat ttc gat caa    192
Tyr Asn Ser Phe Glu Gly Val Leu Tyr Cys Arg Pro His Phe Asp Gln
 50                  55                  60 aac ttc aag aga act gga agt ctt gag aaa agc ttc gaa ggg aca cca    240
Asn Phe Lys Arg Thr Gly Ser Leu Glu Lys Ser Phe Glu Gly Thr Pro
 65                  70                  75                  80 aag att ggg aaa cct gat agg cct ttg gag gga gag aga cct gct gga    288
Lys Ile Gly Lys Pro Asp Arg Pro Leu Glu Gly Glu Arg Pro Ala Gly
                 85                  90                  95 acc aaa gtt tcg aat atg ttt ggt gga aca cga gag aaa tgc gtt ggt    336
Thr Lys Val Ser Asn Met Phe Gly Gly Thr Arg Glu Lys Cys Val Gly
             100                 105                 110 tgc gac aaa acc gtg tat cca att gag aag gta tcg gtg aat gga aca    384
Cys Asp Lys Thr Val Tyr Pro Ile Glu Lys Val Ser Val Asn Gly Thr
             115                 120                 125 ttg tac cac aag agc tgc ttc aag tgt aca cat gga ggc tgc acg ata    432
Leu Tyr His Lys Ser Cys Phe Lys Cys Thr His Gly Gly Cys Thr Ile
130                 135                 140 agc cct tcg aat tac ata gct cac gag ggt aag cta tat tgc aag cat    480
Ser Pro Ser Asn Tyr Ile Ala His Glu Gly Lys Leu Tyr Cys Lys His
145                 150                 155                 160 cat cat att cag ctg atc aag gag aaa gga aac ttg agc cag ctc gaa    528
His His Ile Gln Leu Ile Lys Glu Lys Gly Asn Leu Ser Gln Leu Glu
                 165                 170                 175 gga gga gga gag aat gcc gcc aag gac aaa gtc gtc gct gct taa        573
Gly Gly Gly Glu Asn Ala Ala Lys Asp Lys Val Val Ala Ala
             180                 185                 190

<210> SEQ ID NO 84
<211> LENGTH: 190
<212> TYPE: PRT
<213> ORGANISM: Arabidopsis thaliana

<400> SEQUENCE: 84

Met Ala Phe Ala Gly Thr Thr Gln Lys Cys Met Ala Cys Asp Lys Thr
 1               5                  10                  15

Val Tyr Leu Val Asp Lys Leu Thr Ala Asp Asn Arg Val Tyr His Lys
                 20                  25                  30

Ala Cys Phe Arg Cys His His Cys Lys Gly Thr Leu Lys Leu Ser Asn
             35                  40                  45

Tyr Asn Ser Phe Glu Gly Val Leu Tyr Cys Arg Pro His Phe Asp Gln
 50                  55                  60

Asn Phe Lys Arg Thr Gly Ser Leu Glu Lys Ser Phe Glu Gly Thr Pro
 65                  70                  75                  80

Lys Ile Gly Lys Pro Asp Arg Pro Leu Glu Gly Glu Arg Pro Ala Gly
                 85                  90                  95

Thr Lys Val Ser Asn Met Phe Gly Gly Thr Arg Glu Lys Cys Val Gly
             100                 105                 110

Cys Asp Lys Thr Val Tyr Pro Ile Glu Lys Val Ser Val Asn Gly Thr
             115                 120                 125

Leu Tyr His Lys Ser Cys Phe Lys Cys Thr His Gly Gly Cys Thr Ile
130                 135                 140

Ser Pro Ser Asn Tyr Ile Ala His Glu Gly Lys Leu Tyr Cys Lys His
145                 150                 155                 160
```

```
His His Ile Gln Leu Ile Lys Glu Lys Gly Asn Leu Ser Gln Leu Glu
            165                 170                 175

Gly Gly Gly Glu Asn Ala Ala Lys Asp Lys Val Val Ala Ala
        180                 185                 190
```

<210> SEQ ID NO 85  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 85
gatgggttta gctactacaa cttcttctat                                30

<210> SEQ ID NO 86  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 86
aaaatctcca aagtctctaa cggagaaaga                                30

<210> SEQ ID NO 87  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 87
gatggccgct gaggatcgaa gtgaggaact                                30

<210> SEQ ID NO 88  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 88
gcatatacgt gctctttggc ttttcttttc                                30

<210> SEQ ID NO 89  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 89
gatggctgct tcttcatcct ccgctgcttc                                30

<210> SEQ ID NO 90  
<211> LENGTH: 30  
<212> TYPE: DNA  
<213> ORGANISM: Artificial Sequence  
<220> FEATURE:  
<223> OTHER INFORMATION: Synthetic oligonucleotide

<400> SEQUENCE: 90
gaaactcgca tgatggattc cataaggtgg                                30

<210> SEQ ID NO 91
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 91
aatggaaaaa gccttgagaa acttc                                          25

<210> SEQ ID NO 92
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 92
tccccacgat cttcggcaag taca                                           24

<210> SEQ ID NO 93
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 93
gatggaaagt ctcgcacaca ttcctcccgg                                     30

<210> SEQ ID NO 94
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 94
cgtgtgtgta ttttgagccc aagagtagaa                                     30

<210> SEQ ID NO 95
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 95
atggaagcgg agaagaaaat gg                                             22

<210> SEQ ID NO 96
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 96
aacagctaaa agaggatccg ac                                             22

<210> SEQ ID NO 97
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 97
atggcggatt cgtcttccga c          21

<210> SEQ ID NO 98
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 98
gggaaaatgt ttccaagatt cg          22

<210> SEQ ID NO 99
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 99
atggaagaag caatcatgag ac          22

<210> SEQ ID NO 100
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 100
ataatcatca tgaaagcaat actg          24

<210> SEQ ID NO 101
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 101
gatgtcaaga aagccatgtt gtgtgggaga          30

<210> SEQ ID NO 102
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 102
tatgaagttc ttgtcgtcgt aatcttggct          30

<210> SEQ ID NO 103
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 103
gatggctcgt ggaaagattc agcttaagag          30

<210> SEQ ID NO 104

<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 104
gaactgaaat atttcacttg gcattgttag                                30

<210> SEQ ID NO 105
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 105
gatggcaatg tcttgcaagg atggtaagtt                                30

<210> SEQ ID NO 106
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 106
cacaaaggac caattgatga acacaaagca                                30

<210> SEQ ID NO 107
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 107
atggctgaac gaaagaaacg c                                         21

<210> SEQ ID NO 108
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 108
tgggcacgcg atattaagag g                                         21

<210> SEQ ID NO 109
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 109
gatggggaga cattcttgct gttacaaaca                                30

<210> SEQ ID NO 110
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 110
aagggactga ccaaaagaga cggccattct                                30

<210> SEQ ID NO 111
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 111
gatggccgat gaggtcacaa tcgggtttcg                                30

<210> SEQ ID NO 112
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 112
aggccaagtc agctgttccc agtcccacat                                30

<210> SEQ ID NO 113
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 113
atggcaagac aaatcaacat agag                                      24

<210> SEQ ID NO 114
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 114
ttcagataga aaaacggct cttc                                       24

<210> SEQ ID NO 115
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 115
atggtcatgg agcccaagaa g                                         21

<210> SEQ ID NO 116
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 116
tgaaccattt tcctctgcac tc                                        22

<210> SEQ ID NO 117
<211> LENGTH: 22
<212> TYPE: DNA

```
<213> ORGANISM: Artificial Sequence
<220> FEATURE:
<223> OTHER INFORMATION: Synthetic oligonucleotide

<400> SEQUENCE: 117
atgagatcag gagaatgtga tg                                          22

<210> SEQ ID NO 118
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 118
agaatctgat tcattatcgc tac                                         23

<210> SEQ ID NO 119
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 119
gatgggaaag agagcaacta ctagtgtgag                                  30

<210> SEQ ID NO 120
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 120
acaagtgaag tctcggagcc aatcttcatc                                  30

<210> SEQ ID NO 121
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 121
gatgaagtca agacgtgaac aatcaatcga                                  30

<210> SEQ ID NO 122
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 122
tttatagtaa cctcgaatgt gctgggccaa                                  30

<210> SEQ ID NO 123
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 123
gatgtctggt tcgacccgga aagaaatgga                                  30
```

<210> SEQ ID NO 124
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 124
ctcgatccta cctaatccaa taaactctct                                      30

<210> SEQ ID NO 125
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 125
gatggaggtg gagaagagga ttgtag                                          26

<210> SEQ ID NO 126
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 126
ctcatcagct gaggtaggag gag                                             23

<210> SEQ ID NO 127
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 127
gatggagttg gagcctatat catcgagttg                                      30

<210> SEQ ID NO 128
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 128
tccgacctgc atccgacatt gacggccatg                                      30

<210> SEQ ID NO 129
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 129
gatggaggtt atgagaccgt cgacgtcaca                                      30

<210> SEQ ID NO 130
<211> LENGTH: 30
<212> TYPE: DNA
<213> ORGANISM: Artificial Sequence
<220> FEATURE:

<223> OTHER INFORMATION: Synthetic oligonucleotide

<400> SEQUENCE: 130
tagttgaaac attgtgtttt gggcgtcata             30

<210> SEQ ID NO 131
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 131
atggcgagtt ttgaggaaag c             21

<210> SEQ ID NO 132
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 132
aaatgcatca caggaagatg aag             23

<210> SEQ ID NO 133
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 133
gatgataagc aaggatccaa gatcgagttt             30

<210> SEQ ID NO 134
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 134
gccttgatat tgaaggtgag aactcatcat             30

<210> SEQ ID NO 135
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 135
gatggagggt ggtgcgagta atgaagtagc             30

<210> SEQ ID NO 136
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 136
aacaagttgc agaggtggtt ggtcttggtt             30

```
<210> SEQ ID NO 137
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 137
atggaaactg cttctctttc tttc                                              24

<210> SEQ ID NO 138
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 138
agaattggcc agtttactaa ttgc                                              24

<210> SEQ ID NO 139
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 139
atggcacgac cacaacaacg c                                                 21

<210> SEQ ID NO 140
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 140
cagcgtctga gttggtaaaa cag                                               23

<210> SEQ ID NO 141
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 141
gatgggaaaa tcttcaagct cggaggaaag                                        30

<210> SEQ ID NO 142
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 142
tgatagattc aaagcattat tattatgatc                                        30

<210> SEQ ID NO 143
<211> LENGTH: 30
<212> TYPE: DNA
<213> ORGANISM: Artificial Sequence
<220> FEATURE:
<223> OTHER INFORMATION: Synthetic oligonucleotide
```

<400> SEQUENCE: 143
gatggctgat aggatcaaag gtccatggag                                    30

<210> SEQ ID NO 144
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 144
ctcgattctc ccaactccaa tttgactcat                                    30

<210> SEQ ID NO 145
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 145
atggactttg acgaggagct aaatc                                         25

<210> SEQ ID NO 146
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 146
aaagaaaggc tcataggac aag                                            23

<210> SEQ ID NO 147
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 147
gatgggtaga gggaagatag agataaagaa                                    30

<210> SEQ ID NO 148
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 148
atcattctgg gccgttggat cgttttgaag                                    30

<210> SEQ ID NO 149
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 149
gatggaagta acttcccaat ctaccctccc                                    30

<210> SEQ ID NO 150
<211> LENGTH: 30

```
<212> TYPE: DNA
<213> ORGANISM: Artificial Sequence
<220> FEATURE:
<223> OTHER INFORMATION: Synthetic oligonucleotide

<400> SEQUENCE: 150
aaacttaaac atcgcttgac gatgatggtt                                      30

<210> SEQ ID NO 151
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 151
atgattggag atctaatgaa g                                               21

<210> SEQ ID NO 152
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 152
gttcttgcct ttacccttat g                                               21

<210> SEQ ID NO 153
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 153
atggtacaga cgaagaagtt cag                                             23

<210> SEQ ID NO 154
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 154
gtttgtattg agaagctcct ctatc                                           25

<210> SEQ ID NO 155
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 155
gatggactgc aacatggtat cttcgttccc                                      30

<210> SEQ ID NO 156
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 156
```
gatgaaatga ctagggaaag tgccaaatat                                        30

<210> SEQ ID NO 157
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 157
gatggcagct gctatgaatt tgtac                                             25

<210> SEQ ID NO 158
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 158
agctagaatc gaatcccaat cg                                                22

<210> SEQ ID NO 159
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 159
atggtacatt cgaagaagtt ccg                                               23

<210> SEQ ID NO 160
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 160
gacctgtgca atggatccag                                                   20

<210> SEQ ID NO 161
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 161
gatggtggaa gaaggcggcg tag                                               23

<210> SEQ ID NO 162
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 162
gctagtatat aaatcttccc agaag                                             25

<210> SEQ ID NO 163
<211> LENGTH: 25
<212> TYPE: DNA
<213> ORGANISM: Artificial Sequence

```
<220> FEATURE:
<223> OTHER INFORMATION: Synthetic oligonucleotide

<400> SEQUENCE: 163
atggtgaaaa cacttcaaaa gacac                                              25

<210> SEQ ID NO 164
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 164
gcagaagttc cataatctga tatc                                               24

<210> SEQ ID NO 165
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 165
gatgggagct ccaaagctga agtggacacc                                         30

<210> SEQ ID NO 166
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 166
ccgagtttgg ctatgcattc tatacttcac                                         30

<210> SEQ ID NO 167
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 167
gatgagttac acgagcactg acagtgacca                                         30

<210> SEQ ID NO 168
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 168
acaaactatt tcaagtgatg gtaaggtgaa                                         30

<210> SEQ ID NO 169
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 169
gatggccgac ggtagtacta gttcttcgga                                         30
```

<210> SEQ ID NO 170
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 170
agcgactcca atcgtgttga atgctggatg                                    30

<210> SEQ ID NO 171
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 171
gatgataagc aaggatccaa gatcgagttt                                    30

<210> SEQ ID NO 172
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 172
ctagccttga tattgaaggt gagaactcat                                    30

<210> SEQ ID NO 173
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 173
gatgatgtca aaatctatga gcatatc                                       27

<210> SEQ ID NO 174
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 174
ttatccacta ccattcgaca cgtgacaaaa                                    30

<210> SEQ ID NO 175
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 175
gggatgggaa agagagcaac tactagtgtg agg                                33

<210> SEQ ID NO 176
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 176
tcaacaagtg aagtctcgga gccaatcttc                              30

<210> SEQ ID NO 177
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 177
gatgaacaaa acccgccttc gtgctctctc                              30

<210> SEQ ID NO 178
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 178
tcatcggaat agaagaagcg tttcttgacc                              30

<210> SEQ ID NO 179
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 179
atgagctcat ctgattccgt taataac                                 27

<210> SEQ ID NO 180
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 180
ttatatccga ttatcagaat aagaac                                  26

<210> SEQ ID NO 181
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 181
atgaaataca gaggcgtacg aaag                                    24

<210> SEQ ID NO 182
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 182
gcggtttgcg tcgttacaat tg                                      22

<210> SEQ ID NO 183

```
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 183
gatggtgcgg acaccgtgtt gcaaagctga                                    30

<210> SEQ ID NO 184
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 184
tccaaaatag ttatcaattt cgtcaaacaa                                    30

<210> SEQ ID NO 185
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 185
gatggagacg acgatgaaga agaaagggag                                    30

<210> SEQ ID NO 186
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 186
aatcacatgg tggtcaccat taagcaagtg                                    30

<210> SEQ ID NO 187
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 187
atggcttctt cacatcaaca acag                                          24

<210> SEQ ID NO 188
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 188
agtaactacg agttgagagt gtc                                           23

<210> SEQ ID NO 189
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 189
```
atgcattatc ctaacaacag aacc                                              24

<210> SEQ ID NO 190
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 190
ctggaacata tcagcaattg tatttc                                            26

<210> SEQ ID NO 191
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 191
gatggacacg aaggcggttg gagtttc                                           27

<210> SEQ ID NO 192
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 192
ttctagataa aacaacattg ctatc                                             25

<210> SEQ ID NO 193
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 193
gatggagaat ccggtgggtt taag                                              24

<210> SEQ ID NO 194
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 194
tgttcttgag atagaagaac attgg                                             25

<210> SEQ ID NO 195
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 195
atggattcga aaatggaat taac                                               24

<210> SEQ ID NO 196
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 196
aactgtggtt gtggctgttg ttg                                    23

<210> SEQ ID NO 197
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 197
gatggattac aagtatcaa gaag                                    24

<210> SEQ ID NO 198
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 198
gaatttccaa acgcaatcaa gattc                                  25

<210> SEQ ID NO 199
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 199
atgaatatcg tctcttggaa agatg                                  25

<210> SEQ ID NO 200
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 200
tcacatatgg tgatcacttc ctctacttg                              29

<210> SEQ ID NO 201
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 201
gatggcgtcg gtgtcgtcgt c                                      21

<210> SEQ ID NO 202
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 202
tttctcttgt gggaggtagc tg                                     22
```

<210> SEQ ID NO 203
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 203
atgatcagtt tcagagaaga gaac                                           24

<210> SEQ ID NO 204
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 204
taaaaactta tcgatccaat cagtag                                         26

<210> SEQ ID NO 205
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 205
atggaagaaa gcaatgatat ttttc                                          25

<210> SEQ ID NO 206
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 206
attggcaaga acttcccaaa tcag                                           24

<210> SEQ ID NO 207
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 207
atggagagct caaacaggag c                                              21

<210> SEQ ID NO 208
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 208
tctcttcctt tcttctgaat caag                                           24

<210> SEQ ID NO 209
<211> LENGTH: 25
<212> TYPE: DNA
<213> ORGANISM: Artificial Sequence
<220> FEATURE:

<223> OTHER INFORMATION: Synthetic oligonucleotide

<400> SEQUENCE: 209
gatggaggat caagttgggt ttggg                                          25

<210> SEQ ID NO 210
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 210
accaacaaga atgatccaac taatg                                          25

<210> SEQ ID NO 211
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 211
atggacgaat atattgattt ccgac                                          25

<210> SEQ ID NO 212
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 212
agcaactaat agatctgata tcaatg                                         26

<210> SEQ ID NO 213
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 213
atggcggatc tcttcggtgg                                                20

<210> SEQ ID NO 214
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 214
cgataaaatt gaagcccaat ctatc                                          25

<210> SEQ ID NO 215
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 215
gatgatgaag gttgatcaag attattcgtg                                     30

```
<210> SEQ ID NO 216
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 216
gtcttctcca ctcatcaaaa attgagacgc                                       30

<210> SEQ ID NO 217
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 217
atgaaaagcc gagtgagaaa atc                                              23

<210> SEQ ID NO 218
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 218
ttacttatcc aacaaatgat cttgg                                            25

<210> SEQ ID NO 219
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 219
gatgactcgt cgatgttctc actgcaatca                                       30

<210> SEQ ID NO 220
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 220
taaagcgtgt atcacgcttt tgatgtctga                                       30

<210> SEQ ID NO 221
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 221
gatgaacaaa acccgccttc gtgctctctc                                       30

<210> SEQ ID NO 222
<211> LENGTH: 30
<212> TYPE: DNA
<213> ORGANISM: Artificial Sequence
<220> FEATURE:
<223> OTHER INFORMATION: Synthetic oligonucleotide
```

<400> SEQUENCE: 222
tcggaataga agaagcgttt cttgacctgt                                    30

<210> SEQ ID NO 223
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 223
gatgggaaat cagaagctca aatggacggc                                    30

<210> SEQ ID NO 224
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 224
attcaagtac ataatctttc cctgactaca                                    30

<210> SEQ ID NO 225
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 225
gatggatcca tttttaattc agtccccatt                                    30

<210> SEQ ID NO 226
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 226
ccaagtccca ctattttcag aagaccccaa                                    30

<210> SEQ ID NO 227
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 227
gatggagcca atggaatctt gtagcgttcc                                    30

<210> SEQ ID NO 228
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 228
attatcaaat acgcaaatcc caatatcata                                    30

<210> SEQ ID NO 229
<211> LENGTH: 24

```
<212> TYPE: DNA
<213> ORGANISM: Artificial Sequence
<220> FEATURE:
<223> OTHER INFORMATION: Synthetic oligonucleotide

<400> SEQUENCE: 229
atgggaataa aaaagaaga tcag                                        24

<210> SEQ ID NO 230
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 230
ctcgatatgg tctggttgtg ag                                         22

<210> SEQ ID NO 231
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 231
atggaaaaca gctacaccgt tg                                         22

<210> SEQ ID NO 232
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 232
cttcctagac aacaaccta aac                                         23

<210> SEQ ID NO 233
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 233
gatggcggat tcttcacccg attcg                                      25

<210> SEQ ID NO 234
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 234
gtctttcaag agaagacttc tacc                                       24

<210> SEQ ID NO 235
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 235
```

```
atgtgtgggg gagctatcat ttc                                          23
```

<210> SEQ ID NO 236
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 236

```
attggagtct tgatagctcc                                              20
```

<210> SEQ ID NO 237
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 237

```
atggataatt cagaaaatgt tc                                           22
```

<210> SEQ ID NO 238
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 238

```
tctccaccgc cgtttaattc                                              20
```

<210> SEQ ID NO 239
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 239

```
atgatgatgg atgagtttat ggatc                                        25
```

<210> SEQ ID NO 240
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 240

```
cacaagtaag agatcggata tc                                           22
```

<210> SEQ ID NO 241
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 241

```
ggggatggcg actcctaacg aagt                                         24
```

<210> SEQ ID NO 242
<211> LENGTH: 29
<212> TYPE: DNA
<213> ORGANISM: Artificial Sequence

```
<220> FEATURE:
<223> OTHER INFORMATION: Synthetic oligonucleotide

<400> SEQUENCE: 242
aacaacggtc aactgggaat aaccaaacg                                         29

<210> SEQ ID NO 243
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 243
gatggtgagg cctccttgtt gtgacaaagg                                        30

<210> SEQ ID NO 244
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 244
gaagaaatta gtgttttcat ccaatagaat                                        30

<210> SEQ ID NO 245
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 245
gatggagact ctgcatccat tctctcacct                                        30

<210> SEQ ID NO 246
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 246
agctccggca ctgaagacat tttctccggc                                        30

<210> SEQ ID NO 247
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 247
gatggatttg cctcctggtt ttag                                              24

<210> SEQ ID NO 248
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 248
gtaattccag aaaggttcaa gatc                                              24
```

<210> SEQ ID NO 249
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 249
atgtcggctg tgtctgaatc g                                    21

<210> SEQ ID NO 250
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 250
aaccaaaccg agaggcggtg                                      20

<210> SEQ ID NO 251
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 251
gatgacgggg aagcgatcaa agac                                 24

<210> SEQ ID NO 252
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 252
ggggatataa tagtcgctta gatttc                               26

<210> SEQ ID NO 253
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 253
gatgatgaaa tctggggctg atttgc                               26

<210> SEQ ID NO 254
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 254
gaaagttccc tgcctaacca caagtgg                              27

<210> SEQ ID NO 255
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 255
gatgaaagaa gacatggaag tactatc                                27

<210> SEQ ID NO 256
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 256
tgcgactaga ctgcagaccg acatc                                  25

<210> SEQ ID NO 257
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 257
gatgaagtcg gagctaaatt taccagctgg                             30

<210> SEQ ID NO 258
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 258
cccctgtgga gcaaaactcc aattcaagaa                             30

<210> SEQ ID NO 259
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 259
atgtcgtctt ccaccaatga c                                      21

<210> SEQ ID NO 260
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 260
gtttacaaaa gagtcttgaa tcc                                    23

<210> SEQ ID NO 261
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 261
gatgggtttg aaagatattg ggtcc                                  25

<210> SEQ ID NO 262

```
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 262
ttggaaagcg aggatatttt cggtc                                          25

<210> SEQ ID NO 263
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 263
atgaacacaa catcatcaaa gagc                                           24

<210> SEQ ID NO 264
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 264
ggagccaaag tagttgaaac cttg                                           24

<210> SEQ ID NO 265
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 265
gatgaatcta ccaccgggat ttagg                                          25

<210> SEQ ID NO 266
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 266
cggtaagctt acttcgtcaa gatc                                           24

<210> SEQ ID NO 267
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 267
atgcatagcg ggaagagacc tc                                             22

<210> SEQ ID NO 268
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 268
``` tttcgtcgt ttgtggatac taatg    25

<210> SEQ ID NO 269
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 269
gatgaagaga gatcatcatc atcatcatca    30

<210> SEQ ID NO 270
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 270
atggcgagaa tcggatgaag c    21

<210> SEQ ID NO 271
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 271
gatggagacg gaagaagaga tgaag    25

<210> SEQ ID NO 272
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 272
gcaattccaa acagtgcttg gaatac    26

<210> SEQ ID NO 273
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 273
atgggttttg ctctgatcca cc    22

<210> SEQ ID NO 274
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 274
aaagactgag tagaagcctg tag    23

<210> SEQ ID NO 275
<211> LENGTH: 30
<212> TYPE: DNA

```
<213> ORGANISM: Artificial Sequence
<220> FEATURE:
<223> OTHER INFORMATION: Synthetic oligonucleotide

<400> SEQUENCE: 275
gatgggtgca ccaaagcaga agtggacacc                              30

<210> SEQ ID NO 276
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 276
ccaaggatga ttacggatcc tgaacttcaa                              30

<210> SEQ ID NO 277
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 277
gatggataat tcagctccag attcgttatc                              30

<210> SEQ ID NO 278
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 278
aactctaagg agctgcattt tgttagcaaa                              30

<210> SEQ ID NO 279
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 279
atgattggag atctaatgaa g                                       21

<210> SEQ ID NO 280
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 280
gagactgata accggacacg                                         20

<210> SEQ ID NO 281
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 281
gatgaagaga gatcatcatc atcatcatca                              30
```

<210> SEQ ID NO 282
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 282
tcaggaatga tgactggtgc ttcc                                              24

<210> SEQ ID NO 283
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 283
atggtctccg ctctcagccg                                                   20

<210> SEQ ID NO 284
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 284
ttattctctt gggtagttat aataattg                                          28

<210> SEQ ID NO 285
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 285
atgagatcag gagaatgtga tg                                                22

<210> SEQ ID NO 286
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 286
agaatctgat tcattatcgc tac                                               23

<210> SEQ ID NO 287
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 287
ggggatgtac ggacagtgca atatag                                            26

<210> SEQ ID NO 288
<211> LENGTH: 29
<212> TYPE: DNA
<213> ORGANISM: Artificial Sequence
<220> FEATURE:

<223> OTHER INFORMATION: Synthetic oligonucleotide

<400> SEQUENCE: 288
gggtatgaaa ccaataactc atcaacacg                                29

<210> SEQ ID NO 289
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 289
gatgaattcg ttttcacaag tacctcctgg                               30

<210> SEQ ID NO 290
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 290
gagatcaatc tgacaacttg aagaagtaga                               30

<210> SEQ ID NO 291
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 291
atggtctccg ctctcagccg                                          20

<210> SEQ ID NO 292
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 292
ttctcttggg tagttataat aattg                                    25

<210> SEQ ID NO 293
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 293
atgaaacgaa ttgttcgaat ttcattc                                  27

<210> SEQ ID NO 294
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 294
aacaacttct tcagaagcac cac                                      23

```
<210> SEQ ID NO 295
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 295
gatggggaaa actcaactcg ctcctggatt                                        30

<210> SEQ ID NO 296
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 296 cattttggt ctatgtctca tggaagcaga                                         30

<210> SEQ ID NO 297
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 297
gggatggcgt tcgcaggaac aacccagaaa tg                                     32

<210> SEQ ID NO 298
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 298
agcagcgacg actttgtcct tggcg                                             25

<210> SEQ ID NO 299
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 299
gatggaaaac atgggggatt cgagcatag                                         29

<210> SEQ ID NO 300
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 300
tgagtgccag ttcatgttag gaagctg                                           27

<210> SEQ ID NO 301
<211> LENGTH: 22
<212> TYPE: DNA
<213> ORGANISM: Artificial Sequence
<220> FEATURE:
<223> OTHER INFORMATION: Synthetic oligonucleotide
```

```
<400> SEQUENCE: 301
atggaggttg acgaagacat tg                                              22

<210> SEQ ID NO 302
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 302
tctcctttcc tttgccttgt c                                               21

<210> SEQ ID NO 303
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 303
atgagaatga caagagatgg aaaag                                           25

<210> SEQ ID NO 304
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 304
aaggcaatac ccattagtaa aatccatcat ag                                   32

<210> SEQ ID NO 305
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 305
gatggataat gtcaaacttg ttaagaatgg                                      30

<210> SEQ ID NO 306
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 306
tctgaaacta ttgcaactac tggtctcttc                                      30

<210> SEQ ID NO 307
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 307
gatggagagt acagattctt ccggtggtcc                                      30

<210> SEQ ID NO 308
<211> LENGTH: 30
```

```
<212> TYPE: DNA
<213> ORGANISM: Artificial Sequence
<220> FEATURE:
<223> OTHER INFORMATION: Synthetic oligonucleotide

<400> SEQUENCE: 308
agaataccaa ttcaaaccag gcaattggta                                    30

<210> SEQ ID NO 309
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 309
atggcttttg gcaatatcca ag                                            22

<210> SEQ ID NO 310
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 310
aaaagaagat aataacgtct cc                                            22

<210> SEQ ID NO 311
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 311
atggcgagtt ttgaggaaag c                                             21

<210> SEQ ID NO 312
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 312
aaatgcatca caggaagatg aag                                           23

<210> SEQ ID NO 313
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 313
atggtgaagc aagcgatgaa gg                                            22

<210> SEQ ID NO 314
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 314
```
aaaatcccaa agaatcaaag attc                                          24

<210> SEQ ID NO 315
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 315
gatggaatcg gtggatcaat catgtagtgt                                    30

<210> SEQ ID NO 316
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 316
aacatgtaaa tccctatata agtcatagtc                                    30

<210> SEQ ID NO 317
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 317
atgaacaaca acattttcag tactac                                        26

<210> SEQ ID NO 318
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 318
actgtgtata gctttagata aaacc                                         25

<210> SEQ ID NO 319
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 319
atgtgtgtct taaaagtggc aaatc                                         25

<210> SEQ ID NO 320
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 320
ggaggatgga ctattattgt ag                                            22

<210> SEQ ID NO 321
<211> LENGTH: 23
<212> TYPE: DNA
<213> ORGANISM: Artificial Sequence

```
<220> FEATURE:
<223> OTHER INFORMATION: Synthetic oligonucleotide

<400> SEQUENCE: 321
gatggcggcg ataggagaga aag                                          23

<210> SEQ ID NO 322
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 322
cttaaaagga atattagtat agtg                                         24

<210> SEQ ID NO 323
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 323
gatgaagaga acacatttgg caagttttag                                   30

<210> SEQ ID NO 324
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 324
gaggtagcct agtcgaagct ccaaatcaag                                   30

<210> SEQ ID NO 325
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 325
gatggctgat aggatcaaag gtccatggag                                   30

<210> SEQ ID NO 326
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 326
ctcgattctc ccaactccaa tttgactcat                                   30

<210> SEQ ID NO 327
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 327
atgtttcctt ctttcattac tcac                                         24
```

<210> SEQ ID NO 328
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 328
attagggttt ttagttaaca cattg                                          25

<210> SEQ ID NO 329
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 329
atggaaggaa ttcagcatcc                                                20

<210> SEQ ID NO 330
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 330
ggctttcatt ttcttgctgg                                                20

<210> SEQ ID NO 331
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 331
gatggctggg cgatcatggc tgatc                                          25

<210> SEQ ID NO 332
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 332
cagcagcgtg gcagtgtgtt gcc                                            23

<210> SEQ ID NO 333
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 333
gatggcggtt gtggttgaag aagg                                           24

<210> SEQ ID NO 334
<211> LENGTH: 22
<212> TYPE: DNA
<213> ORGANISM: Artificial Sequence
<220> FEATURE:
<223> OTHER INFORMATION: Synthetic oligonucleotide -continued

```
<400> SEQUENCE: 334
gaagtcccac aagtcccccc tc                                              22

<210> SEQ ID NO 335
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 335
atgagctcat ctgattccgt taataac                                         27

<210> SEQ ID NO 336
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 336
tatccgatta tcagaataag aacattc                                         27

<210> SEQ ID NO 337
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 337
gatgggtctc caagagcttg acccgttagc                                      30

<210> SEQ ID NO 338
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 338
aataaacccg aacccactag attgttgacc                                      30

<210> SEQ ID NO 339
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 339
gatgctgcag tctgcagcac cagag                                           25

<210> SEQ ID NO 340
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 340
tgaactcacc agtgtcctcc atatac                                          26

<210> SEQ ID NO 341
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 341
gatggtgaaa gatctggttg gg                                          22

<210> SEQ ID NO 342
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 342
tctctcgcga tcaaacttca tcgc                                        24

<210> SEQ ID NO 343
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 343
atgaagtctt tttgtgataa tgatg                                       25

<210> SEQ ID NO 344
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 344
agaatcagcc caagcagcga aaaccgg                                     27

<210> SEQ ID NO 345
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 345
gatgggtatc caagaaactg acccgttaac                                  30

<210> SEQ ID NO 346
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 346
cataaaccca aacccaccaa cttgccccga                                  30

<210> SEQ ID NO 347
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 347
```

```
gatggtttac ggtaagagat cgag                                           24

<210> SEQ ID NO 348
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 348
ccaatatatg ttaactattg gtg                                            23

<210> SEQ ID NO 349
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 349
gatggagaag aggagctcta ttaaaaacag                                     30

<210> SEQ ID NO 350
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 350
tagaaacaaa caaaacttat tttcccgata                                     30

<210> SEQ ID NO 351
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 351
gatggattac gaggcatcaa gaatc                                          25

<210> SEQ ID NO 352
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 352
gaaattccaa acgcaatcca attc                                           24

<210> SEQ ID NO 353
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 353
gatggctgat aataaggtca atctttcgat                                     30

<210> SEQ ID NO 354
<211> LENGTH: 30
<212> TYPE: DNA
```

<213> ORGANISM: Artificial Sequence
<220> FEATURE:
<223> OTHER INFORMATION: Synthetic oligonucleotide

<400> SEQUENCE: 354
tacagataaa tgaagaagtg ggtctaaaga                                30

<210> SEQ ID NO 355
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 355
gatgtacgga cagtgcaata tagaatccg                                 29

<210> SEQ ID NO 356
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 356
tgaaaccaat aactcatcaa cacgtgt                                   27

<210> SEQ ID NO 357
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 357
gggatggagg gttcgtccaa agggctgcga aaagg                          35

<210> SEQ ID NO 358
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 358
atcaaatttc acagtctctc catcgaaaag actcc                          35

<210> SEQ ID NO 359
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 359
gatgggtcat cactcatgct gcaaccagca                                30

<210> SEQ ID NO 360
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 360
aaacgaagaa gggaaagaag aagataaggc                                30

<210> SEQ ID NO 361
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 361
gatggagagc accgattctt ccggtggtcc                                    30

<210> SEQ ID NO 362
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 362
agaagagtac caatttaaac cgggtaattg                                    30

<210> SEQ ID NO 363
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 363
atggcgacaa ttcagaagct tg                                            22

<210> SEQ ID NO 364
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 364
gtggttcgat gaccgtgctg                                               20

<210> SEQ ID NO 365
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 365
atgtattcat ctccaagttc ttgg                                          24

<210> SEQ ID NO 366
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 366
acatgagctc ataagaagtt gttc                                          24

<210> SEQ ID NO 367
<211> LENGTH: 30
<212> TYPE: DNA
<213> ORGANISM: Artificial Sequence
<220> FEATURE:

<223> OTHER INFORMATION: Synthetic oligonucleotide

<400> SEQUENCE: 367
gatgaattca ttttcccacg tccctccggg                                30

<210> SEQ ID NO 368
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 368
cttccataga tcaatctgac aactcgaaga                                30

<210> SEQ ID NO 369
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 369
gatgaacata tcagtaaacg gacagtcaca                                30

<210> SEQ ID NO 370
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 370
tccactaccg ttcaacaagt ggcatgtcgt                                30

<210> SEQ ID NO 371
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 371
atggcgaatt caggaaatta tgg                                       23

<210> SEQ ID NO 372
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 372
aaaaccagaa ttaggaggtg aag                                       23

<210> SEQ ID NO 373
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 373
atgtgtggag gagctataat ctc                                       23

```
<210> SEQ ID NO 374
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 374
aaagtctcct tccagcatga aattg                                               25

<210> SEQ ID NO 375
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 375
atggagttca atggtaattt gaatg                                               25

<210> SEQ ID NO 376
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 376
ttggtagaag aatgtggagg g                                                   21

<210> SEQ ID NO 377
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 377
gatgggaagg ggtagggttc aattgaagag                                          30

<210> SEQ ID NO 378
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 378
tgcggcgaag cagccaaggt tgcagttgta                                          30

<210> SEQ ID NO 379
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 379
gatgggtcgc gaatctgtgg ctgttg                                              26

<210> SEQ ID NO 380
<211> LENGTH: 25
<212> TYPE: DNA
<213> ORGANISM: Artificial Sequence
<220> FEATURE:
<223> OTHER INFORMATION: Synthetic oligonucleotide
```

<400> SEQUENCE: 380
ttgtccatta gcattgttct tcttg 25

<210> SEQ ID NO 381
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 381
atggcaacta aacaagaagc tttag 25

<210> SEQ ID NO 382
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 382
agtgacggag ataacggaaa ag 22

<210> SEQ ID NO 383
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 383
atggtgtcta tgctgactaa tg 22

<210> SEQ ID NO 384
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 384
accaaaagag gagtaattgt attg 24

<210> SEQ ID NO 385
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 385
ggggatggcc aagatgggct tgaaac 26

<210> SEQ ID NO 386
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 386
tcaggcctgt tccgatggag gaggc 25

<210> SEQ ID NO 387
<211> LENGTH: 24

<212> TYPE: DNA
<213> ORGANISM: Artificial Sequence
<220> FEATURE:
<223> OTHER INFORMATION: Synthetic oligonucleotide

<400> SEQUENCE: 387
atggaagaat accagcatga caac                                          24

<210> SEQ ID NO 388
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 388
tcatggaccg agacgataag gtcc                                          24

<210> SEQ ID NO 389
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 389
gggatggcgt tcgcaggaac aacccagaaa tg                                 32

<210> SEQ ID NO 390
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 390
ttaagcagcg acgactttgt cc                                            22

<210> SEQ ID NO 391
<211> LENGTH: 13
<212> TYPE: PRT
<213> ORGANISM: Artificial Sequence
<220> FEATURE:
<223> OTHER INFORMATION: Synthetic polypeptide

<400> SEQUENCE: 391

Gly Leu Asp Leu Asp Leu Glu Leu Arg Leu Gly Phe Ala
1               5                   10

<210> SEQ ID NO 392
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (14)..(14)
<223> OTHER INFORMATION: Xaa is Asn or Glu
<220> FEATURE:
<221> NAME/KEY: misc_feature
<222> LOCATION: (16)..(21)
<223> OTHER INFORMATION: Xaa is any amino acid

<400> SEQUENCE: 392

```
Xaa Xaa Xaa Xaa Xaa Xaa Xaa Xaa Xaa Xaa Leu Asp Leu Xaa Leu Xaa
1               5                   10                  15

Xaa Xaa Xaa Xaa Xaa
            20

<210> SEQ ID NO 393
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(10)
<223> OTHER INFORMATION: Xaa is any amino acid
<220> FEATURE:
<221> NAME/KEY: misc_feature
<222> LOCATION: (15)..(15)
<223> OTHER INFORMATION: Xaa is Phe or Ile
<220> FEATURE:
<221> NAME/KEY: misc_feature
<222> LOCATION: (16)..(21)
<223> OTHER INFORMATION: Xaa is any amino acid

<400> SEQUENCE: 393

Xaa Xaa Xaa Xaa Xaa Xaa Xaa Xaa Xaa Xaa Phe Asp Leu Asn Xaa Xaa
1               5                   10                  15

Xaa Xaa Xaa Xaa Xaa
            20

<210> SEQ ID NO 394
<211> LENGTH: 19
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (6)..(6)
<223> OTHER INFORMATION: Xaa is Glu, Gln or Asp
<220> FEATURE:
<221> NAME/KEY: misc_feature
<222> LOCATION: (10)..(19)
<223> OTHER INFORMATION: Xaa is any amino acid

<400> SEQUENCE: 394

Leu Asp Leu Asp Leu Xaa Leu Arg Leu Xaa Xaa Xaa Xaa Xaa Xaa Xaa
1               5                   10                  15

Xaa Xaa Xaa

<210> SEQ ID NO 395
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Asp, Asn, Glu, Gln, Thr or Ser
<220> FEATURE:
<221> NAME/KEY: misc_feature
<222> LOCATION: (3)..(3)
<223> OTHER INFORMATION: Xaa is Asp, Gln, Asn, Arg, Glu, Thr, Ser or His
<220> FEATURE:
<221> NAME/KEY: misc_feature
<222> LOCATION: (5)..(5)
<223> OTHER INFORMATION: Xaa is Arg, Gln, Asn, Thr, Ser, His, Lys or Asp

<400> SEQUENCE: 395
```

```
Xaa Leu Xaa Leu Xaa Leu
1               5

<210> SEQ ID NO 396
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Asp, Asn, Glu, Gln, Thr or Ser
<220> FEATURE:
<221> NAME/KEY: misc_feature
<222> LOCATION: (3)..(3)
<223> OTHER INFORMATION: Xaa is Asp, Gln, Asn, Arg, Glu, Thr, Ser or His
<220> FEATURE:
<221> NAME/KEY: misc_feature
<222> LOCATION: (5)..(5)
<223> OTHER INFORMATION: Xaa is Gln, Asn, Thr, Ser, His, Lys or Asp

<400> SEQUENCE: 396

Xaa Leu Xaa Leu Xaa Leu
1               5

<210> SEQ ID NO 397
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Asp, Asn, Glu, Gln, Thr or Ser
<220> FEATURE:
<221> NAME/KEY: misc_feature
<222> LOCATION: (3)..(3)
<223> OTHER INFORMATION: Xaa is Asn, Arg, Thr, Ser or His

<400> SEQUENCE: 397

Xaa Leu Xaa Leu Arg Leu
1               5

<210> SEQ ID NO 398
<211> LENGTH: 6
<212> TYPE: PRT
<213> ORGANISM: Artificial Sequence
<220> FEATURE:
<223> OTHER INFORMATION: Synthetic polypeptide
<220> FEATURE:
<221> NAME/KEY: misc_feature
<222> LOCATION: (1)..(1)
<223> OTHER INFORMATION: Xaa is Asn, Glu, Gln, Thr or Ser
<220> FEATURE:
<221> NAME/KEY: misc_feature
<222> LOCATION: (3)..(3)
<223> OTHER INFORMATION: Xaa is Asp, Gln, Asn, Arg, Glu, Thr, Ser or His

<400> SEQUENCE: 398

Xaa Leu Xaa Leu Arg Leu
1               5
```

PLANT WITH REDUCED PROTEIN PRODUCTIVITY IN SEEDS AND METHOD FOR PRODUCING SAME

CROSS REFERENCE TO RELATED APPLICATIONS

This application is a Divisional Application of U.S. application Ser. No. 13/376,169, filed Dec. 2, 2011, which is a National Stage of International Application No. PCT/JP2010/059495 filed Jun. 4, 2010, claiming priority based on Japanese Patent Application No. 2009-135195, filed Jun. 4, 2009, the contents of all of which are incorporated herein by reference in their entirety.

BACKGROUND ART

In order to change the amount of protein in seeds, the following have been conventionally used: (1) an improved cultivation method; (2) a method for processing harvested seeds, and particularly grains such as rice grains, with an acid or bacterium; (3) molecular breeding using markers; (4) mutant screening; (5) gene recombination; and other methods.

Problems relating to the above methods and the object achieved by the present invention are described below.

According to the method (1) above, it is possible to change the protein amount, although it is only possible to increase or decrease the amount to a slight extent. In addition, although the method (2) above is effective to a certain extent for reducing the protein amount, processing of harvested seeds is labor- and time-consuming. Further, advantageous results such as an increase in protein amount cannot be obtained according to the method (2) above. According to the method (3) above, the protein amount is determined to be a quantitative trait. In order to modify such trait by a conventional breeding method, it is necessary to identify a plurality of gene loci that contribute highly to trait expression by QTL analysis, to specify the causative gene at each gene locus, and to introduce each causative gene into a desired variety by crossing. Therefore, the method (3) above is also labor- and time-consuming. With the method (4) above, a low-glutelin rice line such as LGC-1 is bred. However, the amount of remaining glutelin accounts for 30% to 50% of that in the original variety. In addition, there are problematic points common to low-glutelin rice lines. In fact, the amount of glutelin, which is an easily digestible protein, decreases to significantly below the level found in the original variety. However, this in turn causes a significant increase in the amount of prolamin, which is an indigestible protein. Therefore, the method (4) above cannot be evaluated as a method for reducing total seed protein content. In the case of the method (5) above, it has been reported that the total expression level of the prolamin multigene group was remarkably reduced, resulting in reduction of the protein content in rice seeds (Patent Document 1:WO2004/056993). However, in this case, the decrease in the total protein content is 15% at maximum, although the amount of prolamin itself decreases to 50% or less of the original amount. In addition, regarding the method (5) above, it has been reported that transcription factors specified by AT1G04550, AT1G66390, AT5G13330, and At2g30420 were overexpressed in *Arabidopsis thaliana* seeds, which resulted in, respectively, 25%, 14%, 39%, and 17% increases in protein content. Also, it has been reported that overexpression of a transcription factor specified by At2g47460 resulted in a decrease in the seed storage protein content of 13% (Patent Document 2: WO 01/35727).

In spite of the development of the above molecular breeding methods for the improvement of a variety of traits, there are still no practically available techniques to increase or decrease seed protein content.

As reasons for the above, it is considered that truly excellent genes remain undiscovered, and that new recombinant varieties that have been confirmed to have desirable effects in the test phase cannot exhibit expected effects upon practical use in different environments. In addition, a number of genes are involved in the expression of quantitative traits such as seed protein content in different steps in the control system, the metabolizing system, and other systems. Thus, it has been difficult to discover or develop truly excellent genes capable of improving quantitative traits. In order to solve such problems, an object of the present invention is to find a novel gene exhibiting remarkably high effects. Another object of the present invention is to develop a gene capable of exerting effects in a practical environment to an extent comparable to the effects exerted in the test phase.

CITATION LIST

Patent Literature

Patent Document 1: WO2004/056993
Patent Document 2: WO 01/35727

SUMMARY OF INVENTION

Technical Problem

In view of the above circumstances, an object of the present invention is to provide a technique for searching for a gene having a novel function that can cause an increase or decrease in seed protein content so as to improve such feature of a plant.

Solution to Problem

As a result of intensive studies to achieve the above objects, the present inventors found that it is possible to improve various quantitative traits and particularly to increase or decrease seed protein content via induction of expression of a chimeric protein obtained by fusing a particular transcription factor and a functional peptide capable of converting an arbitrary transcription factor into a transcriptional repressor (hereinafter sometimes referred to as a "repressor domain"), introduction of a particular gene encoding a particular transcription factor, or modification of an expression control region of an endogenous gene corresponding to the gene. This has led to the completion of the present invention.

The plant of the present invention is obtained by inducing expression of a chimeric protein in a plant, such chimeric protein obtained by fusing a transcription factor consisting of any one of the following proteins (a) to (c) and a functional peptide capable of converting an arbitrary transcription factor into a transcriptional repressor, introducing a gene encoding a transcription factor consisting of any one of the following proteins (d) to (f) into a plant, or modifying an expression control region of an endogenous gene corresponding to the gene in a plant.

(a) A protein comprising an amino acid sequence shown in any of the even-numbered SEQ ID NOS: 1 to 76

(b) A protein having transactivation activity and comprising an amino acid sequence that has a deletion, a substitution, an addition, or an insertion of one or a plurality of amino acids with respect to an amino acid sequence shown in any of the even-numbered SEQ ID NOS: 1 to 76.
(c) A protein having transactivation activity encoded by a polynucleotide that hybridizes under stringent conditions to a polynucleotide consisting of a nucleotide sequence complementary to a nucleotide sequence shown in any of the odd-numbered SEQ ID NOS: 1 to 76.
(d) A protein comprising an amino acid sequence shown in any of the even-numbered SEQ ID NOS: 77 to 84.
(e) A protein having transactivation activity and comprising an amino acid sequence that has a deletion, a substitution, an addition, or an insertion of one or a plurality of amino acids with respect to the amino acid sequence shown in any of the even-numbered SEQ ID NOS: 77 to 84.
(f) A protein having transactivation activity encoded by a polynucleotide that hybridizes under stringent conditions to a polynucleotide consisting of a nucleotide sequence complementary to a nucleotide sequence shown in any of the odd-numbered SEQ ID NOS: 77 to 84.

Preferably, the fusion of a functional peptide with a predetermined transcription factor causes repression of transcriptional regulatory activity, and particularly, transactivation activity, of the transcription factor in the plant of the present invention. Examples of the above functional peptide used herein include peptides expressed by the following formulae (1) to (8).

(1) X1-Leu-Asp-Leu-X2-Leu-X3 (SEQ ID NO: 392 with deletion of 0-10 residues from the N-terminus)
(where X1 denotes a set of 0 to 10 amino acid residues, X2 denotes Asn or Glu, and X3 denotes a set of at least 6 amino acid residues.)
(2) Y1-Phe-Asp-Leu-Asn-Y2-Y3 (SEQ ID NO: 393 with deletion of 0-10 residues from the N-terminus)
(where Y1 denotes a set of 0 to 10 amino acid residues, Y2 denotes Phe or Ile, and Y3 denotes a set of at least 6 amino acid residues.)
(3) Z1-Asp-Leu-Z2-Leu-Arg-Leu-Z3 (SEQ ID NO: 394 with deletion of 0-10 residues from the C-terminus and deletion of 0-2 residues from the N-terminus)
(where Z1 denotes Leu, Asp-Leu, or Leu-Asp-Leu, Z2 denotes Glu, Gln, or Asp, and Z3 denotes a set of 0 to 10 amino acid residues.)

```
       (4) Asp-Leu-Z4-Leu-Arg-Leu
           (residues 4-9 of SEQ ID NO: 394)
```

(where Z4 denotes Glu, Gln, or Asp.)

```
                                          (SEQ ID NO: 395)
       (5) α1-Leu-β1-Leu-γ1-Leu (SEQ ID NO: 396)
       (6) α1-Leu-β1-Leu-γ2-Leu (SEQ ID NO: 397)
       (7) α1-Leu-β2-Leu-Arg-Leu (SEQ ID NO: 398)
       (8) α2-Leu-β1-Leu-Arg-Leu
```

(where α1 denotes Asp, Asn, Glu, Gln, Thr, or Ser, α2 denotes Asn, Glu, Gln, Thr, or Ser, β1 denotes Asp, Gln, Asn, Arg, Glu, Thr, Ser, or His, β2 denotes Asn, Arg, Thr, Ser, or His, γ1 denotes Arg, Gln, Asn, Thr, Ser, His, Lys, or Asp, and γ2 denotes Gln, Asn, Thr, Ser, His, Lys, or Asp in formulae (5) to (8).)

In addition, the plant of the present invention provides significant improvement or reduction of productivity of a protein contained in seeds. Here, the expression "significant improvement or reduction" indicates that the plant of the present invention allows an increase or decrease in the seed protein content associated with a statistically significant difference when compared in terms of material productivity with a plant in which the above chimeric protein is not expressed.

Meanwhile, according to the present invention, the above chimeric protein, the gene encoding the chimeric protein, an expression vector comprising the gene, and a transformant comprising the gene can be provided.

This description includes part or all of the contents as disclosed in the description and/or drawings of Japanese Patent Application No. 2009-135195, which is a priority document of the present application.

Advantageous Effects of Invention

The seed protein content is improved or reduced in the plant of the present invention. Therefore, the use of the plant of the present invention enables mass production of a desired protein in seeds of the plant. Alternatively, seeds that exhibit a significant reduction in the content of a protein contained as an impurity or an allergen can be produced.

DESCRIPTION OF EMBODIMENTS

The present invention will be described in detail as follows.

The plant of the present invention is a plant in which a chimeric protein obtained by fusing a predetermined transcription factor and a functional peptide capable of converting an arbitrary transcription factor into a transcriptional repressor is expressed, a plant in which a gene encoding a predetermined transcription factor is present as a result of gene introduction, or a plant in which an expression control region of an endogenous gene corresponding to the gene is modified. The plant of the present invention is found to exhibit significant improvement or reduction of the productivity of seed protein when compared with a wild-type plant. Specifically, the plant of the present invention is produced by causing a transcription factor to be expressed in the form of a chimeric protein with the functional peptide in a desired plant, introducing a gene encoding a predetermined transcription factor into a desired plant, or modifying an expression control region of an endogenous gene corresponding to the gene in a desired plant so as to significantly improve or reduce the protein content in seeds of the desired plant. Here, the expression level of the gene can be significantly increased compared with that in a wild-type plant by exogenously introducing a predetermined transcription factor into a plant or modifying an expression control region of an endogenous gene corresponding to the gene in a plant. The plant according to the present invention may be produced by causing the expression of the predetermined transcription factor in all plant tissues, or at least in some plant tissues. Here, the term "plant tissue(s)" is meant to include plant organ(s) such as leaves, stems, seeds, roots, and flowers.

Also, the term "expression control region" refers to a promoter region to which RNA polymerase binds and a region to which another transcription factor binds. A transcriptional regulatory region is preferably modified by substituting a promoter region, for example, among endogenous transcriptional regulatory regions with a promoter region that enables a higher expression level. In addition, when replacing, for example, a promoter region with a promoter region that enables a higher expression level, it becomes possible to cause overexpression of the predetermined transcription factor. Further, the term "overexpression" used herein also indicates a case in which a gene encoding a predetermined transcription factor present in a plant as a result of gene introduction is transcribed and thus is expressed at a level at which the gene can be confirmed as a transcription product.

In particular, preferably, the transactivation activity of a transcription factor is repressed in the plant of the present invention by fusing the factor with the above functional peptide. In other words, when a chimeric protein obtained by fusing a transcription factor with the functional peptide is expressed in the plant of the present invention, this preferably results in expression of transcription repression effects originally imparted to the functional peptide as a dominant trait.

A protein contained in a plant used herein may be any protein originally accumulated in seeds and any protein encoded by a gene exogenously introduced into the plant. In addition, genes to be exogenously introduced are introduced under control of, for example, a publicly known seed-specific expression promoter, thereby allowing efficient expression of the genes in seeds.

In particular, if the seed protein content increases, purification cost or transport cost can be reduced. Thus, such plant is highly industrially applicable. Meanwhile, a protein contained in seeds might become an impurity or allergen, depending on the usage of seeds. Therefore, if the productivity of a protein contained in seeds decreases, the impurity content or the allergen content also decreases. In such case, the seeds are highly industrially applicable.

Plants used herein are not particularly limited, and thus any plant can be used as a target plant. Examples of an available target plant include soybean, sesame, olive oil, coconut, rice, cotton, sunflower, corn, sugarcane, Jatropha, palm, tobacco, safflower, and rapeseed. Also, *Arabidopsis thaliana*, which has been widely used as an biological model for plant gene analysis and for which gene expression analysis methods have been established, can be used as a target plant.

In addition, transcription repression activity of a chimeric protein comprising a transcription factor is activity of recognizing a cis sequence that is recognized by the transcription factor or a cis sequence of a different transcription factor that is analogous to such a cis sequence so as to actively repress the expression of downstream genes. Thus, such chimeric protein can also be called a "transcriptional repressor." A method for causing a chimeric protein comprising a transcription factor to have transcription repression activity is not particularly limited. However, the most preferable method may be a method for constructing a chimeric protein (fusion protein) by adding a repressor domain sequence or an SRDX sequence thereto.

In the above method, as a repressor domain sequence, a variety of amino acid sequences discovered by the present inventors, each of which constitutes a peptide capable of converting an arbitrary transcription factor into a transcriptional repressor, can be used. For example, the following can be referred to for a method using a repressor domain sequence: JP Patent Publication (Kokai) No. 2001-269177 A; JP Patent Publication (Kokai) No. 2001-269178 A; JP Patent Publication (Kokai) No. 2001-292776 A; JP Patent Publication (Kokai) No. 2001-292777 A; JP Patent Publication (Kokai) No. 2001-269176 A; JP Patent Publication (Kokai) No. 2001-269179 A; WO03/055903; Ohta, M., Matsui, K., Hiratsu, K., Shinshi, H. and Ohme-Takagi, M., The Plant Cell, Vol. 13, 1959-1968, August, 2001; and Hiratsu, K., Ohta, M., Matsui, K., or Ohme-Takagi, M., FEBS Letters 514 (2002) 351-354. A repressor domain sequence can be excised from a Class II ERF (Ethylene Responsive Element Binding Factor) protein or a plant zinc finger protein (zinc finger protein such as *Arabidopsis thaliana* SUPERMAN protein). The sequence has a very simple structure.

Examples of a transcription factor constituting a chimeric protein to be expressed include transcription factors specified by AGI codes for *Arabidopsis thaliana* listed in tables 1 and 2. In addition, any transcription factor listed in table 1 causes a significant increase in seed protein content when a chimeric protein comprising the transcription factor and a repressor domain is expressed in a plant. Meanwhile, any transcription factor listed in table 2 causes a significant decrease in seed protein content when a chimeric protein comprising the transcription factor and a repressor domain is expressed in a plant.

TABLE 1

| AGI code | Nucleotide sequence | Amino acid sequence |
| --- | --- | --- |
| AT2G23760 | SEQ ID NO: 1 | SEQ ID NO: 2 |
| AT1G18330 | SEQ ID NO: 3 | SEQ ID NO: 4 |
| AT2G02070 | SEQ ID NO: 5 | SEQ ID NO: 6 |
| AT1G12980 | SEQ ID NO: 7 | SEQ ID NO: 8 |
| AT5G62380 | SEQ ID NO: 9 | SEQ ID NO: 10 |
| AT4G23750 | SEQ ID NO: 11 | SEQ ID NO: 12 |
| AT4G32800 | SEQ ID NO: 13 | SEQ ID NO: 14 |
| AT1G24590 | SEQ ID NO: 15 | SEQ ID NO: 16 |
| AT5G07690 | SEQ ID NO: 17 | SEQ ID NO: 18 |
| AT1G71692 | SEQ ID NO: 19 | SEQ ID NO: 20 |
| AT1G52150 | SEQ ID NO: 21 | SEQ ID NO: 22 |
| AT3G25890 | SEQ ID NO: 23 | SEQ ID NO: 24 |
| AT1G09540 | SEQ ID NO: 25 | SEQ ID NO: 26 |
| AT5G22380 | SEQ ID NO: 27 | SEQ ID NO: 28 |
| AT2G44940 | SEQ ID NO: 29 | SEQ ID NO: 30 |
| AT5G41030 | SEQ ID NO: 31 | SEQ ID NO: 32 |
| AT5G60970 | SEQ ID NO: 33 | SEQ ID NO: 34 |
| AT5G35550 | SEQ ID NO: 35 | SEQ ID NO: 36 |
| AT1G60240 | SEQ ID NO: 37 | SEQ ID NO: 38 |
| AT2G23290 | SEQ ID NO: 39 | SEQ ID NO: 40 |
| AT5G14000 | SEQ ID NO: 41 | SEQ ID NO: 42 |
| AT1G19490 | SEQ ID NO: 43 | SEQ ID NO: 44 |

TABLE 2

| AGI code | Nucleotide sequence | Amino acid sequence |
| --- | --- | --- |
| AT1G32770 | SEQ ID NO: 45 | SEQ ID NO: 46 |
| AT5G47220 | SEQ ID NO: 47 | SEQ ID NO: 48 |
| AT1G56650 | SEQ ID NO: 49 | SEQ ID NO: 50 |
| AT1G63910 | SEQ ID NO: 51 | SEQ ID NO: 52 |
| AT3G15510 | SEQ ID NO: 53 | SEQ ID NO: 54 |
| AT2G45680 | SEQ ID NO: 55 | SEQ ID NO: 56 |
| AT2G31230 | SEQ ID NO: 57 | SEQ ID NO: 58 |
| AT1G12260 | SEQ ID NO: 59 | SEQ ID NO: 60 |
| AT3G61910 | SEQ ID NO: 61 | SEQ ID NO: 62 |
| AT5G07310 | SEQ ID NO: 63 | SEQ ID NO: 64 |
| AT3G14230 | SEQ ID NO: 65 | SEQ ID NO: 66 |
| AT1G28160 | SEQ ID NO: 67 | SEQ ID NO: 68 |
| AT1G69120 | SEQ ID NO: 69 | SEQ ID NO: 70 |
| AT3G10490 | SEQ ID NO: 71 | SEQ ID NO: 72 |
| AT5G61600 | SEQ ID NO: 73 | SEQ ID NO: 74 |
| AT1G43160 | SEQ ID NO: 75 | SEQ ID NO: 76 |

Moreover, examples of a transcription factor that is introduced into a plant or in which a transcriptional regulatory region is modified include transcription factors specified by AGI codes for *Arabidopsis thaliana* listed in tables 3 and 4. In addition, any transcription factor listed in table 3 causes a significant increase in seed protein content when it is introduced into a plant or a transcriptional regulatory region thereof is modified. Any transcription factor listed in table 4 causes a significant decrease in seed protein content when it is introduced into a plant or a transcriptional regulatory region thereof is modified.

TABLE 3

| AGI code | Nucleotide sequence | Amino acid sequence |
| --- | --- | --- |
| AT3G04070 | SEQ ID NO: 77 | SEQ ID NO: 78 |
| AT2G46770 | SEQ ID NO: 79 | SEQ ID NO: 80 |
| AT5G35550 | SEQ ID NO: 81 | SEQ ID NO: 82 |

TABLE 4

| AGI code | Nucleotide sequence | Amino acid sequence |
| --- | --- | --- |
| AT1G10200 | SEQ ID NO: 83 | SEQ ID NO: 84 |

In addition, examples of a transcription factor constituting a chimeric protein or a transcription factor subjected to gene introduction or modification of an expression control region are not limited to amino acid sequences (shown in the even-numbered SEQ ID NOS: 1 to 84) listed in tables 1 to 4. Also, it is possible to use a transcription factor having transactivation activity and comprising an amino acid sequence that has a deletion, a substitution, an addition, or an insertion of one or a plurality of amino acid sequences with respect to any of the amino acid sequences. Here, the term "a plurality of amino acids" refers to 1 to 20, preferably 1 to 10, more preferably 1 to 7, further preferably 1 to 5, and particularly preferably 1 to 3 amino acids, for example. In addition, amino acid deletion, substitution, or addition can be performed by modifying a nucleotide sequence encoding any of the above transcription factors by a technique known in the art. Mutation can be introduced into a nucleotide sequence by a known technique such as the Kunkel method or the Gapped duplex method or a method based thereon. For example, mutation is introduced with a mutagenesis kit using site-directed mutagenesis (e.g., Mutant-K or Mutant-G (both are trade names of Takara Bio)) or the like, or a LA PCR in vitro Mutagenesis series kit (trade name, Takara Bio). Also, a mutagenesis method may be: a method using a chemical mutation agent represented by EMS (ethyl methanesulfonate), 5-bromouracil, 2-aminopurine, hydroxylamine, N-methyl-N'-nitro-N nitrosoguanidine, or other carcinogenic compounds; or a method that involves radiation treatment or ultraviolet [UV] treatment typically using X-rays, alpha rays, beta rays, gamma rays, an ion beam, or the like.

Further, examples of a transcription factor constituting a chimeric protein or a transcription factor subjected to gene introduction or modification of an expression control region are not limited to *Arabidopsis thaliana* transcription factors listed in tables 1 to 4. Examples of such transcription factor can include transcription factors that function in a similar manner in non-*Arabidopsis thaliana* plants (e.g., the aforementioned plants) (hereinafter referred to as homologous transcription factors). These homologous transcription factors can be searched for using the genomic information of a search target plant based on amino acid sequences listed in tables 1 to 4 or the nucleotide sequences of individual genes if the plant genomic information has been elucidated. Homologous transcription factors can be identified by searching for amino acid sequences having, for example, 70% or higher, preferably 80% or higher, more preferably 90% or higher, and most preferably 95% or higher homology to the amino acid sequences listed in tables 1 to 4. Here, the value of homology refers to a value that can be found based on default setting using a computer equipped with a BLAST algorithm and a database containing gene sequence information.

In addition, a homologous gene can be identified by, when the plant genome information remains unclarified, extracting the genome from a target plant or constructing a cDNA library for a target plant and then isolating a genomic region or cDNA hybridizing under stringent conditions to at least some portions of the gene encoding any one of the transcription factors listed in tables 1 to 4. Here, the term "stringent conditions" refers to conditions under which namely a specific hybrid is formed, but a non-specific hybrid is never formed. For example, such conditions comprise hybridization at 45° C. with 6×SSC (sodium chloride/sodium citrate), followed by washing at 50° C. to 65° C. with 0.2-1×SSC and 0.1% SDS. Alternatively, such conditions comprise hybridization at 65° C. to 70° C. with 1×SSC, followed by washing at 65° C. to 70° C. with 0.3×SSC. Hybridization can be performed by a conventionally known method such as a method described in J. Sambrook et al. Molecular Cloning, A Laboratory Manual, 2nd Ed., Cold Spring Harbor Laboratory (1989).

A feature of causing the seed protein content to vary significantly (to be improved or reduced significantly) is imparted to the plant of the present invention by causing expression of the aforementioned chimeric protein comprising a transcription factor and a functional peptide in a plant, introducing the aforementioned gene encoding a transcription factor into a plant, or altering an expression control region of such gene in a plant.

In particular, a feature of causing the seed protein content to vary significantly (to be improved or reduced significantly) is imparted to the plant of the present invention by causing expression of a chimeric protein comprising a transcription factor of interest having repressed transactivation activity, further causing expression of transcription repression activity through recognition of a cis sequence homologous to a cis sequence recognized by the transcription factor of interest, and altering the specific affinity of the transcription factor of interest to that of another factor, nucleic acid, lipid, or carbohydrate. In the plant of the present invention, it is possible to create a chimeric protein comprising an endogenous transcription factor by modifying the endogenous transcription factor. Alternatively, it is also possible to introduce a gene encoding a chimeric protein into the plant so as to cause the gene to be expressed therein. For instance, it is preferable to use a method wherein a gene encoding a chimeric protein (fusion protein) obtained by fusing the aforementioned transcription factor and a functional peptide capable of converting an arbitrary transcription factor into a transcriptional repressor is introduced into a target plant to cause the chimeric protein (fusion protein) to be expressed in the plant.

The expression "transcription factor having repressed transactivation activity" used herein is not particularly limited. Such transcription factor has significantly lower transactivation activity than the original transcription factor. In addition, a "functional peptide capable of converting an arbitrary transcription factor into a transcriptional repressor" (sometimes referred to as a "transcription repressor converting peptide") is defined as a peptide having the function of causing an arbitrary transcription factor to have significantly reduced transactivation activity in comparison with the original transcription factor when the peptide is fused with the transcription factor to create a chimeric protein. Such "functional peptide capable of converting an arbitrary transcription factor into a transcriptional repressor" is not particularly limited. However, it is particularly preferable for the functional peptide to consist of an amino acid sequence known as a repressor domain sequence or an SRDX sequence. Examples of such transcription repressor converting peptide are described in detail in JP Patent Publication (Kokai) No. 2005-204657 A. Any example disclosed in such document can be used.

For example, a transcription repressor converting peptide consists of an amino acid sequence expressed by any one of the following formula (1) to (8).

(1) X1-Leu-Asp-Leu-X2-Leu-X3 (SEQ ID NO: 392 with deletion of 0-10 residues from the N-terminus)
(where X1 denotes a set of 0 to 10 amino acid residues, X2 denotes Asn or Glu, and X3 denotes a set of at least 6 amino acid residues.)

(2) Y1-Phe-Asp-Leu-Asn-Y2-Y3 (SEQ ID NO: 393 with deletion of 0-10 residues from the N-terminus)
(where Y1 denotes a set of 0 to 10 amino acid residues, Y2 denotes Phe or Ile, and Y3 denotes a set of at least 6 amino acid residues.)

(3) Z1-Asp-Leu-Z2-Leu-Arg-Leu-Z3 (SEQ ID NO: 394 with deletion of 0-10 residues from the C-terminus and deletion of 0-2 residues from the N-terminus)
(where Z1 denotes Leu, Asp-Leu, or Leu-Asp-Leu, Z2 denotes Glu, Gln, or Asp, and Z3 denotes a set of 0 to 10 amino acid residues.)

(4) Asp-Leu-Z4-Leu-Arg-Leu
(residues 4-9 of SEQ ID NO: 394)

(where Z4 denotes Glu, Gln, or Asp.)

(5) α1-Leu-β1-Leu-γ1-Leu (SEQ ID NO: 395)

(6) α1-Leu-β1-Leu-γ2-Leu (SEQ ID NO: 396)

(7) α1-Leu-β2-Leu-Arg-Leu (SEQ ID NO: 397)

(8) α2-Leu-β1-Leu-Arg-Leu (SEQ ID NO: 398)

(where α1 denotes Asp, Asn, Glu, Gln, Thr, or Ser, α2 denotes Asn, Glu, Gln, Thr, or Ser, β1 denotes Asp, Gln, Asn, Arg, Glu, Thr, Ser, or His, β2 denotes Asn, Arg, Thr, Ser, or His, γ1 denotes Arg, Gln, Asn, Thr, Ser, His, Lys, or Asp, and γ2 denotes Gln, Asn, Thr, Ser, His, Lys, or Asp in formulae (5) to (8).)

Transcription Repressor Converting Peptide of Formula (1)

The number of amino acid residues in the set denoted by "X1" may be 0 to 10 for the transcription repressor converting peptide of formula (1). In addition, types of specific amino acids corresponding to amino acid residues in the set denoted by X1 are not particularly limited. Any amino acid can be used. In view of ease of synthesis of the transcription repressor converting peptide of formula (1), it is preferable to minimize the length of the set of amino acid residues denoted by X1. Specifically, the number of amino acid residues in the set denoted by X1 is preferably not more than 5.

Transcription Repressor Converting Peptide of Formula (2)

As in the case of X1 for the transcription repressor converting peptide of formula (1), the number of amino acid residues in the set denoted by Y1 for the transcription repressor converting peptide of formula (2) may be 0 to 10. In addition, types of specific amino acids corresponding to amino acid residues in the set denoted by Y1 are not particularly limited, and thus any amino acid may be used. The number of specific amino acid residues in the set denoted by Y1 is preferably not more than 5.

Similarly, as in the case of X3 for the transcription repressor converting peptide of formula (1), the number of amino acid residues in the set denoted by Y3 for the transcription repressor converting peptide of formula (2) may be at least 6. In addition, types of specific amino acids corresponding to amino acid residues in the set denoted by Y3 are not particularly limited, and thus any amino acid may be used.

Transcription Repressor Converting Peptide of Formula (3)

For the transcription repressor converting peptide of formula (3), the set of amino acid residues denoted by Z1 contains 1 to 3 "Leu" amino acids. When it contains a single amino acid, Z1 denotes Leu. When it contains two amino acids, Z1 denotes Asp-Leu. When it contains 3 amino acids, Z1 denotes Leu-Asp-Leu.

Meanwhile, for the transcription repressor converting peptide of formula (3), the number of amino acid residues in the set denoted by Z3 may be 0 to 10. In addition, types of specific amino acids corresponding to amino acid residues in the set denoted by Z3 are not particularly limited, and thus any amino acid may be used. Specifically, the number of amino acid residues in the set denoted by Z3 is preferably not more than 5. Specific examples of an amino acid residue in the set denoted by Z3 include, but are not limited to, Gly, Gly-Phe-Phe, Gly-Phe-Ala, Gly-Tyr-Tyr, and Ala-Ala-Ala.

In addition, the number of amino acid residues consisting of a transcription repressor converting peptide as a whole of formula (3) is not particularly limited. However, in view of ease of synthesis, it is preferably not more than 20 amino acids.

Transcription Repressor Converting Peptide of Formula (4)

The transcription repressor converting peptide of formula (4) is a hexamer (6mer) consisting of 6 amino acid residues. In addition, if the amino acid residue denoted by Z4 in the transcription repressor converting peptide of formula (4) is Glu, the amino acid sequence of the peptide corresponds to a region ranging from position 196 to position 201 of the amino acid sequence of the *Arabidopsis thaliana* SUPERMAN protein (SUP protein).

A chimeric protein (fusion protein) is created through fusion of any of the different transcription repressor converting peptides described above and any of the transcription factors described above so as to modify characteristics of the transcription factor. Specifically, a chimeric protein (fusion protein) is created through fusion of the transcription factor and the transcription repressor converting peptide, making it possible to modify the transcription factor into a transcriptional repressor or a negative transcriptional coactivator. In addition, it is possible to further convert a non-dominant transcriptional repressor into a dominant transcriptional repressor.

In addition, a chimeric protein (fusion protein) can be produced by obtaining a fusion gene of a polynucleotide encoding any transcription repressor converting peptide described above and a gene encoding a transcription factor. Specifically, a fusion gene is constructed by linking a polynucleotide encoding the transcription repressor converting peptide (hereinafter referred to as a "transcription repressor converting polynucleotide") and the gene encoding a transcription factor. The fusion gene is introduced into plant cells, thereby allowing production of a chimeric protein (fusion protein). The specific nucleotide sequence of the transcription repressor converting polynucleotide is not particularly limited. It is only necessary for the transcription repressor converting polynucleotide to comprise a nucleotide sequence corresponding to the amino acid sequence of the transcription repressor converting peptide in accordance with the genetic code of the peptide. In addition, if necessary, the transcription repressor converting polynucleotide may have a nucleotide sequence that serves as a linking site via which the transcription repressor converting polynucleotide is linked to a transcription factor gene. Further, if the amino acid reading frame of the transcription repressor converting polynucleotide does not match the reading frame of the transcription factor gene, the transcription repressor converting polynucleotide can comprise an additional nucleotide sequence that allows matching of both reading frames. Furthermore, the transcription repressor converting polynucleotide may comprise a variety of additional polypeptides such as a polypeptide having a linker function to link a transcription factor and a transcription repressor converting peptide and a polypeptide such as His, Myc, or Flag used for epitope labeling of a chimeric protein (fusion protein). Moreover, if necessary, the chimeric protein (fusion protein) may have a construct such as a sugar chain, an isoprenoid group, or the like as well as such polypeptide.

In addition, a conventionally known expression vector or the like can be used when the above gene encoding a transcription factor is introduced into plants.

A method for producing a plant is not particularly limited as long as it comprises a step of producing the above chimeric protein comprising a transcription factor and a transcription repressor converting peptide in a plant or a step of introducing the above gene encoding a transcription factor into a plant or modifying an expression control region of the gene. However, for example, a production method comprising steps such as an expression vector construction step, a transformation step, and a selection step can be used. Each step is specifically described below.

Expression Vector Construction Step

The expression vector construction step is not particularly limited as long as it includes a step of constructing a recombinant expression vector containing the gene encoding a transcription factor, a transcription repressor converting polynucleotide, and a promoter. Also, the expression vector construction step is not particularly limited as long as it is a step of constructing a recombinant expression vector containing the gene encoding a transcription factor to be introduced and a promoter. As a vector serving as a mother body for a recombinant expression vector, various conventionally known vectors can be used. For example, plasmids, phages, cosmids, or the like can be used and such vector can be appropriately selected depending on plant cells into which it is introduced and introduction methods. Specific examples of such vector include pBR322, pBR325, pUC19, pUC119, pBluescript, pBluescriptSK, and pBI vectors. Particularly, when a method for introduction of a vector into a plant uses *Agrobacterium*, a pBI binary vector is preferably used. Specific examples of such pBI binary vector include pBIG, pBIN19, pBI101, pBI121, and pBI221.

A promoter used herein is not particularly limited as long as it can cause gene expression in plants. Any known promoter can be appropriately used. Examples of such promoter include a cauliflower mosaic virus 35S promoter (CaMV35S), various actin gene promoters, various ubiquitin gene promoters, a nopaline synthase gene promoter, a tobacco PR1a gene promoter, a tomato ribulose1,5-bisphosphate carboxylase.oxidase small subunit gene promoter, a napin gene promoter, and an oleosin gene promoter. Of these, a cauliflower mosaic virus 35S promoter, an actin gene promoter, or a ubiquitin gene promoter can be more preferably used. The use of each of the above promoters enables strong expression of any gene when it is introduced into plant cells. The structure of a recombinant expression vector itself is not particularly limited as long as the promoter is linked to a fusion gene obtained by linking a gene encoding a transcription factor and a transcription repressor converting polynucleotide so as to cause expression of the gene and introduced into the vector. Also, the structure of a recombinant expression vector itself is not particularly limited as long as the promoter is linked to a gene encoding a desired transcription factor for gene introduction so as to cause expression of the gene and introduced into the vector.

In addition, a recombinant expression vector may further contain other DNA segments, in addition to a promoter and the fusion gene or the gene encoding a transcription factor. Such other DNA segments are not particularly limited and examples thereof include a terminator, a selection marker, an enhancer, and a nucleotide sequence for enhancing translation efficiency. Also, the above recombinant expression vector may further have a T-DNA region. A T-DNA region can enhance efficiency for gene introduction particularly when the above recombinant expression vector is introduced into a plant using *Agrobacterium*.

A transcription terminator is not particularly limited as long as it has functions as a transcription termination site and may be any known transcription terminator. For example, specifically, a transcription termination region (Nos terminator) of a nopaline synthase gene, a transcription termination region (CaMV35S terminator) of cauliflower mosaic virus 35S, or the like can be preferably used. Of them, the Nos terminator can be more preferably used. In the case of the above recombinant vector, a phenomenon such that an unnecessarily long transcript is synthesized and that a strong promoter decreases the number of copies of a plasmid after introduction into plant cells can be prevented by arranging a transcription terminator at an appropriate position.

As a transformant selection marker, a drug resistance gene can be used, for example. Specific examples of such drug resistance gene include drug resistance genes against hygromycin, bleomycin, kanamycin, gentamicin, chloramphenicol, and the like. Transformed plants can be easily selected by selecting plants that can grow in medium containing the above antibiotics.

An example of a nucleotide sequence for increasing translation efficiency is an omega sequence from tobacco mosaic virus. This omega sequence is arranged in an untranslated region (5'UTR) of a promoter, so that the translation efficiency of the fusion gene can be increased. As such, the recombinant expression vector can contain various DNA segments depending on purposes.

A method for constructing a recombinant expression vector is not particularly limited. To an appropriately selected vector serving as a mother body, the above promoter, a fusion gene consisting of a gene encoding a transcription factor and a transcription repressor converting polynucleotide or a gene encoding a desired transcription factor for gene introduction, and, if necessary, the above other DNA segments may be introduced in a predetermined order. For example, a gene encoding a transcription factor and a transcription repressor converting polynucleotide are linked to construct a fusion gene, and then the fusion gene and the promoter (e.g., a transcription terminator according to need) are then linked to construct an expression cassette and then the cassette may be introduced into a vector.

In construction of a chimeric gene (fusion gene) and an expression cassette, for example, cleavage sites of DNA segments are prepared to have protruding ends complementary to each other and then performing a reaction with a ligation enzyme, making it possible to specify the order of the DNA segments. In addition, when an expression cassette contains a terminator, DNA segments may be arranged in the following order from upstream: a promoter, the fusion gene or the gene encoding a transcription factor, and a terminator. Also, reagents for construction of an expression vector (that is, types of restriction enzymes, ligation enzymes, and the like) are also not particularly limited. Hence, commercially available reagents can be appropriately selected and used.

Also, a method for replicating (a method for producing) the above expression vector is not particularly limited and conventionally known replication methods can be used herein. In general, such expression vector may be replicated within *Escherichia coli* as a host. At this time, preferred types of *Escherichia coli* may be selected depending on the types of vector.

Transformation Step

The transformation step carried out in the present invention is a step of introducing the fusion gene or the gene encoding a transcription factor into plant cells using the above recombinant expression vector so as to cause the expression of the gene. A method for introducing such gene into plant cells (transformation method) using a recombinant expression vector is not particularly limited. Conventionally known appropriate introduction methods can be used depending on plant cells. Specifically, a method using *Agrobacterium* or a method that involves direct introduction into plant cells can be used, for example. As a method using *Agrobacterium*, a method described in the following can be employed, for example: Bechtold, E., Ellis, J. and Pelletier, G. (1993), In Planta *Agrobacterium*-mediated gene transfer by infiltration of adult *Arabidopsis* plants. C. R. Acad. Sci. Paris Sci. Vie, 316, 1194-1199; or Zyprian E, Kado Cl, *Agrobacterium*-mediated plant transformation by novel mini-T vectors in conjunction with a high-copy vir region helper plasmid, Plant Molecular Biology, 1990, 15(2), 245-256.

As a method for directly introducing DNA comprising a recombinant expression vector and a target gene into plant cells, microinjection, electroporation, a polyethylene glycol method, a particle gun method, protoplast fusion, a calcium phosphate method, or the like can be employed.

Also, when a method for directly introducing DNA into plant cells is employed, DNA that can be used herein contains transcriptional units required for the expression of a target gene, such as a promoter and a transcription terminator, and a target gene. Vector functions are not essential in such case. Moreover, a DNA that contains a protein coding region alone of a target gene having no transcriptional unit may be used herein, as long as it is integrated into a host's transcriptional unit and then the target gene can be expressed.

Examples of plant cells into which DNA comprising the above recombinant expression vector and a target gene or DNA containing no expression vector but a target gene DNA is introduced include cells of each tissue of plant organs such as flowers, leaves, and roots, calluses, and suspension-cultured cells. At this time, according to the plant production method of the present invention, an appropriate expression vector may be constructed as the above recombinant expression vector according to the type of plant to be produced or a versatile expression vector may be constructed in advance and then introduced into plant cells. That is to say, the plant production method of the present invention may or may not comprise a step of constructing a DNA for transformation using the recombinant expression vector.

Other Steps and Methods

The plant production method of the present invention needs to comprise at least the transformation step, and the method may further comprise a step of constructing the DNA for transformation using the recombinant expression vector. The method may further comprise other steps. Specifically, for example, a step of selecting an appropriate transformant from among transformed plants can be employed.

A selection method is not particularly limited. For example, selection may be carried based on drug resistance such as hygromycin resistance. Alternatively, selection may be carried out based on the protein content in plant seeds collected from cultivated transformants. For example, a method comprising collecting plant seeds, determining the protein content in the seeds according to a standard method, and comparing the protein content with the protein content in non-transformed plant seeds can be employed in a case in which selection is carried out based on protein content (see the Examples described below).

According to the plant production method of the present invention, the fusion gene or the gene encoding a transcription factor is introduced into a plant. This makes it possible to obtain an offspring plant having a significantly improved or reduced protein content in comparison with the plant via sexual reproduction or asexual reproduction. Also, plant cells or reproductive materials, such as seeds, fruits, stocks, calluses, tubers, cut ears, or lumps, may be obtained from the plant or an offspring plant thereof. The plant can be mass-produced therefrom based on such materials. Therefore, the plant production method of the present invention may comprise a reproduction step (mass production step) for reproducing a selected plant.

In addition, the plant of the present invention may include a matter comprising at least any one of an adult plant, plant cells, plant tissue, callus, and seeds. That is, according to the present invention, any matter in a state that allows it to eventually grow to become a plant can be regarded as a plant. In addition, plant cells include plant cells in various forms. Examples of such plant cells include suspension-cultured cells, protoplasts, and leaf sections. As a result of proliferation/differentiation of such plant cells, a plant can be obtained. In addition, a plant can be reproduced from plant cells by a conventionally known method depending on the types of plant cells. Therefore, the plant production method of the present invention may comprise a regeneration step of regenerating a plant from plant cells or the like.

In addition, the plant production method of the present invention is not limited to a method of transformation using a recombinant expression vector. A different method may be used. Specifically, for example, the chimeric protein (fusion protein) itself or a transcription factor (protein) can be administered to a plant. In this case, the chimeric protein (fusion protein) or a transcription factor (protein) can be administered to a young plant such that the seed protein content can be improved. In addition, a method of administration of a chimeric protein (fusion protein) or a transcription factor (protein) is not particularly limited, and a different known method can be used.

As described above, according to the present invention, it becomes possible to provide a plant for which the seed protein content has been caused to vary significantly (to be improved or reduced significantly) relative to the protein content in a wild-type plant by inducing expression of a chimeric protein comprising a predetermined transcription factor and any functional peptide described above or a predetermined transcription factor. When the chimeric protein is expressed in a plant, it might cause repression of transactivation activity of a target transcription factor or it might cause exhibition of transcription repression effects upon a sequence homologous to a cis sequence recognized by a target transcription factor. Further, in some cases, such chimeric protein functions to change the specific affinity of another factor, DNA, RNA, lipid, or carbohydrate having affinity to a target transcription factor or transcriptional coactivator. Alternatively, in some cases, it functions to cause a substance having no affinity to a target transcription factor to have improved affinity thereto. The following factors can be expressed in a similar manner in the plant of the present invention: a transcription factor that constitutes a chimeric protein; a transcription factor capable of recognizing a cis sequence homologous to a cis sequence recognized by the transcription factor; a transcription factor homologous to a transcription factor that constitutes a chimeric protein; other factors each having affinity to a transcription factor that constitutes a chimeric protein; and the like. However, the above effects of a chimeric protein allow suppression of gene expression to be controlled in a dominant-negative manner. Accordingly, the expression levels of gene groups involved in plant growth and the expression levels of gene groups involved in protein production in seeds and/or gene groups involved in decomposition of a produced protein would vary in the plant of the present invention. This is thought to cause significant variation in seed protein content.

Here, significant variation in the seed protein content exists in a case in which the plant of the present invention exhibits an improvement of the protein amount over a wild-type plant while the single seed mass remains stable, a case in which the plant of the present invention is found to exhibit improvement of protein content with a significantly higher or lower level of single seed mass than that of a wild-type plant, or a case in which the plant of the present invention is found to exhibit improvement or reduction of seed protein content when compared with a wild-type plant. In any case, it corresponds to a variation in the amount of a protein produced by a single individual plant.

More specifically, if a chimeric protein comprising any transcription factor listed in table 1 is expressed in a plant, the protein content in seeds of the plant would be improved by approximately 20% or more compared with a wild-type plant. In addition, if a gene encoding any transcription factor listed in table 3 is introduced into a plant, the protein content in seeds of the plant would be improved by approximately 20% or more compared with a wild-type plant. Among the plants of the present invention, a plant confirmed to have increased protein content can be used for a method for producing a plant-derived protein. For example, a protein can be produced by cultivating the plant of the present invention, taking seeds therefrom, and collecting protein components from the obtained seeds. In particular, it can be said that the protein production method using the plant of the present invention is a method whereby high protein content in seeds can be achieved, resulting in excellent productivity. In other words, assuming that the number of cultivated plant individuals per unit area of cultivated acreage is stable and thus the amount of collected seeds is stable, the amount of protein produced per unit area of cultivated acreage can be remarkably improved with the use of the plant of the present invention. Therefore, production cost necessary for protein production can be significantly reduced with the use of the plant of the present invention.

EXAMPLES

The present invention is hereafter described in greater detail with reference to the following examples, although the technical scope of the present invention is not limited thereto.

Example 1

Transcription Factor Gene Amplification

Each of the following transcription factors was subjected to PCR amplification of a coding region DNA fragment including or excluding a termination codon using the *Arabidopsis thaliana* cDNA library and primers described below: At2g23760, At1g18330, At2g02070, At1g12980, At5g62380, At4g23750, At4g32800, At1g24590, At5g07690, At1g71692, At1g52150, At3g25890, At1g09540, At5g22380, At2g44940, At5g41030, At5g60970, At5g35550, At1g60240, At2g23290, At5g14000, At1g19490, At5g58900, At5g07580, At3g04070, At2g42830, At2g22200, At5g25190, At5g54230, At5g67300, At4g28140, At5g23260, At1g69490, At4g18390, At1g15360, At1g27370, At1g78080, At5g25390, At3g04060, At1g44830, At3g49850, At5g06100, At1g74840, At3g04070, At2g46770, At5g35550, At1g71030, At2g44840, At3g23220, At1g18570, At3g01530, At5g51190, At4g34410, At5g22290, At3g04420, At3g45150, At3g29035, At3g02150, At2g41710, At1g49120, At1g64380, At3g23230, At1g01010, At5g53290, At1g36060, At5g66300, At2g46310, At5g47390, At1g71030, At1g17520, At3g23220, At2g18060, At5g08070, At1g80580, At1g34190, At2g47520, At5g67000, At4g27950, At5g47230, At3g28910, At3g11280, At5g07680, At1g25470, At1g28520, At1g77450, At5g24590, At5g08790, At1g67260, At4g28530, At5g13910, At5g64530, At2g33710, At1g53230, At1g56010, At5g18560, At5g67580, At5g24520, At4g18390, At1g69690, At5g13330, At5g60970, At3g23220, At1g62700, At5g13330, At1g22985, At5g09330, At1g10200, At1g61110, At1g30210, At5g40330, At5g13180, At1g52880, At4g18450, At5g07580, At1g74930, At4g36160, At3g18550, At5g64750, At2g02450, At2g42400, At5g67300, At1g68800, At1g14510, At1g25580, At5g18270, At2g44840, At3g15500, At4g35580, At4g01550, At4g37750, At1g52890, At2g17040, At2g33480, At5g39610, At1g32770, At5g47220, At1g56650, At1g63910, At3g15510, At2g45680, At2g31230, At1g12260, At3g61910, At5g07310, At3g14230, At1g28160, At1g69120, At3g10490, At5g61600, At1g43160, At3g15210, At4g08150, and At1g10200. Note that a coding region DNA fragment including a termination codon was amplified for each of At3g04070, At2g46770, At5g35550, At1g71030, At2g44840, At4g18390, At1g69690, At5g13330, At5g60970, At3g23220, At3g15210, At4g08150, and At1g10200. PCR was carried out under conditions of 94° C. for 1 minute, 47° C. for 2 minutes, and elongation reaction at 74° C. for 1 minute for 25 cycles. Next, each PCR product was isolated by agarose gel electrophoresis and collected.

TABLE 5

| AGI code | Fowerd primer | Nucleotide sequence | Reverse primer | Nucleotide sequence |
|---|---|---|---|---|
| At2g23760 | GATGGGTTTAGCTACTACAACTTCTTCTAT | SEQ ID NO: 85 | AAAATCTCCAAAGTCTCTAACGGAGAAAGA | SEQ ID NO: 86 |
| At1g18330 | GATGGCCGCTGAGGATCGAAGTGAGGAACT | SEQ ID NO: 87 | GCATATACGTGCTCTTTGGCTTTTCTTTTC | SEQ ID NO: 88 |
| At2g02070 | GATGGCTGCTTCTTCATCCTCCGCTGCTTC | SEQ ID NO: 89 | GAAACTCGCATGATGGATTCCATAAGGTGG | SEQ ID NO: 90 |
| At1g12980 | AATGGAAAAAGCCTTGAGAAACTTC | SEQ ID NO: 91 | TCCCCACGATCTTCGGCAAGTACA | SEQ ID NO: 92 |
| At5g62380 | GATGGAAAGTCTCGCACACATTCCTCCCGG | SEQ ID NO: 93 | CGTGTGTGTATTTTGAGCCCAAGAGTAGAA | SEQ ID NO: 94 |
| At4g23750 | ATGGAAGCGGAGAAGAAAATGG | SEQ ID NO: 95 | AACAGCTAAAAGAGGATCCGAC | SEQ ID NO: 96 |
| At4g32800 | ATGGCGGATTCGTCTTCCGAC | SEQ ID NO: 97 | GGGAAAATGTTTCCAAGATTCG | SEQ ID NO: 98 |
| At1g24590 | ATGGAAGAAGCAATCATGAGAC | SEQ ID NO: 99 | ATAATCATCATGAAAGCAATACTG | SEQ ID NO: 100 |
| At5g07690 | GATGTCAAGAAAGCCATGTTGTGTGGGAGA | SEQ ID NO: 101 | TATGAAGTTCTTGTCGTCGTAATCTTGGCT | SEQ ID NO: 102 |
| At1g71692 | GATGGCTCGTGGAAAGATTCAGCTTAAGAG | SEQ ID NO: 103 | GAACTGAAATATTTCACTTGGCATTGTTAG | SEQ ID NO: 104 |
| At1g52150 | GATGGCAATGTCTTGCAAGGATGGTAAGTT | SEQ ID NO: 105 | CACAAAGGACCAATTGATGAACACAAAGCA | SEQ ID NO: 106 |
| At3g25890 | ATGGCTGAACGAAAGAAACGC | SEQ ID NO: 107 | TGGGCACGCGATATTAAGAGG | SEQ ID NO: 108 |
| At1g09540 | GATGGGGAGACATTCTTGCTGTTACAAACA | SEQ ID NO: 109 | AAGGGACTGACCAAAAGAGACGGCCATTCT | SEQ ID NO: 110 |
| At5g22380 | GATGGCCGATGAGGTCACAATCGGGTTTCG | SEQ ID NO: 111 | AGGCCAAGTCAGCTGTTCCCAGTCCCACAT | SEQ ID NO: 112 |
| At2g44940 | ATGGCAAGACAAATCAACATAGAG | SEQ ID NO: 113 | TTCAGATAGAAAAAACGGCTCTTC | SEQ ID NO: 114 |
| At5g41030 | ATGGTCATGGAGCCCAAGAAG | SEQ ID NO: 115 | TGAACCATTTTCCTCTGCACTC | SEQ ID NO: 116 |
| At5g60970 | ATGAGATCAGGAGAATGTGATG | SEQ ID NO: 117 | AGAATCTGATTCATTATCGCTAC | SEQ ID NO: 118 |
| At5g35550 | GATGGGAAAGAGAGCAACTACTAGTGTGAG | SEQ ID NO: 119 | ACAAGTGAAGTCTCGGAGCCAATCTTCATC | SEQ ID NO: 120 |
| At1g60240 | GATGAAGTCAAGACGTGAACAATCAATCGA | SEQ ID NO: 121 | TTTATAGTAACCTCGAATGTGCTGGGCCAA | SEQ ID NO: 122 |
| At2g23290 | GATGTCTGGTTCGACCCGGAAAGAAATGGA | SEQ ID NO: 123 | CTCGATCCTACCTAATCCAATAAACTCTCT | SEQ ID NO: 124 |
| At5g14000 | GATGGAGGTGGAGAAGAGGATTGTAG | SEQ ID NO: 125 | CTCATCAGCTGAGGTAGGAGGAG | SEQ ID NO: 126 |
| At1g19490 | GATGGAGTTGGAGCCTATATCATCGAGTTG | SEQ ID NO: 127 | TCCGACCTGCATCCGACATTGACGGCCATG | SEQ ID NO: 128 |
| At5g58900 | GATGGAGGTTATGAGACCGTCGACGTCACA | SEQ ID NO: 129 | TAGTTGAAACATTGTGTTTTGGGCGTCATA | SEQ ID NO: 130 |
| At5g07580 | ATGGCGAGTTTTGAGGAAAGC | SEQ ID NO: 131 | AAATGCATCACAGGAAGATGAAG | SEQ ID NO: 132 |
| At3g04070 | GATGATAAGCAAGGATCCAAGATCGAGTTT | SEQ ID NO: 133 | GCCTTGATATTGAAGGTGAGAACTCATCAT | SEQ ID NO: 134 |
| At2g42830 | GATGGAGGGTGGTGCGAGTAATGAAGTAGC | SEQ ID NO: 135 | AACAAGTTGCAGAGGTGGTTGGTCTTGGTT | SEQ ID NO: 136 |
| At2g22200 | ATGGAAACTGCTTCTCTTTCTTTC | SEQ ID NO: 137 | AGAATTGGCCAGTTTACTAATTGC | SEQ ID NO: 138 |
| At5g25190 | ATGGCACGACCACAACAACGC | SEQ ID NO: 139 | CAGCGTCTGAGTTGGTAAAACAG | SEQ ID NO: 140 |
| At5g54230 | GATGGGAAAATCTTCAAGCTCGGAGGAAAG | SEQ ID NO: 141 | TGATAGATTCAAAGCATTATTATTATGATC | SEQ ID NO: 142 |
| At5g67300 | GATGGCTGATAGGATCAAAGGTCCATGGAG | SEQ ID NO: 143 | CTCGATTCTCCCAACTCCAATTTGACTCAT | SEQ ID NO: 144 |
| At4g28140 | ATGGACTTTGACGAGGAGCTAAATC | SEQ ID NO: 145 | AAAGAAAGGCCTCATAGGACAAG | SEQ ID NO: 146 |
| At5g23260 | GATGGGTAGAGGGAAGATAGAGATAAAGAA | SEQ ID NO: 147 | ATCATTCTGGGCCGTTGGATCGTTTTGAAG | SEQ ID NO: 148 |
| At1g69490 | GATGGAAGTAACTTCCCAATCTACCCTCCC | SEQ ID NO: 149 | AAACTTAAACATCGCTTGACGATGATGGTT | SEQ ID NO: 150 |
| At4g18390 | ATGATTGGAGATCTAATGAAG | SEQ ID NO: 151 | GTTCTTGCCTTTACCCTTATG | SEQ ID NO: 152 |
| At1g15360 | ATGGTACAGACGAAGAAGTTCAG | SEQ ID NO: 153 | GTTTGTATTGAGAGCTCCTCTATC | SEQ ID NO: 154 |
| At1g27370 | GATGGACTGCAACATGGTATCTTCGTTCCC | SEQ ID NO: 155 | GATGAAATGACTAGGGAAAGTGCCAAATAT | SEQ ID NO: 156 |

TABLE 5-continued

| AGI code | Foward primer | Nucleotide sequence | Reverse primer | Nucleotide sequence |
|---|---|---|---|---|
| At1g78080 | GATGGCAGCTGCTATGAATTTGTAC | SEQ ID NO: 157 | AGCTAGAATCGAATCCCAATCG | SEQ ID NO: 158 |
| At5g25390 | ATGGTACATTCGAAGAAGTTCCG | SEQ ID NO: 159 | GACCTGTGCAATGGATCCAG | SEQ ID NO: 160 |
| At3g04060 | GATGGTGGAAGAAGGCGGCGTAG | SEQ ID NO: 161 | GCTAGTATATAAATCTTCCCAGAAG | SEQ ID NO: 162 |
| At1g44830 | ATGGTGAAAACACTTCAAAAGACAC | SEQ ID NO: 163 | GCAGAAGTTCCATAATCTGATATC | SEQ ID NO: 164 |
| At3g49850 | GATGGGAGCTCCAAAGCTGAAGTGGACACC | SEQ ID NO: 165 | CCGAGTTTGGCTATGCATTCTATACTTCAC | SEQ ID NO: 166 |
| At5g06100 | GATGAGTTACACGAGCACTGACAGTGACCA | SEQ ID NO: 167 | ACAAACATATTTCAAGTGATGGTAAGGTGAA | SEQ ID NO: 168 |
| At1g74840 | GATGGCCGACGGTAGTACTAGTTCTTCGGA | SEQ ID NO: 169 | AGCGACTCCAATCGTGTTGAATGCTGGATG | SEQ ID NO: 170 |
| At3g04070 | GATGATAAGCAAGGATCCAAGATCGAGTTT | SEQ ID NO: 171 | CTAGCCTTGATATTGAAGGTGAGAACTCAT | SEQ ID NO: 172 |
| At2g46770 | GATGATGTCAAAATCTATGAGCATATC | SEQ ID NO: 173 | TTATCCACTACCATTCGACACGTGACAAAA | SEQ ID NO: 174 |
| At5g35550 | GGGATGGGAAAGAGAGCAACTACTAGTGTGAGG | SEQ ID NO: 175 | TCAACAAGTGAAGTCTCGGAGCCAATCTTC | SEQ ID NO: 176 |
| At1g71030 | GATGAACAAAACCCGCCTTCGTGCTCTCTC | SEQ ID NO: 177 | TCATCGGAATAGAAGAAGCGTTTCTTGACC | SEQ ID NO: 178 |
| At2g44840 | ATGAGCTCATCTGATTCCGTTAATAAC | SEQ ID NO: 179 | TTATATCCGATTATCAGAATAAGAAC | SEQ ID NO: 180 |
| At3g23220 | ATGAAATACAGAGGCGTACGAAAG | SEQ ID NO: 181 | GCGGTTTGCGTCGTTACAATTG | SEQ ID NO: 182 |
| At1g18570 | GATGGTGCGGACACCGTGTTGCAAAGCTGA | SEQ ID NO: 183 | TCCAAAATAGTTATCAATTTCGTCAAACAA | SEQ ID NO: 184 |
| At3g01530 | GATGGAGACGACGATGAAGAAGAAAGGGAG | SEQ ID NO: 185 | AATCACATGGTGGTCACCATTAAGCAAGTG | SEQ ID NO: 186 |
| At5g51190 | ATGGCTTCTTCACATCAACAACAG | SEQ ID NO: 187 | AGTAACTACGAGTTGAGAGTGTC | SEQ ID NO: 188 |
| At4g34410 | ATGCATTATCCTAACAACAGAACC | SEQ ID NO: 189 | CTGGAACATATCAGCAATTGTATTTC | SEQ ID NO: 190 |
| At5g22290 | GATGGACACGAAGGCGGTTGGAGTTTC | SEQ ID NO: 191 | TTCTAGATAAAACAACATTGCTATC | SEQ ID NO: 192 |
| At3g04420 | GATGGAGAATCCGGTGGGTTTAAG | SEQ ID NO: 193 | TGTTCTTGAGATAGAAGAACATTGG | SEQ ID NO: 194 |
| At3g45150 | ATGGATTCGAAAAATGGAATTAAC | SEQ ID NO: 195 | AACTGTGGTTGTGGCTGTTGTTG | SEQ ID NO: 196 |
| At3g29035 | GATGGATTACAAGGTATCAAGAAG | SEQ ID NO: 197 | GAATTTCCAAACGCAATCAAGATTC | SEQ ID NO: 198 |
| At3g02150 | ATGAATATCGTCTCTTGGAAAGATG | SEQ ID NO: 199 | TCACATATGGTGATCACTTCCTCTACTTG | SEQ ID NO: 200 |
| At2g41710 | GATGGCGTCGGTGTCGTCGTC | SEQ ID NO: 201 | TTTCTCTTGTGGGAGGTAGCTG | SEQ ID NO: 202 |
| At1g49120 | ATGATCAGTTTCAGAGAAGAGAAC | SEQ ID NO: 203 | TAAAAACTTATCGATCCAATCAGTAG | SEQ ID NO: 204 |
| At1g64380 | ATGGAAGAAAGCAATGATATTTTC | SEQ ID NO: 205 | ATTGGCAAGAACTTCCCAAATCAG | SEQ ID NO: 206 |
| At3g23230 | ATGGAGAGCTCAAACAGGAGC | SEQ ID NO: 207 | TCTCTTCCTTTCTTCTGAATCAAG | SEQ ID NO: 208 |
| At1g01010 | GATGGAGGATCAAGTTGGGTTTGGG | SEQ ID NO: 209 | ACCAACAAGAATGATCCAACTAATG | SEQ ID NO: 210 |
| At5g53290 | ATGGACGAATATATTGATTTCCGAC | SEQ ID NO: 211 | AGCAACTAATAGATCTGATATCAATG | SEQ ID NO: 212 |
| At1g36060 | ATGGCGGATCTCTTCGGTGG | SEQ ID NO: 213 | CGATAAAATTGAAGCCCAATCTATC | SEQ ID NO: 214 |
| At5g66300 | GATGATGAAGGTTGATCAAGATTATTCGTG | SEQ ID NO: 215 | GTCTTCTCCACTCATCAAAAATTGAGACGC | SEQ ID NO: 216 |
| At2g46310 | ATGAAAAGCCGAGTGAGAAAATC | SEQ ID NO: 217 | TTACTTATCCAACAAATGATCTTGG | SEQ ID NO: 218 |
| At5g47390 | GATGACTCGTCGATGTTCTCACTGCAATCA | SEQ ID NO: 219 | TAAAGCGTGTATCACGCTTTTGATGTCTGA | SEQ ID NO: 220 |
| At1g71030 | GATGAACAAAACCCGCCTTCGTGCTCTCTC | SEQ ID NO: 221 | TCGGAATAGAAGAAGCGTTTCTTGACCTGT | SEQ ID NO: 222 |
| At1g17520 | GATGGGAAATCAGAAGCTCAAATGGACGGC | SEQ ID NO: 223 | ATTCAAGTACATAATCTTTCCCTGACTACA | SEQ ID NO: 224 |
| At3g23220 | GATGGATCCATTTTTAATTCAGTCCCCATT | SEQ ID NO: 225 | CCAAGTCCCACTATTTTCAGAAGACCCCAA | SEQ ID NO: 226 |
| At2g18060 | GATGGAGCCAATGGAATCTTGTAGCGTTCC | SEQ ID NO: 227 | ATTATCAAATACGCAAATCCCAATATCATA | SEQ ID NO: 228 |
| At5g08070 | ATGGGAATAAAAAAAGAAGATCAG | SEQ ID NO: 229 | CTCGATATGGTCTGGTTGTGAG | SEQ ID NO: 230 |
| At1g80580 | ATGGAAAACAGCTACACCGTTG | SEQ ID NO: 231 | CTTCCTAGACAACAACCCTAAAC | SEQ ID NO: 232 |
| At1g34190 | GATGGCGGATTCTTCACCCGATTCG | SEQ ID NO: 233 | GTCTTTCAAGAGAAGACTTCTACC | SEQ ID NO: 234 |

TABLE 5-continued

| AGI code | Foword primer | Nucleotide sequence | Reverse primer | Nucleotide sequence |
|---|---|---|---|---|
| At2g47520 | ATGTGTGGGGAGCTATCATTTC | SEQ ID NO: 235 | ATTGGAGTCTTGATAGCTCC | SEQ ID NO: 236 |
| At5g67000 | ATGGATAATTCAGAAAATGTTC | SEQ ID NO: 237 | TCTCCACCGCCGTTTAATTC | SEQ ID NO: 238 |
| At4g27950 | ATGATGATGGATGAGTTTATGGATC | SEQ ID NO: 239 | CACAAGTAAGAGATCGGATATC | SEQ ID NO: 240 |
| At5g47230 | GGGGATGGCGACTCCTAACGAAGT | SEQ ID NO: 241 | AACAACGGTCAACTGGGAATAACCAAACG | SEQ ID NO: 242 |
| At3g28910 | GATGGTGAGGCCTCCTTGTTGTGACAAAGG | SEQ ID NO: 243 | GAAGAAATTAGTGTTTTCATCCAATAGAAT | SEQ ID NO: 244 |
| At3g11280 | GATGGAGACTCTGCATCCATTCTCTCACCT | SEQ ID NO: 245 | AGCTCCGGCACTGAAGACATTTTCTCCGGC | SEQ ID NO: 246 |
| At5g07680 | GATGGATTTGCCTCCTGGTTTTAG | SEQ ID NO: 247 | GTAATTCCAGAAAGGTTCAAGATC | SEQ ID NO: 248 |
| At1g25470 | ATGTCGGCTGTGTCTGAATCG | SEQ ID NO: 249 | AACCAAACCGAGAGGCGGTG | SEQ ID NO: 250 |
| At1g28520 | GATGACGGGGAAGCGATCAAAGAC | SEQ ID NO: 251 | GGGGATATAATAGTCGCTTAGATTTC | SEQ ID NO: 252 |
| At1g77450 | GATGATGAAATCTGGGGCTGATTTGC | SEQ ID NO: 253 | GAAAGTTCCCTGCCTAACCACAAGTGG | SEQ ID NO: 254 |
| At5g24590 | GATGAAAGAAGACATGGAAGTACTATC | SEQ ID NO: 255 | TGCGACTAGACTGCAGACCGACATC | SEQ ID NO: 256 |
| At5g08790 | GATGAAGTCGGAGCTAAATTTACCAGCTGG | SEQ ID NO: 257 | CCCCTGTGGAGCAAAACTCCAATTCAAGAA | SEQ ID NO: 258 |
| At1g67260 | ATGTCGTCTTCCACCAATGAC | SEQ ID NO: 259 | GTTTACAAAAGAGTCTTGAATCC | SEQ ID NO: 260 |
| At4g28530 | GATGGGTTTGAAAGATATTGGGTCC | SEQ ID NO: 261 | TTGGAAAGCGAGGATATTTTCGGTC | SEQ ID NO: 262 |
| At5g13910 | ATGAACACAACATCATCAAAGAGC | SEQ ID NO: 263 | GGAGCCAAAGTAGTTGAAACCTTG | SEQ ID NO: 264 |
| At5g64530 | GATGAATCTACCACCGGGATTAGG | SEQ ID NO: 265 | CGGTAAGCTTACTTCGTCAAGATC | SEQ ID NO: 266 |
| At2g33710 | ATGCATAGCGGGAAGAGACCTC | SEQ ID NO: 267 | TTTTCGTCGTTTGTGGATACTAATG | SEQ ID NO: 268 |
| At1g53230 | GATGAAGAGAGATCATCATCATCATCATCA | SEQ ID NO: 269 | ATGGCGAGAATCGGATGAAGC | SEQ ID NO: 270 |
| At1g56010 | GATGGAGACGGAAGAAGAGATGAAG | SEQ ID NO: 271 | GCAATTCCAAACAGTGCTTGGAATAC | SEQ ID NO: 272 |
| At5g18560 | ATGGGTTTTGCTCTGATCCACC | SEQ ID NO: 273 | AAAGACTGAGTAGAAGCCTGTAG | SEQ ID NO: 274 |
| At5g67580 | GATGGGTGCACCAAAGCAGAAGTGGACACC | SEQ ID NO: 275 | CCAAGGATGATTACGGATCCTGAACTTCAA | SEQ ID NO: 276 |
| At5g24520 | GATGGATAATTCAGCTCCAGATTCGTTATC | SEQ ID NO: 277 | AACTCTAAGGAGCTGCATTTTGTTAGCAAA | SEQ ID NO: 278 |
| At4g18390 | ATGATTGGAGATCTAATGAAG | SEQ ID NO: 279 | GAGACTGATAACCGGACACG | SEQ ID NO: 280 |
| At1g69690 | GATGAAGAGAGATCATCATCATCATCATCA | SEQ ID NO: 281 | TCAGGAATGATGACTGGTGCTTCC | SEQ ID NO: 282 |
| At5g13330 | ATGGTCTCCGCTCTCAGCCG | SEQ ID NO: 283 | TTATTCTCTTGGGTAGTTATAATAATTG | SEQ ID NO: 284 |
| At5g60970 | ATGAGATCAGGAGAATGTGATG | SEQ ID NO: 285 | AGAATCTGATTCATTATCGCTAC | SEQ ID NO: 286 |
| At3g23220 | GGGGATGTACGGACAGTGCAATATAG | SEQ ID NO: 287 | GGGTATGAAACCAATAACTCATCAACACG | SEQ ID NO: 288 |
| At1g62700 | GATGAATTCGTTTTCACAAGTACCTCCTGG | SEQ ID NO: 289 | GAGATCAATCTGACAACTTGAAGAAGTAGA | SEQ ID NO: 290 |
| At5g13330 | ATGGTCTCCGCTCTCAGCCG | SEQ ID NO: 291 | TTCTCTTGGGTAGTTATAATAATTG | SEQ ID NO: 292 |
| At1g22985 | ATGAAACGAATTGTTCGAATTTCATTC | SEQ ID NO: 293 | AACAACTTCTTCAGAAGCACCAC | SEQ ID NO: 294 |
| At5g09330 | GATGGGGAAAACTCAACTCGCTCCTGGATT | SEQ ID NO: 295 | CATTTTGGTCTATGTCTCATGGAAGCAGA | SEQ ID NO: 296 |
| At1g10200 | GGGATGGCGTTCGCAGGAACAACCCAGAAATG | SEQ ID NO: 297 | AGCAGCGACGACTTTGTCCTTGGCG | SEQ ID NO: 298 |
| At1g61110 | GATGGAAAACATGGGGGATTCGAGCATAG | SEQ ID NO: 299 | TGAGTGCCAGTTCATGTTAGGAAGCTG | SEQ ID NO: 300 |
| At1g30210 | ATGGAGGTTGACGAAGACATTG | SEQ ID NO: 301 | TCTCCTTTCCTTTGCCTTGTC | SEQ ID NO: 302 |
| At5g40330 | ATGAGAATGACAAGAGATGGAAAAG | SEQ ID NO: 303 | AAGGCAATACCCATTAGTAAAATCCATCA TAG | SEQ ID NO: 304 |
| At5g13180 | GATGGATAATGTCAAACTTGTTAAGAATGG | SEQ ID NO: 305 | TCTGAAACTATTGCAACTACTGGTCTCTTC | SEQ ID NO: 306 |
| At1g52880 | GATGGAGAGTACAGATTCTTCCGGTGTCC | SEQ ID NO: 307 | AGAATACCAATTCAAACCAGGCAATTGGTA | SEQ ID NO: 308 |
| At4g18450 | ATGGCTTTTGGCAATATCCAAG | SEQ ID NO: 309 | AAAAGAAGATAATAACGTCTCC | SEQ ID NO: 310 |

TABLE 5-continued

| AGI code | Foward primer | Nucleotide sequence | Reverse primer | Nucleotide sequence |
|---|---|---|---|---|
| At5g07580 | ATGGCGAGTTTTGAGGAAAGC | SEQ ID NO: 311 | AAATGCATCACAGGAAGATGAAG | SEQ ID NO: 312 |
| At1g74930 | ATGGTGAAGCAAGCGATGAAGG | SEQ ID NO: 313 | AAAATCCCAAAGAATCAAAGATTC | SEQ ID NO: 314 |
| At4g36160 | GATGGAATCGGTGGATCAATCATGTAGTGT | SEQ ID NO: 315 | AACATGTAAATCCCTATATAAGTCATAGTC | SEQ ID NO: 316 |
| At3g18550 | ATGAACAACAACATTTTCAGTACTAC | SEQ ID NO: 317 | ACTGTGTATAGCTTTAGATAAAACC | SEQ ID NO: 318 |
| At5g64750 | ATGTGTGTCTTAAAAGTGGCAAATC | SEQ ID NO: 319 | GGAGGATGGACTATTATTGTAG | SEQ ID NO: 320 |
| At2g02450 | GATGGCGGCGATAGGAGAGAAAG | SEQ ID NO: 321 | CTTAAAAGGAATATTAGTATAGTG | SEQ ID NO: 322 |
| At2g42400 | GATGAAGAGAACACATTTGGCAAGTTTTAG | SEQ ID NO: 323 | GAGGTAGCCTAGTCGAAGCTCCAAATCAAG | SEQ ID NO: 324 |
| At5g67300 | GATGGCTGATAGGATCAAAGGTCCATGGAG | SEQ ID NO: 325 | CTCGATTCTCCCAACTCCAATTTGACTCAT | SEQ ID NO: 326 |
| At1g68800 | ATGTTTCCTTCTTTCATTACTCAC | SEQ ID NO: 327 | ATTAGGGTTTTTAGTTAACACATTG | SEQ ID NO: 328 |
| At1g14510 | ATGGAAGGAATTCAGCATCC | SEQ ID NO: 329 | GGCTTTCATTTTCTTGCTGG | SEQ ID NO: 330 |
| At1g25580 | GATGGCTGGGCGATCATGGCTGATC | SEQ ID NO: 331 | CAGCAGCGTGGCAGTGTGTTGCC | SEQ ID NO: 332 |
| At5g18270 | GATGGCGGTTGTGGTTGAAGAAGG | SEQ ID NO: 333 | GAAGTCCCACAAGTCCCCCCTC | SEQ ID NO: 334 |
| At2g44840 | ATGAGCTCATCTGATTCCGTTAATAAC | SEQ ID NO: 335 | TATCCGATTATCAGAATAAGAACATTC | SEQ ID NO: 336 |
| At3g15500 | GATGGGTCTCCAAGAGCTTGACCCGTTAGC | SEQ ID NO: 337 | AATAAACCCGAACCCACTAGATTGTGACC | SEQ ID NO: 338 |
| At4g35580 | GATGCTGCAGTCTGCAGCACCAGAG | SEQ ID NO: 339 | TGAACTCACCAGTGTCCTCCATATAC | SEQ ID NO: 340 |
| At4g01550 | GATGGTGAAAGATCTGGTTGGG | SEQ ID NO: 341 | TCTCTCGCGATCAAACTTCATCGC | SEQ ID NO: 342 |
| At4g37750 | ATGAAGTCTTTTTGTGATAATGATG | SEQ ID NO: 343 | AGAATCAGCCCAAGCAGCGAAAACCGG | SEQ ID NO: 344 |
| At1g52890 | GATGGGTATCCAAGAAACTGACCCGTTAAC | SEQ ID NO: 345 | CATAAACCCAAACCCACCAACTTGCCCCGA | SEQ ID NO: 346 |
| At2g17040 | GATGGTTTACGGTAAGAGATCGAG | SEQ ID NO: 347 | CCAATATATGTTAACTATTGGTG | SEQ ID NO: 348 |
| At2g33480 | GATGGAGAAGAGGAGCTCTATTAAAAACAG | SEQ ID NO: 349 | TAGAAACAAACAAAACTTATTTTCCCGATA | SEQ ID NO: 350 |
| At5g39610 | GATGGATTACGAGGCATCAAGAATC | SEQ ID NO: 351 | GAAATTCCAAACGCAATCCAATTC | SEQ ID NO: 352 |
| At1g32770 | GATGGCTGATAATAAGGTCAATCTTTCGAT | SEQ ID NO: 353 | TACAGATAAATGAAGAAGTGGGTCTAAAGA | SEQ ID NO: 354 |
| At5g47220 | GATGTACGGACAGTGCAATATAGAATCCG | SEQ ID NO: 355 | TGAAACCAATAACTCATCAACACGTGT | SEQ ID NO: 356 |
| At1g56650 | GGGATGGAGGGTTCGTCCAAAGGGCTGCG AAAAGG | SEQ ID NO: 357 | ATCAAATTTCACAGTCTCTCCATCGAAAA GACTCC | SEQ ID NO: 358 |
| At1g63910 | GATGGGTCATCACTCATGCTGCAACCAGCA | SEQ ID NO: 359 | AAACGAAGAAGGGAAAGAAGAAGATAAGGC | SEQ ID NO: 360 |
| At3g15510 | GATGGAGAGCACCGATTCTTCCGGTGGTCC | SEQ ID NO: 361 | AGAAGAGTACCAATTTAAACCGGGTAATTG | SEQ ID NO: 362 |
| At2g45680 | ATGGCGACAATTCAGAAGCTTG | SEQ ID NO: 363 | GTGGTTCGATGACCGTGCTG | SEQ ID NO: 364 |
| At2g31230 | ATGTATTCATCTCCAAGTTCTTGG | SEQ ID NO: 365 | ACATGAGCTCATAAGAAGTTGTTC | SEQ ID NO: 366 |
| At1g12260 | GATGAATTCATTTTCCCACGTCCCTCCGGG | SEQ ID NO: 367 | CTTCCATAGATCAATCTGACAACTCGAAGA | SEQ ID NO: 368 |
| At3g61910 | GATGAACATATCAGTAAACGGACAGTCACA | SEQ ID NO: 369 | TCCACTACCGTTCAACAAGTGGCATGTCGT | SEQ ID NO: 370 |
| At5g07310 | ATGGCGAATTCAGGAAATTATGG | SEQ ID NO: 371 | AAAACCAGAATTAGGAGGTGAAG | SEQ ID NO: 372 |
| At3g14230 | ATGTGTGGAGGAGCTATAATCTC | SEQ ID NO: 373 | AAAGTCTCCTTCCAGCATGAAATTG | SEQ ID NO: 374 |
| At1g28160 | ATGGAGTTCAATGGTAATTTGAATG | SEQ ID NO: 375 | TTGGTAGAAGAATGTGGAGGG | SEQ ID NO: 376 |
| At1g69120 | GATGGGAAGGGGTAGGGTTCAATTGAAGAG | SEQ ID NO: 377 | TGCGGCGAAGCAGCCAAGGTTGCAGTTGTA | SEQ ID NO: 378 |
| At3g10490 | GATGGGTCGCGAATCTGTGGCTGTTG | SEQ ID NO: 379 | TTGTCCATTAGCATTGTTCTTCTTG | SEQ ID NO: 380 |
| At5g61600 | ATGGCAACTAAACAAGAAGCTTTAG | SEQ ID NO: 381 | AGTGACGGAGATAACGGAAAAG | SEQ ID NO: 382 |
| At1g43160 | ATGGTGTCTATGCTGACTAATG | SEQ ID NO: 383 | ACCAAAAGAGGAGTAATTGTATTG | SEQ ID NO: 384 |
| At3g15210 | GGGGATGGCCAAGATGGGCTTGAAAC | SEQ ID NO: 385 | TCAGGCCTGTTCCGATGGAGGAGGC | SEQ ID NO: 386 |

TABLE 5-continued

| AGI code | Fowerd primer | Nucleotide sequence | Reverse primer | Nucleotide sequence |
|---|---|---|---|---|
| At4g08150 | ATGGAAGAATACCAGCATGACAAC | SEQ ID NO: 387 | TCATGGACCGAGACGATAAGGTCC | SEQ ID NO: 388 |
| At1g10200 | GGGATGGCGTTCGCAGGAACAACCCAGAAATG | SEQ ID NO: 389 | TTAAGCAGCGACGACTTTGTCC | SEQ ID NO: 390 |

Production of Improved Transcription Factors

In order to add a repressor domain sequence to the 3' terminal of a transcription factor gene encoded by a coding region DNA fragment excluding a termination codon, p35SSXG, which is a vector having an SmaI site and a repressor domain sequence (amino acid sequence: GLDLD-LELRLGFA (SEQ ID NO: 391)) downstream of a CaMV35S promoter, was used. In order to link a transcription factor gene sequence and a repressor domain sequence, p35SSXG was cleaved with SmaI. Each PCR amplification fragment encoding the relevant transcription factor obtained above was separately inserted at the cleavage site. Thus, vectors (each denoted by p35SSXG(TFs)) were produced. Here, each vector is denoted by p35SSXG(TFs), provided that "TFs" represents the AGI code for each transcription factor. For example, a vector having the transcription factor specified by At2g23760 is denoted by p35SSXG (At2g23760). Also, in the descriptions below, "TFs" is used in a similar manner to denote vectors and the like.

Construction of Improved Transcription Factor Expression Vectors pBCKH was used as a binary vector for gene introduction into plants with *Agrobacterium*. This vector was obtained by incorporating a casset of the Gateway vector conversion system (Invitrogen) into the HindIII site of pBIG(Hygr) (Nucleic Acids Res. 18,203 (1990)). In order to incorporate an improved transcription factor gene sequence into the vector, 181 types of p35SSXG(TFs) were each separately mixed with the vector, followed by a recombination reaction using GATEWAY LR clonase (Invitrogen). Thus, vectors (each denoted by pBCKH-p35SSXG(TFs)) were produced.

In addition, for each transcription factor encoded by the relevant coding region DNA fragment including a termination codon, the gene encoding the transcription factor was selected for introduction. Thus, vectors, in each of which the relevant DNA fragment was linked downstream of a 35S promoter in the manner described above, were produced.

Introduction of Improved Transcription Factor Gene Expression Vectors and Transcription Factor Expression Vectors into Plants

*Arabidopsis thaliana* (Columbia (Col-0)) was used as a plant for introduction of a transcription factor or an improved transcription factor. Gene introduction was carried out in accordance with "Transformation of *Arabidopsis thaliana* by vacuum infiltration" (www.bch.msu.edu/pamgreen/protocol.htm). Note that each plant was infected only by immersing it in an *Agrobacterium* bacterial liquid without conducting depressurization treatment. Specifically, a transcription factor expression vector or an improved transcription factor expression vector (pBCKH-p35SSXG (TFs)) was introduced into the soil bacterium (*Agrobacterium tumefaciens*) strain (GV3101 (C58C1Rifr) pMP90 (Gmr), Koncz and Schell 1986)) by electroporation. For each vector, gene-transfected bacterial cells were cultured in 1 liter of a YEP medium containing antibiotics (kanamycin (Km): 50 µg/ml; gentamicin (Gm): 25 µg/ml; and rifampicin (Rif): 50 µg/ml)) until OD600 became 1. Subsequently, bacterial cells were recovered from each culture solution and suspended in 1 liter of an infection medium (an infiltration medium containing 2.2 g of an MS salt, 1× B5 vitamins, 50 g of sucrose, 0.5 g of MES, 0.044 µM of benzylaminopurine, and 400 µl of Silwet per litter (pH 5.7)).

*Arabidopsis thaliana* plants cultivated for 14 days were immersed in each solution for 1 minute for infection. Thereafter, the plants were continuously cultivated to result in seed setting. The collected seeds (T1 seeds) were sterilized in a solution containing 50% bleach and 0.02% Triton X-100 for 7 minutes, rinsed 3 times with sterilized water, and seeded on a sterilized hygromycin selection medium (containing a 4.3 g/l MS salt, 0.5% sucrose, 0.5 g/l MES (pH 5.7), 0.8% agar, 30 mg/l hygromycin, and 250 mg/l vancomycin). Five to ten lines of the transformed plants (T1 plants) growing on the hygromycin plate were selected for each improved transcription gene and transplanted into pots (each with a diameter of 50 mm) containing vermiculite mixed soil. Then, the plants were cultivated under conditions of 22° C. for 16 hours in the light and 8 hours in the dark at a light intensity ranging from about 60 to 80 µE/cm$^2$. Thus, seeds (T2 seeds) were obtained.

Analysis of T2 Seeds

Forty seeds were weighed and put into a 1.5-ml PP microtest tube for each of the transformants and wild-type *Arabidopsis thaliana*, which had been transfected with the relevant improved transcription factor or transcription factor. Further, a Tungsten Carbide Bead (3 mm) (QIAGEN) was put into each tube, followed by disruption by shaking at a frequency of 1/30 for 1 minute using a Mixer Mill MM 300 (Qiagen). After disruption, 50 µl of extraction buffer (62.5 mM Tris-HCl, 2% SDS, 10% glycerol, and 5% 2-mercaptethanol) was added thereto, followed by another instance of disruption by shaking for 1 minute. After disruption, each tube was allowed to stand on ice for 10 minutes, followed by centrifugation at 15000 rpm for 10 minutes. Each obtained supernatant was subjected to quantitative protein determination.

Quantitative protein determination for the prepared extracts was carried out using RC DC Protein Assay Kits (Bio-Rad) according to the manufacturer's instructions. The protein concentration was determined based on a calibration curve derived from BSA (bovine serum albumin).

In addition, 34 individuals of the wild strain (Col-0) were cultivated and seeds were collected from each individual. The protein content was determined for each line by quantitative analysis. Then, the average protein content was obtained. Thereafter, the average protein content of each transgenic individual was compared with the average protein content of the wild strain. The protein content increase rate for each gene-transfected line and the t-test P value were determined. Each line was found to exhibit improvement or reduction of seed protein content by 20% or more when compared with a wild-type strain. However, the P value was found to be 5% or less for each comparison.

Table 6 lists the analysis results for each line that was found to exhibit improvement of seed protein content by 20% or more as a result of introduction of the relevant improved transcription factor when compared with the wild-type strain. Table 7 lists the analysis results for each line that were found to exhibit improvement of seed protein content by 20% or more as a result of introduction of the gene encoding the relevant transcription factor when compared with the wild-type strain.

TABLE 6

|  | AGI code | Reference number | Protein content (%) | Increase-decrease rate (%) |
|---|---|---|---|---|
|  |  | WT(Col-0) | 16.3% | — |
| 1 | At2g23760 | HR0530 | 25.7% | 57.5% |
| 2 | At1g18330 | CR711 | 25.2% | 54.2% |
| 3 | At2g02070 | HR0489 | 23.9% | 46.3% |
| 4 | At1g12980 | TP120 | 22.6% | 38.7% |
| 5 | At5g62380 | CR604 | 22.5% | 38.2% |
| 6 | At4g23750 | CR034 | 21.8% | 33.7% |
| 7 | At4g32800 | CR504 | 21.6% | 32.1% |
| 8 | At1g24590 | CR019 | 21.4% | 31.3% |
| 9 | At5g07690 | HR0040 | 21.2% | 29.8% |
| 10 | At1g71692 | CR412 | 21.0% | 28.9% |
| 11 | At1g52150 | HR0611 | 20.9% | 27.9% |
| 12 | At3g25890 | CR029 | 20.4% | 24.9% |
| 13 | At1g09540 | CR705 | 20.4% | 24.8% |
| 14 | At5g22380 | CR229 | 20.3% | 24.5% |
| 15 | At2g44940 | CR505 | 20.3% | 24.1% |
| 16 | At5g41030 | CR131 | 20.2% | 23.6% |
| 17 | At5g60970 | CR116 | 20.1% | 23.1% |
| 18 | At5g35550 | CR701 | 20.0% | 22.4% |
| 19 | At1g60240 | CR623 | 19.9% | 22.2% |
| 20 | At2g23290 | HR0018 | 19.9% | 21.8% |
| 21 | At5g14000 | CR223 | 19.7% | 20.9% |
| 22 | At1g19490 | HR0001 | 19.6% | 20.2% |

TABLE 7

|  | AGI code | Reference number | Protein content (%) | Increase-decrease rate (%) |
|---|---|---|---|---|
|  |  | WT(Col-0) | 16.3% | — |
| 1 | At3g04070 | CR312 | 22.1% | 35.7% |
| 2 | At2g46770 | CR308 | 21.0% | 28.6% |
| 3 | At5g35550 | CR903 | 21.0% | 28.5% |

Table 8 lists the analysis results for each line that was found to exhibit reduction of seed protein content by 20% or more as a result of introduction of the relevant improved transcription factor when compared with the wild-type strain. Table 9 lists the analysis results for each line that were found to exhibit reduction of seed protein content by 20% or more as a result of introduction of the gene encoding the relevant transcription factor when compared with a wild-type strain.

TABLE 8

|  | AGI code | Reference number | Protein content (%) | Increase-decrease rate (%) |
|---|---|---|---|---|
|  |  | WT(Col-0) | 16.3% | 0.0% |
| 1 | At1g32770 | CR250 | 12.8% | −21.6% |
| 2 | At5g47220 | TP100 | 12.8% | −21.6% |
| 3 | At1g56650 | TP107 | 12.7% | −22.2% |
| 4 | At1g63910 | HR1722 | 12.5% | −23.5% |
| 5 | At3g15510 | CR245 | 12.5% | −23.7% |
| 6 | At2g45680 | CR121 | 12.4% | −24.3% |
| 7 | At2g31230 | CR006 | 12.2% | −25.2% |
| 8 | At1g12260 | CR232 | 12.1% | −25.6% |
| 9 | At3g61910 | CR601 | 11.9% | −27.3% |
| 10 | At5g07310 | CR008 | 11.9% | −27.3% |
| 11 | At3g14230 | CR014 | 11.9% | −27.3% |
| 12 | At1g28160 | CR020 | 11.8% | −27.4% |
| 13 | At1g69120 | CR404 | 11.8% | −27.6% |
| 14 | At3g10490 | CR220 | 11.8% | −27.7% |
| 15 | At5g61600 | CR001 | 11.5% | −29.7% |
| 16 | At1g43160 | CR015 | 10.9% | −33.1% |

TABLE 9

|  | AGI code | Reference number | Protein content (%) | Increase-decrease rate (%) |
|---|---|---|---|---|
|  |  | WT(Col-0) | 16.3% | 0.0% |
| 1 | At1g10200 | TP106 | 13.0% | −20.5% |

In addition, T2 seeds of a line (HR0530) (into which the improved transcription factor (At2g23760) listed in fig. 6 with the results demonstrating the largest increase in protein content had been introduced) were cultivated, followed by re-evaluation of the protein content. Table 10 lists the results. As shown in table 10, it was also possible to confirm an increase in protein content for T3 seeds. In particular, the protein content was found to be up to 43% higher than that of the wild-type line. In addition, it was confirmed that SDS-PAGE caused no changes in seed protein composition (not shown).

TABLE 10

|  | Protein concentration (mg/ml) | Increasing rate (%) | Protein content (%) | Increasing rate (%) | Total protein amount (mg) | Increasing rate (%) |
|---|---|---|---|---|---|---|
| Average of WT (10 individuals) | 1.6 |  | 26.6 |  | 71.8 |  |
| HR0530-23-4 | 2.4 | 46.3 | 36.9 | 38.5 | 90.7 | 26.3 |
| HR0530-23-10 | 2.3 | 43.0 | 39.4 | 48.2 | 130.1 | 81.1 |
| HR0530-23-8 | 2.3 | 39.6 | 39.0 | 46.7 | 103.9 | 44.7 |

As described above, the expression of SRDX-added chimeric proteins formed with 141 types of transcription factors was induced in this analysis. Results showed that the seed storage protein content increased by 20% or more as a result of expression of 22 types of chimeric proteins (accounting for 15.6% of the analyzed transcription factors), while the seed storage protein content decreased by 20% or more as a result of expression of 16 types of chimeric proteins (accounting for 11.3% of the analyzed transcription factors). That is to say, the seed storage protein content was found to have remarkably increased or decreased as a result of expression of approximately 27% of the chimeric proteins. In other words, it was found that approximately 73% of the transcription factors (e.g., At3g23220, At1g18570, At3g01530, At5g51190, At4g34410, At5g22290, and At3g04420) subjected to the experiments in the Examples do not cause remarkable changes in seed protein content even when a chimeric protein comprising such a transcription factor and a repressor domain is expressed or such a transcription factor is overexpressed.

As described above, the Examples revealed that the seed protein content can be significantly modified by causing expression of a particular transcription factor fused with a repressor domain, introducing a gene encoding a particular transcription factor, or modifying an expression control region of such gene.

In addition, in order to increase or decrease the seed protein content with the use of the above functionally improved transcription factors, it is expected that it will become possible to further modify the storage protein content to a remarkable extent with the simultaneous use of transcription factors and a known method for modifying a seed storage protein by modifying the nitrogen metabolic pathway, the fatty acid metabolic pathway, or transcription factors.

All publications, patents, and patent applications cited herein are incorporated herein by reference in their entirety.

The invention claimed is:

1. A method for increasing protein productivity in seeds, comprising expressing, in a plant, a chimeric protein obtained by fusing a transcription factor and a functional peptide capable of converting an arbitrary transcription factor into a transcriptional repressor, wherein said transcription factor is a protein comprising the amino acid sequence of SEQ ID NO: 4, or a protein having transactivation activity and comprising the amino acid sequence of SEQ ID NO: 4 but in which 1-10 amino acids have been deleted, substituted, added, or inserted, and wherein the functional peptide has an amino acid sequence expressed by any one of the following formulae (1) to (8):
(1) X1-Leu-Asp-Leu-X2-Leu-X3 (SEQ ID NO: 392 with deletion of 0-10 residues from the N-terminus) (where X1 denotes a set of 0 to 10 amino acid residues, X2 denotes Asn or Glu, and X3 denotes a set of at least 6 amino acid residues);
(2) Y1-Phe-Asp-Leu-Asn-Y2-Y3 (SEQ ID NO: 393 with deletion of 0-10 residues from the N-terminus (where Y1 denotes a set of 0 to 10 amino acid residues, Y2 denotes Phe or Ile, and Y3 denotes a set of at least 6 amino acid residues);
(3) Z1-Asp-Leu-Z2-Leu-Arg-Leu-Z3 (SEQ ID NO: 394 with deletion of 0-10 residues from the C-terminus and deletion of 0-2 residues from the N-terminus) (where Z1 denotes Leu, Asp-Leu, or Leu-Asp-Leu, Z2 denotes Glu, Gln, or Asp, and Z3 denotes a set of 0 to 10 amino acid residues);
(4) Asp-Leu-Z4-Leu-Arg-Leu (where Z4 denotes Glu, Gln, or Asp) (residues 4-9 of SEQ ID NO.: 394);

(5) α1-Leu-β1-Leu-γ1-Leu; (SEQ ID NO: 395)

(6) α1-Leu-β1-Leu-γ2-Leu; (SEQ ID NO: 396)

(7) α1-Leu-β2-Leu-Arg-Leu; (SEQ ID NO: 397)
and (8) α2-Leu-β1-Leu-Arg-Leu (SEQ ID NO: 398)

(where α1 denotes Asp, Asn, Glu, Gln, Thr, or Ser; α2 denotes Asn, Glu, Gln, Thr, or Ser; β1 denotes Asp, Gln, Asn, Arg, Glu, Thr, Ser, or His; β2 denotes Asn, Arg, Thr, Ser, or His; γ1 denotes Arg, Gln, Asn, Thr, Ser, His, Lys, or Asp; and γ2 denotes Gln, Asn, Thr, Ser, His, Lys, or Asp, in formulae (5) to (8)).

2. The method according to claim 1, wherein trans activation activity of the transcription factor is repressed.

3. The method according to claim 1, wherein the chimeric protein has transcriptional repressor activity.

4. A plant exhibiting increased protein productivity in seeds, wherein said plant expresses a chimeric protein obtained by fusing a transcription factor and a functional peptide capable of converting an arbitrary transcription factor into a transcriptional repressor,
wherein said transcription factor is a protein comprising the amino acid sequence of SEQ ID NO: 4, or a protein having transactivation activity and comprising the amino acid sequence of SEQ ID NO: 4 but in which 1-10 amino acids have been deleted, substituted, added, or inserted, and wherein the functional peptide has an amino acid sequence expressed by any one of the following formulae (1) to (8):
(1) X1-Leu-Asp-Leu-X2-Leu-X3 (SEQ ID NO: 392 with deletion of 0-10 residues from the N-terminus) (where X1 denotes a set of 0 to 10 amino acid residues, X2 denotes Asn or Glu, and X3 denotes a set of at least 6 amino acid residues);
(2) Y1-Phe-Asp-Leu-Asn-Y2-Y3 (SEQ ID NO: 393 with deletion of 0-10 residues from the N-terminus (where Y1 denotes a set of 0 to 10 amino acid residues, Y2 denotes Phe or Ile, and Y3 denotes a set of at least 6 amino acid residues);
(3) Z1-Asp-Leu-Z2-Leu-Arg-Leu-Z3 (SEQ ID NO: 394 with deletion of 0-10 residues from the C-terminus and deletion of 0-2 residues from the N-terminus) (where Z1 denotes Leu, Asp-Leu, or Leu-Asp-Leu, Z2 denotes Glu, Gln, or Asp, and Z3 denotes a set of 0 to 10 amino acid residues);
(4) Asp-Leu-Z4-Leu-Arg-Leu (where Z4 denotes Glu, Gln, or Asp) (residues 4-9 of SEQ ID NO.: 394);

(5) α1-Leu-β1-Leu-γ1-Leu; (SEQ ID NO: 395)

(6) α1-Leu-β1-Leu-γ2-Leu; (SEQ ID NO: 396)

(7) α1-Leu-β2-Leu-Arg-Leu; (SEQ ID NO: 397)
and (8) α2-Leu-β1-Leu-Arg-Leu (SEQ ID NO: 398)

(where α1 denotes Asp, Asn, Glu, Gln, Thr, or Ser; α2 denotes Asn, Glu, Gln, Thr, or Ser; β1 denotes Asp, Gln, Asn, Arg, Glu, Thr, Ser, or His; β2 denotes Asn, Arg, Thr, Ser, or His; y1 denotes Arg, Gln, Asn, Thr, Ser, His, Lys, or Asp; and y2 denotes Gln, Asn, Thr, Ser, His, Lys, or Asp, in formulae (5) to (8)).

* * * * *